(12) United States Patent
Cavaco Paulo et al.

(10) Patent No.: US 12,115,242 B2
(45) Date of Patent: *Oct. 15, 2024

(54) PEPTIDE COMPOSITION AND RESPECTIVE USES

(71) Applicant: Universidade do Minho, Braga (PT)

(72) Inventors: Artur Manuel Cavaco Paulo, Braga (PT); Celia Freitas Da Cruz, Guimaraes (PT); Margarida Maria Macedo Francesko Fernandes, Braga (PT)

(73) Assignee: UNIVERSIDADE DO MINHO, Braga (PT)

( * ) Notice: Subject to any disclaimer, the term of this patent is extended or adjusted under 35 U.S.C. 154(b) by 0 days.

This patent is subject to a terminal disclaimer.

(21) Appl. No.: 18/334,287

(22) Filed: Jun. 13, 2023

(65) Prior Publication Data

US 2023/0301894 A1    Sep. 28, 2023

Related U.S. Application Data

(63) Continuation of application No. 18/194,372, filed on Mar. 31, 2023, which is a continuation of application No. 16/439,889, filed on Jun. 13, 2019, now Pat. No. 11,642,298, which is a continuation of application No. 15/030,313, filed as application No. PCT/IB2014/065375 on Oct. 16, 2014, now Pat. No. 10,709,655.

(30) Foreign Application Priority Data

Oct. 18, 2013 (PT) .......................... 107244

(51) Int. Cl.
| | | |
|---|---|---|
| *A61K 8/64* | (2006.01) | |
| *A61Q 5/00* | (2006.01) | |
| *A61Q 5/04* | (2006.01) | |
| *A61Q 5/06* | (2006.01) | |

(52) U.S. Cl.
CPC ............... *A61K 8/64* (2013.01); *A61K 8/645* (2013.01); *A61Q 5/002* (2013.01); *A61Q 5/04* (2013.01); *A61Q 5/06* (2013.01); *A61Q 5/065* (2013.01); *A61K 2800/30* (2013.01)

(58) Field of Classification Search
CPC ...... A61K 8/64; A61K 8/645; A61K 2800/30; A61K 38/08; A61K 38/10; A61Q 5/002; A61Q 5/04; A61Q 5/06; A61Q 5/065; A61Q 5/00; A61Q 5/10; A61P 17/00; A61P 17/14

See application file for complete search history.

(56) References Cited

U.S. PATENT DOCUMENTS

| | | |
|---|---|---|
| 5,028,419 A | 7/1991 | Pigiet |
| 5,635,170 A | 6/1997 | Lang et al. |
| 8,383,580 B2 | 2/2013 | Rui et al. |
| 10,709,655 B2 | 7/2020 | Cavaco et al. |
| 11,642,298 B2 | 5/2023 | Cavaco Paulo et al. |
| 2006/0223728 A1 | 10/2006 | Tokunaga |
| 2006/0272103 A1 | 12/2006 | Barbarat |
| 2006/0286655 A1 | 12/2006 | Philippe |
| 2008/0107614 A1 | 5/2008 | Fahnestock et al. |
| 2009/0130154 A1 | 5/2009 | Gupta |
| 2010/0015070 A1 | 1/2010 | Bollschweiler et al. |
| 2010/0272666 A1 | 10/2010 | Breakspear et al. |
| 2013/0059772 A1 | 3/2013 | Kumar |
| 2013/0224269 A1 | 8/2013 | Khan et al. |
| 2016/0175209 A1 | 6/2016 | Walker et al. |
| 2016/0271043 A1 | 9/2016 | Cavaco Paulo et al. |
| 2020/0069551 A1 | 3/2020 | Sahib et al. |
| 2020/0121581 A1 | 4/2020 | Shoseyov et al. |
| 2021/0393500 A1 | 12/2021 | Cavaco Paulo et al. |
| 2022/0287944 A1 | 9/2022 | Costache et al. |

(Continued)

FOREIGN PATENT DOCUMENTS

| | | |
|---|---|---|
| CA | 2309413 A1 | 11/2000 |
| CN | 103126949 A | 6/2013 |

(Continued)

OTHER PUBLICATIONS

English Translation of JP11012138, accessed on Oct. 3, 2023, JPO website.*

(Continued)

*Primary Examiner* — Jeanette M Lieb
*Assistant Examiner* — Erinne R Dabkowski
(74) *Attorney, Agent, or Firm* — WILSON SONSINI GOODRICH & ROSATI

(57) ABSTRACT

The current application discloses a composition that comprises at least one peptide with a sequence length of 6-12 amino acids, where 2-5 of those amino acids are cysteines for the treatment and cosmetics of animal hair, in preference human hair. There are several hair styling methods that involve breakage and reestablishment of disulfide bonds, allowing relaxation and straightening of the hair. However, the most effective methods currently used to modulate hair contain harmful chemicals. Thus, there is a constant demand for formulations that efficiently model the hair fiber without damage. Thus, the present invention aims to provide a composition for treatment of the hair, including animal and human hair, without the use of chemicals harmful to the hair fiber and consumer health and uses of said compositions in shampoo, lotion, serum, cream, conditioner, foam, elixir, oil, aerosol or mask.

20 Claims, No Drawings

Specification includes a Sequence Listing.

(56) References Cited

U.S. PATENT DOCUMENTS

| | | |
|---|---|---|
| 2023/0248627 A1 | 8/2023 | Cavaco et al. |
| 2023/0248631 A1 | 8/2023 | Cavaco Paulo et al. |
| 2023/0338263 A1 | 10/2023 | Cavaco Paulo et al. |
| 2023/0355499 A1 | 11/2023 | Sahib et al. |
| 2023/0414478 A1 | 12/2023 | Cavaco et al. |
| 2023/0414479 A1 | 12/2023 | Cavaco et al. |
| 2023/0415070 A1 | 12/2023 | Cavaco et al. |
| 2024/0082135 A1 | 3/2024 | Cavaco Paulo et al. |
| 2024/0108560 A1 | 4/2024 | Staley et al. |
| 2024/0115481 A1 | 4/2024 | Cavaco Paulo et al. |

FOREIGN PATENT DOCUMENTS

| | | | |
|---|---|---|---|
| CN | 104940071 A | | 9/2015 |
| EP | 0335654 A2 | | 10/1989 |
| EP | 0488242 A1 | | 6/1992 |
| EP | 1046390 A1 | | 10/2000 |
| EP | 1238645 A2 | | 9/2002 |
| EP | 1705188 A1 | | 9/2006 |
| FR | 2706300 A1 | | 12/1994 |
| FR | 2876286 A1 | | 4/2006 |
| GB | 103484 A | | 1/1918 |
| JP | H0656889 A | | 3/1994 |
| JP | 1112138 | * | 1/1999 |
| JP | H1112138 A | | 1/1999 |
| JP | 2005151849 A | | 6/2005 |
| KR | 20090070272 A | | 7/2009 |
| PT | 103484 A | | 11/2007 |
| WO | WO-9711672 A1 | | 4/1997 |
| WO | WO-0023039 A2 | | 4/2000 |
| WO | WO-0051556 A1 | | 9/2000 |
| WO | WO-0064405 A2 | | 11/2000 |
| WO | WO-0112806 A2 | | 2/2001 |
| WO | WO-0123890 A1 | | 4/2001 |
| WO | WO-2004048399 A2 | | 6/2004 |
| WO | WO-2005049834 A1 | | 6/2005 |
| WO | WO-2006001536 A1 | | 1/2006 |
| WO | WO-2007136286 A1 | | 11/2007 |
| WO | WO-2008081348 A2 | | 7/2008 |
| WO | WO-2010010145 A1 | | 1/2010 |
| WO | WO-2010089228 A1 | | 8/2010 |
| WO | WO-2011072991 A1 | | 6/2011 |
| WO | WO-2012013593 A1 | | 2/2012 |
| WO | WO-2015056216 A2 | | 4/2015 |
| WO | WO-2018095813 A1 | | 5/2018 |
| WO | WO-2021001289 A1 | | 1/2021 |
| WO | WO-2022003655 A1 | | 1/2022 |
| WO | WO-2022029147 A1 | | 2/2022 |
| WO | WO-2022072696 A1 | | 4/2022 |
| WO | WO-2023081711 A1 | | 5/2023 |
| WO | WO-2023161711 A1 | | 8/2023 |
| WO | WO-2023250104 A2 | | 12/2023 |
| WO | WO-2023250105 A1 | | 12/2023 |
| WO | WO-2024073683 A2 | | 4/2024 |

OTHER PUBLICATIONS

BLAST glossary downloaded from www.ncbi.nlm.nih.gov on May 2, 2020.
BLAST search for SEQ ID No. 1, downloaded May 2, 2020 (2020).
BLAST search for SEQ ID No. 2, downloaded May 2, 2020 (2020).
Dow, Carbowax Sentry Polyethylene Glycols, published online 2011.
Fernanda Reis Gavazzoni Dias. Hair Cosmetics: An Overview. International Journal of Trichology 7:2-15 (2015).
Fernandes et al. Keratin-based peptide: biological evaluation and strengthening properties on relaxed hair. International Journal of Cosmetic Science 34:338-346 (2012).
Koonin et al. Chapter 2 Evolutionary Concept in Genetics and Genomics. MY. Sequence—Evolution—Function: Computational Approaches in Comparative Genomics. Boston: Kluwer Academic. Available from: https:// www.ncbi.nlnn.nih.gov/books/NBK20260/ (pp. 3 ) (2003).
Marabotti et al. The misuse of terms in scientific literature. Bioinformatics 26(19):2498 (2010).
Naturally Curly, http://www.naturallycurly.com/curlreading/kinky-hair-type-4a/ingredients-commonly-used-in-hair-care-productspeg-modified-materials/, published online Jun. 8, 2010.
PCT/IB2014/065375 International Search Report and Written Opinion dated Jun. 7, 2015.
Romanowski. An introduction to cosmetic technology. American Oil Chemists' Society. Available at https://www.aocs.org/stay-informed/inform-magazine/featured-articles/an-introduction-to-cosmetic-technology-april-2015?SSO=True (8 pgs.) (2015).
Shimomura et al. Human Hair Keratin-Associated Proteins. J Investig Dermatol Symp Proc 10:230-233 (2005).
Thesis from Celia Freitas Da Cruz, Unraveling and modulating human hair morphology features (192 pgs) (2012).
Uniprot Protein Database, protein accession A8MUX0 , Keratin-associated protein 16-1, accessed on Dec. 18, 2019.
Uniprot Protein Database, protein accession P26371 , Keratin-associated protein 5-9, accessed on Dec. 18, 2019.
Uniprot Protein Database, protein accession Q9NSB0, Type II hair keratin 6, accessed on Dec. 18, 2019.
Uniprot Protein Database, protein Accession Q9NSB5, accessed on Nov. 8, 2019.
Uniprot protein database, protein Type II hair keratin 1, protein accession Q9NSB5, accessed on Aug. 28, 2017.
U.S. Forest Service entry on soaps at www.fs.fed.us/wildflowers/ethnobotany/soaps.shtra, downloaded Sep. 29, 2020 (2020).
U.S. Appl. No. 15/030,313 Office Action dated Aug. 29, 2018.
U.S. Appl. No. 15/030,313 Office Action dated Aug. 31, 2017.
U.S. Appl. No. 15/030,313 Office Action dated Jan. 11, 2019.
U.S. Appl. No. 15/030,313 Office Action dated Jan. 24, 2018.
U.S. Appl. No. 15/030,313 Office Action dated Jul. 18, 2019.
U.S. Appl. No. 15/030,313 Office Action dated Mar. 2, 2017.
U.S. Appl. No. 16/122,796 Office Action dated Apr. 15, 2021.
U.S. Appl. No. 16/122,796 Office Action dated Apr. 28, 2023.
U.S. Appl. No. 16/122,796 Office Action dated Jan. 5, 2023.
U.S. Appl. No. 16/122,796 Office Action dated May 4, 2020.
U.S. Appl. No. 16/122,796 Office Action dated Oct. 1, 2020.
U.S. Appl. No. 16/122,796 Office Action dated Sep. 20, 2022.
U.S. Appl. No. 16/439,889 Office Action dated Apr. 1, 2022.
U.S. Appl. No. 16/439,889 Office Action dated Jan. 3, 2020.
U.S. Appl. No. 16/439,889 Office Action dated Sep. 15, 2022.
Yang. Chapter 36: Hair Care Cosmetics. Cosmetic Science and Technology: Theoretical Principles and Applications (pp. 601-615) (2017).
Co-pending U.S. Appl. No. 18/164,515, inventors Sahib; Suveen [Us] et al., filed Feb. 3, 2023.
Co-pending U.S. Appl. No. 18/194,372, inventors Cavaco Paulo; Arthur Manuel et al., filed Mar. 31, 2023.
Co-pending U.S. Appl. No. 18/339,889, inventors Cavaco; Paulo Artur Manuel et al., filed Jun. 22, 2023.
Co-pending U.S. Appl. No. 18/339,927, inventors Cavaco; Paulo Artur Manuel et al., filed Jun. 22, 2023.
Altschul et al., Basic Local Alignment Search Tool. J Mol Biol 215(3):403-410 (1990).
Archunan. Odorant Binding Proteins: a key player in the sense of smell. Bioinformation 14(1):36-37 (2018).
Bignetti et al. Purification and characterisation of an odorant-binding protein from cow nasal tissue. Eur. J. Biochem. 149:227-231 (1985).
Bignetti et al. The pyrazine-binding protein and olfaction. Comp. Biochem. Physiol., 90(1):1-5 (1988).
Breer. Olfactory receptors: molecular basis for recognition and discrimination of odors. Anal Bioanal Chem 377(3):427-33 (2003).
Briand et al. Evidence of an Odorant-Binding Protein in the Human Olfactory Mucus: Location, Structural Characterization, and Odorant-Binding Properties. Biochemistry 41:7241-7252 (2002).
Campanella et al., MatGAT: An application that generates similarity/identity matrices using protein or DNA sequences. BMC Bioinformatics 4:29 (2003).
Capo et al. The porcine odorant-binding protein as molecular probe for benzene detection. PloS One 13(9):e0202630 (2018).

(56) References Cited

OTHER PUBLICATIONS

Castro et al. The Structural Properties of Odorants Modulate Their Association to Human Odorant Binding Protein. Biomolecules 11(2):145 (2021).

Cave et al. Progress in the development of olfactory-based bioelectronic chemosensors. Biosens Bioelectron 123:211-222 (2019).

Cennamo et al. Easy to Use Plastic Optical Fiber-Based Biosensor for Detection of Butanal. PloS One 10(3):e0116770 (2015).

Co-pending U.S. Appl. No. 18/478,320, inventors Staley; Karis et al., filed Sep. 29, 2023.

Co-pending U.S. Appl. No. 18/497,900, inventors Cavaco Paulo; Arthur Manuel et al., filed Oct. 30, 2023.

Co-pending U.S. Appl. No. 18/520,428, inventors Cavaco Paulo; Artur Manuel et al., filed Nov. 27, 2023.

Dal Monte et al. Purification and characterization of two odorant-binding proteins from nasal tisue of rabbit and pig. Comp Biochem Physiol 99(2):445-451 (1991).

Di Pietrantonio et al. Detection of odorant molecules via surface acoustic wave biosensor array based on odorant-binding proteins. Biosens Bioelectron 41:328-34 (2013).

Flower. Beyond the superfamily: the lipocalin receptors. Biochim Biophys Acta 1482:327-336 (2000).

Flower. The lipocalin protein family : structure and function. Biochem. J. 318(Pt 1)(Pt 1):1-14 (1996).

Garibotti et al. Three Odorant-binding Proteins from Rabbit Nasal Mucosa. Chem Senses 22(4):383-390 (1997).

Goncalves et al. OBP fused with cell-penetrating peptides promotes liposomal transduction. Colloids Surf B Biointerfaces 161:645-653 (2018).

Goncalves et al. Release of Fragrances from Cotton Functionalized with Carbohydrate-Binding Module Proteins. ACS Applied Mater Interfaces 11(31):28499-28506 (2019).

Goncalves et al. Two Engineered OBPs with opposite temperature-dependent affinities towards 1-aminoanthracene. Sci Rep 8 (1):14844 (2018).

Gongalves et al. 1-Aminoanthracene Transduction into Liposomes Driven by Odorant-Binding Protein Proximity. ACS Applied Mater Interfaces 10(32):27531-27539 (2018).

Han et al. Operating Mechanism and Molecular Dynamics of Pheromone-Binding Protein ASP1 as Influenced by pH. PLoS One 9(10):e110565 (2014).

Kozlowski. IPC—Isoelectric Point Calculator. Biol Direct 11(1):55 (2016).

Lazar et al. Molecular and Functional Characterization of an Odorant Binding Protein of the Asian Elephant, *Elephas maximus*: Implications for the Role of Lipocalins in Mammalian Olfaction. Biochemistry 41:11786-11794 (2002).

Lobel et al. Odorant of different chemical classes interact with distinct odorant binding protein subtypes. Chem Senses 27:39-44 (2002).

Malpeli et al. Chapter 9: Purification and Fluorescent Titration of Cellular Retinol-Binding Protein. In Methods in Molecular Biology; Redfern, C. P. F., Ed.; pp. 111-122 (1998).

Mazzini et al. Dissociation and unfolding of bovine odorant binding protein at acidic pH. J Struct Biol 159(1):82-91 (2007).

Mulla et al. Capacitance-modulated transistor detects odorant binding protein chiral interactions. Nature Commun 6:6010 (2015).

Needleman et al. A general method applicable to the search for similarities in the amino acid sequence of two proteins. J. Mol. Biol. 48:443-453 (1970).

Nogueira et al. Peptide anchor for folate-targeted liposomal delivery. Biomacromolecules 16(9):2904-2910 (2015).

Ozeki et al. A study of the suppression of body odour in elderly subjects by anti-fungal agents. Int J Cosmet Sci 38(3):312-8 (2016).

Paolini et al. Porcine odorant-binding protein: structural stability and ligand affinities measured by Fourier-transform infrared spectroscopy and fluorescence spectroscopy. Biochim Biophys Acta 1431:179-188 (1999).

Parisi et al. Unfolding and refolding of porcine odorant binding protein in guanidinium hydrochloride: equilibrium studies at neutral pH. Biochim Biophys Acta 652(2):115-125 (2003).

PCT/IB2021/056011 International Search Report and Written Opinion dated Oct. 6, 2021.

PCT/US2023/026017 International Search Report and Written Opinion dated Dec. 13, 2023.

PCT/US2023/026019 International Search Report and Written Opinion dated Dec. 5, 2023.

Pelosi et al. Odorant-Binding Proteins as Sensing Elements for Odour Monitoring. Sensors (Basel) 18(10):3248 (2018).

Pelosi et al. Structure and biotechnological applications of odorant-binding proteins. Appl Microbiol Biotechnol 98(1):61-70 (2014).

Pelosi. Odorant-Binding Proteins: Structural Aspects. In Annals New York academy of sciences; Olfaction and Taste XII: an international symposium, pp. 281-293 (1998).

Perduca et al. Crystal Structure of a Truncated Form of Porcine Odorant-Binding Protein. Proteins 42:201-209 (2001).

Pes et al. Isolation of two odorant-binding proteins from mouse nasal tissue. Comp. Biochem. Physiol. 103 (4):1011-1017 (1992).

Pevsner et al. Odorant-binding protein: characterization of ligand binding. J Biol Chem 265(11):6118-6125 (1990).

Sankaran et al. Biology and applications of olfactory sensing system: A review. Sensors and Actuators B: Chemical 171-172:1-17 (2012).

Silva et al. Odorant binding proteins: a biotechnological tool for odour control. Appl Microbiol Biotechnol 98(8):3629-3638 (2014).

Sorokowska et al. Does Personality Smell? Accuracy of Personality Assessments Based on Body Odour. European Journal of Personality 26(5):496-503 (2012).

Spinelli et al. The Structure of the Monomeric Porcine Odorant Binding Protein Sheds Light on the Domain Swapping Mechanism. Biochemistry 37:7913-7918 (1998).

Tegoni et al. Mammalian odorant binding proteins. Biochim Biophys Acta 1482:229-240 (2000).

U.S. Appl. No. 18/164,515 Office Action dated Oct. 12, 2023.

U.S. Appl. No. 18/194,372 Office Action dated Dec. 14, 2023.

U.S. Appl. No. 18/339,889 Office Action dated Dec. 19, 2023.

Vincent et al. Crystal structures of bovine odorant-binding protein in complex with odorant molecules. Eur J Biochem 271(19):3832-42 (2004).

What is wrong with CANTU shampoo. https://forums.longhaircommunity.com/showthread.php?t=149761. Published: May 5, 2019.

Whitson et al. Human Odorant Binding Protein 2a has Two Affinity States and is Capable of Binding Some Uremic Toxins. Biochem Anal Biochem 3:2 (2014).

CN104940071A English Translation Published: Sep. 30, 2015.

EP1238645A2 English Translation Published: Sep. 11, 2002.

U.S. Appl. No. 18/339,927 Office Action dated Jan. 24, 2024.

U.S. Appl. No. 18/339,927 Office Action dated May 8, 2024.

Berendsen, HJ., A glimpse of the Holy Grail? Science 282(5389):642-643 (1998).

Bradley et al. Limits of cooperativity in a structurally modular protein: response of the Notch ankyrin domain to analogous alanine substitutions in each repeat. J Mol Biol. 324(2):373-386 (2002).

Chemists Corner, https://chemistscorner.com/cosmeticsciencetalk/discussion/sodium-pca-vs-glycerin/. Published: Dec. 1, 2020.

Ngo, Thomas, et al., Computational Complexity, Protein Structure Prediction, and the Levinthal Paradox. Birkhauser Boston 491-495 (1994).

Rudinger, J., Characteristics of the amino acids as components of a peptide hormone sequence. Peptide Hormones, J.A, Parsons , MA, BM, BCh, 1-7 (1976).

Schinzel, R, et al., The Phosphate Recognition Site of *Escherichia coli* Maltodextrin Phosphorylase. FEBS Letters 286(1-2):125-128 (1991).

Sigma, Designing Custom Peptides, pp. 1-2. (2004).

SOLU Shampoo. https://web.archive.Org/web/20200929001233/https://www.thekindestcut.com/product-page/solu-shampoo. Published: Sep. 29, 2020.

U.S. Appl. No. 18/164,515 Office Action dated Feb. 15, 2024.

U.S. Appl. No. 18/497,900 Office Action dated Mar. 11, 2024.

(56) References Cited

OTHER PUBLICATIONS

U.S. Appl. No. 18/520,428 Office Action dated Mar. 25, 2024.
U.S. Appl. No. 18/339,889 Office Action dated Mar. 27, 2024.
Voet, Judith., Biochemistry, Second Edition, John Wiley & Sons, Inc., 235-241 (1995).
Yampolsky, Lev, et al., The Exchangeability of Amino Acids in Proteins. Genetics 170(4): 1459-1472 (2005).

* cited by examiner

SEQUENCE LISTING

```
Sequence total quantity: 1239
SEQ ID NO: 1          moltype = AA  length = 10
FEATURE               Location/Qualifiers
source                1..10
```

```
                            mol_type = protein
                            organism = Homo sapiens
SEQUENCE: 1
APCAPRPSCG                                                                  10

SEQ ID NO: 2                moltype = AA   length = 10
FEATURE                     Location/Qualifiers
source                      1..10
                            mol_type = protein
                            organism = Homo sapiens
SEQUENCE: 2
EACVPSVPCP                                                                  10

SEQ ID NO: 3                moltype = AA   length = 10
FEATURE                     Location/Qualifiers
source                      1..10
                            mol_type = protein
                            organism = Homo sapiens
SEQUENCE: 3
ESCGTASGCA                                                                  10

SEQ ID NO: 4                moltype = AA   length = 10
FEATURE                     Location/Qualifiers
source                      1..10
                            mol_type = protein
                            organism = Homo sapiens
SEQUENCE: 4
GLCAGTSACL                                                                  10

SEQ ID NO: 5                moltype = AA   length = 10
FEATURE                     Location/Qualifiers
source                      1..10
                            mol_type = protein
                            organism = Homo sapiens
SEQUENCE: 5
GVCGPSPPCI                                                                  10

SEQ ID NO: 6                moltype = AA   length = 10
FEATURE                     Location/Qualifiers
source                      1..10
                            mol_type = protein
                            organism = Homo sapiens
SEQUENCE: 6
HGCTLPGACN                                                                  10

SEQ ID NO: 7                moltype = AA   length = 10
FEATURE                     Location/Qualifiers
source                      1..10
                            mol_type = protein
                            organism = Homo sapiens
SEQUENCE: 7
HSCTLPGACN                                                                  10

SEQ ID NO: 8                moltype = AA   length = 10
FEATURE                     Location/Qualifiers
source                      1..10
                            mol_type = protein
                            organism = Homo sapiens
SEQUENCE: 8
KDCLQNSLCE                                                                  10

SEQ ID NO: 9                moltype = AA   length = 10
FEATURE                     Location/Qualifiers
source                      1..10
                            mol_type = protein
                            organism = Homo sapiens
SEQUENCE: 9
LPCLPAASCG                                                                  10

SEQ ID NO: 10               moltype = AA   length = 10
FEATURE                     Location/Qualifiers
source                      1..10
                            mol_type = protein
                            organism = Homo sapiens
SEQUENCE: 10
LPCYFTGSCN                                                                  10

SEQ ID NO: 11               moltype = AA   length = 10
FEATURE                     Location/Qualifiers
```

| | | |
|---|---|---|
| source | 1..10<br>mol_type = protein<br>organism = Homo sapiens | |
| SEQUENCE: 11<br>NFCLPSLSCR | | 10 |
| SEQ ID NO: 12<br>FEATURE<br>source | moltype = AA   length = 10<br>Location/Qualifiers<br>1..10<br>mol_type = protein<br>organism = Homo sapiens | |
| SEQUENCE: 12<br>NPCATTNACD | | 10 |
| SEQ ID NO: 13<br>FEATURE<br>source | moltype = AA   length = 10<br>Location/Qualifiers<br>1..10<br>mol_type = protein<br>organism = Homo sapiens | |
| SEQUENCE: 13<br>NPCATTNACE | | 10 |
| SEQ ID NO: 14<br>FEATURE<br>source | moltype = AA   length = 10<br>Location/Qualifiers<br>1..10<br>mol_type = protein<br>organism = Homo sapiens | |
| SEQUENCE: 14<br>NPCATTNACS | | 10 |
| SEQ ID NO: 15<br>FEATURE<br>source | moltype = AA   length = 10<br>Location/Qualifiers<br>1..10<br>mol_type = protein<br>organism = Homo sapiens | |
| SEQUENCE: 15<br>NPCGLRARCG | | 10 |
| SEQ ID NO: 16<br>FEATURE<br>source | moltype = AA   length = 10<br>Location/Qualifiers<br>1..10<br>mol_type = protein<br>organism = Homo sapiens | |
| SEQUENCE: 16<br>NPCGPRSRCG | | 10 |
| SEQ ID NO: 17<br>FEATURE<br>source | moltype = AA   length = 10<br>Location/Qualifiers<br>1..10<br>mol_type = protein<br>organism = Homo sapiens | |
| SEQUENCE: 17<br>NPCSTPASCT | | 10 |
| SEQ ID NO: 18<br>FEATURE<br>source | moltype = AA   length = 10<br>Location/Qualifiers<br>1..10<br>mol_type = protein<br>organism = Homo sapiens | |
| SEQUENCE: 18<br>NPCSTSPSCV | | 10 |
| SEQ ID NO: 19<br>FEATURE<br>source | moltype = AA   length = 10<br>Location/Qualifiers<br>1..10<br>mol_type = protein<br>organism = Homo sapiens | |
| SEQUENCE: 19<br>PACTSSSPCS | | 10 |
| SEQ ID NO: 20<br>FEATURE<br>source | moltype = AA   length = 10<br>Location/Qualifiers<br>1..10<br>mol_type = protein<br>organism = Homo sapiens | |
| SEQUENCE: 20<br>SKCHESTVCP | | 10 |
| SEQ ID NO: 21 | moltype = AA   length = 10 | |

```
FEATURE             Location/Qualifiers
source              1..10
                    mol_type = protein
                    organism = Homo sapiens
SEQUENCE: 21
SPCVPRTVCV                                                              10

SEQ ID NO: 22       moltype = AA  length = 10
FEATURE             Location/Qualifiers
source              1..10
                    mol_type = protein
                    organism = Homo sapiens
SEQUENCE: 22
SSCSVETACL                                                              10

SEQ ID NO: 23       moltype = AA  length = 10
FEATURE             Location/Qualifiers
source              1..10
                    mol_type = protein
                    organism = Homo sapiens
SEQUENCE: 23
SVCSSGVNCR                                                              10

SEQ ID NO: 24       moltype = AA  length = 10
FEATURE             Location/Qualifiers
source              1..10
                    mol_type = protein
                    organism = Homo sapiens
SEQUENCE: 24
TACPLPGTCH                                                              10

SEQ ID NO: 25       moltype = AA  length = 10
FEATURE             Location/Qualifiers
source              1..10
                    mol_type = protein
                    organism = Homo sapiens
SEQUENCE: 25
TNCSPRPICV                                                              10

SEQ ID NO: 26       moltype = AA  length = 10
FEATURE             Location/Qualifiers
source              1..10
                    mol_type = protein
                    organism = Homo sapiens
SEQUENCE: 26
TSCVPPAPCT                                                              10

SEQ ID NO: 27       moltype = AA  length = 10
FEATURE             Location/Qualifiers
source              1..10
                    mol_type = protein
                    organism = Homo sapiens
SEQUENCE: 27
TTCTSSNTCE                                                              10

SEQ ID NO: 28       moltype = AA  length = 10
FEATURE             Location/Qualifiers
source              1..10
                    mol_type = protein
                    organism = Homo sapiens
SEQUENCE: 28
VPCVPSVPCT                                                              10

SEQ ID NO: 29       moltype = AA  length = 10
FEATURE             Location/Qualifiers
source              1..10
                    mol_type = protein
                    organism = Homo sapiens
SEQUENCE: 29
ATCGPSACIT                                                              10

SEQ ID NO: 30       moltype = AA  length = 10
FEATURE             Location/Qualifiers
source              1..10
                    mol_type = protein
                    organism = Homo sapiens
SEQUENCE: 30
GPCISNPCGL                                                              10
```

```
SEQ ID NO: 31            moltype = AA   length = 10
FEATURE                  Location/Qualifiers
source                   1..10
                         mol_type = protein
                         organism = Homo sapiens
SEQUENCE: 31
GPCLSNPCTS                                                                10

SEQ ID NO: 32            moltype = AA   length = 10
FEATURE                  Location/Qualifiers
source                   1..10
                         mol_type = protein
                         organism = Homo sapiens
SEQUENCE: 32
GSCVTNPCGP                                                                10

SEQ ID NO: 33            moltype = AA   length = 10
FEATURE                  Location/Qualifiers
source                   1..10
                         mol_type = protein
                         organism = Homo sapiens
SEQUENCE: 33
LTCFSITCSS                                                                10

SEQ ID NO: 34            moltype = AA   length = 10
FEATURE                  Location/Qualifiers
source                   1..10
                         mol_type = protein
                         organism = Homo sapiens
SEQUENCE: 34
NPCSTPSCTT                                                                10

SEQ ID NO: 35            moltype = AA   length = 10
FEATURE                  Location/Qualifiers
source                   1..10
                         mol_type = protein
                         organism = Homo sapiens
SEQUENCE: 35
PSCVTAPCAP                                                                10

SEQ ID NO: 36            moltype = AA   length = 10
FEATURE                  Location/Qualifiers
source                   1..10
                         mol_type = protein
                         organism = Homo sapiens
SEQUENCE: 36
SDCSSTHCSP                                                                10

SEQ ID NO: 37            moltype = AA   length = 10
FEATURE                  Location/Qualifiers
source                   1..10
                         mol_type = protein
                         organism = Homo sapiens
SEQUENCE: 37
SLCLPPTCHT                                                                10

SEQ ID NO: 38            moltype = AA   length = 10
FEATURE                  Location/Qualifiers
source                   1..10
                         mol_type = protein
                         organism = Homo sapiens
SEQUENCE: 38
SLCNLGSCGP                                                                10

SEQ ID NO: 39            moltype = AA   length = 10
FEATURE                  Location/Qualifiers
source                   1..10
                         mol_type = protein
                         organism = Homo sapiens
SEQUENCE: 39
SPCLVGNCAW                                                                10

SEQ ID NO: 40            moltype = AA   length = 10
FEATURE                  Location/Qualifiers
source                   1..10
                         mol_type = protein
                         organism = Homo sapiens
SEQUENCE: 40
TACLPGTCAT                                                                10
```

| | | |
|---|---|---|
| SEQ ID NO: 41<br>FEATURE<br>source | moltype = AA   length = 10<br>Location/Qualifiers<br>1..10<br>mol_type = protein<br>organism = Homo sapiens | |
| SEQUENCE: 41<br>TSCLPALCLP | | 10 |
| SEQ ID NO: 42<br>FEATURE<br>source | moltype = AA   length = 10<br>Location/Qualifiers<br>1..10<br>mol_type = protein<br>organism = Homo sapiens | |
| SEQUENCE: 42<br>TSCSSRPCVP | | 10 |
| SEQ ID NO: 43<br>FEATURE<br>source | moltype = AA   length = 10<br>Location/Qualifiers<br>1..10<br>mol_type = protein<br>organism = Homo sapiens | |
| SEQUENCE: 43<br>TTCGGGSCGV | | 10 |
| SEQ ID NO: 44<br>FEATURE<br>source | moltype = AA   length = 10<br>Location/Qualifiers<br>1..10<br>mol_type = protein<br>organism = Homo sapiens | |
| SEQUENCE: 44<br>VNCRPELCLG | | 10 |
| SEQ ID NO: 45<br>FEATURE<br>source | moltype = AA   length = 10<br>Location/Qualifiers<br>1..10<br>mol_type = protein<br>organism = Homo sapiens | |
| SEQUENCE: 45<br>YVCQPMACLP | | 10 |
| SEQ ID NO: 46<br>FEATURE<br>source | moltype = AA   length = 10<br>Location/Qualifiers<br>1..10<br>mol_type = protein<br>organism = Homo sapiens | |
| SEQUENCE: 46<br>AFSCISACGP | | 10 |
| SEQ ID NO: 47<br>FEATURE<br>source | moltype = AA   length = 10<br>Location/Qualifiers<br>1..10<br>mol_type = protein<br>organism = Homo sapiens | |
| SEQUENCE: 47<br>GSVCSAPCNG | | 10 |
| SEQ ID NO: 48<br>FEATURE<br>source | moltype = AA   length = 10<br>Location/Qualifiers<br>1..10<br>mol_type = protein<br>organism = Homo sapiens | |
| SEQUENCE: 48<br>GVVCGDLCAS | | 10 |
| SEQ ID NO: 49<br>FEATURE<br>source | moltype = AA   length = 10<br>Location/Qualifiers<br>1..10<br>mol_type = protein<br>organism = Homo sapiens | |
| SEQUENCE: 49<br>GVVCGDLCVS | | 10 |
| SEQ ID NO: 50<br>FEATURE<br>source | moltype = AA   length = 10<br>Location/Qualifiers<br>1..10<br>mol_type = protein<br>organism = Homo sapiens | |
| SEQUENCE: 50 | | |

```
LTGCLLPCYF                                                                                       10

SEQ ID NO: 51           moltype = AA   length = 10
FEATURE                 Location/Qualifiers
source                  1..10
                        mol_type = protein
                        organism = Homo sapiens SEQUENCE: 51
NEDCKLPCNP                                                                                       10

SEQ ID NO: 52           moltype = AA   length = 10
FEATURE                 Location/Qualifiers
source                  1..10
                        mol_type = protein
                        organism = Homo sapiens SEQUENCE: 52
NFSCVSACGP                                                                                       10

SEQ ID NO: 53           moltype = AA   length = 10
FEATURE                 Location/Qualifiers
source                  1..10
                        mol_type = protein
                        organism = Homo sapiens SEQUENCE: 53
PPTCHTACPL                                                                                       10

SEQ ID NO: 54           moltype = AA   length = 10
FEATURE                 Location/Qualifiers
source                  1..10
                        mol_type = protein
                        organism = Homo sapiens SEQUENCE: 54
PQPCATACKP                                                                                       10

SEQ ID NO: 55           moltype = AA   length = 10
FEATURE                 Location/Qualifiers
source                  1..10
                        mol_type = protein
                        organism = Homo sapiens SEQUENCE: 55
SEDCKLPCNP                                                                                       10

SEQ ID NO: 56           moltype = AA   length = 10
FEATURE                 Location/Qualifiers
source                  1..10
                        mol_type = protein
                        organism = Homo sapiens SEQUENCE: 56
SLGCRTSCSS                                                                                       10

SEQ ID NO: 57           moltype = AA   length = 10
FEATURE                 Location/Qualifiers
source                  1..10
                        mol_type = protein
                        organism = Homo sapiens SEQUENCE: 57
SLSCRTSCSS                                                                                       10

SEQ ID NO: 58           moltype = AA   length = 10
FEATURE                 Location/Qualifiers
source                  1..10
                        mol_type = protein
                        organism = Homo sapiens SEQUENCE: 58
SSSCPLGCTM                                                                                       10

SEQ ID NO: 59           moltype = AA   length = 10
FEATURE                 Location/Qualifiers
source                  1..10
                        mol_type = protein
                        organism = Homo sapiens SEQUENCE: 59
TGSCNSPCLV                                                                                       10

SEQ ID NO: 60           moltype = AA   length = 10
FEATURE                 Location/Qualifiers
source                  1..10
                        mol_type = protein
                        organism = Homo sapiens
```

```
SEQUENCE: 60
TSSCPLGCTM                                                                            10

SEQ ID NO: 61          moltype = AA  length = 10
FEATURE                Location/Qualifiers
source                 1..10
                       mol_type = protein
                       organism = Homo sapiens
SEQUENCE: 61
VGSCGSSCRK                                                                            10

SEQ ID NO: 62          moltype = AA  length = 10
FEATURE                Location/Qualifiers
source                 1..10
                       mol_type = protein
                       organism = Homo sapiens
SEQUENCE: 62
VGVCGGSCKR                                                                            10

SEQ ID NO: 63          moltype = AA  length = 10
FEATURE                Location/Qualifiers
source                 1..10
                       mol_type = protein
                       organism = Homo sapiens
SEQUENCE: 63
VSNCNWFCEG                                                                            10

SEQ ID NO: 64          moltype = AA  length = 10
FEATURE                Location/Qualifiers
source                 1..10
                       mol_type = protein
                       organism = Homo sapiens
SEQUENCE: 64
ACGPRPGRCC                                                                            10

SEQ ID NO: 65          moltype = AA  length = 10
FEATURE                Location/Qualifiers
source                 1..10
                       mol_type = protein
                       organism = Homo sapiens
SEQUENCE: 65
ACGPRPSRCC                                                                            10

SEQ ID NO: 66          moltype = AA  length = 10
FEATURE                Location/Qualifiers
source                 1..10
                       mol_type = protein
                       organism = Homo sapiens
SEQUENCE: 66
CAPRPSCGPC                                                                            10

SEQ ID NO: 67          moltype = AA  length = 10
FEATURE                Location/Qualifiers
source                 1..10
                       mol_type = protein
                       organism = Homo sapiens
SEQUENCE: 67
CEPCSAYVIC                                                                            10

SEQ ID NO: 68          moltype = AA  length = 10
FEATURE                Location/Qualifiers
source                 1..10
                       mol_type = protein
                       organism = Homo sapiens
SEQUENCE: 68
CGLRARCGPC                                                                            10

SEQ ID NO: 69          moltype = AA  length = 10
FEATURE                Location/Qualifiers
source                 1..10
                       mol_type = protein
                       organism = Homo sapiens
SEQUENCE: 69
CGPRPGRCCI                                                                            10

SEQ ID NO: 70          moltype = AA  length = 10
FEATURE                Location/Qualifiers
source                 1..10
                       mol_type = protein
```

```
                              organism = Homo sapiens
SEQUENCE: 70
CGPRPSRCCI                                                                    10

SEQ ID NO: 71             moltype = AA   length = 10
FEATURE                   Location/Qualifiers
source                    1..10
                          mol_type = protein
                          organism = Homo sapiens
SEQUENCE: 71
CGPRSRCGPC                                                                    10

SEQ ID NO: 72             moltype = AA   length = 10
FEATURE                   Location/Qualifiers
source                    1..10
                          mol_type = protein
                          organism = Homo sapiens
SEQUENCE: 72
CGTSQKGCCN                                                                    10

SEQ ID NO: 73             moltype = AA   length = 10
FEATURE                   Location/Qualifiers
source                    1..10
                          mol_type = protein
                          organism = Homo sapiens
SEQUENCE: 73
CHGCTLPGAC                                                                    10

SEQ ID NO: 74             moltype = AA   length = 10
FEATURE                   Location/Qualifiers
source                    1..10
                          mol_type = protein
                          organism = Homo sapiens
SEQUENCE: 74
CHSCTLPGAC                                                                    10

SEQ ID NO: 75             moltype = AA   length = 10
FEATURE                   Location/Qualifiers
source                    1..10
                          mol_type = protein
                          organism = Homo sapiens
SEQUENCE: 75
CLPCLPAASC                                                                    10

SEQ ID NO: 76             moltype = AA   length = 10
FEATURE                   Location/Qualifiers
source                    1..10
                          mol_type = protein
                          organism = Homo sapiens
SEQUENCE: 76
CLPPTCHTAC                                                                    10

SEQ ID NO: 77             moltype = AA   length = 10
FEATURE                   Location/Qualifiers
source                    1..10
                          mol_type = protein
                          organism = Homo sapiens
SEQUENCE: 77
CLSNPCTSCV                                                                    10

SEQ ID NO: 78             moltype = AA   length = 10
FEATURE                   Location/Qualifiers
source                    1..10
                          mol_type = protein
                          organism = Homo sapiens
SEQUENCE: 78
CLVGNCAWCE                                                                    10

SEQ ID NO: 79             moltype = AA   length = 10
FEATURE                   Location/Qualifiers
source                    1..10
                          mol_type = protein
                          organism = Homo sapiens
SEQUENCE: 79
CNPCSTPASC                                                                    10

SEQ ID NO: 80             moltype = AA   length = 10
FEATURE                   Location/Qualifiers
source                    1..10
```

```
                            mol_type = protein
                            organism = Homo sapiens
SEQUENCE: 80
CNPCSTPSCT                                                              10

SEQ ID NO: 81               moltype = AA  length = 10
FEATURE                     Location/Qualifiers
source                      1..10
                            mol_type = protein
                            organism = Homo sapiens
SEQUENCE: 81
CNPCSTSPSC                                                              10

SEQ ID NO: 82               moltype = AA  length = 10
FEATURE                     Location/Qualifiers
source                      1..10
                            mol_type = protein
                            organism = Homo sapiens
SEQUENCE: 82
CNSPCLVGNC                                                              10

SEQ ID NO: 83               moltype = AA  length = 10
FEATURE                     Location/Qualifiers
source                      1..10
                            mol_type = protein
                            organism = Homo sapiens
SEQUENCE: 83
CRTSCSSRPC                                                              10

SEQ ID NO: 84               moltype = AA  length = 10
FEATURE                     Location/Qualifiers
source                      1..10
                            mol_type = protein
                            organism = Homo sapiens
SEQUENCE: 84
CSLKEHCSAC                                                              10

SEQ ID NO: 85               moltype = AA  length = 10
FEATURE                     Location/Qualifiers
source                      1..10
                            mol_type = protein
                            organism = Homo sapiens
SEQUENCE: 85
CSPRPICVPC                                                              10

SEQ ID NO: 86               moltype = AA  length = 10
FEATURE                     Location/Qualifiers
source                      1..10
                            mol_type = protein
                            organism = Homo sapiens
SEQUENCE: 86
CSSTMSYSCC                                                              10

SEQ ID NO: 87               moltype = AA  length = 10
FEATURE                     Location/Qualifiers
source                      1..10
                            mol_type = protein
                            organism = Homo sapiens
SEQUENCE: 87
CSTPASCTSC                                                              10

SEQ ID NO: 88               moltype = AA  length = 10
FEATURE                     Location/Qualifiers
source                      1..10
                            mol_type = protein
                            organism = Homo sapiens
SEQUENCE: 88
CSTPSCTTCV                                                              10

SEQ ID NO: 89               moltype = AA  length = 10
FEATURE                     Location/Qualifiers
source                      1..10
                            mol_type = protein
                            organism = Homo sapiens
SEQUENCE: 89
CTSCVPPAPC                                                              10

SEQ ID NO: 90               moltype = AA  length = 10
FEATURE                     Location/Qualifiers
```

```
source                          1..10
                                mol_type = protein
                                organism = Homo sapiens
SEQUENCE: 90
CTSSNTCEPC                                                                      10

SEQ ID NO: 91                   moltype = AA  length = 10
FEATURE                         Location/Qualifiers
source                          1..10
                                mol_type = protein
                                organism = Homo sapiens
SEQUENCE: 91
CVPPAPCTPC                                                                      10

SEQ ID NO: 92                   moltype = AA  length = 10
FEATURE                         Location/Qualifiers
source                          1..10
                                mol_type = protein
                                organism = Homo sapiens
SEQUENCE: 92
CVPPSCHGCT                                                                      10

SEQ ID NO: 93                   moltype = AA  length = 10
FEATURE                         Location/Qualifiers
source                          1..10
                                mol_type = protein
                                organism = Homo sapiens
SEQUENCE: 93
CVPPSCHSCT                                                                      10

SEQ ID NO: 94                   moltype = AA  length = 10
FEATURE                         Location/Qualifiers
source                          1..10
                                mol_type = protein
                                organism = Homo sapiens
SEQUENCE: 94
DCKLPCNPCA                                                                      10

SEQ ID NO: 95                   moltype = AA  length = 10
FEATURE                         Location/Qualifiers
source                          1..10
                                mol_type = protein
                                organism = Homo sapiens
SEQUENCE: 95
DCKLPCNPCS                                                                      10

SEQ ID NO: 96                   moltype = AA  length = 10
FEATURE                         Location/Qualifiers
source                          1..10
                                mol_type = protein
                                organism = Homo sapiens
SEQUENCE: 96
PCGTSQKGCC                                                                      10

SEQ ID NO: 97                   moltype = AA  length = 10
FEATURE                         Location/Qualifiers
source                          1..10
                                mol_type = protein
                                organism = Homo sapiens
SEQUENCE: 97
PCLSNPCTSC                                                                      10

SEQ ID NO: 98                   moltype = AA  length = 10
FEATURE                         Location/Qualifiers
source                          1..10
                                mol_type = protein
                                organism = Homo sapiens
SEQUENCE: 98
PCLVGNCAWC                                                                      10

SEQ ID NO: 99                   moltype = AA  length = 10
FEATURE                         Location/Qualifiers
source                          1..10
                                mol_type = protein
                                organism = Homo sapiens
SEQUENCE: 99
PCNPCSTPSC                                                                      10

SEQ ID NO: 100                  moltype = AA  length = 10
```

-continued

```
FEATURE                 Location/Qualifiers
source                  1..10
                        mol_type = protein
                        organism = Homo sapiens
SEQUENCE: 100
PCSTPSCTTC                                                              10

SEQ ID NO: 101          moltype = AA   length = 10
FEATURE                 Location/Qualifiers
source                  1..10
                        mol_type = protein
                        organism = Homo sapiens
SEQUENCE: 101
PCTTCGPTCG                                                              10

SEQ ID NO: 102          moltype = AA   length = 10
FEATURE                 Location/Qualifiers
source                  1..10
                        mol_type = protein
                        organism = Homo sapiens
SEQUENCE: 102
PCVPPSCHGC                                                              10

SEQ ID NO: 103          moltype = AA   length = 10
FEATURE                 Location/Qualifiers
source                  1..10
                        mol_type = protein
                        organism = Homo sapiens
SEQUENCE: 103
PCVPPSCHSC                                                              10

SEQ ID NO: 104          moltype = AA   length = 10
FEATURE                 Location/Qualifiers
source                  1..10
                        mol_type = protein
                        organism = Homo sapiens
SEQUENCE: 104
SCCLPSLGCR                                                              10

SEQ ID NO: 105          moltype = AA   length = 10
FEATURE                 Location/Qualifiers
source                  1..10
                        mol_type = protein
                        organism = Homo sapiens
SEQUENCE: 105
SCSEELQCCQ                                                              10

SEQ ID NO: 106          moltype = AA   length = 10
FEATURE                 Location/Qualifiers
source                  1..10
                        mol_type = protein
                        organism = Homo sapiens
SEQUENCE: 106
SCSPCSTTCT                                                              10

SEQ ID NO: 107          moltype = AA   length = 10
FEATURE                 Location/Qualifiers
source                  1..10
                        mol_type = protein
                        organism = Homo sapiens
SEQUENCE: 107
ASCSTSGTCG                                                              10

SEQ ID NO: 108          moltype = AA   length = 10
FEATURE                 Location/Qualifiers
source                  1..10
                        mol_type = protein
                        organism = Homo sapiens
SEQUENCE: 108
ASCYIPVGCQ                                                              10

SEQ ID NO: 109          moltype = AA   length = 10
FEATURE                 Location/Qualifiers
source                  1..10
                        mol_type = protein
                        organism = Homo sapiens
SEQUENCE: 109
ASCYVPVSCQ                                                              10
```

-continued

```
SEQ ID NO: 110        moltype = AA   length = 10
FEATURE               Location/Qualifiers
source                1..10
                      mol_type = protein
                      organism = Homo sapiens
SEQUENCE: 110
AVCTLPSSCQ                                                                    10

SEQ ID NO: 111        moltype = AA   length = 10
FEATURE               Location/Qualifiers
source                1..10
                      mol_type = protein
                      organism = Homo sapiens
SEQUENCE: 111
DLCPTSVSCG                                                                    10

SEQ ID NO: 112        moltype = AA   length = 10
FEATURE               Location/Qualifiers
source                1..10
                      mol_type = protein
                      organism = Homo sapiens
SEQUENCE: 112
EICWEPTSCQ                                                                    10

SEQ ID NO: 113        moltype = AA   length = 10
FEATURE               Location/Qualifiers
source                1..10
                      mol_type = protein
                      organism = Homo sapiens
SEQUENCE: 113
ETCGEPTSCQ                                                                    10

SEQ ID NO: 114        moltype = AA   length = 10
FEATURE               Location/Qualifiers
source                1..10
                      mol_type = protein
                      organism = Homo sapiens
SEQUENCE: 114
ETCNETTSCQ                                                                    10

SEQ ID NO: 115        moltype = AA   length = 10
FEATURE               Location/Qualifiers
source                1..10
                      mol_type = protein
                      organism = Homo sapiens
SEQUENCE: 115
ETCWRPNSCQ                                                                    10

SEQ ID NO: 116        moltype = AA   length = 10
FEATURE               Location/Qualifiers
source                1..10
                      mol_type = protein
                      organism = Homo sapiens
SEQUENCE: 116
GYCGYRPFCF                                                                    10

SEQ ID NO: 117        moltype = AA   length = 10
FEATURE               Location/Qualifiers
source                1..10
                      mol_type = protein
                      organism = Homo sapiens
SEQUENCE: 117
KTCWEPASCQ                                                                    10

SEQ ID NO: 118        moltype = AA   length = 10
FEATURE               Location/Qualifiers
source                1..10
                      mol_type = protein
                      organism = Homo sapiens
SEQUENCE: 118
KTCWEPTSCQ                                                                    10

SEQ ID NO: 119        moltype = AA   length = 10
FEATURE               Location/Qualifiers
source                1..10
                      mol_type = protein
                      organism = Homo sapiens
SEQUENCE: 119
LDCVDTTPCK                                                                    10
```

| | | |
|---|---|---|
| SEQ ID NO: 120<br>FEATURE<br>source<br><br>SEQUENCE: 120<br>LGCGYGSFCG | moltype = AA   length = 10<br>Location/Qualifiers<br>1..10<br>mol_type = protein<br>organism = Homo sapiens | 10 |
| SEQ ID NO: 121<br>FEATURE<br>source<br><br>SEQUENCE: 121<br>NSCGYGSGCG | moltype = AA   length = 10<br>Location/Qualifiers<br>1..10<br>mol_type = protein<br>organism = Homo sapiens | 10 |
| SEQ ID NO: 122<br>FEATURE<br>source<br><br>SEQUENCE: 122<br>NYCPSNTMCE | moltype = AA   length = 10<br>Location/Qualifiers<br>1..10<br>mol_type = protein<br>organism = Homo sapiens | 10 |
| SEQ ID NO: 123<br>FEATURE<br>source<br><br>SEQUENCE: 123<br>PACVTSYSCR | moltype = AA   length = 10<br>Location/Qualifiers<br>1..10<br>mol_type = protein<br>organism = Homo sapiens | 10 |
| SEQ ID NO: 124<br>FEATURE<br>source<br><br>SEQUENCE: 124<br>PDCHVEGTCL | moltype = AA   length = 10<br>Location/Qualifiers<br>1..10<br>mol_type = protein<br>organism = Homo sapiens | 10 |
| SEQ ID NO: 125<br>FEATURE<br>source<br><br>SEQUENCE: 125<br>PDCRVEGTCL | moltype = AA   length = 10<br>Location/Qualifiers<br>1..10<br>mol_type = protein<br>organism = Homo sapiens | 10 |
| SEQ ID NO: 126<br>FEATURE<br>source<br><br>SEQUENCE: 126<br>PICSEPSPCS | moltype = AA   length = 10<br>Location/Qualifiers<br>1..10<br>mol_type = protein<br>organism = Homo sapiens | 10 |
| SEQ ID NO: 127<br>FEATURE<br>source<br><br>SEQUENCE: 127<br>PICYIFKPCQ | moltype = AA   length = 10<br>Location/Qualifiers<br>1..10<br>mol_type = protein<br>organism = Homo sapiens | 10 |
| SEQ ID NO: 128<br>FEATURE<br>source<br><br>SEQUENCE: 128<br>PLCYISNSCQ | moltype = AA   length = 10<br>Location/Qualifiers<br>1..10<br>mol_type = protein<br>organism = Homo sapiens | 10 |
| SEQ ID NO: 129<br>FEATURE<br>source<br><br>SEQUENCE: 129 | moltype = AA   length = 10<br>Location/Qualifiers<br>1..10<br>mol_type = protein<br>organism = Homo sapiens | |

|  |  |  |
|---|---|---|
| PPCGQPTPCS | | 10 |
| SEQ ID NO: 130<br>FEATURE<br>source<br><br>SEQUENCE: 130<br>PPCHIPQPCV | moltype = AA  length = 10<br>Location/Qualifiers<br>1..10<br>mol_type = protein<br>organism = Homo sapiens | 10 |
| SEQ ID NO: 131<br>FEATURE<br>source<br><br>SEQUENCE: 131<br>PSCGRLASCG | moltype = AA  length = 10<br>Location/Qualifiers<br>1..10<br>mol_type = protein<br>organism = Homo sapiens | 10 |
| SEQ ID NO: 132<br>FEATURE<br>source<br><br>SEQUENCE: 132<br>PSCSESSICQ | moltype = AA  length = 10<br>Location/Qualifiers<br>1..10<br>mol_type = protein<br>organism = Homo sapiens | 10 |
| SEQ ID NO: 133<br>FEATURE<br>source<br><br>SEQUENCE: 133<br>PSCSEVTSCP | moltype = AA  length = 10<br>Location/Qualifiers<br>1..10<br>mol_type = protein<br>organism = Homo sapiens | 10 |
| SEQ ID NO: 134<br>FEATURE<br>source<br><br>SEQUENCE: 134<br>PSCSTSGTCG | moltype = AA  length = 10<br>Location/Qualifiers<br>1..10<br>mol_type = protein<br>organism = Homo sapiens | 10 |
| SEQ ID NO: 135<br>FEATURE<br>source<br><br>SEQUENCE: 135<br>PSCSVSSGCQ | moltype = AA  length = 10<br>Location/Qualifiers<br>1..10<br>mol_type = protein<br>organism = Homo sapiens | 10 |
| SEQ ID NO: 136<br>FEATURE<br>source<br><br>SEQUENCE: 136<br>PSCTESDSCK | moltype = AA  length = 10<br>Location/Qualifiers<br>1..10<br>mol_type = protein<br>organism = Homo sapiens | 10 |
| SEQ ID NO: 137<br>FEATURE<br>source<br><br>SEQUENCE: 137<br>PSCYQTSSCG | moltype = AA  length = 10<br>Location/Qualifiers<br>1..10<br>mol_type = protein<br>organism = Homo sapiens | 10 |
| SEQ ID NO: 138<br>FEATURE<br>source<br><br>SEQUENCE: 138<br>PTCFLLNSCQ | moltype = AA  length = 10<br>Location/Qualifiers<br>1..10<br>mol_type = protein<br>organism = Homo sapiens | 10 |
| SEQ ID NO: 139<br>FEATURE<br>source | moltype = AA  length = 10<br>Location/Qualifiers<br>1..10<br>mol_type = protein<br>organism = Homo sapiens | |

```
SEQUENCE: 139
PTCSVTSSCQ                                                                                    10

SEQ ID NO: 140          moltype = AA  length = 10
FEATURE                 Location/Qualifiers
source                  1..10
                        mol_type = protein
                        organism = Homo sapiens
SEQUENCE: 140
PTCWLLNNCH                                                                                    10

SEQ ID NO: 141          moltype = AA  length = 10
FEATURE                 Location/Qualifiers
source                  1..10
                        mol_type = protein
                        organism = Homo sapiens
SEQUENCE: 141
PTCYQRTSCV                                                                                    10

SEQ ID NO: 142          moltype = AA  length = 10
FEATURE                 Location/Qualifiers
source                  1..10
                        mol_type = protein
                        organism = Homo sapiens
SEQUENCE: 142
PTCYRRTSCV                                                                                    10

SEQ ID NO: 143          moltype = AA  length = 10
FEATURE                 Location/Qualifiers
source                  1..10
                        mol_type = protein
                        organism = Homo sapiens
SEQUENCE: 143
PTCYVVKRCP                                                                                    10

SEQ ID NO: 144          moltype = AA  length = 10
FEATURE                 Location/Qualifiers
source                  1..10
                        mol_type = protein
                        organism = Homo sapiens
SEQUENCE: 144
PVCFEATICE                                                                                    10

SEQ ID NO: 145          moltype = AA  length = 10
FEATURE                 Location/Qualifiers
source                  1..10
                        mol_type = protein
                        organism = Homo sapiens
SEQUENCE: 145
PVCFEATVCE                                                                                    10

SEQ ID NO: 146          moltype = AA  length = 10
FEATURE                 Location/Qualifiers
source                  1..10
                        mol_type = protein
                        organism = Homo sapiens
SEQUENCE: 146
PVCSRPASCS                                                                                    10

SEQ ID NO: 147          moltype = AA  length = 10
FEATURE                 Location/Qualifiers
source                  1..10
                        mol_type = protein
                        organism = Homo sapiens
SEQUENCE: 147
PVCSWVPACS                                                                                    10

SEQ ID NO: 148          moltype = AA  length = 10
FEATURE                 Location/Qualifiers
source                  1..10
                        mol_type = protein
                        organism = Homo sapiens
SEQUENCE: 148
QTCNESSYCL                                                                                    10

SEQ ID NO: 149          moltype = AA  length = 10
FEATURE                 Location/Qualifiers
source                  1..10
                        mol_type = protein
```

```
                       organism = Homo sapiens
SEQUENCE: 149
QTCWEPTSCQ                                                                    10

SEQ ID NO: 150         moltype = AA  length = 10
FEATURE                Location/Qualifiers
source                 1..10
                       mol_type = protein
                       organism = Homo sapiens
SEQUENCE: 150
SFCRLGYGCG                                                                    10

SEQ ID NO: 151         moltype = AA  length = 10
FEATURE                Location/Qualifiers
source                 1..10
                       mol_type = protein
                       organism = Homo sapiens
SEQUENCE: 151
SFCRRGSGCG                                                                    10

SEQ ID NO: 152         moltype = AA  length = 10
FEATURE                Location/Qualifiers
source                 1..10
                       mol_type = protein
                       organism = Homo sapiens
SEQUENCE: 152
SLCGYGYGCG                                                                    10

SEQ ID NO: 153         moltype = AA  length = 10
FEATURE                Location/Qualifiers
source                 1..10
                       mol_type = protein
                       organism = Homo sapiens
SEQUENCE: 153
SLCSTEVSCG                                                                    10

SEQ ID NO: 154         moltype = AA  length = 10
FEATURE                Location/Qualifiers
source                 1..10
                       mol_type = protein
                       organism = Homo sapiens
SEQUENCE: 154
SNCFGQLNCL                                                                    10

SEQ ID NO: 155         moltype = AA  length = 10
FEATURE                Location/Qualifiers
source                 1..10
                       mol_type = protein
                       organism = Homo sapiens
SEQUENCE: 155
SPCGQPTPCS                                                                    10

SEQ ID NO: 156         moltype = AA  length = 10
FEATURE                Location/Qualifiers
source                 1..10
                       mol_type = protein
                       organism = Homo sapiens
SEQUENCE: 156
SSCDQSSSCA                                                                    10

SEQ ID NO: 157         moltype = AA  length = 10
FEATURE                Location/Qualifiers
source                 1..10
                       mol_type = protein
                       organism = Homo sapiens
SEQUENCE: 157
SSCGQSSSCA                                                                    10

SEQ ID NO: 158         moltype = AA  length = 10
FEATURE                Location/Qualifiers
source                 1..10
                       mol_type = protein
                       organism = Homo sapiens
SEQUENCE: 158
SVCPEPVSCP                                                                    10

SEQ ID NO: 159         moltype = AA  length = 10
FEATURE                Location/Qualifiers
source                 1..10
```

```
                        mol_type = protein
                        organism = Homo sapiens
SEQUENCE: 159
TFCSFDKSCR                                                              10

SEQ ID NO: 160          moltype = AA  length = 10
FEATURE                 Location/Qualifiers
source                  1..10
                        mol_type = protein
                        organism = Homo sapiens
SEQUENCE: 160
TICSSDKSCR                                                              10

SEQ ID NO: 161          moltype = AA  length = 10
FEATURE                 Location/Qualifiers
source                  1..10
                        mol_type = protein
                        organism = Homo sapiens
SEQUENCE: 161
TLCVESSPCH                                                              10

SEQ ID NO: 162          moltype = AA  length = 10
FEATURE                 Location/Qualifiers
source                  1..10
                        mol_type = protein
                        organism = Homo sapiens
SEQUENCE: 162
TPCYQQSSCQ                                                              10

SEQ ID NO: 163          moltype = AA  length = 10
FEATURE                 Location/Qualifiers
source                  1..10
                        mol_type = protein
                        organism = Homo sapiens
SEQUENCE: 163
VTCSRQTTCI                                                              10

SEQ ID NO: 164          moltype = AA  length = 10
FEATURE                 Location/Qualifiers
source                  1..10
                        mol_type = protein
                        organism = Homo sapiens
SEQUENCE: 164
YGCGYGSGCG                                                              10

SEQ ID NO: 165          moltype = AA  length = 10
FEATURE                 Location/Qualifiers
source                  1..10
                        mol_type = protein
                        organism = Homo sapiens
SEQUENCE: 165
YGCGYGSGCR                                                              10

SEQ ID NO: 166          moltype = AA  length = 10
FEATURE                 Location/Qualifiers
source                  1..10
                        mol_type = protein
                        organism = Homo sapiens
SEQUENCE: 166
YGCIHSTHCG                                                              10

SEQ ID NO: 167          moltype = AA  length = 10
FEATURE                 Location/Qualifiers
source                  1..10
                        mol_type = protein
                        organism = Homo sapiens
SEQUENCE: 167
AACEPSACQS                                                              10

SEQ ID NO: 168          moltype = AA  length = 10
FEATURE                 Location/Qualifiers
source                  1..10
                        mol_type = protein
                        organism = Homo sapiens
SEQUENCE: 168
AACEPSPCQS                                                              10

SEQ ID NO: 169          moltype = AA  length = 10
FEATURE                 Location/Qualifiers
```

```
source                      1..10
                            mol_type = protein
                            organism = Homo sapiens
SEQUENCE: 169
AACTMSVCSS                                                                          10

SEQ ID NO: 170              moltype = AA  length = 10
FEATURE                     Location/Qualifiers
source                      1..10
                            mol_type = protein
                            organism = Homo sapiens
SEQUENCE: 170
ADCLGGICLP                                                                          10

SEQ ID NO: 171              moltype = AA  length = 10
FEATURE                     Location/Qualifiers
source                      1..10
                            mol_type = protein
                            organism = Homo sapiens
SEQUENCE: 171
ALCLPSSCHS                                                                          10

SEQ ID NO: 172              moltype = AA  length = 10
FEATURE                     Location/Qualifiers
source                      1..10
                            mol_type = protein
                            organism = Homo sapiens
SEQUENCE: 172
ALCSPSTCQL                                                                          10

SEQ ID NO: 173              moltype = AA  length = 10
FEATURE                     Location/Qualifiers
source                      1..10
                            mol_type = protein
                            organism = Homo sapiens
SEQUENCE: 173
APCLALVCAP                                                                          10

SEQ ID NO: 174              moltype = AA  length = 10
FEATURE                     Location/Qualifiers
source                      1..10
                            mol_type = protein
                            organism = Homo sapiens
SEQUENCE: 174
APCLSLVCTP                                                                          10

SEQ ID NO: 175              moltype = AA  length = 10
FEATURE                     Location/Qualifiers
source                      1..10
                            mol_type = protein
                            organism = Homo sapiens
SEQUENCE: 175
APCLTLVCTP                                                                          10

SEQ ID NO: 176              moltype = AA  length = 10
FEATURE                     Location/Qualifiers
source                      1..10
                            mol_type = protein
                            organism = Homo sapiens
SEQUENCE: 176
APCVALLCRP                                                                          10

SEQ ID NO: 177              moltype = AA  length = 10
FEATURE                     Location/Qualifiers
source                      1..10
                            mol_type = protein
                            organism = Homo sapiens
SEQUENCE: 177
ASCGSLLCRP                                                                          10

SEQ ID NO: 178              moltype = AA  length = 10
FEATURE                     Location/Qualifiers
source                      1..10
                            mol_type = protein
                            organism = Homo sapiens
SEQUENCE: 178
ASCLSFLCRP                                                                          10

SEQ ID NO: 179              moltype = AA  length = 10
```

```
FEATURE                    Location/Qualifiers
source                     1..10
                           mol_type = protein
                           organism = Homo sapiens
SEQUENCE: 179
ASCVSLLCRP                                                                      10

SEQ ID NO: 180             moltype = AA  length = 10
FEATURE                    Location/Qualifiers
source                     1..10
                           mol_type = protein
                           organism = Homo sapiens
SEQUENCE: 180
AVCEPSPCQS                                                                      10

SEQ ID NO: 181             moltype = AA  length = 10
FEATURE                    Location/Qualifiers
source                     1..10
                           mol_type = protein
                           organism = Homo sapiens
SEQUENCE: 181
AVCLPVSCQS                                                                      10

SEQ ID NO: 182             moltype = AA  length = 10
FEATURE                    Location/Qualifiers
source                     1..10
                           mol_type = protein
                           organism = Homo sapiens
SEQUENCE: 182
AVCVPVRCQS                                                                      10

SEQ ID NO: 183             moltype = AA  length = 10
FEATURE                    Location/Qualifiers
source                     1..10
                           mol_type = protein
                           organism = Homo sapiens
SEQUENCE: 183
AVCVPVSCQS                                                                      10

SEQ ID NO: 184             moltype = AA  length = 10
FEATURE                    Location/Qualifiers
source                     1..10
                           mol_type = protein
                           organism = Homo sapiens
SEQUENCE: 184
DLCSPSTCQL                                                                      10

SEQ ID NO: 185             moltype = AA  length = 10
FEATURE                    Location/Qualifiers
source                     1..10
                           mol_type = protein
                           organism = Homo sapiens
SEQUENCE: 185
DSCGSSSCGP                                                                      10

SEQ ID NO: 186             moltype = AA  length = 10
FEATURE                    Location/Qualifiers
source                     1..10
                           mol_type = protein
                           organism = Homo sapiens
SEQUENCE: 186
DSCVQSNCFP                                                                      10

SEQ ID NO: 187             moltype = AA  length = 10
FEATURE                    Location/Qualifiers
source                     1..10
                           mol_type = protein
                           organism = Homo sapiens
SEQUENCE: 187
FNCSTRNCSS                                                                      10

SEQ ID NO: 188             moltype = AA  length = 10
FEATURE                    Location/Qualifiers
source                     1..10
                           mol_type = protein
                           organism = Homo sapiens
SEQUENCE: 188
GGCGSYGCSQ                                                                      10
```

| | | |
|---|---|---|
| SEQ ID NO: 189<br>FEATURE<br>source<br><br>SEQUENCE: 189<br>GSCGFGSCYG | moltype = AA   length = 10<br>Location/Qualifiers<br>1..10<br>mol_type = protein<br>organism = Homo sapiens | 10 |
| SEQ ID NO: 190<br>FEATURE<br>source<br><br>SEQUENCE: 190<br>GSCSSRKCFS | moltype = AA   length = 10<br>Location/Qualifiers<br>1..10<br>mol_type = protein<br>organism = Homo sapiens | 10 |
| SEQ ID NO: 191<br>FEATURE<br>source<br><br>SEQUENCE: 191<br>GVCLPSTCPH | moltype = AA   length = 10<br>Location/Qualifiers<br>1..10<br>mol_type = protein<br>organism = Homo sapiens | 10 |
| SEQ ID NO: 192<br>FEATURE<br>source<br><br>SEQUENCE: 192<br>HSCEGYLCYS | moltype = AA   length = 10<br>Location/Qualifiers<br>1..10<br>mol_type = protein<br>organism = Homo sapiens | 10 |
| SEQ ID NO: 193<br>FEATURE<br>source<br><br>SEQUENCE: 193<br>IVCAAPSCQS | moltype = AA   length = 10<br>Location/Qualifiers<br>1..10<br>mol_type = protein<br>organism = Homo sapiens | 10 |
| SEQ ID NO: 194<br>FEATURE<br>source<br><br>SEQUENCE: 194<br>KTCSTTGCDP | moltype = AA   length = 10<br>Location/Qualifiers<br>1..10<br>mol_type = protein<br>organism = Homo sapiens | 10 |
| SEQ ID NO: 195<br>FEATURE<br>source<br><br>SEQUENCE: 195<br>LACVSQPCQS | moltype = AA   length = 10<br>Location/Qualifiers<br>1..10<br>mol_type = protein<br>organism = Homo sapiens | 10 |
| SEQ ID NO: 196<br>FEATURE<br>source<br><br>SEQUENCE: 196<br>LGCGYGGCGY | moltype = AA   length = 10<br>Location/Qualifiers<br>1..10<br>mol_type = protein<br>organism = Homo sapiens | 10 |
| SEQ ID NO: 197<br>FEATURE<br>source<br><br>SEQUENCE: 197<br>LSCGSRSCSS | moltype = AA   length = 10<br>Location/Qualifiers<br>1..10<br>mol_type = protein<br>organism = Homo sapiens | 10 |
| SEQ ID NO: 198<br>FEATURE<br>source<br><br>SEQUENCE: 198<br>LVCTPVSCVS | moltype = AA   length = 10<br>Location/Qualifiers<br>1..10<br>mol_type = protein<br>organism = Homo sapiens | 10 |

| | | |
|---|---|---|
| SEQ ID NO: 199<br>FEATURE<br>source<br><br>SEQUENCE: 199<br>NGCQETYCEP | moltype = AA   length = 10<br>Location/Qualifiers<br>1..10<br>mol_type = protein<br>organism = Homo sapiens | <br><br><br><br><br>10 |
| SEQ ID NO: 200<br>FEATURE<br>source<br><br>SEQUENCE: 200<br>NSCRSLSCGS | moltype = AA   length = 10<br>Location/Qualifiers<br>1..10<br>mol_type = protein<br>organism = Homo sapiens | <br><br><br><br><br>10 |
| SEQ ID NO: 201<br>FEATURE<br>source<br><br>SEQUENCE: 201<br>PACVISTCPR | moltype = AA   length = 10<br>Location/Qualifiers<br>1..10<br>mol_type = protein<br>organism = Homo sapiens | <br><br><br><br><br>10 |
| SEQ ID NO: 202<br>FEATURE<br>source<br><br>SEQUENCE: 202<br>PGCLNQSCGS | moltype = AA   length = 10<br>Location/Qualifiers<br>1..10<br>mol_type = protein<br>organism = Homo sapiens | <br><br><br><br><br>10 |
| SEQ ID NO: 203<br>FEATURE<br>source<br><br>SEQUENCE: 203<br>PPCGTAPCLT | moltype = AA   length = 10<br>Location/Qualifiers<br>1..10<br>mol_type = protein<br>organism = Homo sapiens | <br><br><br><br><br>10 |
| SEQ ID NO: 204<br>FEATURE<br>source<br><br>SEQUENCE: 204<br>PPCTTALCRP | moltype = AA   length = 10<br>Location/Qualifiers<br>1..10<br>mol_type = protein<br>organism = Homo sapiens | <br><br><br><br><br>10 |
| SEQ ID NO: 205<br>FEATURE<br>source<br><br>SEQUENCE: 205<br>PPCYLVSCTP | moltype = AA   length = 10<br>Location/Qualifiers<br>1..10<br>mol_type = protein<br>organism = Homo sapiens | <br><br><br><br><br>10 |
| SEQ ID NO: 206<br>FEATURE<br>source<br><br>SEQUENCE: 206<br>PRCTRPICEP | moltype = AA   length = 10<br>Location/Qualifiers<br>1..10<br>mol_type = protein<br>organism = Homo sapiens | <br><br><br><br><br>10 |
| SEQ ID NO: 207<br>FEATURE<br>source<br><br>SEQUENCE: 207<br>PSCPVSSCAQ | moltype = AA   length = 10<br>Location/Qualifiers<br>1..10<br>mol_type = protein<br>organism = Homo sapiens | <br><br><br><br><br>10 |
| SEQ ID NO: 208<br>FEATURE<br>source<br><br>SEQUENCE: 208 | moltype = AA   length = 10<br>Location/Qualifiers<br>1..10<br>mol_type = protein<br>organism = Homo sapiens | |

PSCQPSVCVP 10

SEQ ID NO: 209         moltype = AA  length = 10
FEATURE                Location/Qualifiers
source                 1..10
                       mol_type = protein
                       organism = Homo sapiens

SEQUENCE: 209
PSCSVSNCYQ 10

SEQ ID NO: 210         moltype = AA  length = 10
FEATURE                Location/Qualifiers
source                 1..10
                       mol_type = protein
                       organism = Homo sapiens

SEQUENCE: 210
PSCSVSSCAQ 10

SEQ ID NO: 211         moltype = AA  length = 10
FEATURE                Location/Qualifiers
source                 1..10
                       mol_type = protein
                       organism = Homo sapiens

SEQUENCE: 211
PSCTSVLCRP 10

SEQ ID NO: 212         moltype = AA  length = 10
FEATURE                Location/Qualifiers
source                 1..10
                       mol_type = protein
                       organism = Homo sapiens

SEQUENCE: 212
PTCKSPSCEP 10

SEQ ID NO: 213         moltype = AA  length = 10
FEATURE                Location/Qualifiers
source                 1..10
                       mol_type = protein
                       organism = Homo sapiens

SEQUENCE: 213
PTCVISSCPR 10

SEQ ID NO: 214         moltype = AA  length = 10
FEATURE                Location/Qualifiers
source                 1..10
                       mol_type = protein
                       organism = Homo sapiens

SEQUENCE: 214
PTCVISTCPR 10

SEQ ID NO: 215         moltype = AA  length = 10
FEATURE                Location/Qualifiers
source                 1..10
                       mol_type = protein
                       organism = Homo sapiens

SEQUENCE: 215
PTCYQTICFR 10

SEQ ID NO: 216         moltype = AA  length = 10
FEATURE                Location/Qualifiers
source                 1..10
                       mol_type = protein
                       organism = Homo sapiens

SEQUENCE: 216
PVCGGVSCHT 10

SEQ ID NO: 217         moltype = AA  length = 10
FEATURE                Location/Qualifiers
source                 1..10
                       mol_type = protein
                       organism = Homo sapiens

SEQUENCE: 217
PVCGRVSCHT 10

SEQ ID NO: 218         moltype = AA  length = 10
FEATURE                Location/Qualifiers
source                 1..10
                       mol_type = protein
                       organism = Homo sapiens

```
SEQUENCE: 218
PVCNKPVCFV                                                                                          10

SEQ ID NO: 219          moltype = AA  length = 10
FEATURE                 Location/Qualifiers
source                  1..10
                        mol_type = protein
                        organism = Homo sapiens
SEQUENCE: 219
PVCPTPTCSV                                                                                          10

SEQ ID NO: 220          moltype = AA  length = 10
FEATURE                 Location/Qualifiers
source                  1..10
                        mol_type = protein
                        organism = Homo sapiens
SEQUENCE: 220
PVCRSTYCVP                                                                                          10

SEQ ID NO: 221          moltype = AA  length = 10
FEATURE                 Location/Qualifiers
source                  1..10
                        mol_type = protein
                        organism = Homo sapiens
SEQUENCE: 221
PVCSKSVCYV                                                                                          10

SEQ ID NO: 222          moltype = AA  length = 10
FEATURE                 Location/Qualifiers
source                  1..10
                        mol_type = protein
                        organism = Homo sapiens
SEQUENCE: 222
PVCSRPACYS                                                                                          10

SEQ ID NO: 223          moltype = AA  length = 10
FEATURE                 Location/Qualifiers
source                  1..10
                        mol_type = protein
                        organism = Homo sapiens
SEQUENCE: 223
PVCYVPTCSE                                                                                          10

SEQ ID NO: 224          moltype = AA  length = 10
FEATURE                 Location/Qualifiers
source                  1..10
                        mol_type = protein
                        organism = Homo sapiens
SEQUENCE: 224
QFCLSKSCQP                                                                                          10

SEQ ID NO: 225          moltype = AA  length = 10
FEATURE                 Location/Qualifiers
source                  1..10
                        mol_type = protein
                        organism = Homo sapiens
SEQUENCE: 225
RPCERTACQS                                                                                          10

SEQ ID NO: 226          moltype = AA  length = 10
FEATURE                 Location/Qualifiers
source                  1..10
                        mol_type = protein
                        organism = Homo sapiens
SEQUENCE: 226
RSCQTSFCGF                                                                                          10

SEQ ID NO: 227          moltype = AA  length = 10
FEATURE                 Location/Qualifiers
source                  1..10
                        mol_type = protein
                        organism = Homo sapiens
SEQUENCE: 227
RSCSSLGCGS                                                                                          10

SEQ ID NO: 228          moltype = AA  length = 10
FEATURE                 Location/Qualifiers
source                  1..10
                        mol_type = protein
```

```
                              organism = Homo sapiens
SEQUENCE: 228
RSCYSVGCGS                                                                          10

SEQ ID NO: 229                moltype = AA   length = 10
FEATURE                       Location/Qualifiers
source                        1..10
                              mol_type = protein
                              organism = Homo sapiens
SEQUENCE: 229
RVCLPGSCDS                                                                          10

SEQ ID NO: 230                moltype = AA   length = 10
FEATURE                       Location/Qualifiers
source                        1..10
                              mol_type = protein
                              organism = Homo sapiens
SEQUENCE: 230
SFCGFPSCST                                                                          10

SEQ ID NO: 231                moltype = AA   length = 10
FEATURE                       Location/Qualifiers
source                        1..10
                              mol_type = protein
                              organism = Homo sapiens
SEQUENCE: 231
SFCGYPSCST                                                                          10

SEQ ID NO: 232                moltype = AA   length = 10
FEATURE                       Location/Qualifiers
source                        1..10
                              mol_type = protein
                              organism = Homo sapiens
SEQUENCE: 232
SGCDPASCQP                                                                          10

SEQ ID NO: 233                moltype = AA   length = 10
FEATURE                       Location/Qualifiers
source                        1..10
                              mol_type = protein
                              organism = Homo sapiens
SEQUENCE: 233
SGCGGSGCGG                                                                          10

SEQ ID NO: 234                moltype = AA   length = 10
FEATURE                       Location/Qualifiers
source                        1..10
                              mol_type = protein
                              organism = Homo sapiens
SEQUENCE: 234
SGCQPSSCLA                                                                          10

SEQ ID NO: 235                moltype = AA   length = 10
FEATURE                       Location/Qualifiers
source                        1..10
                              mol_type = protein
                              organism = Homo sapiens
SEQUENCE: 235
SHCQPPHCQL                                                                          10

SEQ ID NO: 236                moltype = AA   length = 10
FEATURE                       Location/Qualifiers
source                        1..10
                              mol_type = protein
                              organism = Homo sapiens
SEQUENCE: 236
SICQPATCVA                                                                          10

SEQ ID NO: 237                moltype = AA   length = 10
FEATURE                       Location/Qualifiers
source                        1..10
                              mol_type = protein
                              organism = Homo sapiens
SEQUENCE: 237
SLCVPVSCRP                                                                          10

SEQ ID NO: 238                moltype = AA   length = 10
FEATURE                       Location/Qualifiers
source                        1..10
```

```
                        mol_type = protein
                        organism = Homo sapiens
SEQUENCE: 238
SNCLPTSCQP                                                              10

SEQ ID NO: 239          moltype = AA  length = 10
FEATURE                 Location/Qualifiers
source                  1..10
                        mol_type = protein
                        organism = Homo sapiens
SEQUENCE: 239
SPCLVSSCQP                                                              10

SEQ ID NO: 240          moltype = AA  length = 10
FEATURE                 Location/Qualifiers
source                  1..10
                        mol_type = protein
                        organism = Homo sapiens
SEQUENCE: 240
SPCQQSSCQE                                                              10

SEQ ID NO: 241          moltype = AA  length = 10
FEATURE                 Location/Qualifiers
source                  1..10
                        mol_type = protein
                        organism = Homo sapiens
SEQUENCE: 241
SPCQQSYCVP                                                              10

SEQ ID NO: 242          moltype = AA  length = 10
FEATURE                 Location/Qualifiers
source                  1..10
                        mol_type = protein
                        organism = Homo sapiens
SEQUENCE: 242
SPCSPAVCVS                                                              10

SEQ ID NO: 243          moltype = AA  length = 10
FEATURE                 Location/Qualifiers
source                  1..10
                        mol_type = protein
                        organism = Homo sapiens
SEQUENCE: 243
SRCQQPSCQP                                                              10

SEQ ID NO: 244          moltype = AA  length = 10
FEATURE                 Location/Qualifiers
source                  1..10
                        mol_type = protein
                        organism = Homo sapiens
SEQUENCE: 244
SRCYRPHCGQ                                                              10

SEQ ID NO: 245          moltype = AA  length = 10
FEATURE                 Location/Qualifiers
source                  1..10
                        mol_type = protein
                        organism = Homo sapiens
SEQUENCE: 245
SSCAPIYCRR                                                              10

SEQ ID NO: 246          moltype = AA  length = 10
FEATURE                 Location/Qualifiers
source                  1..10
                        mol_type = protein
                        organism = Homo sapiens
SEQUENCE: 246
SSCAPVYCRR                                                              10

SEQ ID NO: 247          moltype = AA  length = 10
FEATURE                 Location/Qualifiers
source                  1..10
                        mol_type = protein
                        organism = Homo sapiens
SEQUENCE: 247
SSCGKGGCGS                                                              10

SEQ ID NO: 248          moltype = AA  length = 10
FEATURE                 Location/Qualifiers
```

```
source                  1..10
                        mol_type = protein
                        organism = Homo sapiens
SEQUENCE: 248
SSCGKRGCGS                                                                  10

SEQ ID NO: 249          moltype = AA   length = 10
FEATURE                 Location/Qualifiers
source                  1..10
                        mol_type = protein
                        organism = Homo sapiens
SEQUENCE: 249
SSCLPVSCRP                                                                  10

SEQ ID NO: 250          moltype = AA   length = 10
FEATURE                 Location/Qualifiers
source                  1..10
                        mol_type = protein
                        organism = Homo sapiens
SEQUENCE: 250
SSCQPAYCTS                                                                  10

SEQ ID NO: 251          moltype = AA   length = 10
FEATURE                 Location/Qualifiers
source                  1..10
                        mol_type = protein
                        organism = Homo sapiens
SEQUENCE: 251
SSCQPSYCRQ                                                                  10

SEQ ID NO: 252          moltype = AA   length = 10
FEATURE                 Location/Qualifiers
source                  1..10
                        mol_type = protein
                        organism = Homo sapiens
SEQUENCE: 252
SSCQPVVCEP                                                                  10

SEQ ID NO: 253          moltype = AA   length = 10
FEATURE                 Location/Qualifiers
source                  1..10
                        mol_type = protein
                        organism = Homo sapiens
SEQUENCE: 253
SSCTAVVCRP                                                                  10

SEQ ID NO: 254          moltype = AA   length = 10
FEATURE                 Location/Qualifiers
source                  1..10
                        mol_type = protein
                        organism = Homo sapiens
SEQUENCE: 254
SSCYQPFCRS                                                                  10

SEQ ID NO: 255          moltype = AA   length = 10
FEATURE                 Location/Qualifiers
source                  1..10
                        mol_type = protein
                        organism = Homo sapiens
SEQUENCE: 255
SSCYRPICGS                                                                  10

SEQ ID NO: 256          moltype = AA   length = 10
FEATURE                 Location/Qualifiers
source                  1..10
                        mol_type = protein
                        organism = Homo sapiens
SEQUENCE: 256
SSCYRPTCGS                                                                  10

SEQ ID NO: 257          moltype = AA   length = 10
FEATURE                 Location/Qualifiers
source                  1..10
                        mol_type = protein
                        organism = Homo sapiens
SEQUENCE: 257
SVCMSGSCQA                                                                  10

SEQ ID NO: 258          moltype = AA   length = 10
```

```
                        -continued

FEATURE                 Location/Qualifiers
source                  1..10
                        mol_type = protein
                        organism = Homo sapiens
SEQUENCE: 258
SVCSDQGCDQ                                                              10

SEQ ID NO: 259          moltype = AA  length = 10
FEATURE                 Location/Qualifiers
source                  1..10
                        mol_type = protein
                        organism = Homo sapiens
SEQUENCE: 259
SVCSDQGCGL                                                              10

SEQ ID NO: 260          moltype = AA  length = 10
FEATURE                 Location/Qualifiers
source                  1..10
                        mol_type = protein
                        organism = Homo sapiens
SEQUENCE: 260
SVCSDQGCGQ                                                              10

SEQ ID NO: 261          moltype = AA  length = 10
FEATURE                 Location/Qualifiers
source                  1..10
                        mol_type = protein
                        organism = Homo sapiens
SEQUENCE: 261
SVCSDQGCSQ                                                              10

SEQ ID NO: 262          moltype = AA  length = 10
FEATURE                 Location/Qualifiers
source                  1..10
                        mol_type = protein
                        organism = Homo sapiens
SEQUENCE: 262
SVCSDQSCGQ                                                              10

SEQ ID NO: 263          moltype = AA  length = 10
FEATURE                 Location/Qualifiers
source                  1..10
                        mol_type = protein
                        organism = Homo sapiens
SEQUENCE: 263
SVCSHQGCGQ                                                              10

SEQ ID NO: 264          moltype = AA  length = 10
FEATURE                 Location/Qualifiers
source                  1..10
                        mol_type = protein
                        organism = Homo sapiens
SEQUENCE: 264
SVCSHQGCGR                                                              10

SEQ ID NO: 265          moltype = AA  length = 10
FEATURE                 Location/Qualifiers
source                  1..10
                        mol_type = protein
                        organism = Homo sapiens
SEQUENCE: 265
SVCVPVSCRP                                                              10

SEQ ID NO: 266          moltype = AA  length = 10
FEATURE                 Location/Qualifiers
source                  1..10
                        mol_type = protein
                        organism = Homo sapiens
SEQUENCE: 266
SYCRQASCVS                                                              10

SEQ ID NO: 267          moltype = AA  length = 10
FEATURE                 Location/Qualifiers
source                  1..10
                        mol_type = protein
                        organism = Homo sapiens
SEQUENCE: 267
TACEPSACQS                                                              10
```

```
SEQ ID NO: 268          moltype = AA   length = 10
FEATURE                 Location/Qualifiers
source                  1..10
                        mol_type = protein
                        organism = Homo sapiens
SEQUENCE: 268
TICTASPCQP                                                                10

SEQ ID NO: 269          moltype = AA   length = 10
FEATURE                 Location/Qualifiers
source                  1..10
                        mol_type = protein
                        organism = Homo sapiens
SEQUENCE: 269
TSCPETSCLP                                                                10

SEQ ID NO: 270          moltype = AA   length = 10
FEATURE                 Location/Qualifiers
source                  1..10
                        mol_type = protein
                        organism = Homo sapiens
SEQUENCE: 270
TSCQMTNCEQ                                                                10

SEQ ID NO: 271          moltype = AA   length = 10
FEATURE                 Location/Qualifiers
source                  1..10
                        mol_type = protein
                        organism = Homo sapiens
SEQUENCE: 271
TSCQPVHCET                                                                10

SEQ ID NO: 272          moltype = AA   length = 10
FEATURE                 Location/Qualifiers
source                  1..10
                        mol_type = protein
                        organism = Homo sapiens
SEQUENCE: 272
TSCQPVLCKS                                                                10

SEQ ID NO: 273          moltype = AA   length = 10
FEATURE                 Location/Qualifiers
source                  1..10
                        mol_type = protein
                        organism = Homo sapiens
SEQUENCE: 273
TSCQPVLCVP                                                                10

SEQ ID NO: 274          moltype = AA   length = 10
FEATURE                 Location/Qualifiers
source                  1..10
                        mol_type = protein
                        organism = Homo sapiens
SEQUENCE: 274
TSCVGFVCQP                                                                10

SEQ ID NO: 275          moltype = AA   length = 10
FEATURE                 Location/Qualifiers
source                  1..10
                        mol_type = protein
                        organism = Homo sapiens
SEQUENCE: 275
TSCVSNPCQV                                                                10

SEQ ID NO: 276          moltype = AA   length = 10
FEATURE                 Location/Qualifiers
source                  1..10
                        mol_type = protein
                        organism = Homo sapiens
SEQUENCE: 276
TTCFQPTCVS                                                                10

SEQ ID NO: 277          moltype = AA   length = 10
FEATURE                 Location/Qualifiers
source                  1..10
                        mol_type = protein
                        organism = Homo sapiens
SEQUENCE: 277
TTCFQPTCVT                                                                10
```

| | | |
|---|---|---|
| SEQ ID NO: 278<br>FEATURE<br>source<br><br>SEQUENCE: 278<br>TTCFQPTCVY | moltype = AA   length = 10<br>Location/Qualifiers<br>1..10<br>mol_type = protein<br>organism = Homo sapiens | <br><br><br><br><br>10 |
| SEQ ID NO: 279<br>FEATURE<br>source<br><br>SEQUENCE: 279<br>TTCISNPCST | moltype = AA   length = 10<br>Location/Qualifiers<br>1..10<br>mol_type = protein<br>organism = Homo sapiens | <br><br><br><br><br>10 |
| SEQ ID NO: 280<br>FEATURE<br>source<br><br>SEQUENCE: 280<br>TWCQGSSCQP | moltype = AA   length = 10<br>Location/Qualifiers<br>1..10<br>mol_type = protein<br>organism = Homo sapiens | <br><br><br><br><br>10 |
| SEQ ID NO: 281<br>FEATURE<br>source<br><br>SEQUENCE: 281<br>VGCQSSVCVP | moltype = AA   length = 10<br>Location/Qualifiers<br>1..10<br>mol_type = protein<br>organism = Homo sapiens | <br><br><br><br><br>10 |
| SEQ ID NO: 282<br>FEATURE<br>source<br><br>SEQUENCE: 282<br>VPCQPSTCVF | moltype = AA   length = 10<br>Location/Qualifiers<br>1..10<br>mol_type = protein<br>organism = Homo sapiens | <br><br><br><br><br>10 |
| SEQ ID NO: 283<br>FEATURE<br>source<br><br>SEQUENCE: 283<br>VSCEPSPCQS | moltype = AA   length = 10<br>Location/Qualifiers<br>1..10<br>mol_type = protein<br>organism = Homo sapiens | <br><br><br><br><br>10 |
| SEQ ID NO: 284<br>FEATURE<br>source<br><br>SEQUENCE: 284<br>VSCGGPICLP | moltype = AA   length = 10<br>Location/Qualifiers<br>1..10<br>mol_type = protein<br>organism = Homo sapiens | <br><br><br><br><br>10 |
| SEQ ID NO: 285<br>FEATURE<br>source<br><br>SEQUENCE: 285<br>VSCKPVLCVA | moltype = AA   length = 10<br>Location/Qualifiers<br>1..10<br>mol_type = protein<br>organism = Homo sapiens | <br><br><br><br><br>10 |
| SEQ ID NO: 286<br>FEATURE<br>source<br><br>SEQUENCE: 286<br>VSCPSTSCRP | moltype = AA   length = 10<br>Location/Qualifiers<br>1..10<br>mol_type = protein<br>organism = Homo sapiens | <br><br><br><br><br>10 |
| SEQ ID NO: 287<br>FEATURE<br>source<br><br>SEQUENCE: 287 | moltype = AA   length = 10<br>Location/Qualifiers<br>1..10<br>mol_type = protein<br>organism = Homo sapiens | |

-continued

```
VSCQSSVCMP                                                                    10

SEQ ID NO: 288          moltype = AA  length = 10
FEATURE                 Location/Qualifiers
source                  1..10
                        mol_type = protein
                        organism = Homo sapiens
SEQUENCE: 288
VSCTRIVCVA                                                                    10

SEQ ID NO: 289          moltype = AA  length = 10
FEATURE                 Location/Qualifiers
source                  1..10
                        mol_type = protein
                        organism = Homo sapiens
SEQUENCE: 289
VTCEPSPCQS                                                                    10

SEQ ID NO: 290          moltype = AA  length = 10
FEATURE                 Location/Qualifiers
source                  1..10
                        mol_type = protein
                        organism = Homo sapiens
SEQUENCE: 290
VTCQTTVCRP                                                                    10

SEQ ID NO: 291          moltype = AA  length = 10
FEATURE                 Location/Qualifiers
source                  1..10
                        mol_type = protein
                        organism = Homo sapiens
SEQUENCE: 291
YGCGYEGCRY                                                                    10

SEQ ID NO: 292          moltype = AA  length = 10
FEATURE                 Location/Qualifiers
source                  1..10
                        mol_type = protein
                        organism = Homo sapiens
SEQUENCE: 292
AGSCQPSCSE                                                                    10

SEQ ID NO: 293          moltype = AA  length = 10
FEATURE                 Location/Qualifiers
source                  1..10
                        mol_type = protein
                        organism = Homo sapiens
SEQUENCE: 293
ALLCRPLCGV                                                                    10

SEQ ID NO: 294          moltype = AA  length = 10
FEATURE                 Location/Qualifiers
source                  1..10
                        mol_type = protein
                        organism = Homo sapiens
SEQUENCE: 294
ALVCEPVCLR                                                                    10

SEQ ID NO: 295          moltype = AA  length = 10
FEATURE                 Location/Qualifiers
source                  1..10
                        mol_type = protein
                        organism = Homo sapiens
SEQUENCE: 295
ATICEPSCSV                                                                    10

SEQ ID NO: 296          moltype = AA  length = 10
FEATURE                 Location/Qualifiers
source                  1..10
                        mol_type = protein
                        organism = Homo sapiens
SEQUENCE: 296
ATTCEPSCSV                                                                    10

SEQ ID NO: 297          moltype = AA  length = 10
FEATURE                 Location/Qualifiers
source                  1..10
                        mol_type = protein
                        organism = Homo sapiens
```

| | | |
|---|---|---|
| SEQUENCE: 297<br>ATVCEPSCSV | | 10 |
| SEQ ID NO: 298<br>FEATURE<br>source | moltype = AA  length = 10<br>Location/Qualifiers<br>1..10<br>mol_type = protein<br>organism = Homo sapiens | |
| SEQUENCE: 298<br>EGTCLPPCYL | | 10 |
| SEQ ID NO: 299<br>FEATURE<br>source | moltype = AA  length = 10<br>Location/Qualifiers<br>1..10<br>mol_type = protein<br>organism = Homo sapiens | |
| SEQUENCE: 299<br>FSTCRPSCSG | | 10 |
| SEQ ID NO: 300<br>FEATURE<br>source | moltype = AA  length = 10<br>Location/Qualifiers<br>1..10<br>mol_type = protein<br>organism = Homo sapiens | |
| SEQUENCE: 300<br>GFVCQPMCSH | | 10 |
| SEQ ID NO: 301<br>FEATURE<br>source | moltype = AA  length = 10<br>Location/Qualifiers<br>1..10<br>mol_type = protein<br>organism = Homo sapiens | |
| SEQUENCE: 301<br>GLDCGYGCGY | | 10 |
| SEQ ID NO: 302<br>FEATURE<br>source | moltype = AA  length = 10<br>Location/Qualifiers<br>1..10<br>mol_type = protein<br>organism = Homo sapiens | |
| SEQUENCE: 302<br>GLGCGYGCGY | | 10 |
| SEQ ID NO: 303<br>FEATURE<br>source | moltype = AA  length = 10<br>Location/Qualifiers<br>1..10<br>mol_type = protein<br>organism = Homo sapiens | |
| SEQUENCE: 303<br>GLGCSYGCGH | | 10 |
| SEQ ID NO: 304<br>FEATURE<br>source | moltype = AA  length = 10<br>Location/Qualifiers<br>1..10<br>mol_type = protein<br>organism = Homo sapiens | |
| SEQUENCE: 304<br>GLGCSYGCGL | | 10 |
| SEQ ID NO: 305<br>FEATURE<br>source | moltype = AA  length = 10<br>Location/Qualifiers<br>1..10<br>mol_type = protein<br>organism = Homo sapiens | |
| SEQUENCE: 305<br>GSGCGYGCGY | | 10 |
| SEQ ID NO: 306<br>FEATURE<br>source | moltype = AA  length = 10<br>Location/Qualifiers<br>1..10<br>mol_type = protein<br>organism = Homo sapiens | |
| SEQUENCE: 306<br>GTGCGYGCGY | | 10 |
| SEQ ID NO: 307<br>FEATURE<br>source | moltype = AA  length = 10<br>Location/Qualifiers<br>1..10<br>mol_type = protein | |

```
                               -continued organism = Homo sapiens
SEQUENCE: 307
GVSCHTTCYR                                                              10

SEQ ID NO: 308        moltype = AA  length = 10
FEATURE               Location/Qualifiers
source                1..10
                      mol_type = protein
                      organism = Homo sapiens
SEQUENCE: 308
GYACNFPCSY                                                              10

SEQ ID NO: 309        moltype = AA  length = 10
FEATURE               Location/Qualifiers
source                1..10
                      mol_type = protein
                      organism = Homo sapiens
SEQUENCE: 309
GYGCGYGCGF                                                              10

SEQ ID NO: 310        moltype = AA  length = 10
FEATURE               Location/Qualifiers
source                1..10
                      mol_type = protein
                      organism = Homo sapiens
SEQUENCE: 310
HSPCQASCYV                                                              10

SEQ ID NO: 311        moltype = AA  length = 10
FEATURE               Location/Qualifiers
source                1..10
                      mol_type = protein
                      organism = Homo sapiens
SEQUENCE: 311
HTSCSPACQP                                                              10

SEQ ID NO: 312        moltype = AA  length = 10
FEATURE               Location/Qualifiers
source                1..10
                      mol_type = protein
                      organism = Homo sapiens
SEQUENCE: 312
HTSCSSGCQP                                                              10

SEQ ID NO: 313        moltype = AA  length = 10
FEATURE               Location/Qualifiers
source                1..10
                      mol_type = protein
                      organism = Homo sapiens
SEQUENCE: 313
IRWCHPDCHV                                                              10

SEQ ID NO: 314        moltype = AA  length = 10
FEATURE               Location/Qualifiers
source                1..10
                      mol_type = protein
                      organism = Homo sapiens
SEQUENCE: 314
IRWCRPDCRV                                                              10

SEQ ID NO: 315        moltype = AA  length = 10
FEATURE               Location/Qualifiers
source                1..10
                      mol_type = protein
                      organism = Homo sapiens
SEQUENCE: 315
ISSCGTGCGI                                                              10

SEQ ID NO: 316        moltype = AA  length = 10
FEATURE               Location/Qualifiers
source                1..10
                      mol_type = protein
                      organism = Homo sapiens
SEQUENCE: 316
KGGCGSGCGG                                                              10

SEQ ID NO: 317        moltype = AA  length = 10
FEATURE               Location/Qualifiers
source                1..10
```

```
                              mol_type = protein
                              organism = Homo sapiens
SEQUENCE: 317
KGGCGSSCSQ                                                                    10

SEQ ID NO: 318                moltype = AA  length = 10
FEATURE                       Location/Qualifiers
source                        1..10
                              mol_type = protein
                              organism = Homo sapiens
SEQUENCE: 318
LVTCQDSCGS                                                                    10

SEQ ID NO: 319                moltype = AA  length = 10
FEATURE                       Location/Qualifiers
source                        1..10
                              mol_type = protein
                              organism = Homo sapiens
SEQUENCE: 319
LVTCQESCQP                                                                    10

SEQ ID NO: 320                moltype = AA  length = 10
FEATURE                       Location/Qualifiers
source                        1..10
                              mol_type = protein
                              organism = Homo sapiens
SEQUENCE: 320
MSICSSACTD                                                                    10

SEQ ID NO: 321                moltype = AA  length = 10
FEATURE                       Location/Qualifiers
source                        1..10
                              mol_type = protein
                              organism = Homo sapiens
SEQUENCE: 321
MSICSSACTN                                                                    10

SEQ ID NO: 322                moltype = AA  length = 10
FEATURE                       Location/Qualifiers
source                        1..10
                              mol_type = protein
                              organism = Homo sapiens
SEQUENCE: 322
MSVCSSACSD                                                                    10

SEQ ID NO: 323                moltype = AA  length = 10
FEATURE                       Location/Qualifiers
source                        1..10
                              mol_type = protein
                              organism = Homo sapiens
SEQUENCE: 323
PAICEPSCSV                                                                    10

SEQ ID NO: 324                moltype = AA  length = 10
FEATURE                       Location/Qualifiers
source                        1..10
                              mol_type = protein
                              organism = Homo sapiens
SEQUENCE: 324
PASCQKSCYR                                                                    10

SEQ ID NO: 325                moltype = AA  length = 10
FEATURE                       Location/Qualifiers
source                        1..10
                              mol_type = protein
                              organism = Homo sapiens
SEQUENCE: 325
PIYCRRTCYH                                                                    10

SEQ ID NO: 326                moltype = AA  length = 10
FEATURE                       Location/Qualifiers
source                        1..10
                              mol_type = protein
                              organism = Homo sapiens
SEQUENCE: 326
PNSCQTLCVE                                                                    10

SEQ ID NO: 327                moltype = AA  length = 10
FEATURE                       Location/Qualifiers
```

-continued

```
source                  1..10
                        mol_type = protein
                        organism = Homo sapiens
SEQUENCE: 327
PQPCVPTCFL                                                              10

SEQ ID NO: 328          moltype = AA   length = 10
FEATURE                 Location/Qualifiers
source                  1..10
                        mol_type = protein
                        organism = Homo sapiens
SEQUENCE: 328
PSACQSGCTS                                                              10

SEQ ID NO: 329          moltype = AA   length = 10
FEATURE                 Location/Qualifiers
source                  1..10
                        mol_type = protein
                        organism = Homo sapiens
SEQUENCE: 329
PSPCEPSCSE                                                              10

SEQ ID NO: 330          moltype = AA   length = 10
FEATURE                 Location/Qualifiers
source                  1..10
                        mol_type = protein
                        organism = Homo sapiens
SEQUENCE: 330
PSPCQASCYI                                                              10

SEQ ID NO: 331          moltype = AA   length = 10
FEATURE                 Location/Qualifiers
source                  1..10
                        mol_type = protein
                        organism = Homo sapiens
SEQUENCE: 331
PSPCQSGCIS                                                              10

SEQ ID NO: 332          moltype = AA   length = 10
FEATURE                 Location/Qualifiers
source                  1..10
                        mol_type = protein
                        organism = Homo sapiens
SEQUENCE: 332
PSPCQSGCTD                                                              10

SEQ ID NO: 333          moltype = AA   length = 10
FEATURE                 Location/Qualifiers
source                  1..10
                        mol_type = protein
                        organism = Homo sapiens
SEQUENCE: 333
PSPCQSGCTS                                                              10

SEQ ID NO: 334          moltype = AA   length = 10
FEATURE                 Location/Qualifiers
source                  1..10
                        mol_type = protein
                        organism = Homo sapiens
SEQUENCE: 334
PTACQPTCYQ                                                              10

SEQ ID NO: 335          moltype = AA   length = 10
FEATURE                 Location/Qualifiers
source                  1..10
                        mol_type = protein
                        organism = Homo sapiens
SEQUENCE: 335
PTACQPTCYR                                                              10

SEQ ID NO: 336          moltype = AA   length = 10
FEATURE                 Location/Qualifiers
source                  1..10
                        mol_type = protein
                        organism = Homo sapiens
SEQUENCE: 336
PTPCSTTCRT                                                              10

SEQ ID NO: 337          moltype = AA   length = 10
```

```
FEATURE                 Location/Qualifiers
source                  1..10
                        mol_type = protein
                        organism = Homo sapiens
SEQUENCE: 337
PTSCQKSCYR                                                          10

SEQ ID NO: 338          moltype = AA   length = 10
FEATURE                 Location/Qualifiers
source                  1..10
                        mol_type = protein
                        organism = Homo sapiens
SEQUENCE: 338
PTSCQPSCES                                                          10

SEQ ID NO: 339          moltype = AA   length = 10
FEATURE                 Location/Qualifiers
source                  1..10
                        mol_type = protein
                        organism = Homo sapiens
SEQUENCE: 339
PTSCQTSCTL                                                          10

SEQ ID NO: 340          moltype = AA   length = 10
FEATURE                 Location/Qualifiers
source                  1..10
                        mol_type = protein
                        organism = Homo sapiens
SEQUENCE: 340
PVICEPSCSV                                                          10

SEQ ID NO: 341          moltype = AA   length = 10
FEATURE                 Location/Qualifiers
source                  1..10
                        mol_type = protein
                        organism = Homo sapiens
SEQUENCE: 341
PVSCVPVCSG                                                          10

SEQ ID NO: 342          moltype = AA   length = 10
FEATURE                 Location/Qualifiers
source                  1..10
                        mol_type = protein
                        organism = Homo sapiens
SEQUENCE: 342
PVTCVPRCTR                                                          10

SEQ ID NO: 343          moltype = AA   length = 10
FEATURE                 Location/Qualifiers
source                  1..10
                        mol_type = protein
                        organism = Homo sapiens
SEQUENCE: 343
PVYCRRTCYH                                                          10

SEQ ID NO: 344          moltype = AA   length = 10
FEATURE                 Location/Qualifiers
source                  1..10
                        mol_type = protein
                        organism = Homo sapiens
SEQUENCE: 344
PVYCRRTCYY                                                          10

SEQ ID NO: 345          moltype = AA   length = 10
FEATURE                 Location/Qualifiers
source                  1..10
                        mol_type = protein
                        organism = Homo sapiens
SEQUENCE: 345
PVYCVPVCSG                                                          10

SEQ ID NO: 346          moltype = AA   length = 10
FEATURE                 Location/Qualifiers
source                  1..10
                        mol_type = protein
                        organism = Homo sapiens
SEQUENCE: 346
QPGCESPCEP                                                          10
```

```
SEQ ID NO: 347          moltype = AA   length = 10
FEATURE                 Location/Qualifiers
source                  1..10
                        mol_type = protein
                        organism = Homo sapiens
SEQUENCE: 347
QQSCVSSCRR                                                              10

SEQ ID NO: 348          moltype = AA   length = 10
FEATURE                 Location/Qualifiers
source                  1..10
                        mol_type = protein
                        organism = Homo sapiens
SEQUENCE: 348
QTSCGSSCGQ                                                              10

SEQ ID NO: 349          moltype = AA   length = 10
FEATURE                 Location/Qualifiers
source                  1..10
                        mol_type = protein
                        organism = Homo sapiens
SEQUENCE: 349
QTTCHPSCGM                                                              10

SEQ ID NO: 350          moltype = AA   length = 10
FEATURE                 Location/Qualifiers
source                  1..10
                        mol_type = protein
                        organism = Homo sapiens
SEQUENCE: 350
QTTCRPSCGV                                                              10

SEQ ID NO: 351          moltype = AA   length = 10
FEATURE                 Location/Qualifiers
source                  1..10
                        mol_type = protein
                        organism = Homo sapiens
SEQUENCE: 351
RGGCGSGCGG                                                              10

SEQ ID NO: 352          moltype = AA   length = 10
FEATURE                 Location/Qualifiers
source                  1..10
                        mol_type = protein
                        organism = Homo sapiens
SEQUENCE: 352
RLACYSLCSG                                                              10

SEQ ID NO: 353          moltype = AA   length = 10
FEATURE                 Location/Qualifiers
source                  1..10
                        mol_type = protein
                        organism = Homo sapiens
SEQUENCE: 353
RPACYRPCYS                                                              10

SEQ ID NO: 354          moltype = AA   length = 10
FEATURE                 Location/Qualifiers
source                  1..10
                        mol_type = protein
                        organism = Homo sapiens
SEQUENCE: 354
RPFCFRRCYS                                                              10

SEQ ID NO: 355          moltype = AA   length = 10
FEATURE                 Location/Qualifiers
source                  1..10
                        mol_type = protein
                        organism = Homo sapiens
SEQUENCE: 355
RPICRPICSG                                                              10

SEQ ID NO: 356          moltype = AA   length = 10
FEATURE                 Location/Qualifiers
source                  1..10
                        mol_type = protein
                        organism = Homo sapiens
SEQUENCE: 356
RPLCYRRCYS                                                              10
```

| | | |
|---|---|---|
| SEQ ID NO: 357<br>FEATURE<br>source<br><br>SEQUENCE: 357<br>RSPCQASCYV | moltype = AA   length = 10<br>Location/Qualifiers<br>1..10<br>mol_type = protein<br>organism = Homo sapiens | 10 |
| SEQ ID NO: 358<br>FEATURE<br>source<br><br>SEQUENCE: 358<br>RVSCHTTCYR | moltype = AA   length = 10<br>Location/Qualifiers<br>1..10<br>mol_type = protein<br>organism = Homo sapiens | 10 |
| SEQ ID NO: 359<br>FEATURE<br>source<br><br>SEQUENCE: 359<br>SAICRPTCPR | moltype = AA   length = 10<br>Location/Qualifiers<br>1..10<br>mol_type = protein<br>organism = Homo sapiens | 10 |
| SEQ ID NO: 360<br>FEATURE<br>source<br><br>SEQUENCE: 360<br>SDSCKRDCKK | moltype = AA   length = 10<br>Location/Qualifiers<br>1..10<br>mol_type = protein<br>organism = Homo sapiens | 10 |
| SEQ ID NO: 361<br>FEATURE<br>source<br><br>SEQUENCE: 361<br>SEGCGSGCGG | moltype = AA   length = 10<br>Location/Qualifiers<br>1..10<br>mol_type = protein<br>organism = Homo sapiens | 10 |
| SEQ ID NO: 362<br>FEATURE<br>source<br><br>SEQUENCE: 362<br>SFLCRPACSR | moltype = AA   length = 10<br>Location/Qualifiers<br>1..10<br>mol_type = protein<br>organism = Homo sapiens | 10 |
| SEQ ID NO: 363<br>FEATURE<br>source<br><br>SEQUENCE: 363<br>SGGCGSGCGG | moltype = AA   length = 10<br>Location/Qualifiers<br>1..10<br>mol_type = protein<br>organism = Homo sapiens | 10 |
| SEQ ID NO: 364<br>FEATURE<br>source<br><br>SEQUENCE: 364<br>SGGCGSSCGG | moltype = AA   length = 10<br>Location/Qualifiers<br>1..10<br>mol_type = protein<br>organism = Homo sapiens | 10 |
| SEQ ID NO: 365<br>FEATURE<br>source<br><br>SEQUENCE: 365<br>SGSCQAACGQ | moltype = AA   length = 10<br>Location/Qualifiers<br>1..10<br>mol_type = protein<br>organism = Homo sapiens | 10 |
| SEQ ID NO: 366<br>FEATURE<br>source<br><br>SEQUENCE: 366 | moltype = AA   length = 10<br>Location/Qualifiers<br>1..10<br>mol_type = protein<br>organism = Homo sapiens | |

```
SLLCHPVCKS                                                                              10

SEQ ID NO: 367           moltype = AA  length = 10
FEATURE                  Location/Qualifiers
source                   1..10
                         mol_type = protein
                         organism = Homo sapiens SEQUENCE: 367
SLLCHPVCRS                                                                              10

SEQ ID NO: 368           moltype = AA  length = 10
FEATURE                  Location/Qualifiers
source                   1..10
                         mol_type = protein
                         organism = Homo sapiens SEQUENCE: 368
SLLCRPACSP                                                                              10

SEQ ID NO: 369           moltype = AA  length = 10
FEATURE                  Location/Qualifiers
source                   1..10
                         mol_type = protein
                         organism = Homo sapiens SEQUENCE: 369
SLLCRPACSR                                                                              10

SEQ ID NO: 370           moltype = AA  length = 10
FEATURE                  Location/Qualifiers
source                   1..10
                         mol_type = protein
                         organism = Homo sapiens SEQUENCE: 370
SLLCRPICRP                                                                              10

SEQ ID NO: 371           moltype = AA  length = 10
FEATURE                  Location/Qualifiers
source                   1..10
                         mol_type = protein
                         organism = Homo sapiens SEQUENCE: 371
SLLCRPMCSR                                                                              10

SEQ ID NO: 372           moltype = AA  length = 10
FEATURE                  Location/Qualifiers
source                   1..10
                         mol_type = protein
                         organism = Homo sapiens SEQUENCE: 372
SLLCRPTCSR                                                                              10

SEQ ID NO: 373           moltype = AA  length = 10
FEATURE                  Location/Qualifiers
source                   1..10
                         mol_type = protein
                         organism = Homo sapiens SEQUENCE: 373
SLLCRPVCQP                                                                              10

SEQ ID NO: 374           moltype = AA  length = 10
FEATURE                  Location/Qualifiers
source                   1..10
                         mol_type = protein
                         organism = Homo sapiens SEQUENCE: 374
SLLCRPVCRP                                                                              10

SEQ ID NO: 375           moltype = AA  length = 10
FEATURE                  Location/Qualifiers
source                   1..10
                         mol_type = protein
                         organism = Homo sapiens SEQUENCE: 375
SLLCRPVCRS                                                                              10

SEQ ID NO: 376           moltype = AA  length = 10
FEATURE                  Location/Qualifiers
source                   1..10
                         mol_type = protein
                         organism = Homo sapiens
```

| | | | |
|---|---|---|---|
| SEQUENCE: 376<br>SLLCRPVCSR | | | 10 |
| SEQ ID NO: 377<br>FEATURE<br>source | moltype = AA length = 10<br>Location/Qualifiers<br>1..10<br>mol_type = protein<br>organism = Homo sapiens | | |
| SEQUENCE: 377<br>SNPCQVTCSR | | | 10 |
| SEQ ID NO: 378<br>FEATURE<br>source | moltype = AA length = 10<br>Location/Qualifiers<br>1..10<br>mol_type = protein<br>organism = Homo sapiens | | |
| SEQUENCE: 378<br>SRGCGSGCGG | | | 10 |
| SEQ ID NO: 379<br>FEATURE<br>source | moltype = AA length = 10<br>Location/Qualifiers<br>1..10<br>mol_type = protein<br>organism = Homo sapiens | | |
| SEQUENCE: 379<br>SRSCQSPCYR | | | 10 |
| SEQ ID NO: 380<br>FEATURE<br>source | moltype = AA length = 10<br>Location/Qualifiers<br>1..10<br>mol_type = protein<br>organism = Homo sapiens | | |
| SEQUENCE: 380<br>SRSCQSSCYR | | | 10 |
| SEQ ID NO: 381<br>FEATURE<br>source | moltype = AA length = 10<br>Location/Qualifiers<br>1..10<br>mol_type = protein<br>organism = Homo sapiens | | |
| SEQUENCE: 381<br>SSGCGYGCGY | | | 10 |
| SEQ ID NO: 382<br>FEATURE<br>source | moltype = AA length = 10<br>Location/Qualifiers<br>1..10<br>mol_type = protein<br>organism = Homo sapiens | | |
| SEQUENCE: 382<br>SSGCPMACPG | | | 10 |
| SEQ ID NO: 383<br>FEATURE<br>source | moltype = AA length = 10<br>Location/Qualifiers<br>1..10<br>mol_type = protein<br>organism = Homo sapiens | | |
| SEQUENCE: 383<br>SSICQPICSE | | | 10 |
| SEQ ID NO: 384<br>FEATURE<br>source | moltype = AA length = 10<br>Location/Qualifiers<br>1..10<br>mol_type = protein<br>organism = Homo sapiens | | |
| SEQUENCE: 384<br>SSPCHTSCYY | | | 10 |
| SEQ ID NO: 385<br>FEATURE<br>source | moltype = AA length = 10<br>Location/Qualifiers<br>1..10<br>mol_type = protein<br>organism = Homo sapiens | | |
| SEQUENCE: 385<br>SSPCQPTCYV | | | 10 |
| SEQ ID NO: 386<br>FEATURE<br>source | moltype = AA length = 10<br>Location/Qualifiers<br>1..10<br>mol_type = protein | | |

-continued

```
                           organism = Homo sapiens
SEQUENCE: 386
SSPCQQSCYV                                                                  10

SEQ ID NO: 387             moltype = AA   length = 10
FEATURE                    Location/Qualifiers
source                     1..10
                           mol_type = protein
                           organism = Homo sapiens
SEQUENCE: 387
SSPCQTSCYR                                                                  10

SEQ ID NO: 388             moltype = AA   length = 10
FEATURE                    Location/Qualifiers
source                     1..10
                           mol_type = protein
                           organism = Homo sapiens
SEQUENCE: 388
SSSCQQSCRV                                                                  10

SEQ ID NO: 389             moltype = AA   length = 10
FEATURE                    Location/Qualifiers
source                     1..10
                           mol_type = protein
                           organism = Homo sapiens
SEQUENCE: 389
STVCQPACGV                                                                  10

SEQ ID NO: 390             moltype = AA   length = 10
FEATURE                    Location/Qualifiers
source                     1..10
                           mol_type = protein
                           organism = Homo sapiens
SEQUENCE: 390
TDNCQETCGE                                                                  10

SEQ ID NO: 391             moltype = AA   length = 10
FEATURE                    Location/Qualifiers
source                     1..10
                           mol_type = protein
                           organism = Homo sapiens
SEQUENCE: 391
TQPCYEPCLP                                                                  10

SEQ ID NO: 392             moltype = AA   length = 10
FEATURE                    Location/Qualifiers
source                     1..10
                           mol_type = protein
                           organism = Homo sapiens
SEQUENCE: 392
TSSCGTGCGI                                                                  10

SEQ ID NO: 393             moltype = AA   length = 10
FEATURE                    Location/Qualifiers
source                     1..10
                           mol_type = protein
                           organism = Homo sapiens
SEQUENCE: 393
TSSCQPSCGR                                                                  10

SEQ ID NO: 394             moltype = AA   length = 10
FEATURE                    Location/Qualifiers
source                     1..10
                           mol_type = protein
                           organism = Homo sapiens
SEQUENCE: 394
TSSCTTPCYQ                                                                  10

SEQ ID NO: 395             moltype = AA   length = 10
FEATURE                    Location/Qualifiers
source                     1..10
                           mol_type = protein
                           organism = Homo sapiens
SEQUENCE: 395
TSVCLPGCLN                                                                  10

SEQ ID NO: 396             moltype = AA   length = 10
FEATURE                    Location/Qualifiers
source                     1..10
```

```
                        mol_type = protein
                        organism = Homo sapiens
SEQUENCE: 396
TTVCLPGCLN                                                              10

SEQ ID NO: 397          moltype = AA  length = 10
FEATURE                 Location/Qualifiers
source                  1..10
                        mol_type = protein
                        organism = Homo sapiens
SEQUENCE: 397
VANCQAPCST                                                              10

SEQ ID NO: 398          moltype = AA  length = 10
FEATURE                 Location/Qualifiers
source                  1..10
                        mol_type = protein
                        organism = Homo sapiens
SEQUENCE: 398
VDDCPESCWP                                                              10

SEQ ID NO: 399          moltype = AA  length = 10
FEATURE                 Location/Qualifiers
source                  1..10
                        mol_type = protein
                        organism = Homo sapiens
SEQUENCE: 399
VKRCPSVCPE                                                              10

SEQ ID NO: 400          moltype = AA  length = 10
FEATURE                 Location/Qualifiers
source                  1..10
                        mol_type = protein
                        organism = Homo sapiens
SEQUENCE: 400
VSSCQPSCSE                                                              10

SEQ ID NO: 401          moltype = AA  length = 10
FEATURE                 Location/Qualifiers
source                  1..10
                        mol_type = protein
                        organism = Homo sapiens
SEQUENCE: 401
YEGCRYGCGH                                                              10

SEQ ID NO: 402          moltype = AA  length = 10
FEATURE                 Location/Qualifiers
source                  1..10
                        mol_type = protein
                        organism = Homo sapiens
SEQUENCE: 402
YGRCRHGCHS                                                              10

SEQ ID NO: 403          moltype = AA  length = 10
FEATURE                 Location/Qualifiers
source                  1..10
                        mol_type = protein
                        organism = Homo sapiens
SEQUENCE: 403
YGYCRPSCYG                                                              10

SEQ ID NO: 404          moltype = AA  length = 10
FEATURE                 Location/Qualifiers
source                  1..10
                        mol_type = protein
                        organism = Homo sapiens
SEQUENCE: 404
YRDCQKTCWE                                                              10

SEQ ID NO: 405          moltype = AA  length = 10
FEATURE                 Location/Qualifiers
source                  1..10
                        mol_type = protein
                        organism = Homo sapiens
SEQUENCE: 405
YRGCQEICWE                                                              10

SEQ ID NO: 406          moltype = AA  length = 10
FEATURE                 Location/Qualifiers
```

|   |   |   |
|---|---|---|
| source | 1..10<br>mol_type = protein<br>organism = Homo sapiens | |
| SEQUENCE: 406<br>YRGCQETCWR | | 10 |
| SEQ ID NO: 407<br>FEATURE<br>source | moltype = AA   length = 10<br>Location/Qualifiers<br>1..10<br>mol_type = protein<br>organism = Homo sapiens | |
| SEQUENCE: 407<br>YRGCQQTCWE | | 10 |
| SEQ ID NO: 408<br>FEATURE<br>source | moltype = AA   length = 10<br>Location/Qualifiers<br>1..10<br>mol_type = protein<br>organism = Homo sapiens | |
| SEQUENCE: 408<br>YRSCRPSCYG | | 10 |
| SEQ ID NO: 409<br>FEATURE<br>source | moltype = AA   length = 10<br>Location/Qualifiers<br>1..10<br>mol_type = protein<br>organism = Homo sapiens | |
| SEQUENCE: 409<br>GGVCGPSPPC | | 10 |
| SEQ ID NO: 410<br>FEATURE<br>source | moltype = AA   length = 10<br>Location/Qualifiers<br>1..10<br>mol_type = protein<br>organism = Homo sapiens | |
| SEQUENCE: 410<br>GVCGPSPPCI | | 10 |
| SEQ ID NO: 411<br>FEATURE<br>source | moltype = AA   length = 10<br>Location/Qualifiers<br>1..10<br>mol_type = protein<br>organism = Homo sapiens | |
| SEQUENCE: 411<br>VCGPSPPCIT | | 10 |
| SEQ ID NO: 412<br>FEATURE<br>source | moltype = AA   length = 10<br>Location/Qualifiers<br>1..10<br>mol_type = protein<br>organism = Homo sapiens | |
| SEQUENCE: 412<br>CGPSPPCITT | | 10 |
| SEQ ID NO: 413<br>FEATURE<br>source | moltype = AA   length = 10<br>Location/Qualifiers<br>1..10<br>mol_type = protein<br>organism = Homo sapiens | |
| SEQUENCE: 413<br>CAPIYCRRTC | | 10 |
| SEQ ID NO: 414<br>FEATURE<br>source | moltype = AA   length = 10<br>Location/Qualifiers<br>1..10<br>mol_type = protein<br>organism = Homo sapiens | |
| SEQUENCE: 414<br>CAPSPCQASC | | 10 |
| SEQ ID NO: 415<br>FEATURE<br>source | moltype = AA   length = 10<br>Location/Qualifiers<br>1..10<br>mol_type = protein<br>organism = Homo sapiens | |
| SEQUENCE: 415<br>CAPSPCQPAC | | 10 |
| SEQ ID NO: 416 | moltype = AA   length = 10 | |

```
FEATURE                 Location/Qualifiers
source                  1..10
                        mol_type = protein
                        organism = Homo sapiens
SEQUENCE: 416
CAPVYCRRTC                                                                      10

SEQ ID NO: 417          moltype = AA  length = 10
FEATURE                 Location/Qualifiers
source                  1..10
                        mol_type = protein
                        organism = Homo sapiens
SEQUENCE: 417
CASSPCQQAC                                                                      10

SEQ ID NO: 418          moltype = AA  length = 10
FEATURE                 Location/Qualifiers
source                  1..10
                        mol_type = protein
                        organism = Homo sapiens
SEQUENCE: 418
CASSSCQPAC                                                                      10

SEQ ID NO: 419          moltype = AA  length = 10
FEATURE                 Location/Qualifiers
source                  1..10
                        mol_type = protein
                        organism = Homo sapiens
SEQUENCE: 419
CASSSCQQSC                                                                      10

SEQ ID NO: 420          moltype = AA  length = 10
FEATURE                 Location/Qualifiers
source                  1..10
                        mol_type = protein
                        organism = Homo sapiens
SEQUENCE: 420
CCGNFSSHSC                                                                      10

SEQ ID NO: 421          moltype = AA  length = 10
FEATURE                 Location/Qualifiers
source                  1..10
                        mol_type = protein
                        organism = Homo sapiens
SEQUENCE: 421
CCGYGGLGCG                                                                      10

SEQ ID NO: 422          moltype = AA  length = 10
FEATURE                 Location/Qualifiers
source                  1..10
                        mol_type = protein
                        organism = Homo sapiens
SEQUENCE: 422
CCNYYGNSCG                                                                      10

SEQ ID NO: 423          moltype = AA  length = 10
FEATURE                 Location/Qualifiers
source                  1..10
                        mol_type = protein
                        organism = Homo sapiens
SEQUENCE: 423
CCNYYRNSCG                                                                      10

SEQ ID NO: 424          moltype = AA  length = 10
FEATURE                 Location/Qualifiers
source                  1..10
                        mol_type = protein
                        organism = Homo sapiens
SEQUENCE: 424
CCSRNFSSCS                                                                      10

SEQ ID NO: 425          moltype = AA  length = 10
FEATURE                 Location/Qualifiers
source                  1..10
                        mol_type = protein
                        organism = Homo sapiens
SEQUENCE: 425
CDAGSCQPSC                                                                      10
```

| | | |
|---|---|---|
| SEQ ID NO: 426<br>FEATURE<br>source | moltype = AA   length = 10<br>Location/Qualifiers<br>1..10<br>mol_type = protein<br>organism = Homo sapiens | |
| SEQUENCE: 426<br>CDPCSLQEGC | | 10 |
| SEQ ID NO: 427<br>FEATURE<br>source | moltype = AA   length = 10<br>Location/Qualifiers<br>1..10<br>mol_type = protein<br>organism = Homo sapiens | |
| SEQUENCE: 427<br>CDPSPCEPSC | | 10 |
| SEQ ID NO: 428<br>FEATURE<br>source | moltype = AA   length = 10<br>Location/Qualifiers<br>1..10<br>mol_type = protein<br>organism = Homo sapiens | |
| SEQUENCE: 428<br>CDPVICEPSC | | 10 |
| SEQ ID NO: 429<br>FEATURE<br>source | moltype = AA   length = 10<br>Location/Qualifiers<br>1..10<br>mol_type = protein<br>organism = Homo sapiens | |
| SEQUENCE: 429<br>CDQGLCQETC | | 10 |
| SEQ ID NO: 430<br>FEATURE<br>source | moltype = AA   length = 10<br>Location/Qualifiers<br>1..10<br>mol_type = protein<br>organism = Homo sapiens | |
| SEQUENCE: 430<br>CEATTCEPSC | | 10 |
| SEQ ID NO: 431<br>FEATURE<br>source | moltype = AA   length = 10<br>Location/Qualifiers<br>1..10<br>mol_type = protein<br>organism = Homo sapiens | |
| SEQUENCE: 431<br>CELPCGTPSC | | 10 |
| SEQ ID NO: 432<br>FEATURE<br>source | moltype = AA   length = 10<br>Location/Qualifiers<br>1..10<br>mol_type = protein<br>organism = Homo sapiens | |
| SEQUENCE: 432<br>CEPAICEPSC | | 10 |
| SEQ ID NO: 433<br>FEATURE<br>source | moltype = AA   length = 10<br>Location/Qualifiers<br>1..10<br>mol_type = protein<br>organism = Homo sapiens | |
| SEQUENCE: 433<br>CEPPCGTAPC | | 10 |
| SEQ ID NO: 434<br>FEATURE<br>source | moltype = AA   length = 10<br>Location/Qualifiers<br>1..10<br>mol_type = protein<br>organism = Homo sapiens | |
| SEQUENCE: 434<br>CEPPCSAPSC | | 10 |
| SEQ ID NO: 435<br>FEATURE<br>source | moltype = AA   length = 10<br>Location/Qualifiers<br>1..10<br>mol_type = protein<br>organism = Homo sapiens | |
| SEQUENCE: 435<br>CEPRSCASSC | | 10 |

| | | |
|---|---|---|
| SEQ ID NO: 436<br>FEATURE<br>source<br><br>SEQUENCE: 436<br>CEPSACQSGC | moltype = AA   length = 10<br>Location/Qualifiers<br>1..10<br>mol_type = protein<br>organism = Homo sapiens | 10 |
| SEQ ID NO: 437<br>FEATURE<br>source<br><br>SEQUENCE: 437<br>CEPSCSVSNC | moltype = AA   length = 10<br>Location/Qualifiers<br>1..10<br>mol_type = protein<br>organism = Homo sapiens | 10 |
| SEQ ID NO: 438<br>FEATURE<br>source<br><br>SEQUENCE: 438<br>CEPSCSVSSC | moltype = AA   length = 10<br>Location/Qualifiers<br>1..10<br>mol_type = protein<br>organism = Homo sapiens | 10 |
| SEQ ID NO: 439<br>FEATURE<br>source<br><br>SEQUENCE: 439<br>CEPSPCQSGC | moltype = AA   length = 10<br>Location/Qualifiers<br>1..10<br>mol_type = protein<br>organism = Homo sapiens | 10 |
| SEQ ID NO: 440<br>FEATURE<br>source<br><br>SEQUENCE: 440<br>CEPTACQPTC | moltype = AA   length = 10<br>Location/Qualifiers<br>1..10<br>mol_type = protein<br>organism = Homo sapiens | 10 |
| SEQ ID NO: 441<br>FEATURE<br>source<br><br>SEQUENCE: 441<br>CEPTSCQTSC | moltype = AA   length = 10<br>Location/Qualifiers<br>1..10<br>mol_type = protein<br>organism = Homo sapiens | 10 |
| SEQ ID NO: 442<br>FEATURE<br>source<br><br>SEQUENCE: 442<br>CEPVCLRPVC | moltype = AA   length = 10<br>Location/Qualifiers<br>1..10<br>mol_type = protein<br>organism = Homo sapiens | 10 |
| SEQ ID NO: 443<br>FEATURE<br>source<br><br>SEQUENCE: 443<br>CETSSCQPRC | moltype = AA   length = 10<br>Location/Qualifiers<br>1..10<br>mol_type = protein<br>organism = Homo sapiens | 10 |
| SEQ ID NO: 444<br>FEATURE<br>source<br><br>SEQUENCE: 444<br>CETTCFQPTC | moltype = AA   length = 10<br>Location/Qualifiers<br>1..10<br>mol_type = protein<br>organism = Homo sapiens | 10 |
| SEQ ID NO: 445<br>FEATURE<br>source<br><br>SEQUENCE: 445 | moltype = AA   length = 10<br>Location/Qualifiers<br>1..10<br>mol_type = protein<br>organism = Homo sapiens | |

CFQPTCVSSC                                                                       10

SEQ ID NO: 446        moltype = AA  length = 10
FEATURE               Location/Qualifiers
source                1..10
                      mol_type = protein
                      organism = Homo sapiens SEQUENCE: 446
CFQPTCVTSC                                                                       10

SEQ ID NO: 447        moltype = AA  length = 10
FEATURE               Location/Qualifiers
source                1..10
                      mol_type = protein
                      organism = Homo sapiens SEQUENCE: 447
CFQPTCVYSC                                                                       10

SEQ ID NO: 448        moltype = AA  length = 10
FEATURE               Location/Qualifiers
source                1..10
                      mol_type = protein
                      organism = Homo sapiens SEQUENCE: 448
CGCGFRRLGC                                                                       10

SEQ ID NO: 449        moltype = AA  length = 10
FEATURE               Location/Qualifiers
source                1..10
                      mol_type = protein
                      organism = Homo sapiens SEQUENCE: 449
CGCGYRGLDC                                                                       10

SEQ ID NO: 450        moltype = AA  length = 10
FEATURE               Location/Qualifiers
source                1..10
                      mol_type = protein
                      organism = Homo sapiens SEQUENCE: 450
CGCNGYYGCY                                                                       10

SEQ ID NO: 451        moltype = AA  length = 10
FEATURE               Location/Qualifiers
source                1..10
                      mol_type = protein
                      organism = Homo sapiens SEQUENCE: 451
CGFGSCYGCG                                                                       10

SEQ ID NO: 452        moltype = AA  length = 10
FEATURE               Location/Qualifiers
source                1..10
                      mol_type = protein
                      organism = Homo sapiens SEQUENCE: 452
CGGSGCGGSC                                                                       10

SEQ ID NO: 453        moltype = AA  length = 10
FEATURE               Location/Qualifiers
source                1..10
                      mol_type = protein
                      organism = Homo sapiens SEQUENCE: 453
CGGSGSSCCV                                                                       10

SEQ ID NO: 454        moltype = AA  length = 10
FEATURE               Location/Qualifiers
source                1..10
                      mol_type = protein
                      organism = Homo sapiens SEQUENCE: 454
CGGVSCHTTC                                                                       10

SEQ ID NO: 455        moltype = AA  length = 10
FEATURE               Location/Qualifiers
source                1..10
                      mol_type = protein
                      organism = Homo sapiens

```
SEQUENCE: 455
CGKGGCGSCG                                                                              10

SEQ ID NO: 456          moltype = AA  length = 10
FEATURE                 Location/Qualifiers
source                  1..10
                        mol_type = protein
                        organism = Homo sapiens
SEQUENCE: 456
CGKRGCGSCG                                                                              10

SEQ ID NO: 457          moltype = AA  length = 10
FEATURE                 Location/Qualifiers
source                  1..10
                        mol_type = protein
                        organism = Homo sapiens
SEQUENCE: 457
CGQDLCQETC                                                                              10

SEQ ID NO: 458          moltype = AA  length = 10
FEATURE                 Location/Qualifiers
source                  1..10
                        mol_type = protein
                        organism = Homo sapiens
SEQUENCE: 458
CGQTSCGSSC                                                                              10

SEQ ID NO: 459          moltype = AA  length = 10
FEATURE                 Location/Qualifiers
source                  1..10
                        mol_type = protein
                        organism = Homo sapiens
SEQUENCE: 459
CGQVLCQETC                                                                              10

SEQ ID NO: 460          moltype = AA  length = 10
FEATURE                 Location/Qualifiers
source                  1..10
                        mol_type = protein
                        organism = Homo sapiens
SEQUENCE: 460
CGRDLCQETC                                                                              10

SEQ ID NO: 461          moltype = AA  length = 10
FEATURE                 Location/Qualifiers
source                  1..10
                        mol_type = protein
                        organism = Homo sapiens
SEQUENCE: 461
CGRVSCHTTC                                                                              10

SEQ ID NO: 462          moltype = AA  length = 10
FEATURE                 Location/Qualifiers
source                  1..10
                        mol_type = protein
                        organism = Homo sapiens
SEQUENCE: 462
CGSCGFGSCY                                                                              10

SEQ ID NO: 463          moltype = AA  length = 10
FEATURE                 Location/Qualifiers
source                  1..10
                        mol_type = protein
                        organism = Homo sapiens
SEQUENCE: 463
CGSCGGSKGC                                                                              10

SEQ ID NO: 464          moltype = AA  length = 10
FEATURE                 Location/Qualifiers
source                  1..10
                        mol_type = protein
                        organism = Homo sapiens
SEQUENCE: 464
CGSGCGVPVC                                                                              10

SEQ ID NO: 465          moltype = AA  length = 10
FEATURE                 Location/Qualifiers
source                  1..10
                        mol_type = protein
```

```
                        organism = Homo sapiens
SEQUENCE: 465
CGSLLCRPTC                                                              10

SEQ ID NO: 466          moltype = AA   length = 10
FEATURE                 Location/Qualifiers
source                  1..10
                        mol_type = protein
                        organism = Homo sapiens
SEQUENCE: 466
CGSRCYVPVC                                                              10

SEQ ID NO: 467          moltype = AA   length = 10
FEATURE                 Location/Qualifiers
source                  1..10
                        mol_type = protein
                        organism = Homo sapiens
SEQUENCE: 467
CGSSSCGPQC                                                              10

SEQ ID NO: 468          moltype = AA   length = 10
FEATURE                 Location/Qualifiers
source                  1..10
                        mol_type = protein
                        organism = Homo sapiens
SEQUENCE: 468
CGSVCSDQGC                                                              10

SEQ ID NO: 469          moltype = AA   length = 10
FEATURE                 Location/Qualifiers
source                  1..10
                        mol_type = protein
                        organism = Homo sapiens
SEQUENCE: 469
CGSVCSDQSC                                                              10

SEQ ID NO: 470          moltype = AA   length = 10
FEATURE                 Location/Qualifiers
source                  1..10
                        mol_type = protein
                        organism = Homo sapiens
SEQUENCE: 470
CGSVCSHQGC                                                              10

SEQ ID NO: 471          moltype = AA   length = 10
FEATURE                 Location/Qualifiers
source                  1..10
                        mol_type = protein
                        organism = Homo sapiens
SEQUENCE: 471
CGSYGCSQCS                                                              10

SEQ ID NO: 472          moltype = AA   length = 10
FEATURE                 Location/Qualifiers
source                  1..10
                        mol_type = protein
                        organism = Homo sapiens
SEQUENCE: 472
CGVCLPSTCP                                                              10

SEQ ID NO: 473          moltype = AA   length = 10
FEATURE                 Location/Qualifiers
source                  1..10
                        mol_type = protein
                        organism = Homo sapiens
SEQUENCE: 473
CGYEGCRYGC                                                              10

SEQ ID NO: 474          moltype = AA   length = 10
FEATURE                 Location/Qualifiers
source                  1..10
                        mol_type = protein
                        organism = Homo sapiens
SEQUENCE: 474
CGYGCGYGCG                                                              10

SEQ ID NO: 475          moltype = AA   length = 10
FEATURE                 Location/Qualifiers
source                  1..10
```

```
                            mol_type = protein
                            organism = Homo sapiens
SEQUENCE: 475
CGYGGCGYGC                                                              10

SEQ ID NO: 476              moltype = AA  length = 10
FEATURE                     Location/Qualifiers
source                      1..10
                            mol_type = protein
                            organism = Homo sapiens
SEQUENCE: 476
CGYGSFCGCG                                                              10

SEQ ID NO: 477              moltype = AA  length = 10
FEATURE                     Location/Qualifiers
source                      1..10
                            mol_type = protein
                            organism = Homo sapiens
SEQUENCE: 477
CGYGSGCGCG                                                              10

SEQ ID NO: 478              moltype = AA  length = 10
FEATURE                     Location/Qualifiers
source                      1..10
                            mol_type = protein
                            organism = Homo sapiens
SEQUENCE: 478
CHPSCGMSSC                                                              10

SEQ ID NO: 479              moltype = AA  length = 10
FEATURE                     Location/Qualifiers
source                      1..10
                            mol_type = protein
                            organism = Homo sapiens
SEQUENCE: 479
CHPSCSISSC                                                              10

SEQ ID NO: 480              moltype = AA  length = 10
FEATURE                     Location/Qualifiers
source                      1..10
                            mol_type = protein
                            organism = Homo sapiens
SEQUENCE: 480
CHPTCYQTIC                                                              10

SEQ ID NO: 481              moltype = AA  length = 10
FEATURE                     Location/Qualifiers
source                      1..10
                            mol_type = protein
                            organism = Homo sapiens
SEQUENCE: 481
CHTSCSPACQ                                                              10

SEQ ID NO: 482              moltype = AA  length = 10
FEATURE                     Location/Qualifiers
source                      1..10
                            mol_type = protein
                            organism = Homo sapiens
SEQUENCE: 482
CHTSCSSGCQ                                                              10

SEQ ID NO: 483              moltype = AA  length = 10
FEATURE                     Location/Qualifiers
source                      1..10
                            mol_type = protein
                            organism = Homo sapiens
SEQUENCE: 483
CHTTCYRPAC                                                              10

SEQ ID NO: 484              moltype = AA  length = 10
FEATURE                     Location/Qualifiers
source                      1..10
                            mol_type = protein
                            organism = Homo sapiens
SEQUENCE: 484
CHTTCYRPTC                                                              10

SEQ ID NO: 485              moltype = AA  length = 10
FEATURE                     Location/Qualifiers
```

```
                        -continued source                  1..10
                        mol_type = protein
                        organism = Homo sapiens
SEQUENCE: 485
CIHSPCQASC                                                          10

SEQ ID NO: 486          moltype = AA   length = 10
FEATURE                 Location/Qualifiers
source                  1..10
                        mol_type = protein
                        organism = Homo sapiens
SEQUENCE: 486
CIHSTHCGCN                                                          10

SEQ ID NO: 487          moltype = AA   length = 10
FEATURE                 Location/Qualifiers
source                  1..10
                        mol_type = protein
                        organism = Homo sapiens
SEQUENCE: 487
CIRSPCQASC                                                          10

SEQ ID NO: 488          moltype = AA   length = 10
FEATURE                 Location/Qualifiers
source                  1..10
                        mol_type = protein
                        organism = Homo sapiens
SEQUENCE: 488
CISSCYRPQC                                                          10

SEQ ID NO: 489          moltype = AA   length = 10
FEATURE                 Location/Qualifiers
source                  1..10
                        mol_type = protein
                        organism = Homo sapiens
SEQUENCE: 489
CISSPCQQSC                                                          10

SEQ ID NO: 490          moltype = AA   length = 10
FEATURE                 Location/Qualifiers
source                  1..10
                        mol_type = protein
                        organism = Homo sapiens
SEQUENCE: 490
CKPCSSQSSC                                                          10

SEQ ID NO: 491          moltype = AA   length = 10
FEATURE                 Location/Qualifiers
source                  1..10
                        mol_type = protein
                        organism = Homo sapiens
SEQUENCE: 491
CKPSCSQSSC                                                          10

SEQ ID NO: 492          moltype = AA   length = 10
FEATURE                 Location/Qualifiers
source                  1..10
                        mol_type = protein
                        organism = Homo sapiens
SEQUENCE: 492
CKPVCFKPIC                                                          10

SEQ ID NO: 493          moltype = AA   length = 10
FEATURE                 Location/Qualifiers
source                  1..10
                        mol_type = protein
                        organism = Homo sapiens
SEQUENCE: 493
CKPVCYVPTC                                                          10

SEQ ID NO: 494          moltype = AA   length = 10
FEATURE                 Location/Qualifiers
source                  1..10
                        mol_type = protein
                        organism = Homo sapiens
SEQUENCE: 494
CKPVSCVPVC                                                          10

SEQ ID NO: 495          moltype = AA   length = 10
```

```
                        -continued

FEATURE                 Location/Qualifiers
source                  1..10
                        mol_type = protein
                        organism = Homo sapiens
SEQUENCE: 495
CKPVYCVPVC                                                              10

SEQ ID NO: 496          moltype = AA   length = 10
FEATURE                 Location/Qualifiers
source                  1..10
                        mol_type = protein
                        organism = Homo sapiens
SEQUENCE: 496
CKTVYCKPIC                                                              10

SEQ ID NO: 497          moltype = AA   length = 10
FEATURE                 Location/Qualifiers
source                  1..10
                        mol_type = protein
                        organism = Homo sapiens
SEQUENCE: 497
CLNQSCGSNC                                                              10

SEQ ID NO: 498          moltype = AA   length = 10
FEATURE                 Location/Qualifiers
source                  1..10
                        mol_type = protein
                        organism = Homo sapiens
SEQUENCE: 498
CLNQSCGSSC                                                              10

SEQ ID NO: 499          moltype = AA   length = 10
FEATURE                 Location/Qualifiers
source                  1..10
                        mol_type = protein
                        organism = Homo sapiens
SEQUENCE: 499
CLPGCLNQSC                                                              10

SEQ ID NO: 500          moltype = AA   length = 10
FEATURE                 Location/Qualifiers
source                  1..10
                        mol_type = protein
                        organism = Homo sapiens
SEQUENCE: 500
CLPGSCDSCS                                                              10

SEQ ID NO: 501          moltype = AA   length = 10
FEATURE                 Location/Qualifiers
source                  1..10
                        mol_type = protein
                        organism = Homo sapiens
SEQUENCE: 501
CLPPCYLVSC                                                              10

SEQ ID NO: 502          moltype = AA   length = 10
FEATURE                 Location/Qualifiers
source                  1..10
                        mol_type = protein
                        organism = Homo sapiens
SEQUENCE: 502
CLPTSCQPSC                                                              10

SEQ ID NO: 503          moltype = AA   length = 10
FEATURE                 Location/Qualifiers
source                  1..10
                        mol_type = protein
                        organism = Homo sapiens
SEQUENCE: 503
CLSFLCRPAC                                                              10

SEQ ID NO: 504          moltype = AA   length = 10
FEATURE                 Location/Qualifiers
source                  1..10
                        mol_type = protein
                        organism = Homo sapiens
SEQUENCE: 504
CLVSSCQPSC                                                              10
```

| | | |
|---|---|---|
| SEQ ID NO: 505<br>FEATURE<br>source | moltype = AA   length = 10<br>Location/Qualifiers<br>1..10<br>mol_type = protein<br>organism = Homo sapiens | |
| SEQUENCE: 505<br>CMPSPCQPAC | | 10 |
| SEQ ID NO: 506<br>FEATURE<br>source | moltype = AA   length = 10<br>Location/Qualifiers<br>1..10<br>mol_type = protein<br>organism = Homo sapiens | |
| SEQUENCE: 506<br>CMSGSCQAAC | | 10 |
| SEQ ID NO: 507<br>FEATURE<br>source | moltype = AA   length = 10<br>Location/Qualifiers<br>1..10<br>mol_type = protein<br>organism = Homo sapiens | |
| SEQUENCE: 507<br>CNESSYCLPC | | 10 |
| SEQ ID NO: 508<br>FEATURE<br>source | moltype = AA   length = 10<br>Location/Qualifiers<br>1..10<br>mol_type = protein<br>organism = Homo sapiens | |
| SEQUENCE: 508<br>CPASCVSLLC | | 10 |
| SEQ ID NO: 509<br>FEATURE<br>source | moltype = AA   length = 10<br>Location/Qualifiers<br>1..10<br>mol_type = protein<br>organism = Homo sapiens | |
| SEQUENCE: 509<br>CPMACPGSPC | | 10 |
| SEQ ID NO: 510<br>FEATURE<br>source | moltype = AA   length = 10<br>Location/Qualifiers<br>1..10<br>mol_type = protein<br>organism = Homo sapiens | |
| SEQUENCE: 510<br>CPSSCTAVVC | | 10 |
| SEQ ID NO: 511<br>FEATURE<br>source | moltype = AA   length = 10<br>Location/Qualifiers<br>1..10<br>mol_type = protein<br>organism = Homo sapiens | |
| SEQUENCE: 511<br>CPVTCEPSPC | | 10 |
| SEQ ID NO: 512<br>FEATURE<br>source | moltype = AA   length = 10<br>Location/Qualifiers<br>1..10<br>mol_type = protein<br>organism = Homo sapiens | |
| SEQUENCE: 512<br>CQAACEPSAC | | 10 |
| SEQ ID NO: 513<br>FEATURE<br>source | moltype = AA   length = 10<br>Location/Qualifiers<br>1..10<br>mol_type = protein<br>organism = Homo sapiens | |
| SEQUENCE: 513<br>CQAACEPSPC | | 10 |
| SEQ ID NO: 514<br>FEATURE<br>source | moltype = AA   length = 10<br>Location/Qualifiers<br>1..10<br>mol_type = protein<br>organism = Homo sapiens | |
| SEQUENCE: 514<br>CQAACGQSVC | | 10 |

```
SEQ ID NO: 515            moltype = AA  length = 10
FEATURE                   Location/Qualifiers
source                    1..10
                          mol_type = protein
                          organism = Homo sapiens SEQUENCE: 515
CQAPCSTKNC                                                                10

SEQ ID NO: 516            moltype = AA  length = 10
FEATURE                   Location/Qualifiers
source                    1..10
                          mol_type = protein
                          organism = Homo sapiens SEQUENCE: 516
CQAVCEPSPC                                                                10

SEQ ID NO: 517            moltype = AA  length = 10
FEATURE                   Location/Qualifiers
source                    1..10
                          mol_type = protein
                          organism = Homo sapiens SEQUENCE: 517
CQDSCGSSSC                                                                10

SEQ ID NO: 518            moltype = AA  length = 10
FEATURE                   Location/Qualifiers
source                    1..10
                          mol_type = protein
                          organism = Homo sapiens SEQUENCE: 518
CQHSSCQPTC                                                                10

SEQ ID NO: 519            moltype = AA  length = 10
FEATURE                   Location/Qualifiers
source                    1..10
                          mol_type = protein
                          organism = Homo sapiens SEQUENCE: 519
CQISSCGTGC                                                                10

SEQ ID NO: 520            moltype = AA  length = 10
FEATURE                   Location/Qualifiers
source                    1..10
                          mol_type = protein
                          organism = Homo sapiens SEQUENCE: 520
CQKSSCQPAC                                                                10

SEQ ID NO: 521            moltype = AA  length = 10
FEATURE                   Location/Qualifiers
source                    1..10
                          mol_type = protein
                          organism = Homo sapiens SEQUENCE: 521
CQPMCSHAAC                                                                10

SEQ ID NO: 522            moltype = AA  length = 10
FEATURE                   Location/Qualifiers
source                    1..10
                          mol_type = protein
                          organism = Homo sapiens SEQUENCE: 522
CQPPCTTALC                                                                10

SEQ ID NO: 523            moltype = AA  length = 10
FEATURE                   Location/Qualifiers
source                    1..10
                          mol_type = protein
                          organism = Homo sapiens SEQUENCE: 523
CQPSCESSFC                                                                10

SEQ ID NO: 524            moltype = AA  length = 10
FEATURE                   Location/Qualifiers
source                    1..10
                          mol_type = protein
                          organism = Homo sapiens

SEQUENCE: 524
```

| | | |
|---|---|---|
| CQPSCSESTC | | 10 |
| SEQ ID NO: 525<br>FEATURE<br>source<br><br>SEQUENCE: 525<br>CQPSCTSVLC | moltype = AA length = 10<br>Location/Qualifiers<br>1..10<br>mol_type = protein<br>organism = Homo sapiens | 10 |
| SEQ ID NO: 526<br>FEATURE<br>source<br><br>SEQUENCE: 526<br>CQPTCGGSSC | moltype = AA length = 10<br>Location/Qualifiers<br>1..10<br>mol_type = protein<br>organism = Homo sapiens | 10 |
| SEQ ID NO: 527<br>FEATURE<br>source<br><br>SEQUENCE: 527<br>CQPTCSRPSC | moltype = AA length = 10<br>Location/Qualifiers<br>1..10<br>mol_type = protein<br>organism = Homo sapiens | 10 |
| SEQ ID NO: 528<br>FEATURE<br>source<br><br>SEQUENCE: 528<br>CQPVCPTPTC | moltype = AA length = 10<br>Location/Qualifiers<br>1..10<br>mol_type = protein<br>organism = Homo sapiens | 10 |
| SEQ ID NO: 529<br>FEATURE<br>source<br><br>SEQUENCE: 529<br>CQPVLCKSSC | moltype = AA length = 10<br>Location/Qualifiers<br>1..10<br>mol_type = protein<br>organism = Homo sapiens | 10 |
| SEQ ID NO: 530<br>FEATURE<br>source<br><br>SEQUENCE: 530<br>CQPVVCEPSC | moltype = AA length = 10<br>Location/Qualifiers<br>1..10<br>mol_type = protein<br>organism = Homo sapiens | 10 |
| SEQ ID NO: 531<br>FEATURE<br>source<br><br>SEQUENCE: 531<br>CQQPSCQPAC | moltype = AA length = 10<br>Location/Qualifiers<br>1..10<br>mol_type = protein<br>organism = Homo sapiens | 10 |
| SEQ ID NO: 532<br>FEATURE<br>source<br><br>SEQUENCE: 532<br>CQQSCRVPVC | moltype = AA length = 10<br>Location/Qualifiers<br>1..10<br>mol_type = protein<br>organism = Homo sapiens | 10 |
| SEQ ID NO: 533<br>FEATURE<br>source<br><br>SEQUENCE: 533<br>CQQSCYVPVC | moltype = AA length = 10<br>Location/Qualifiers<br>1..10<br>mol_type = protein<br>organism = Homo sapiens | 10 |
| SEQ ID NO: 534<br>FEATURE<br>source | moltype = AA length = 10<br>Location/Qualifiers<br>1..10<br>mol_type = protein<br>organism = Homo sapiens | |

```
SEQUENCE: 534
CQQSGCQPAC                                                                      10

SEQ ID NO: 535          moltype = AA  length = 10
FEATURE                 Location/Qualifiers
source                  1..10
                        mol_type = protein
                        organism = Homo sapiens
SEQUENCE: 535
CQQSSCHPAC                                                                      10

SEQ ID NO: 536          moltype = AA  length = 10
FEATURE                 Location/Qualifiers
source                  1..10
                        mol_type = protein
                        organism = Homo sapiens
SEQUENCE: 536
CQQSSCKPAC                                                                      10

SEQ ID NO: 537          moltype = AA  length = 10
FEATURE                 Location/Qualifiers
source                  1..10
                        mol_type = protein
                        organism = Homo sapiens
SEQUENCE: 537
CQQSSCQLAC                                                                      10

SEQ ID NO: 538          moltype = AA  length = 10
FEATURE                 Location/Qualifiers
source                  1..10
                        mol_type = protein
                        organism = Homo sapiens
SEQUENCE: 538
CQQSSCQPAC                                                                      10

SEQ ID NO: 539          moltype = AA  length = 10
FEATURE                 Location/Qualifiers
source                  1..10
                        mol_type = protein
                        organism = Homo sapiens
SEQUENCE: 539
CQQSSCQPTC                                                                      10

SEQ ID NO: 540          moltype = AA  length = 10
FEATURE                 Location/Qualifiers
source                  1..10
                        mol_type = protein
                        organism = Homo sapiens
SEQUENCE: 540
CQQSSCQSAC                                                                      10

SEQ ID NO: 541          moltype = AA  length = 10
FEATURE                 Location/Qualifiers
source                  1..10
                        mol_type = protein
                        organism = Homo sapiens
SEQUENCE: 541
CQQSSCVSCV                                                                      10

SEQ ID NO: 542          moltype = AA  length = 10
FEATURE                 Location/Qualifiers
source                  1..10
                        mol_type = protein
                        organism = Homo sapiens
SEQUENCE: 542
CQQSYCVPVC                                                                      10

SEQ ID NO: 543          moltype = AA  length = 10
FEATURE                 Location/Qualifiers
source                  1..10
                        mol_type = protein
                        organism = Homo sapiens
SEQUENCE: 543
CQSGCISSCT                                                                      10

SEQ ID NO: 544          moltype = AA  length = 10
FEATURE                 Location/Qualifiers
source                  1..10
                        mol_type = protein
```

```
                          organism = Homo sapiens
SEQUENCE: 544
CQSGCTDSCT                                                                  10

SEQ ID NO: 545            moltype = AA   length = 10
FEATURE                   Location/Qualifiers
source                    1..10
                          mol_type = protein
                          organism = Homo sapiens
SEQUENCE: 545
CQSGCTSSCT                                                                  10

SEQ ID NO: 546            moltype = AA   length = 10
FEATURE                   Location/Qualifiers
source                    1..10
                          mol_type = protein
                          organism = Homo sapiens
SEQUENCE: 546
CQSSCYRPTC                                                                  10

SEQ ID NO: 547            moltype = AA   length = 10
FEATURE                   Location/Qualifiers
source                    1..10
                          mol_type = protein
                          organism = Homo sapiens
SEQUENCE: 547
CQSVCYQPTC                                                                  10

SEQ ID NO: 548            moltype = AA   length = 10
FEATURE                   Location/Qualifiers
source                    1..10
                          mol_type = protein
                          organism = Homo sapiens
SEQUENCE: 548
CQSVYCQPTC                                                                  10

SEQ ID NO: 549            moltype = AA   length = 10
FEATURE                   Location/Qualifiers
source                    1..10
                          mol_type = protein
                          organism = Homo sapiens
SEQUENCE: 549
CQTACEPSAC                                                                  10

SEQ ID NO: 550            moltype = AA   length = 10
FEATURE                   Location/Qualifiers
source                    1..10
                          mol_type = protein
                          organism = Homo sapiens
SEQUENCE: 550
CQTSSCGTGC                                                                  10

SEQ ID NO: 551            moltype = AA   length = 10
FEATURE                   Location/Qualifiers
source                    1..10
                          mol_type = protein
                          organism = Homo sapiens
SEQUENCE: 551
CQTTCHPSCG                                                                  10

SEQ ID NO: 552            moltype = AA   length = 10
FEATURE                   Location/Qualifiers
source                    1..10
                          mol_type = protein
                          organism = Homo sapiens
SEQUENCE: 552
CQTTCRPSCG                                                                  10

SEQ ID NO: 553            moltype = AA   length = 10
FEATURE                   Location/Qualifiers
source                    1..10
                          mol_type = protein
                          organism = Homo sapiens
SEQUENCE: 553
CQTTCYRTTC                                                                  10

SEQ ID NO: 554            moltype = AA   length = 10
FEATURE                   Location/Qualifiers
source                    1..10
```

```
                            mol_type = protein
                            organism = Homo sapiens
SEQUENCE: 554
CQTTRCRTTC                                                              10

SEQ ID NO: 555              moltype = AA  length = 10
FEATURE                     Location/Qualifiers
source                      1..10
                            mol_type = protein
                            organism = Homo sapiens
SEQUENCE: 555
CQVTCEPSPC                                                              10

SEQ ID NO: 556              moltype = AA  length = 10
FEATURE                     Location/Qualifiers
source                      1..10
                            mol_type = protein
                            organism = Homo sapiens
SEQUENCE: 556
CRNTSCQPTC                                                              10

SEQ ID NO: 557              moltype = AA  length = 10
FEATURE                     Location/Qualifiers
source                      1..10
                            mol_type = protein
                            organism = Homo sapiens
SEQUENCE: 557
CRPACSPLAC                                                              10

SEQ ID NO: 558              moltype = AA  length = 10
FEATURE                     Location/Qualifiers
source                      1..10
                            mol_type = protein
                            organism = Homo sapiens
SEQUENCE: 558
CRPACSRLAC                                                              10

SEQ ID NO: 559              moltype = AA  length = 10
FEATURE                     Location/Qualifiers
source                      1..10
                            mol_type = protein
                            organism = Homo sapiens
SEQUENCE: 559
CRPACSRPAC                                                              10

SEQ ID NO: 560              moltype = AA  length = 10
FEATURE                     Location/Qualifiers
source                      1..10
                            mol_type = protein
                            organism = Homo sapiens
SEQUENCE: 560
CRPMCSRPAC                                                              10

SEQ ID NO: 561              moltype = AA  length = 10
FEATURE                     Location/Qualifiers
source                      1..10
                            mol_type = protein
                            organism = Homo sapiens
SEQUENCE: 561
CRPSCGQTTC                                                              10

SEQ ID NO: 562              moltype = AA  length = 10
FEATURE                     Location/Qualifiers
source                      1..10
                            mol_type = protein
                            organism = Homo sapiens
SEQUENCE: 562
CRPSCGVSSC                                                              10

SEQ ID NO: 563              moltype = AA  length = 10
FEATURE                     Location/Qualifiers
source                      1..10
                            mol_type = protein
                            organism = Homo sapiens
SEQUENCE: 563
CRPSCSISSC                                                              10

SEQ ID NO: 564              moltype = AA  length = 10
FEATURE                     Location/Qualifiers
```

-continued

| | | |
|---|---|---|
| source | 1..10<br>mol_type = protein<br>organism = Homo sapiens | |
| SEQUENCE: 564<br>CRPSCSQTTC | | 10 |
| SEQ ID NO: 565<br>FEATURE<br>source | moltype = AA length = 10<br>Location/Qualifiers<br>1..10<br>mol_type = protein<br>organism = Homo sapiens | |
| SEQUENCE: 565<br>CRPSYCGQSC | | 10 |
| SEQ ID NO: 566<br>FEATURE<br>source | moltype = AA length = 10<br>Location/Qualifiers<br>1..10<br>mol_type = protein<br>organism = Homo sapiens | |
| SEQUENCE: 566<br>CRPSYCISSC | | 10 |
| SEQ ID NO: 567<br>FEATURE<br>source | moltype = AA length = 10<br>Location/Qualifiers<br>1..10<br>mol_type = protein<br>organism = Homo sapiens | |
| SEQUENCE: 567<br>CRPSYCQTTC | | 10 |
| SEQ ID NO: 568<br>FEATURE<br>source | moltype = AA length = 10<br>Location/Qualifiers<br>1..10<br>mol_type = protein<br>organism = Homo sapiens | |
| SEQUENCE: 568<br>CRPTCSRLAC | | 10 |
| SEQ ID NO: 569<br>FEATURE<br>source | moltype = AA length = 10<br>Location/Qualifiers<br>1..10<br>mol_type = protein<br>organism = Homo sapiens | |
| SEQUENCE: 569<br>CRPTCSSGSC | | 10 |
| SEQ ID NO: 570<br>FEATURE<br>source | moltype = AA length = 10<br>Location/Qualifiers<br>1..10<br>mol_type = protein<br>organism = Homo sapiens | |
| SEQUENCE: 570<br>CRPTSCQNTC | | 10 |
| SEQ ID NO: 571<br>FEATURE<br>source | moltype = AA length = 10<br>Location/Qualifiers<br>1..10<br>mol_type = protein<br>organism = Homo sapiens | |
| SEQUENCE: 571<br>CRPVCRSTYC | | 10 |
| SEQ ID NO: 572<br>FEATURE<br>source | moltype = AA length = 10<br>Location/Qualifiers<br>1..10<br>mol_type = protein<br>organism = Homo sapiens | |
| SEQUENCE: 572<br>CRPVCSRPAC | | 10 |
| SEQ ID NO: 573<br>FEATURE<br>source | moltype = AA length = 10<br>Location/Qualifiers<br>1..10<br>mol_type = protein<br>organism = Homo sapiens | |
| SEQUENCE: 573<br>CRPVTCVPRC | | 10 |
| SEQ ID NO: 574 | moltype = AA length = 10 | |

```
FEATURE                 Location/Qualifiers
source                  1..10
                        mol_type = protein
                        organism = Homo sapiens
SEQUENCE: 574
CRQSSCQPAC                                                                      10

SEQ ID NO: 575          moltype = AA   length = 10
FEATURE                 Location/Qualifiers
source                  1..10
                        mol_type = protein
                        organism = Homo sapiens
SEQUENCE: 575
CRTTCFHPIC                                                                      10

SEQ ID NO: 576          moltype = AA   length = 10
FEATURE                 Location/Qualifiers
source                  1..10
                        mol_type = protein
                        organism = Homo sapiens
SEQUENCE: 576
CRTTCFQPTC                                                                      10

SEQ ID NO: 577          moltype = AA   length = 10
FEATURE                 Location/Qualifiers
source                  1..10
                        mol_type = protein
                        organism = Homo sapiens
SEQUENCE: 577
CRTTCYRPSC                                                                      10

SEQ ID NO: 578          moltype = AA   length = 10
FEATURE                 Location/Qualifiers
source                  1..10
                        mol_type = protein
                        organism = Homo sapiens
SEQUENCE: 578
CRTTYCRPSC                                                                      10

SEQ ID NO: 579          moltype = AA   length = 10
FEATURE                 Location/Qualifiers
source                  1..10
                        mol_type = protein
                        organism = Homo sapiens
SEQUENCE: 579
CRVTCEPSPC                                                                      10

SEQ ID NO: 580          moltype = AA   length = 10
FEATURE                 Location/Qualifiers
source                  1..10
                        mol_type = protein
                        organism = Homo sapiens
SEQUENCE: 580
CRYGCGHRGC                                                                      10

SEQ ID NO: 581          moltype = AA   length = 10
FEATURE                 Location/Qualifiers
source                  1..10
                        mol_type = protein
                        organism = Homo sapiens
SEQUENCE: 581
CSAPCVALLC                                                                      10

SEQ ID NO: 582          moltype = AA   length = 10
FEATURE                 Location/Qualifiers
source                  1..10
                        mol_type = protein
                        organism = Homo sapiens
SEQUENCE: 582
CSDDSGSCCQ                                                                      10

SEQ ID NO: 583          moltype = AA   length = 10
FEATURE                 Location/Qualifiers
source                  1..10
                        mol_type = protein
                        organism = Homo sapiens
SEQUENCE: 583
CSEDSSSCCQ                                                                      10
```

| | | |
|---|---|---|
| SEQ ID NO: 584<br>FEATURE<br>source | moltype = AA   length = 10<br>Location/Qualifiers<br>1..10<br>mol_type = protein<br>organism = Homo sapiens | |
| SEQUENCE: 584<br>CSEDSYSCCQ | | 10 |
| SEQ ID NO: 585<br>FEATURE<br>source | moltype = AA   length = 10<br>Location/Qualifiers<br>1..10<br>mol_type = protein<br>organism = Homo sapiens | |
| SEQUENCE: 585<br>CSEGCGSGCG | | 10 |
| SEQ ID NO: 586<br>FEATURE<br>source | moltype = AA   length = 10<br>Location/Qualifiers<br>1..10<br>mol_type = protein<br>organism = Homo sapiens | |
| SEQUENCE: 586<br>CSESSPSCCQ | | 10 |
| SEQ ID NO: 587<br>FEATURE<br>source | moltype = AA   length = 10<br>Location/Qualifiers<br>1..10<br>mol_type = protein<br>organism = Homo sapiens | |
| SEQUENCE: 587<br>CSESSSSCCQ | | 10 |
| SEQ ID NO: 588<br>FEATURE<br>source | moltype = AA   length = 10<br>Location/Qualifiers<br>1..10<br>mol_type = protein<br>organism = Homo sapiens | |
| SEQUENCE: 588<br>CSFDKSCRCG | | 10 |
| SEQ ID NO: 589<br>FEATURE<br>source | moltype = AA   length = 10<br>Location/Qualifiers<br>1..10<br>mol_type = protein<br>organism = Homo sapiens | |
| SEQUENCE: 589<br>CSGASSLCCQ | | 10 |
| SEQ ID NO: 590<br>FEATURE<br>source | moltype = AA   length = 10<br>Location/Qualifiers<br>1..10<br>mol_type = protein<br>organism = Homo sapiens | |
| SEQUENCE: 590<br>CSGASSPCCQ | | 10 |
| SEQ ID NO: 591<br>FEATURE<br>source | moltype = AA   length = 10<br>Location/Qualifiers<br>1..10<br>mol_type = protein<br>organism = Homo sapiens | |
| SEQUENCE: 591<br>CSGASSSCCQ | | 10 |
| SEQ ID NO: 592<br>FEATURE<br>source | moltype = AA   length = 10<br>Location/Qualifiers<br>1..10<br>mol_type = protein<br>organism = Homo sapiens | |
| SEQUENCE: 592<br>CSGASTSCCQ | | 10 |
| SEQ ID NO: 593<br>FEATURE<br>source | moltype = AA   length = 10<br>Location/Qualifiers<br>1..10<br>mol_type = protein<br>organism = Homo sapiens | |
| SEQUENCE: 593<br>CSGGCGSGCG | | 10 |

```
SEQ ID NO: 594            moltype = AA   length = 10
FEATURE                   Location/Qualifiers
source                    1..10
                          mol_type = protein
                          organism = Homo sapiens SEQUENCE: 594
CSGGCGSSCG                                                                10

SEQ ID NO: 595            moltype = AA   length = 10
FEATURE                   Location/Qualifiers
source                    1..10
                          mol_type = protein
                          organism = Homo sapiens SEQUENCE: 595
CSGISSSCCQ                                                                10

SEQ ID NO: 596            moltype = AA   length = 10
FEATURE                   Location/Qualifiers
source                    1..10
                          mol_type = protein
                          organism = Homo sapiens SEQUENCE: 596
CSKDSSSCCQ                                                                10

SEQ ID NO: 597            moltype = AA   length = 10
FEATURE                   Location/Qualifiers
source                    1..10
                          mol_type = protein
                          organism = Homo sapiens SEQUENCE: 597
CSKGACGSCG                                                                10

SEQ ID NO: 598            moltype = AA   length = 10
FEATURE                   Location/Qualifiers
source                    1..10
                          mol_type = protein
                          organism = Homo sapiens SEQUENCE: 598
CSLSCGSRSC                                                                10

SEQ ID NO: 599            moltype = AA   length = 10
FEATURE                   Location/Qualifiers
source                    1..10
                          mol_type = protein
                          organism = Homo sapiens SEQUENCE: 599
CSQDLCQETC                                                                10

SEQ ID NO: 600            moltype = AA   length = 10
FEATURE                   Location/Qualifiers
source                    1..10
                          mol_type = protein
                          organism = Homo sapiens SEQUENCE: 600
CSRGCGSGCG                                                                10

SEQ ID NO: 601            moltype = AA   length = 10
FEATURE                   Location/Qualifiers
source                    1..10
                          mol_type = protein
                          organism = Homo sapiens SEQUENCE: 601
CSRLSSACCG                                                                10

SEQ ID NO: 602            moltype = AA   length = 10
FEATURE                   Location/Qualifiers
source                    1..10
                          mol_type = protein
                          organism = Homo sapiens SEQUENCE: 602
CSSCGKGGCG                                                                10

SEQ ID NO: 603            moltype = AA   length = 10
FEATURE                   Location/Qualifiers
source                    1..10
                          mol_type = protein
                          organism = Homo sapiens

SEQUENCE: 603
```

| | | |
|---|---|---|
| CSSCGKRGCG | | 10 |
| SEQ ID NO: 604<br>FEATURE<br>source<br><br>SEQUENCE: 604<br>CSSDKSCRCG | moltype = AA  length = 10<br>Location/Qualifiers<br>1..10<br>mol_type = protein<br>organism = Homo sapiens | <br><br><br><br><br>10 |
| SEQ ID NO: 605<br>FEATURE<br>source<br><br>SEQUENCE: 605<br>CSSGNFSSCC | moltype = AA  length = 10<br>Location/Qualifiers<br>1..10<br>mol_type = protein<br>organism = Homo sapiens | <br><br><br><br><br>10 |
| SEQ ID NO: 606<br>FEATURE<br>source<br><br>SEQUENCE: 606<br>CSSSGCGSFC | moltype = AA  length = 10<br>Location/Qualifiers<br>1..10<br>mol_type = protein<br>organism = Homo sapiens | <br><br><br><br><br>10 |
| SEQ ID NO: 607<br>FEATURE<br>source<br><br>SEQUENCE: 607<br>CSSSGCGSSC | moltype = AA  length = 10<br>Location/Qualifiers<br>1..10<br>mol_type = protein<br>organism = Homo sapiens | <br><br><br><br><br>10 |
| SEQ ID NO: 608<br>FEATURE<br>source<br><br>SEQUENCE: 608<br>CSTPCYQPIC | moltype = AA  length = 10<br>Location/Qualifiers<br>1..10<br>mol_type = protein<br>organism = Homo sapiens | <br><br><br><br><br>10 |
| SEQ ID NO: 609<br>FEATURE<br>source<br><br>SEQUENCE: 609<br>CSTTCRTSSC | moltype = AA  length = 10<br>Location/Qualifiers<br>1..10<br>mol_type = protein<br>organism = Homo sapiens | <br><br><br><br><br>10 |
| SEQ ID NO: 610<br>FEATURE<br>source<br><br>SEQUENCE: 610<br>CSWVPACSCT | moltype = AA  length = 10<br>Location/Qualifiers<br>1..10<br>mol_type = protein<br>organism = Homo sapiens | <br><br><br><br><br>10 |
| SEQ ID NO: 611<br>FEATURE<br>source<br><br>SEQUENCE: 611<br>CTFSPCQQAC | moltype = AA  length = 10<br>Location/Qualifiers<br>1..10<br>mol_type = protein<br>organism = Homo sapiens | <br><br><br><br><br>10 |
| SEQ ID NO: 612<br>FEATURE<br>source<br><br>SEQUENCE: 612<br>CTMSVCSSAC | moltype = AA  length = 10<br>Location/Qualifiers<br>1..10<br>mol_type = protein<br>organism = Homo sapiens | <br><br><br><br><br>10 |
| SEQ ID NO: 613<br>FEATURE<br>source | moltype = AA  length = 10<br>Location/Qualifiers<br>1..10<br>mol_type = protein<br>organism = Homo sapiens | |

```
SEQUENCE: 613
CTRPICEPCR                                                                              10

SEQ ID NO: 614          moltype = AA  length = 10
FEATURE                 Location/Qualifiers
source                  1..10
                        mol_type = protein
                        organism = Homo sapiens
SEQUENCE: 614
CTSSPCQHAC                                                                              10

SEQ ID NO: 615          moltype = AA  length = 10
FEATURE                 Location/Qualifiers
source                  1..10
                        mol_type = protein
                        organism = Homo sapiens
SEQUENCE: 615
CTSSPCQQAC                                                                              10

SEQ ID NO: 616          moltype = AA  length = 10
FEATURE                 Location/Qualifiers
source                  1..10
                        mol_type = protein
                        organism = Homo sapiens
SEQUENCE: 616
CTSSPCQQSC                                                                              10

SEQ ID NO: 617          moltype = AA  length = 10
FEATURE                 Location/Qualifiers
source                  1..10
                        mol_type = protein
                        organism = Homo sapiens
SEQUENCE: 617
CTSSSCQQAC                                                                              10

SEQ ID NO: 618          moltype = AA  length = 10
FEATURE                 Location/Qualifiers
source                  1..10
                        mol_type = protein
                        organism = Homo sapiens
SEQUENCE: 618
CVALLCRPLC                                                                              10

SEQ ID NO: 619          moltype = AA  length = 10
FEATURE                 Location/Qualifiers
source                  1..10
                        mol_type = protein
                        organism = Homo sapiens
SEQUENCE: 619
CVALVCEPVC                                                                              10

SEQ ID NO: 620          moltype = AA  length = 10
FEATURE                 Location/Qualifiers
source                  1..10
                        mol_type = protein
                        organism = Homo sapiens
SEQUENCE: 620
CVFSSCNTTC                                                                              10

SEQ ID NO: 621          moltype = AA  length = 10
FEATURE                 Location/Qualifiers
source                  1..10
                        mol_type = protein
                        organism = Homo sapiens
SEQUENCE: 621
CVGFVCQPMC                                                                              10

SEQ ID NO: 622          moltype = AA  length = 10
FEATURE                 Location/Qualifiers
source                  1..10
                        mol_type = protein
                        organism = Homo sapiens
SEQUENCE: 622
CVPRCTRPIC                                                                              10

SEQ ID NO: 623          moltype = AA  length = 10
FEATURE                 Location/Qualifiers
source                  1..10
                        mol_type = protein
```

```
                        organism = Homo sapiens
SEQUENCE: 623
CVPSPCQVAC                                                              10

SEQ ID NO: 624          moltype = AA   length = 10
FEATURE                 Location/Qualifiers
source                  1..10
                        mol_type = protein
                        organism = Homo sapiens
SEQUENCE: 624
CVPSRCQASC                                                              10

SEQ ID NO: 625          moltype = AA   length = 10
FEATURE                 Location/Qualifiers
source                  1..10
                        mol_type = protein
                        organism = Homo sapiens
SEQUENCE: 625
CVPSSCQASC                                                              10

SEQ ID NO: 626          moltype = AA   length = 10
FEATURE                 Location/Qualifiers
source                  1..10
                        mol_type = protein
                        organism = Homo sapiens
SEQUENCE: 626
CVPVCNKPVC                                                              10

SEQ ID NO: 627          moltype = AA   length = 10
FEATURE                 Location/Qualifiers
source                  1..10
                        mol_type = protein
                        organism = Homo sapiens
SEQUENCE: 627
CVPVCSKSVC                                                              10

SEQ ID NO: 628          moltype = AA   length = 10
FEATURE                 Location/Qualifiers
source                  1..10
                        mol_type = protein
                        organism = Homo sapiens
SEQUENCE: 628
CVPVRCKPVC                                                              10

SEQ ID NO: 629          moltype = AA   length = 10
FEATURE                 Location/Qualifiers
source                  1..10
                        mol_type = protein
                        organism = Homo sapiens
SEQUENCE: 629
CVSLLCRPAC                                                              10

SEQ ID NO: 630          moltype = AA   length = 10
FEATURE                 Location/Qualifiers
source                  1..10
                        mol_type = protein
                        organism = Homo sapiens
SEQUENCE: 630
CVSLLCRPMC                                                              10

SEQ ID NO: 631          moltype = AA   length = 10
FEATURE                 Location/Qualifiers
source                  1..10
                        mol_type = protein
                        organism = Homo sapiens
SEQUENCE: 631
CVSLLCRPTC                                                              10

SEQ ID NO: 632          moltype = AA   length = 10
FEATURE                 Location/Qualifiers
source                  1..10
                        mol_type = protein
                        organism = Homo sapiens
SEQUENCE: 632
CVSLLCRPVC                                                              10

SEQ ID NO: 633          moltype = AA   length = 10
FEATURE                 Location/Qualifiers
source                  1..10
```

```
                              mol_type = protein
                              organism = Homo sapiens
SEQUENCE: 633
CVSNPCQVTC                                                                10

SEQ ID NO: 634                moltype = AA  length = 10
FEATURE                       Location/Qualifiers
source                        1..10
                              mol_type = protein
                              organism = Homo sapiens
SEQUENCE: 634
CVSRCYRPHC                                                                10

SEQ ID NO: 635                moltype = AA  length = 10
FEATURE                       Location/Qualifiers
source                        1..10
                              mol_type = protein
                              organism = Homo sapiens
SEQUENCE: 635
CVSSCFRPQC                                                                10

SEQ ID NO: 636                moltype = AA  length = 10
FEATURE                       Location/Qualifiers
source                        1..10
                              mol_type = protein
                              organism = Homo sapiens
SEQUENCE: 636
CVSSICQPIC                                                                10

SEQ ID NO: 637                moltype = AA  length = 10
FEATURE                       Location/Qualifiers
source                        1..10
                              mol_type = protein
                              organism = Homo sapiens
SEQUENCE: 637
CVSSPCQPTC                                                                10

SEQ ID NO: 638                moltype = AA  length = 10
FEATURE                       Location/Qualifiers
source                        1..10
                              mol_type = protein
                              organism = Homo sapiens
SEQUENCE: 638
CVVSCTPPSC                                                                10

SEQ ID NO: 639                moltype = AA  length = 10
FEATURE                       Location/Qualifiers
source                        1..10
                              mol_type = protein
                              organism = Homo sapiens
SEQUENCE: 639
CVVSCTPPTC                                                                10

SEQ ID NO: 640                moltype = AA  length = 10
FEATURE                       Location/Qualifiers
source                        1..10
                              mol_type = protein
                              organism = Homo sapiens
SEQUENCE: 640
CYCPKNSIFC                                                                10

SEQ ID NO: 641                moltype = AA  length = 10
FEATURE                       Location/Qualifiers
source                        1..10
                              mol_type = protein
                              organism = Homo sapiens
SEQUENCE: 641
CYEPCLPRGC                                                                10

SEQ ID NO: 642                moltype = AA  length = 10
FEATURE                       Location/Qualifiers
source                        1..10
                              mol_type = protein
                              organism = Homo sapiens
SEQUENCE: 642
CYRRCYSSCY                                                                10

SEQ ID NO: 643                moltype = AA  length = 10
FEATURE                       Location/Qualifiers
```

| | | |
|---|---|---|
| source | 1..10<br>mol_type = protein<br>organism = Homo sapiens | |
| SEQUENCE: 643<br>GCCGYGGLGC | | 10 |
| SEQ ID NO: 644<br>FEATURE<br>source | moltype = AA  length = 10<br>Location/Qualifiers<br>1..10<br>mol_type = protein<br>organism = Homo sapiens | |
| SEQUENCE: 644<br>GCGGCGSGCA | | 10 |
| SEQ ID NO: 645<br>FEATURE<br>source | moltype = AA  length = 10<br>Location/Qualifiers<br>1..10<br>mol_type = protein<br>organism = Homo sapiens | |
| SEQUENCE: 645<br>GCGGCGSGCG | | 10 |
| SEQ ID NO: 646<br>FEATURE<br>source | moltype = AA  length = 10<br>Location/Qualifiers<br>1..10<br>mol_type = protein<br>organism = Homo sapiens | |
| SEQUENCE: 646<br>GCGGCGSSCG | | 10 |
| SEQ ID NO: 647<br>FEATURE<br>source | moltype = AA  length = 10<br>Location/Qualifiers<br>1..10<br>mol_type = protein<br>organism = Homo sapiens | |
| SEQUENCE: 647<br>GCGGCSSSCG | | 10 |
| SEQ ID NO: 648<br>FEATURE<br>source | moltype = AA  length = 10<br>Location/Qualifiers<br>1..10<br>mol_type = protein<br>organism = Homo sapiens | |
| SEQUENCE: 648<br>GCGGSGSSCC | | 10 |
| SEQ ID NO: 649<br>FEATURE<br>source | moltype = AA  length = 10<br>Location/Qualifiers<br>1..10<br>mol_type = protein<br>organism = Homo sapiens | |
| SEQUENCE: 649<br>GCGSGCAGCG | | 10 |
| SEQ ID NO: 650<br>FEATURE<br>source | moltype = AA  length = 10<br>Location/Qualifiers<br>1..10<br>mol_type = protein<br>organism = Homo sapiens | |
| SEQUENCE: 650<br>GCGSGCGGCG | | 10 |
| SEQ ID NO: 651<br>FEATURE<br>source | moltype = AA  length = 10<br>Location/Qualifiers<br>1..10<br>mol_type = protein<br>organism = Homo sapiens | |
| SEQUENCE: 651<br>GCGSGCGGCS | | 10 |
| SEQ ID NO: 652<br>FEATURE<br>source | moltype = AA  length = 10<br>Location/Qualifiers<br>1..10<br>mol_type = protein<br>organism = Homo sapiens | |
| SEQUENCE: 652<br>GCGSSCGGCD | | 10 |
| SEQ ID NO: 653 | moltype = AA  length = 10 | |

```
                    FEATURE            Location/Qualifiers
                    source             1..10
                                       mol_type = protein
                                       organism = Homo sapiens
SEQUENCE: 653
GCGSSCGGCG                                                                             10

SEQ ID NO: 654                         moltype = AA   length = 10
FEATURE                                Location/Qualifiers
source                                 1..10
                                       mol_type = protein
                                       organism = Homo sapiens
SEQUENCE: 654
GCGSSCSQCS                                                                             10

SEQ ID NO: 655                         moltype = AA   length = 10
FEATURE                                Location/Qualifiers
source                                 1..10
                                       mol_type = protein
                                       organism = Homo sapiens
SEQUENCE: 655
GCGYSSSCCG                                                                             10

SEQ ID NO: 656                         moltype = AA   length = 10
FEATURE                                Location/Qualifiers
source                                 1..10
                                       mol_type = protein
                                       organism = Homo sapiens
SEQUENCE: 656
GCKGGCGSCG                                                                             10

SEQ ID NO: 657                         moltype = AA   length = 10
FEATURE                                Location/Qualifiers
source                                 1..10
                                       mol_type = protein
                                       organism = Homo sapiens
SEQUENCE: 657
GCSGCSGGCG                                                                             10

SEQ ID NO: 658                         moltype = AA   length = 10
FEATURE                                Location/Qualifiers
source                                 1..10
                                       mol_type = protein
                                       organism = Homo sapiens
SEQUENCE: 658
ICSGASSLCC                                                                             10

SEQ ID NO: 659                         moltype = AA   length = 10
FEATURE                                Location/Qualifiers
source                                 1..10
                                       mol_type = protein
                                       organism = Homo sapiens
SEQUENCE: 659
ICSGASSPCC                                                                             10

SEQ ID NO: 660                         moltype = AA   length = 10
FEATURE                                Location/Qualifiers
source                                 1..10
                                       mol_type = protein
                                       organism = Homo sapiens
SEQUENCE: 660
MCCNYYGNSC                                                                             10

SEQ ID NO: 661                         moltype = AA   length = 10
FEATURE                                Location/Qualifiers
source                                 1..10
                                       mol_type = protein
                                       organism = Homo sapiens
SEQUENCE: 661
MCCNYYRNSC                                                                             10

SEQ ID NO: 662                         moltype = AA   length = 10
FEATURE                                Location/Qualifiers
source                                 1..10
                                       mol_type = protein
                                       organism = Homo sapiens
SEQUENCE: 662
MCYGYGCGCG                                                                             10
```

| | | |
|---|---|---|
| SEQ ID NO: 663<br>FEATURE<br>source | moltype = AA length = 10<br>Location/Qualifiers<br>1..10<br>mol_type = protein<br>organism = Homo sapiens | |
| SEQUENCE: 663<br>NCCSRNFSSC | | 10 |
| SEQ ID NO: 664<br>FEATURE<br>source | moltype = AA length = 10<br>Location/Qualifiers<br>1..10<br>mol_type = protein<br>organism = Homo sapiens | |
| SEQUENCE: 664<br>PCSLQEGCCR | | 10 |
| SEQ ID NO: 665<br>FEATURE<br>source | moltype = AA length = 10<br>Location/Qualifiers<br>1..10<br>mol_type = protein<br>organism = Homo sapiens | |
| SEQUENCE: 665<br>PCSSQSSCCV | | 10 |
| SEQ ID NO: 666<br>FEATURE<br>source | moltype = AA length = 10<br>Location/Qualifiers<br>1..10<br>mol_type = protein<br>organism = Homo sapiens | |
| SEQUENCE: 666<br>SCCAPASSCQ | | 10 |
| SEQ ID NO: 667<br>FEATURE<br>source | moltype = AA length = 10<br>Location/Qualifiers<br>1..10<br>mol_type = protein<br>organism = Homo sapiens | |
| SEQUENCE: 667<br>SCCAPASTCQ | | 10 |
| SEQ ID NO: 668<br>FEATURE<br>source | moltype = AA length = 10<br>Location/Qualifiers<br>1..10<br>mol_type = protein<br>organism = Homo sapiens | |
| SEQUENCE: 668<br>SCCAPTSSCQ | | 10 |
| SEQ ID NO: 669<br>FEATURE<br>source | moltype = AA length = 10<br>Location/Qualifiers<br>1..10<br>mol_type = protein<br>organism = Homo sapiens | |
| SEQUENCE: 669<br>SCCGYRPLCY | | 10 |
| SEQ ID NO: 670<br>FEATURE<br>source | moltype = AA length = 10<br>Location/Qualifiers<br>1..10<br>mol_type = protein<br>organism = Homo sapiens | |
| SEQUENCE: 670<br>SCCVPASSCQ | | 10 |
| SEQ ID NO: 671<br>FEATURE<br>source | moltype = AA length = 10<br>Location/Qualifiers<br>1..10<br>mol_type = protein<br>organism = Homo sapiens | |
| SEQUENCE: 671<br>SCCVPTSSCQ | | 10 |
| SEQ ID NO: 672<br>FEATURE<br>source | moltype = AA length = 10<br>Location/Qualifiers<br>1..10<br>mol_type = protein<br>organism = Homo sapiens | |
| SEQUENCE: 672<br>SCGCSKGACG | | 10 |

| SEQ ID NO: 673 | moltype = AA   length = 10 |
| --- | --- |
| FEATURE | Location/Qualifiers |
| source | 1..10 |
| | mol_type = protein |
| | organism = Homo sapiens |

SEQUENCE: 673
SCGGCDSSCG                                                                10

| SEQ ID NO: 674 | moltype = AA   length = 10 |
| --- | --- |
| FEATURE | Location/Qualifiers |
| source | 1..10 |
| | mol_type = protein |
| | organism = Homo sapiens |

SEQUENCE: 674
SCGGCGSGCG                                                                10

| SEQ ID NO: 675 | moltype = AA   length = 10 |
| --- | --- |
| FEATURE | Location/Qualifiers |
| source | 1..10 |
| | mol_type = protein |
| | organism = Homo sapiens |

SEQUENCE: 675
SCGGCGSSCG                                                                10

| SEQ ID NO: 676 | moltype = AA   length = 10 |
| --- | --- |
| FEATURE | Location/Qualifiers |
| source | 1..10 |
| | mol_type = protein |
| | organism = Homo sapiens |

SEQUENCE: 676
SCGGCKGGCG                                                                10

| SEQ ID NO: 677 | moltype = AA   length = 10 |
| --- | --- |
| FEATURE | Location/Qualifiers |
| source | 1..10 |
| | mol_type = protein |
| | organism = Homo sapiens |

SEQUENCE: 677
SCGGSKGCCG                                                                10

| SEQ ID NO: 678 | moltype = AA   length = 10 |
| --- | --- |
| FEATURE | Location/Qualifiers |
| source | 1..10 |
| | mol_type = protein |
| | organism = Homo sapiens |

SEQUENCE: 678
SCGSGCRGCG                                                                10

| SEQ ID NO: 679 | moltype = AA   length = 10 |
| --- | --- |
| FEATURE | Location/Qualifiers |
| source | 1..10 |
| | mol_type = protein |
| | organism = Homo sapiens |

SEQUENCE: 679
SCYGCGYGCI                                                                10

| SEQ ID NO: 680 | moltype = AA   length = 10 |
| --- | --- |
| FEATURE | Location/Qualifiers |
| source | 1..10 |
| | mol_type = protein |
| | organism = Homo sapiens |

SEQUENCE: 680
TCCVPVPSCG                                                                10

| SEQ ID NO: 681 | moltype = AA   length = 10 |
| --- | --- |
| FEATURE | Location/Qualifiers |
| source | 1..10 |
| | mol_type = protein |
| | organism = Homo sapiens |

SEQUENCE: 681
TCSDDSGSCC                                                                10

| SEQ ID NO: 682 | moltype = AA   length = 10 |
| --- | --- |
| FEATURE | Location/Qualifiers |
| source | 1..10 |
| | mol_type = protein |
| | organism = Homo sapiens |

SEQUENCE: 682

| | | |
|---|---|---|
| TCSEDSSSCC | | 10 |
| SEQ ID NO: 683<br>FEATURE<br>source<br><br>SEQUENCE: 683<br>TCSEDSYSCC | moltype = AA  length = 10<br>Location/Qualifiers<br>1..10<br>mol_type = protein<br>organism = Homo sapiens | 10 |
| SEQ ID NO: 684<br>FEATURE<br>source<br><br>SEQUENCE: 684<br>TCSESSPSCC | moltype = AA  length = 10<br>Location/Qualifiers<br>1..10<br>mol_type = protein<br>organism = Homo sapiens | 10 |
| SEQ ID NO: 685<br>FEATURE<br>source<br><br>SEQUENCE: 685<br>TCSESSSSCC | moltype = AA  length = 10<br>Location/Qualifiers<br>1..10<br>mol_type = protein<br>organism = Homo sapiens | 10 |
| SEQ ID NO: 686<br>FEATURE<br>source<br><br>SEQUENCE: 686<br>TCSKDSSSCC | moltype = AA  length = 10<br>Location/Qualifiers<br>1..10<br>mol_type = protein<br>organism = Homo sapiens | 10 |
| SEQ ID NO: 687<br>FEATURE<br>source<br><br>SEQUENCE: 687<br>TCSRLSSACC | moltype = AA  length = 10<br>Location/Qualifiers<br>1..10<br>mol_type = protein<br>organism = Homo sapiens | 10 |
| SEQ ID NO: 688<br>FEATURE<br>source<br><br>SEQUENCE: 688<br>VCCQPTPICD | moltype = AA  length = 10<br>Location/Qualifiers<br>1..10<br>mol_type = protein<br>organism = Homo sapiens | 10 |
| SEQ ID NO: 689<br>FEATURE<br>source<br><br>SEQUENCE: 689<br>VCSEDSSSCC | moltype = AA  length = 10<br>Location/Qualifiers<br>1..10<br>mol_type = protein<br>organism = Homo sapiens | 10 |
| SEQ ID NO: 690<br>FEATURE<br>source<br><br>SEQUENCE: 690<br>VCSGASSLCC | moltype = AA  length = 10<br>Location/Qualifiers<br>1..10<br>mol_type = protein<br>organism = Homo sapiens | 10 |
| SEQ ID NO: 691<br>FEATURE<br>source<br><br>SEQUENCE: 691<br>VCSGASSPCC | moltype = AA  length = 10<br>Location/Qualifiers<br>1..10<br>mol_type = protein<br>organism = Homo sapiens | 10 |
| SEQ ID NO: 692<br>FEATURE<br>source | moltype = AA  length = 10<br>Location/Qualifiers<br>1..10<br>mol_type = protein<br>organism = Homo sapiens | |

```
SEQUENCE: 692
VCSGASSSCC                                                                          10

SEQ ID NO: 693          moltype = AA  length = 10
FEATURE                 Location/Qualifiers
source                  1..10
                        mol_type = protein
                        organism = Homo sapiens
SEQUENCE: 693
VCSGASTSCC                                                                          10

SEQ ID NO: 694          moltype = AA  length = 10
FEATURE                 Location/Qualifiers
source                  1..10
                        mol_type = protein
                        organism = Homo sapiens
SEQUENCE: 694
VCSGDSSCCQ                                                                          10

SEQ ID NO: 695          moltype = AA  length = 10
FEATURE                 Location/Qualifiers
source                  1..10
                        mol_type = protein
                        organism = Homo sapiens
SEQUENCE: 695
VCSGISSSCC                                                                          10

SEQ ID NO: 696          moltype = AA  length = 10
FEATURE                 Location/Qualifiers
source                  1..10
                        mol_type = protein
                        organism = Homo sapiens
SEQUENCE: 696
YCVPIPSCCA                                                                          10

SEQ ID NO: 697          moltype = AA  length = 10
FEATURE                 Location/Qualifiers
source                  1..10
                        mol_type = protein
                        organism = Homo sapiens
SEQUENCE: 697
CASSCCTPSC                                                                          10

SEQ ID NO: 698          moltype = AA  length = 10
FEATURE                 Location/Qualifiers
source                  1..10
                        mol_type = protein
                        organism = Homo sapiens
SEQUENCE: 698
CCDNCPPPCH                                                                          10

SEQ ID NO: 699          moltype = AA  length = 10
FEATURE                 Location/Qualifiers
source                  1..10
                        mol_type = protein
                        organism = Homo sapiens
SEQUENCE: 699
CCEPCLPRGC                                                                          10

SEQ ID NO: 700          moltype = AA  length = 10
FEATURE                 Location/Qualifiers
source                  1..10
                        mol_type = protein
                        organism = Homo sapiens
SEQUENCE: 700
CCGAASSCCR                                                                          10

SEQ ID NO: 701          moltype = AA  length = 10
FEATURE                 Location/Qualifiers
source                  1..10
                        mol_type = protein
                        organism = Homo sapiens
SEQUENCE: 701
CCGCGGSGCG                                                                          10

SEQ ID NO: 702          moltype = AA  length = 10
FEATURE                 Location/Qualifiers
source                  1..10
                        mol_type = protein
```

```
                                organism = Homo sapiens
SEQUENCE: 702
CCGPSSSCCQ                                                                              10

SEQ ID NO: 703          moltype = AA   length = 10
FEATURE                 Location/Qualifiers
source                  1..10
                        mol_type = protein
                        organism = Homo sapiens
SEQUENCE: 703
CCGSGCGGCG                                                                              10

SEQ ID NO: 704          moltype = AA   length = 10
FEATURE                 Location/Qualifiers
source                  1..10
                        mol_type = protein
                        organism = Homo sapiens
SEQUENCE: 704
CCKPYCSQCS                                                                              10

SEQ ID NO: 705          moltype = AA   length = 10
FEATURE                 Location/Qualifiers
source                  1..10
                        mol_type = protein
                        organism = Homo sapiens
SEQUENCE: 705
CCMPVSSCCA                                                                              10

SEQ ID NO: 706          moltype = AA   length = 10
FEATURE                 Location/Qualifiers
source                  1..10
                        mol_type = protein
                        organism = Homo sapiens
SEQUENCE: 706
CCNYYRNCCG                                                                              10

SEQ ID NO: 707          moltype = AA   length = 10
FEATURE                 Location/Qualifiers
source                  1..10
                        mol_type = protein
                        organism = Homo sapiens
SEQUENCE: 707
CCPSCVVSSC                                                                              10

SEQ ID NO: 708          moltype = AA   length = 10
FEATURE                 Location/Qualifiers
source                  1..10
                        mol_type = protein
                        organism = Homo sapiens
SEQUENCE: 708
CCPSYCVSSC                                                                              10

SEQ ID NO: 709          moltype = AA   length = 10
FEATURE                 Location/Qualifiers
source                  1..10
                        mol_type = protein
                        organism = Homo sapiens
SEQUENCE: 709
CCQPICGSSC                                                                              10

SEQ ID NO: 710          moltype = AA   length = 10
FEATURE                 Location/Qualifiers
source                  1..10
                        mol_type = protein
                        organism = Homo sapiens
SEQUENCE: 710
CCQPICVTSC                                                                              10

SEQ ID NO: 711          moltype = AA   length = 10
FEATURE                 Location/Qualifiers
source                  1..10
                        mol_type = protein
                        organism = Homo sapiens
SEQUENCE: 711
CCQPTCLSSC                                                                              10

SEQ ID NO: 712          moltype = AA   length = 10
FEATURE                 Location/Qualifiers
source                  1..10
```

-continued

```
                        mol_type = protein
                        organism = Homo sapiens
SEQUENCE: 712
CCQPTCLTSC                                                          10

SEQ ID NO: 713          moltype = AA   length = 10
FEATURE                 Location/Qualifiers
source                  1..10
                        mol_type = protein
                        organism = Homo sapiens
SEQUENCE: 713
CCQPTCVASC                                                          10

SEQ ID NO: 714          moltype = AA   length = 10
FEATURE                 Location/Qualifiers
source                  1..10
                        mol_type = protein
                        organism = Homo sapiens
SEQUENCE: 714
CCQPTCVTSC                                                          10

SEQ ID NO: 715          moltype = AA   length = 10
FEATURE                 Location/Qualifiers
source                  1..10
                        mol_type = protein
                        organism = Homo sapiens
SEQUENCE: 715
CCQPYCHPTC                                                          10

SEQ ID NO: 716          moltype = AA   length = 10
FEATURE                 Location/Qualifiers
source                  1..10
                        mol_type = protein
                        organism = Homo sapiens
SEQUENCE: 716
CCQQSSCVSC                                                          10

SEQ ID NO: 717          moltype = AA   length = 10
FEATURE                 Location/Qualifiers
source                  1..10
                        mol_type = protein
                        organism = Homo sapiens
SEQUENCE: 717
CCQSSCFKPC                                                          10

SEQ ID NO: 718          moltype = AA   length = 10
FEATURE                 Location/Qualifiers
source                  1..10
                        mol_type = protein
                        organism = Homo sapiens
SEQUENCE: 718
CCQSSCSKPC                                                          10

SEQ ID NO: 719          moltype = AA   length = 10
FEATURE                 Location/Qualifiers
source                  1..10
                        mol_type = protein
                        organism = Homo sapiens
SEQUENCE: 719
CCQSSCYKPC                                                          10

SEQ ID NO: 720          moltype = AA   length = 10
FEATURE                 Location/Qualifiers
source                  1..10
                        mol_type = protein
                        organism = Homo sapiens
SEQUENCE: 720
CCQTICRSTC                                                          10

SEQ ID NO: 721          moltype = AA   length = 10
FEATURE                 Location/Qualifiers
source                  1..10
                        mol_type = protein
                        organism = Homo sapiens
SEQUENCE: 721
CCQTTCHPSC                                                          10

SEQ ID NO: 722          moltype = AA   length = 10
FEATURE                 Location/Qualifiers
```

```
source                    1..10
                          mol_type = protein
                          organism = Homo sapiens
SEQUENCE: 722
CCQTTCRPSC                                                               10

SEQ ID NO: 723            moltype = AA   length = 10
FEATURE                   Location/Qualifiers
source                    1..10
                          mol_type = protein
                          organism = Homo sapiens
SEQUENCE: 723
CCRVPTCSCS                                                               10

SEQ ID NO: 724            moltype = AA   length = 10
FEATURE                   Location/Qualifiers
source                    1..10
                          mol_type = protein
                          organism = Homo sapiens
SEQUENCE: 724
CCSPGCQPTC                                                               10

SEQ ID NO: 725            moltype = AA   length = 10
FEATURE                   Location/Qualifiers
source                    1..10
                          mol_type = protein
                          organism = Homo sapiens
SEQUENCE: 725
CCSSGCGSSC                                                               10

SEQ ID NO: 726            moltype = AA   length = 10
FEATURE                   Location/Qualifiers
source                    1..10
                          mol_type = protein
                          organism = Homo sapiens
SEQUENCE: 726
CCSSSCGSCG                                                               10

SEQ ID NO: 727            moltype = AA   length = 10
FEATURE                   Location/Qualifiers
source                    1..10
                          mol_type = protein
                          organism = Homo sapiens
SEQUENCE: 727
CCTQEQNCCE                                                               10

SEQ ID NO: 728            moltype = AA   length = 10
FEATURE                   Location/Qualifiers
source                    1..10
                          mol_type = protein
                          organism = Homo sapiens
SEQUENCE: 728
CCVPIPSCCA                                                               10

SEQ ID NO: 729            moltype = AA   length = 10
FEATURE                   Location/Qualifiers
source                    1..10
                          mol_type = protein
                          organism = Homo sapiens
SEQUENCE: 729
CCVPISSCCA                                                               10

SEQ ID NO: 730            moltype = AA   length = 10
FEATURE                   Location/Qualifiers
source                    1..10
                          mol_type = protein
                          organism = Homo sapiens
SEQUENCE: 730
CCVPVCYQCK                                                               10

SEQ ID NO: 731            moltype = AA   length = 10
FEATURE                   Location/Qualifiers
source                    1..10
                          mol_type = protein
                          organism = Homo sapiens
SEQUENCE: 731
CCVPVPSCCA                                                               10

SEQ ID NO: 732            moltype = AA   length = 10
```

```
FEATURE              Location/Qualifiers
source               1..10
                     mol_type = protein
                     organism = Homo sapiens
SEQUENCE: 732
CCVPVPSCCV                                                              10

SEQ ID NO: 733       moltype = AA  length = 10
FEATURE              Location/Qualifiers
source               1..10
                     mol_type = protein
                     organism = Homo sapiens
SEQUENCE: 733
CCVPVSSCCA                                                              10

SEQ ID NO: 734       moltype = AA  length = 10
FEATURE              Location/Qualifiers
source               1..10
                     mol_type = protein
                     organism = Homo sapiens
SEQUENCE: 734
CDSSCCQPSC                                                              10

SEQ ID NO: 735       moltype = AA  length = 10
FEATURE              Location/Qualifiers
source               1..10
                     mol_type = protein
                     organism = Homo sapiens
SEQUENCE: 735
CDTCPPPCCK                                                              10

SEQ ID NO: 736       moltype = AA  length = 10
FEATURE              Location/Qualifiers
source               1..10
                     mol_type = protein
                     organism = Homo sapiens
SEQUENCE: 736
CEPCRRPVCC                                                              10

SEQ ID NO: 737       moltype = AA  length = 10
FEATURE              Location/Qualifiers
source               1..10
                     mol_type = protein
                     organism = Homo sapiens
SEQUENCE: 737
CEPSCCQPVC                                                              10

SEQ ID NO: 738       moltype = AA  length = 10
FEATURE              Location/Qualifiers
source               1..10
                     mol_type = protein
                     organism = Homo sapiens
SEQUENCE: 738
CEPSCCSAVC                                                              10

SEQ ID NO: 739       moltype = AA  length = 10
FEATURE              Location/Qualifiers
source               1..10
                     mol_type = protein
                     organism = Homo sapiens
SEQUENCE: 739
CETSCCQPSC                                                              10

SEQ ID NO: 740       moltype = AA  length = 10
FEATURE              Location/Qualifiers
source               1..10
                     mol_type = protein
                     organism = Homo sapiens
SEQUENCE: 740
CETTCCRTTC                                                              10

SEQ ID NO: 741       moltype = AA  length = 10
FEATURE              Location/Qualifiers
source               1..10
                     mol_type = protein
                     organism = Homo sapiens
SEQUENCE: 741
CFSGCGSSCC                                                              10
```

```
SEQ ID NO: 742            moltype = AA   length = 10
FEATURE                   Location/Qualifiers
source                    1..10
                          mol_type = protein
                          organism = Homo sapiens
SEQUENCE: 742
CGCSQSNCCK                                                                10

SEQ ID NO: 743            moltype = AA   length = 10
FEATURE                   Location/Qualifiers
source                    1..10
                          mol_type = protein
                          organism = Homo sapiens
SEQUENCE: 743
CGCSQSSCCK                                                                10

SEQ ID NO: 744            moltype = AA   length = 10
FEATURE                   Location/Qualifiers
source                    1..10
                          mol_type = protein
                          organism = Homo sapiens
SEQUENCE: 744
CGGCGGCGGC                                                                10

SEQ ID NO: 745            moltype = AA   length = 10
FEATURE                   Location/Qualifiers
source                    1..10
                          mol_type = protein
                          organism = Homo sapiens
SEQUENCE: 745
CGGCGGGCCG                                                                10

SEQ ID NO: 746            moltype = AA   length = 10
FEATURE                   Location/Qualifiers
source                    1..10
                          mol_type = protein
                          organism = Homo sapiens
SEQUENCE: 746
CGGCGSGCCV                                                                10

SEQ ID NO: 747            moltype = AA   length = 10
FEATURE                   Location/Qualifiers
source                    1..10
                          mol_type = protein
                          organism = Homo sapiens
SEQUENCE: 747
CGGCGSSCCV                                                                10

SEQ ID NO: 748            moltype = AA   length = 10
FEATURE                   Location/Qualifiers
source                    1..10
                          mol_type = protein
                          organism = Homo sapiens
SEQUENCE: 748
CGGGCCGSSC                                                                10

SEQ ID NO: 749            moltype = AA   length = 10
FEATURE                   Location/Qualifiers
source                    1..10
                          mol_type = protein
                          organism = Homo sapiens
SEQUENCE: 749
CGGSCCGSSC                                                                10

SEQ ID NO: 750            moltype = AA   length = 10
FEATURE                   Location/Qualifiers
source                    1..10
                          mol_type = protein
                          organism = Homo sapiens
SEQUENCE: 750
CGQSCCRPAC                                                                10

SEQ ID NO: 751            moltype = AA   length = 10
FEATURE                   Location/Qualifiers
source                    1..10
                          mol_type = protein
                          organism = Homo sapiens
SEQUENCE: 751
CGQSCCRPVC                                                                10
```

```
SEQ ID NO: 752            moltype = AA   length = 10
FEATURE                   Location/Qualifiers
source                    1..10
                          mol_type = protein
                          organism = Homo sapiens
SEQUENCE: 752
CGSCGCSQCN                                                                10

SEQ ID NO: 753            moltype = AA   length = 10
FEATURE                   Location/Qualifiers
source                    1..10
                          mol_type = protein
                          organism = Homo sapiens
SEQUENCE: 753
CGSCGCSQCS                                                                10

SEQ ID NO: 754            moltype = AA   length = 10
FEATURE                   Location/Qualifiers
source                    1..10
                          mol_type = protein
                          organism = Homo sapiens
SEQUENCE: 754
CGSFCCQSSC                                                                10

SEQ ID NO: 755            moltype = AA   length = 10
FEATURE                   Location/Qualifiers
source                    1..10
                          mol_type = protein
                          organism = Homo sapiens
SEQUENCE: 755
CGSGCCVPVC                                                                10

SEQ ID NO: 756            moltype = AA   length = 10
FEATURE                   Location/Qualifiers
source                    1..10
                          mol_type = protein
                          organism = Homo sapiens
SEQUENCE: 756
CGSSCCGSGC                                                                10

SEQ ID NO: 757            moltype = AA   length = 10
FEATURE                   Location/Qualifiers
source                    1..10
                          mol_type = protein
                          organism = Homo sapiens
SEQUENCE: 757
CGSSCCQPCY                                                                10

SEQ ID NO: 758            moltype = AA   length = 10
FEATURE                   Location/Qualifiers
source                    1..10
                          mol_type = protein
                          organism = Homo sapiens
SEQUENCE: 758
CGSSCCQPIC                                                                10

SEQ ID NO: 759            moltype = AA   length = 10
FEATURE                   Location/Qualifiers
source                    1..10
                          mol_type = protein
                          organism = Homo sapiens
SEQUENCE: 759
CGSSCCQPSC                                                                10

SEQ ID NO: 760            moltype = AA   length = 10
FEATURE                   Location/Qualifiers
source                    1..10
                          mol_type = protein
                          organism = Homo sapiens
SEQUENCE: 760
CGSSCCQSSC                                                                10

SEQ ID NO: 761            moltype = AA   length = 10
FEATURE                   Location/Qualifiers
source                    1..10
                          mol_type = protein
                          organism = Homo sapiens
SEQUENCE: 761
```

```
CGSSCCVPIC                                                                      10

SEQ ID NO: 762         moltype = AA  length = 10
FEATURE                Location/Qualifiers
source                 1..10
                       mol_type = protein
                       organism = Homo sapiens SEQUENCE: 762
CGSSCCVPVC                                                                      10

SEQ ID NO: 763         moltype = AA  length = 10
FEATURE                Location/Qualifiers
source                 1..10
                       mol_type = protein
                       organism = Homo sapiens SEQUENCE: 763
CGSSCSQCSC                                                                      10

SEQ ID NO: 764         moltype = AA  length = 10
FEATURE                Location/Qualifiers
source                 1..10
                       mol_type = protein
                       organism = Homo sapiens SEQUENCE: 764
CGYGSCCGCG                                                                      10

SEQ ID NO: 765         moltype = AA  length = 10
FEATURE                Location/Qualifiers
source                 1..10
                       mol_type = protein
                       organism = Homo sapiens SEQUENCE: 765
CHPRCCISSC                                                                      10

SEQ ID NO: 766         moltype = AA  length = 10
FEATURE                Location/Qualifiers
source                 1..10
                       mol_type = protein
                       organism = Homo sapiens SEQUENCE: 766
CHPSCCESSC                                                                      10

SEQ ID NO: 767         moltype = AA  length = 10
FEATURE                Location/Qualifiers
source                 1..10
                       mol_type = protein
                       organism = Homo sapiens SEQUENCE: 767
CHPSCCISSC                                                                      10

SEQ ID NO: 768         moltype = AA  length = 10
FEATURE                Location/Qualifiers
source                 1..10
                       mol_type = protein
                       organism = Homo sapiens SEQUENCE: 768
CHPTCCQNTC                                                                      10

SEQ ID NO: 769         moltype = AA  length = 10
FEATURE                Location/Qualifiers
source                 1..10
                       mol_type = protein
                       organism = Homo sapiens SEQUENCE: 769
CHPTCCQTIC                                                                      10

SEQ ID NO: 770         moltype = AA  length = 10
FEATURE                Location/Qualifiers
source                 1..10
                       mol_type = protein
                       organism = Homo sapiens SEQUENCE: 770
CHPVCCQTTC                                                                      10

SEQ ID NO: 771         moltype = AA  length = 10
FEATURE                Location/Qualifiers
source                 1..10
                       mol_type = protein
                       organism = Homo sapiens
```

```
SEQUENCE: 771
CHPVCKSTCC                                                                              10

SEQ ID NO: 772         moltype = AA  length = 10
FEATURE                Location/Qualifiers
source                 1..10
                       mol_type = protein
                       organism = Homo sapiens
SEQUENCE: 772
CHPVCRSTCC                                                                              10

SEQ ID NO: 773         moltype = AA  length = 10
FEATURE                Location/Qualifiers
source                 1..10
                       mol_type = protein
                       organism = Homo sapiens
SEQUENCE: 773
CISSCCHPSC                                                                              10

SEQ ID NO: 774         moltype = AA  length = 10
FEATURE                Location/Qualifiers
source                 1..10
                       mol_type = protein
                       organism = Homo sapiens
SEQUENCE: 774
CISSCCKPSC                                                                              10

SEQ ID NO: 775         moltype = AA  length = 10
FEATURE                Location/Qualifiers
source                 1..10
                       mol_type = protein
                       organism = Homo sapiens
SEQUENCE: 775
CISSCCRPSC                                                                              10

SEQ ID NO: 776         moltype = AA  length = 10
FEATURE                Location/Qualifiers
source                 1..10
                       mol_type = protein
                       organism = Homo sapiens
SEQUENCE: 776
CISSCTPSCC                                                                              10

SEQ ID NO: 777         moltype = AA  length = 10
FEATURE                Location/Qualifiers
source                 1..10
                       mol_type = protein
                       organism = Homo sapiens
SEQUENCE: 777
CISSSCCPSC                                                                              10

SEQ ID NO: 778         moltype = AA  length = 10
FEATURE                Location/Qualifiers
source                 1..10
                       mol_type = protein
                       organism = Homo sapiens
SEQUENCE: 778
CKAVCCVPTC                                                                              10

SEQ ID NO: 779         moltype = AA  length = 10
FEATURE                Location/Qualifiers
source                 1..10
                       mol_type = protein
                       organism = Homo sapiens
SEQUENCE: 779
CKPCCSQASC                                                                              10

SEQ ID NO: 780         moltype = AA  length = 10
FEATURE                Location/Qualifiers
source                 1..10
                       mol_type = protein
                       organism = Homo sapiens
SEQUENCE: 780
CKPCCSQSRC                                                                              10

SEQ ID NO: 781         moltype = AA  length = 10
FEATURE                Location/Qualifiers
source                 1..10
                       mol_type = protein
```

```
                                organism = Homo sapiens
SEQUENCE: 781
CKPCCSQSSC                                                                          10

SEQ ID NO: 782           moltype = AA  length = 10
FEATURE                  Location/Qualifiers
source                   1..10
                         mol_type = protein
                         organism = Homo sapiens
SEQUENCE: 782
CKPCCSSSGC                                                                          10

SEQ ID NO: 783           moltype = AA  length = 10
FEATURE                  Location/Qualifiers
source                   1..10
                         mol_type = protein
                         organism = Homo sapiens
SEQUENCE: 783
CKPCSCFSGC                                                                          10

SEQ ID NO: 784           moltype = AA  length = 10
FEATURE                  Location/Qualifiers
source                   1..10
                         mol_type = protein
                         organism = Homo sapiens
SEQUENCE: 784
CKPCSCSSGC                                                                          10

SEQ ID NO: 785           moltype = AA  length = 10
FEATURE                  Location/Qualifiers
source                   1..10
                         mol_type = protein
                         organism = Homo sapiens
SEQUENCE: 785
CKPCYCSSGC                                                                          10

SEQ ID NO: 786           moltype = AA  length = 10
FEATURE                  Location/Qualifiers
source                   1..10
                         mol_type = protein
                         organism = Homo sapiens
SEQUENCE: 786
CKPICCVPVC                                                                          10

SEQ ID NO: 787           moltype = AA  length = 10
FEATURE                  Location/Qualifiers
source                   1..10
                         mol_type = protein
                         organism = Homo sapiens
SEQUENCE: 787
CKPQCCQSVC                                                                          10

SEQ ID NO: 788           moltype = AA  length = 10
FEATURE                  Location/Qualifiers
source                   1..10
                         mol_type = protein
                         organism = Homo sapiens
SEQUENCE: 788
CKPSCCQTTC                                                                          10

SEQ ID NO: 789           moltype = AA  length = 10
FEATURE                  Location/Qualifiers
source                   1..10
                         mol_type = protein
                         organism = Homo sapiens
SEQUENCE: 789
CKPVCCAPTC                                                                          10

SEQ ID NO: 790           moltype = AA  length = 10
FEATURE                  Location/Qualifiers
source                   1..10
                         mol_type = protein
                         organism = Homo sapiens
SEQUENCE: 790
CKPVCCKPIC                                                                          10

SEQ ID NO: 791           moltype = AA  length = 10
FEATURE                  Location/Qualifiers
source                   1..10
```

```
                            mol_type = protein
                            organism = Homo sapiens
SEQUENCE: 791
CKPVCCKSIC                                                                  10

SEQ ID NO: 792             moltype = AA  length = 10
FEATURE                    Location/Qualifiers
source                     1..10
                           mol_type = protein
                           organism = Homo sapiens
SEQUENCE: 792
CKPVCCLPTC                                                                  10

SEQ ID NO: 793             moltype = AA  length = 10
FEATURE                    Location/Qualifiers
source                     1..10
                           mol_type = protein
                           organism = Homo sapiens
SEQUENCE: 793
CKPVCCVPTC                                                                  10

SEQ ID NO: 794             moltype = AA  length = 10
FEATURE                    Location/Qualifiers
source                     1..10
                           mol_type = protein
                           organism = Homo sapiens
SEQUENCE: 794
CKPVCCVPVC                                                                  10

SEQ ID NO: 795             moltype = AA  length = 10
FEATURE                    Location/Qualifiers
source                     1..10
                           mol_type = protein
                           organism = Homo sapiens
SEQUENCE: 795
CKPVCCVSTC                                                                  10

SEQ ID NO: 796             moltype = AA  length = 10
FEATURE                    Location/Qualifiers
source                     1..10
                           mol_type = protein
                           organism = Homo sapiens
SEQUENCE: 796
CKPYCCQSSC                                                                  10

SEQ ID NO: 797             moltype = AA  length = 10
FEATURE                    Location/Qualifiers
source                     1..10
                           mol_type = protein
                           organism = Homo sapiens
SEQUENCE: 797
CKPYCSQCSC                                                                  10

SEQ ID NO: 798             moltype = AA  length = 10
FEATURE                    Location/Qualifiers
source                     1..10
                           mol_type = protein
                           organism = Homo sapiens
SEQUENCE: 798
CKSNCCKPVC                                                                  10

SEQ ID NO: 799             moltype = AA  length = 10
FEATURE                    Location/Qualifiers
source                     1..10
                           mol_type = protein
                           organism = Homo sapiens
SEQUENCE: 799
CKTVCCKPVC                                                                  10

SEQ ID NO: 800             moltype = AA  length = 10
FEATURE                    Location/Qualifiers
source                     1..10
                           mol_type = protein
                           organism = Homo sapiens
SEQUENCE: 800
CLPPCCVVSC                                                                  10

SEQ ID NO: 801             moltype = AA  length = 10
FEATURE                    Location/Qualifiers
```

```
                                -continued source                    1..10
                          mol_type = protein
                          organism = Homo sapiens
SEQUENCE: 801
CLTSCCQPSC                                                              10

SEQ ID NO: 802            moltype = AA   length = 10
FEATURE                   Location/Qualifiers
source                    1..10
                          mol_type = protein
                          organism = Homo sapiens
SEQUENCE: 802
CNPCCSQSSC                                                              10

SEQ ID NO: 803            moltype = AA   length = 10
FEATURE                   Location/Qualifiers
source                    1..10
                          mol_type = protein
                          organism = Homo sapiens
SEQUENCE: 803
CPESCCELPC                                                              10

SEQ ID NO: 804            moltype = AA   length = 10
FEATURE                   Location/Qualifiers
source                    1..10
                          mol_type = protein
                          organism = Homo sapiens
SEQUENCE: 804
CPESCCEPHC                                                              10

SEQ ID NO: 805            moltype = AA   length = 10
FEATURE                   Location/Qualifiers
source                    1..10
                          mol_type = protein
                          organism = Homo sapiens
SEQUENCE: 805
CPESCCEPPC                                                              10

SEQ ID NO: 806            moltype = AA   length = 10
FEATURE                   Location/Qualifiers
source                    1..10
                          mol_type = protein
                          organism = Homo sapiens
SEQUENCE: 806
CPFSCPTTCC                                                              10

SEQ ID NO: 807            moltype = AA   length = 10
FEATURE                   Location/Qualifiers
source                    1..10
                          mol_type = protein
                          organism = Homo sapiens
SEQUENCE: 807
CPGDCFTCCT                                                              10

SEQ ID NO: 808            moltype = AA   length = 10
FEATURE                   Location/Qualifiers
source                    1..10
                          mol_type = protein
                          organism = Homo sapiens
SEQUENCE: 808
CPSCVVSSCC                                                              10

SEQ ID NO: 809            moltype = AA   length = 10
FEATURE                   Location/Qualifiers
source                    1..10
                          mol_type = protein
                          organism = Homo sapiens
SEQUENCE: 809
CPSYCVSSCC                                                              10

SEQ ID NO: 810            moltype = AA   length = 10
FEATURE                   Location/Qualifiers
source                    1..10
                          mol_type = protein
                          organism = Homo sapiens
SEQUENCE: 810
CPTTCCRTTC                                                              10

SEQ ID NO: 811            moltype = AA   length = 10
```

| | | |
|---|---|---|
| FEATURE | Location/Qualifiers | |
| source | 1..10 | |
| | mol_type = protein | |
| | organism = Homo sapiens | |
| SEQUENCE: 811 | | |
| CQETCCRPSC | | 10 |
| | | |
| SEQ ID NO: 812 | moltype = AA  length = 10 | |
| FEATURE | Location/Qualifiers | |
| source | 1..10 | |
| | mol_type = protein | |
| | organism = Homo sapiens | |
| SEQUENCE: 812 | | |
| CQHACCVPVC | | 10 |
| | | |
| SEQ ID NO: 813 | moltype = AA  length = 10 | |
| FEATURE | Location/Qualifiers | |
| source | 1..10 | |
| | mol_type = protein | |
| | organism = Homo sapiens | |
| SEQUENCE: 813 | | |
| CQNTCCRTTC | | 10 |
| | | |
| SEQ ID NO: 814 | moltype = AA  length = 10 | |
| FEATURE | Location/Qualifiers | |
| source | 1..10 | |
| | mol_type = protein | |
| | organism = Homo sapiens | |
| SEQUENCE: 814 | | |
| CQPACCQPTC | | 10 |
| | | |
| SEQ ID NO: 815 | moltype = AA  length = 10 | |
| FEATURE | Location/Qualifiers | |
| source | 1..10 | |
| | mol_type = protein | |
| | organism = Homo sapiens | |
| SEQUENCE: 815 | | |
| CQPACCTASC | | 10 |
| | | |
| SEQ ID NO: 816 | moltype = AA  length = 10 | |
| FEATURE | Location/Qualifiers | |
| source | 1..10 | |
| | mol_type = protein | |
| | organism = Homo sapiens | |
| SEQUENCE: 816 | | |
| CQPACCTSSC | | 10 |
| | | |
| SEQ ID NO: 817 | moltype = AA  length = 10 | |
| FEATURE | Location/Qualifiers | |
| source | 1..10 | |
| | mol_type = protein | |
| | organism = Homo sapiens | |
| SEQUENCE: 817 | | |
| CQPACCTTSC | | 10 |
| | | |
| SEQ ID NO: 818 | moltype = AA  length = 10 | |
| FEATURE | Location/Qualifiers | |
| source | 1..10 | |
| | mol_type = protein | |
| | organism = Homo sapiens | |
| SEQUENCE: 818 | | |
| CQPACCVPVC | | 10 |
| | | |
| SEQ ID NO: 819 | moltype = AA  length = 10 | |
| FEATURE | Location/Qualifiers | |
| source | 1..10 | |
| | mol_type = protein | |
| | organism = Homo sapiens | |
| SEQUENCE: 819 | | |
| CQPACCVSSC | | 10 |
| | | |
| SEQ ID NO: 820 | moltype = AA  length = 10 | |
| FEATURE | Location/Qualifiers | |
| source | 1..10 | |
| | mol_type = protein | |
| | organism = Homo sapiens | |
| SEQUENCE: 820 | | |
| CQPCCHPTCY | | 10 |

```
SEQ ID NO: 821          moltype = AA   length = 10
FEATURE                 Location/Qualifiers
source                  1..10
                        mol_type = protein
                        organism = Homo sapiens
SEQUENCE: 821
CQPCCRPTSC                                                                    10

SEQ ID NO: 822          moltype = AA   length = 10
FEATURE                 Location/Qualifiers
source                  1..10
                        mol_type = protein
                        organism = Homo sapiens
SEQUENCE: 822
CQPICCGSSC                                                                    10

SEQ ID NO: 823          moltype = AA   length = 10
FEATURE                 Location/Qualifiers
source                  1..10
                        mol_type = protein
                        organism = Homo sapiens
SEQUENCE: 823
CQPICGSSCC                                                                    10

SEQ ID NO: 824          moltype = AA   length = 10
FEATURE                 Location/Qualifiers
source                  1..10
                        mol_type = protein
                        organism = Homo sapiens
SEQUENCE: 824
CQPICVTSCC                                                                    10

SEQ ID NO: 825          moltype = AA   length = 10
FEATURE                 Location/Qualifiers
source                  1..10
                        mol_type = protein
                        organism = Homo sapiens
SEQUENCE: 825
CQPNCCRPSC                                                                    10

SEQ ID NO: 826          moltype = AA   length = 10
FEATURE                 Location/Qualifiers
source                  1..10
                        mol_type = protein
                        organism = Homo sapiens
SEQUENCE: 826
CQPRCCETSC                                                                    10

SEQ ID NO: 827          moltype = AA   length = 10
FEATURE                 Location/Qualifiers
source                  1..10
                        mol_type = protein
                        organism = Homo sapiens
SEQUENCE: 827
CQPSCCRPAC                                                                    10

SEQ ID NO: 828          moltype = AA   length = 10
FEATURE                 Location/Qualifiers
source                  1..10
                        mol_type = protein
                        organism = Homo sapiens
SEQUENCE: 828
CQPSCCSTPC                                                                    10

SEQ ID NO: 829          moltype = AA   length = 10
FEATURE                 Location/Qualifiers
source                  1..10
                        mol_type = protein
                        organism = Homo sapiens
SEQUENCE: 829
CQPSCCSTTC                                                                    10

SEQ ID NO: 830          moltype = AA   length = 10
FEATURE                 Location/Qualifiers
source                  1..10
                        mol_type = protein
                        organism = Homo sapiens
SEQUENCE: 830
CQPSCCVPSC                                                                    10
```

| | | |
|---|---|---|
| SEQ ID NO: 831<br>FEATURE<br>source<br><br>SEQUENCE: 831<br>CQPSCCVSSC | moltype = AA   length = 10<br>Location/Qualifiers<br>1..10<br>mol_type = protein<br>organism = Homo sapiens | <br><br><br><br><br>10 |
| SEQ ID NO: 832<br>FEATURE<br>source<br><br>SEQUENCE: 832<br>CQPTCCGSSC | moltype = AA   length = 10<br>Location/Qualifiers<br>1..10<br>mol_type = protein<br>organism = Homo sapiens | <br><br><br><br><br>10 |
| SEQ ID NO: 833<br>FEATURE<br>source<br><br>SEQUENCE: 833<br>CQPTCCHPSC | moltype = AA   length = 10<br>Location/Qualifiers<br>1..10<br>mol_type = protein<br>organism = Homo sapiens | <br><br><br><br><br>10 |
| SEQ ID NO: 834<br>FEATURE<br>source<br><br>SEQUENCE: 834<br>CQPTCCQPTC | moltype = AA   length = 10<br>Location/Qualifiers<br>1..10<br>mol_type = protein<br>organism = Homo sapiens | <br><br><br><br><br>10 |
| SEQ ID NO: 835<br>FEATURE<br>source<br><br>SEQUENCE: 835<br>CQPTCCRPRC | moltype = AA   length = 10<br>Location/Qualifiers<br>1..10<br>mol_type = protein<br>organism = Homo sapiens | <br><br><br><br><br>10 |
| SEQ ID NO: 836<br>FEATURE<br>source<br><br>SEQUENCE: 836<br>CQPTCCRPSC | moltype = AA   length = 10<br>Location/Qualifiers<br>1..10<br>mol_type = protein<br>organism = Homo sapiens | <br><br><br><br><br>10 |
| SEQ ID NO: 837<br>FEATURE<br>source<br><br>SEQUENCE: 837<br>CQPTCCRTTC | moltype = AA   length = 10<br>Location/Qualifiers<br>1..10<br>mol_type = protein<br>organism = Homo sapiens | <br><br><br><br><br>10 |
| SEQ ID NO: 838<br>FEATURE<br>source<br><br>SEQUENCE: 838<br>CQPTCLSSCC | moltype = AA   length = 10<br>Location/Qualifiers<br>1..10<br>mol_type = protein<br>organism = Homo sapiens | <br><br><br><br><br>10 |
| SEQ ID NO: 839<br>FEATURE<br>source<br><br>SEQUENCE: 839<br>CQPTCLTSCC | moltype = AA   length = 10<br>Location/Qualifiers<br>1..10<br>mol_type = protein<br>organism = Homo sapiens | <br><br><br><br><br>10 |
| SEQ ID NO: 840<br>FEATURE<br>source<br><br>SEQUENCE: 840 | moltype = AA   length = 10<br>Location/Qualifiers<br>1..10<br>mol_type = protein<br>organism = Homo sapiens | |

CQPTCVASCC 10

SEQ ID NO: 841  moltype = AA  length = 10
FEATURE         Location/Qualifiers
source          1..10
                mol_type = protein
                organism = Homo sapiens
SEQUENCE: 841
CQPTCVTSCC 10

SEQ ID NO: 842  moltype = AA  length = 10
FEATURE         Location/Qualifiers
source          1..10
                mol_type = protein
                organism = Homo sapiens
SEQUENCE: 842
CQPVCCQPTC 10

SEQ ID NO: 843  moltype = AA  length = 10
FEATURE         Location/Qualifiers
source          1..10
                mol_type = protein
                organism = Homo sapiens
SEQUENCE: 843
CQPYCHPTCC 10

SEQ ID NO: 844  moltype = AA  length = 10
FEATURE         Location/Qualifiers
source          1..10
                mol_type = protein
                organism = Homo sapiens
SEQUENCE: 844
CQQACCMPVC 10

SEQ ID NO: 845  moltype = AA  length = 10
FEATURE         Location/Qualifiers
source          1..10
                mol_type = protein
                organism = Homo sapiens
SEQUENCE: 845
CQQACCVPIC 10

SEQ ID NO: 846  moltype = AA  length = 10
FEATURE         Location/Qualifiers
source          1..10
                mol_type = protein
                organism = Homo sapiens
SEQUENCE: 846
CQQACCVPVC 10

SEQ ID NO: 847  moltype = AA  length = 10
FEATURE         Location/Qualifiers
source          1..10
                mol_type = protein
                organism = Homo sapiens
SEQUENCE: 847
CQQSCCVPVC 10

SEQ ID NO: 848  moltype = AA  length = 10
FEATURE         Location/Qualifiers
source          1..10
                mol_type = protein
                organism = Homo sapiens
SEQUENCE: 848
CQQSCCVSVC 10

SEQ ID NO: 849  moltype = AA  length = 10
FEATURE         Location/Qualifiers
source          1..10
                mol_type = protein
                organism = Homo sapiens
SEQUENCE: 849
CQSMCCQPTC 10

SEQ ID NO: 850  moltype = AA  length = 10
FEATURE         Location/Qualifiers
source          1..10
                mol_type = protein
                organism = Homo sapiens

```
SEQUENCE: 850
CQSNCCVPVC                                                                                10

SEQ ID NO: 851          moltype = AA   length = 10
FEATURE                 Location/Qualifiers
source                  1..10
                        mol_type = protein
                        organism = Homo sapiens
SEQUENCE: 851
CQSSCCKPCS                                                                                10

SEQ ID NO: 852          moltype = AA   length = 10
FEATURE                 Location/Qualifiers
source                  1..10
                        mol_type = protein
                        organism = Homo sapiens
SEQUENCE: 852
CQSSCCQSSC                                                                                10

SEQ ID NO: 853          moltype = AA   length = 10
FEATURE                 Location/Qualifiers
source                  1..10
                        mol_type = protein
                        organism = Homo sapiens
SEQUENCE: 853
CQSSCCVPVC                                                                                10

SEQ ID NO: 854          moltype = AA   length = 10
FEATURE                 Location/Qualifiers
source                  1..10
                        mol_type = protein
                        organism = Homo sapiens
SEQUENCE: 854
CQSSCFKPCC                                                                                10

SEQ ID NO: 855          moltype = AA   length = 10
FEATURE                 Location/Qualifiers
source                  1..10
                        mol_type = protein
                        organism = Homo sapiens
SEQUENCE: 855
CQSSCSKPCC                                                                                10

SEQ ID NO: 856          moltype = AA   length = 10
FEATURE                 Location/Qualifiers
source                  1..10
                        mol_type = protein
                        organism = Homo sapiens
SEQUENCE: 856
CQSVCCQPTC                                                                                10

SEQ ID NO: 857          moltype = AA   length = 10
FEATURE                 Location/Qualifiers
source                  1..10
                        mol_type = protein
                        organism = Homo sapiens
SEQUENCE: 857
CQTICRSTCC                                                                                10

SEQ ID NO: 858          moltype = AA   length = 10
FEATURE                 Location/Qualifiers
source                  1..10
                        mol_type = protein
                        organism = Homo sapiens
SEQUENCE: 858
CQTTCCRPSC                                                                                10

SEQ ID NO: 859          moltype = AA   length = 10
FEATURE                 Location/Qualifiers
source                  1..10
                        mol_type = protein
                        organism = Homo sapiens
SEQUENCE: 859
CQTTCCRTTC                                                                                10

SEQ ID NO: 860          moltype = AA   length = 10
FEATURE                 Location/Qualifiers
source                  1..10
                        mol_type = protein
```

```
                       organism = Homo sapiens
SEQUENCE: 860
CRATCCRPSC                                                                10

SEQ ID NO: 861         moltype = AA   length = 10
FEATURE                Location/Qualifiers
source                 1..10
                       mol_type = protein
                       organism = Homo sapiens
SEQUENCE: 861
CRGCGPSCCA                                                                10

SEQ ID NO: 862         moltype = AA   length = 10
FEATURE                Location/Qualifiers
source                 1..10
                       mol_type = protein
                       organism = Homo sapiens
SEQUENCE: 862
CRPACCETTC                                                                10

SEQ ID NO: 863         moltype = AA   length = 10
FEATURE                Location/Qualifiers
source                 1..10
                       mol_type = protein
                       organism = Homo sapiens
SEQUENCE: 863
CRPACCQNTC                                                                10

SEQ ID NO: 864         moltype = AA   length = 10
FEATURE                Location/Qualifiers
source                 1..10
                       mol_type = protein
                       organism = Homo sapiens
SEQUENCE: 864
CRPCCWATTC                                                                10

SEQ ID NO: 865         moltype = AA   length = 10
FEATURE                Location/Qualifiers
source                 1..10
                       mol_type = protein
                       organism = Homo sapiens
SEQUENCE: 865
CRPICRPACC                                                                10

SEQ ID NO: 866         moltype = AA   length = 10
FEATURE                Location/Qualifiers
source                 1..10
                       mol_type = protein
                       organism = Homo sapiens
SEQUENCE: 866
CRPLCCQTTC                                                                10

SEQ ID NO: 867         moltype = AA   length = 10
FEATURE                Location/Qualifiers
source                 1..10
                       mol_type = protein
                       organism = Homo sapiens
SEQUENCE: 867
CRPQCCQSVC                                                                10

SEQ ID NO: 868         moltype = AA   length = 10
FEATURE                Location/Qualifiers
source                 1..10
                       mol_type = protein
                       organism = Homo sapiens
SEQUENCE: 868
CRPQCCQTTC                                                                10

SEQ ID NO: 869         moltype = AA   length = 10
FEATURE                Location/Qualifiers
source                 1..10
                       mol_type = protein
                       organism = Homo sapiens
SEQUENCE: 869
CRPRCCISSC                                                                10

SEQ ID NO: 870         moltype = AA   length = 10
FEATURE                Location/Qualifiers
source                 1..10
```

```
                        mol_type = protein
                        organism = Homo sapiens
SEQUENCE: 870
CRPSCCESSC                                                              10

SEQ ID NO: 871          moltype = AA   length = 10
FEATURE                 Location/Qualifiers
source                  1..10
                        mol_type = protein
                        organism = Homo sapiens
SEQUENCE: 871
CRPSCCETTC                                                              10

SEQ ID NO: 872          moltype = AA   length = 10
FEATURE                 Location/Qualifiers
source                  1..10
                        mol_type = protein
                        organism = Homo sapiens
SEQUENCE: 872
CRPSCCISSC                                                              10

SEQ ID NO: 873          moltype = AA   length = 10
FEATURE                 Location/Qualifiers
source                  1..10
                        mol_type = protein
                        organism = Homo sapiens
SEQUENCE: 873
CRPSCCKPQC                                                              10

SEQ ID NO: 874          moltype = AA   length = 10
FEATURE                 Location/Qualifiers
source                  1..10
                        mol_type = protein
                        organism = Homo sapiens
SEQUENCE: 874
CRPSCCMSSC                                                              10

SEQ ID NO: 875          moltype = AA   length = 10
FEATURE                 Location/Qualifiers
source                  1..10
                        mol_type = protein
                        organism = Homo sapiens
SEQUENCE: 875
CRPSCCQTTC                                                              10

SEQ ID NO: 876          moltype = AA   length = 10
FEATURE                 Location/Qualifiers
source                  1..10
                        mol_type = protein
                        organism = Homo sapiens
SEQUENCE: 876
CRPSCCRPSC                                                              10

SEQ ID NO: 877          moltype = AA   length = 10
FEATURE                 Location/Qualifiers
source                  1..10
                        mol_type = protein
                        organism = Homo sapiens
SEQUENCE: 877
CRPSCCVSRC                                                              10

SEQ ID NO: 878          moltype = AA   length = 10
FEATURE                 Location/Qualifiers
source                  1..10
                        mol_type = protein
                        organism = Homo sapiens
SEQUENCE: 878
CRPSCCVSSC                                                              10

SEQ ID NO: 879          moltype = AA   length = 10
FEATURE                 Location/Qualifiers
source                  1..10
                        mol_type = protein
                        organism = Homo sapiens
SEQUENCE: 879
CRPTCCETTC                                                              10

SEQ ID NO: 880          moltype = AA   length = 10
FEATURE                 Location/Qualifiers
```

```
source                          1..10
                                mol_type = protein
                                organism = Homo sapiens
SEQUENCE: 880
CRPTCCQNTC                                                                      10

SEQ ID NO: 881                  moltype = AA   length = 10
FEATURE                         Location/Qualifiers
source                          1..10
                                mol_type = protein
                                organism = Homo sapiens
SEQUENCE: 881
CRPTCCQTTC                                                                      10

SEQ ID NO: 882                  moltype = AA   length = 10
FEATURE                         Location/Qualifiers
source                          1..10
                                mol_type = protein
                                organism = Homo sapiens
SEQUENCE: 882
CRPVCCDPCS                                                                      10

SEQ ID NO: 883                  moltype = AA   length = 10
FEATURE                         Location/Qualifiers
source                          1..10
                                mol_type = protein
                                organism = Homo sapiens
SEQUENCE: 883
CRPVCCQTTC                                                                      10

SEQ ID NO: 884                  moltype = AA   length = 10
FEATURE                         Location/Qualifiers
source                          1..10
                                mol_type = protein
                                organism = Homo sapiens
SEQUENCE: 884
CRPVCQPACC                                                                      10

SEQ ID NO: 885                  moltype = AA   length = 10
FEATURE                         Location/Qualifiers
source                          1..10
                                mol_type = protein
                                organism = Homo sapiens
SEQUENCE: 885
CRPVCRPACC                                                                      10

SEQ ID NO: 886                  moltype = AA   length = 10
FEATURE                         Location/Qualifiers
source                          1..10
                                mol_type = protein
                                organism = Homo sapiens
SEQUENCE: 886
CRPVCRPTCC                                                                      10

SEQ ID NO: 887                  moltype = AA   length = 10
FEATURE                         Location/Qualifiers
source                          1..10
                                mol_type = protein
                                organism = Homo sapiens
SEQUENCE: 887
CRPVCRSTCC                                                                      10

SEQ ID NO: 888                  moltype = AA   length = 10
FEATURE                         Location/Qualifiers
source                          1..10
                                mol_type = protein
                                organism = Homo sapiens
SEQUENCE: 888
CRPYCCESSC                                                                      10

SEQ ID NO: 889                  moltype = AA   length = 10
FEATURE                         Location/Qualifiers
source                          1..10
                                mol_type = protein
                                organism = Homo sapiens
SEQUENCE: 889
CRRPVCCDPC                                                                      10

SEQ ID NO: 890                  moltype = AA   length = 10
```

```
FEATURE                 Location/Qualifiers
source                  1..10
                        mol_type = protein
                        organism = Homo sapiens
SEQUENCE: 890
CRSQCCQSVC                                                                      10

SEQ ID NO: 891          moltype = AA   length = 10
FEATURE                 Location/Qualifiers
source                  1..10
                        mol_type = protein
                        organism = Homo sapiens
SEQUENCE: 891
CRTTCCHPSC                                                                      10

SEQ ID NO: 892          moltype = AA   length = 10
FEATURE                 Location/Qualifiers
source                  1..10
                        mol_type = protein
                        organism = Homo sapiens
SEQUENCE: 892
CRTTCCQPIC                                                                      10

SEQ ID NO: 893          moltype = AA   length = 10
FEATURE                 Location/Qualifiers
source                  1..10
                        mol_type = protein
                        organism = Homo sapiens
SEQUENCE: 893
CRTTCCQPTC                                                                      10

SEQ ID NO: 894          moltype = AA   length = 10
FEATURE                 Location/Qualifiers
source                  1..10
                        mol_type = protein
                        organism = Homo sapiens
SEQUENCE: 894
CRTTCCRPSC                                                                      10

SEQ ID NO: 895          moltype = AA   length = 10
FEATURE                 Location/Qualifiers
source                  1..10
                        mol_type = protein
                        organism = Homo sapiens
SEQUENCE: 895
CRTTCCRTTC                                                                      10

SEQ ID NO: 896          moltype = AA   length = 10
FEATURE                 Location/Qualifiers
source                  1..10
                        mol_type = protein
                        organism = Homo sapiens
SEQUENCE: 896
CSCSSCGSCA                                                                      10

SEQ ID NO: 897          moltype = AA   length = 10
FEATURE                 Location/Qualifiers
source                  1..10
                        mol_type = protein
                        organism = Homo sapiens
SEQUENCE: 897
CSCSSCGSCG                                                                      10

SEQ ID NO: 898          moltype = AA   length = 10
FEATURE                 Location/Qualifiers
source                  1..10
                        mol_type = protein
                        organism = Homo sapiens
SEQUENCE: 898
CSCTSCGSCG                                                                      10

SEQ ID NO: 899          moltype = AA   length = 10
FEATURE                 Location/Qualifiers
source                  1..10
                        mol_type = protein
                        organism = Homo sapiens
SEQUENCE: 899
CSPACQPTCC                                                                      10
```

| | | |
|---|---|---|
| SEQ ID NO: 900<br>FEATURE<br>source | moltype = AA   length = 10<br>Location/Qualifiers<br>1..10<br>mol_type = protein<br>organism = Homo sapiens | |
| SEQUENCE: 900<br>CSPGCQPTCC | | 10 |
| SEQ ID NO: 901<br>FEATURE<br>source | moltype = AA   length = 10<br>Location/Qualifiers<br>1..10<br>mol_type = protein<br>organism = Homo sapiens | |
| SEQUENCE: 901<br>CSPSCCQTTC | | 10 |
| SEQ ID NO: 902<br>FEATURE<br>source | moltype = AA   length = 10<br>Location/Qualifiers<br>1..10<br>mol_type = protein<br>organism = Homo sapiens | |
| SEQUENCE: 902<br>CSQCSCYKPC | | 10 |
| SEQ ID NO: 903<br>FEATURE<br>source | moltype = AA   length = 10<br>Location/Qualifiers<br>1..10<br>mol_type = protein<br>organism = Homo sapiens | |
| SEQUENCE: 903<br>CSQSNCCKPC | | 10 |
| SEQ ID NO: 904<br>FEATURE<br>source | moltype = AA   length = 10<br>Location/Qualifiers<br>1..10<br>mol_type = protein<br>organism = Homo sapiens | |
| SEQUENCE: 904<br>CSQSSCCKPC | | 10 |
| SEQ ID NO: 905<br>FEATURE<br>source | moltype = AA   length = 10<br>Location/Qualifiers<br>1..10<br>mol_type = protein<br>organism = Homo sapiens | |
| SEQUENCE: 905<br>CSSGCGSCCQ | | 10 |
| SEQ ID NO: 906<br>FEATURE<br>source | moltype = AA   length = 10<br>Location/Qualifiers<br>1..10<br>mol_type = protein<br>organism = Homo sapiens | |
| SEQUENCE: 906<br>CSSGCGSSCC | | 10 |
| SEQ ID NO: 907<br>FEATURE<br>source | moltype = AA   length = 10<br>Location/Qualifiers<br>1..10<br>mol_type = protein<br>organism = Homo sapiens | |
| SEQUENCE: 907<br>CSSGCQPACC | | 10 |
| SEQ ID NO: 908<br>FEATURE<br>source | moltype = AA   length = 10<br>Location/Qualifiers<br>1..10<br>mol_type = protein<br>organism = Homo sapiens | |
| SEQUENCE: 908<br>CSSSCCQPSC | | 10 |
| SEQ ID NO: 909<br>FEATURE<br>source | moltype = AA   length = 10<br>Location/Qualifiers<br>1..10<br>mol_type = protein<br>organism = Homo sapiens | |
| SEQUENCE: 909<br>CSTPCCQPTC | | 10 |

| | | |
|---|---|---|
| SEQ ID NO: 910<br>FEATURE<br>source<br><br>SEQUENCE: 910<br>CSTTCCQPIC | moltype = AA  length = 10<br>Location/Qualifiers<br>1..10<br>mol_type = protein<br>organism = Homo sapiens | 10 |
| SEQ ID NO: 911<br>FEATURE<br>source<br><br>SEQUENCE: 911<br>CTAVVCRPCC | moltype = AA  length = 10<br>Location/Qualifiers<br>1..10<br>mol_type = protein<br>organism = Homo sapiens | 10 |
| SEQ ID NO: 912<br>FEATURE<br>source<br><br>SEQUENCE: 912<br>CTDSCTPSCC | moltype = AA  length = 10<br>Location/Qualifiers<br>1..10<br>mol_type = protein<br>organism = Homo sapiens | 10 |
| SEQ ID NO: 913<br>FEATURE<br>source<br><br>SEQUENCE: 913<br>CTPSCCQPAC | moltype = AA  length = 10<br>Location/Qualifiers<br>1..10<br>mol_type = protein<br>organism = Homo sapiens | 10 |
| SEQ ID NO: 914<br>FEATURE<br>source<br><br>SEQUENCE: 914<br>CTRPICEPCC | moltype = AA  length = 10<br>Location/Qualifiers<br>1..10<br>mol_type = protein<br>organism = Homo sapiens | 10 |
| SEQ ID NO: 915<br>FEATURE<br>source<br><br>SEQUENCE: 915<br>CTSSCTPSCC | moltype = AA  length = 10<br>Location/Qualifiers<br>1..10<br>mol_type = protein<br>organism = Homo sapiens | 10 |
| SEQ ID NO: 916<br>FEATURE<br>source<br><br>SEQUENCE: 916<br>CVPACSCSSC | moltype = AA  length = 10<br>Location/Qualifiers<br>1..10<br>mol_type = protein<br>organism = Homo sapiens | 10 |
| SEQ ID NO: 917<br>FEATURE<br>source<br><br>SEQUENCE: 917<br>CVPACSCTSC | moltype = AA  length = 10<br>Location/Qualifiers<br>1..10<br>mol_type = protein<br>organism = Homo sapiens | 10 |
| SEQ ID NO: 918<br>FEATURE<br>source<br><br>SEQUENCE: 918<br>CVPVCCKPVC | moltype = AA  length = 10<br>Location/Qualifiers<br>1..10<br>mol_type = protein<br>organism = Homo sapiens | 10 |
| SEQ ID NO: 919<br>FEATURE<br>source<br><br>SEQUENCE: 919 | moltype = AA  length = 10<br>Location/Qualifiers<br>1..10<br>mol_type = protein<br>organism = Homo sapiens | |

```
CVPVCCVPTC                                                                           10

SEQ ID NO: 920          moltype = AA  length = 10
FEATURE                 Location/Qualifiers
source                  1..10
                        mol_type = protein
                        organism = Homo sapiens
SEQUENCE: 920
CVPVCCVPVC                                                                           10

SEQ ID NO: 921          moltype = AA  length = 10
FEATURE                 Location/Qualifiers
source                  1..10
                        mol_type = protein
                        organism = Homo sapiens
SEQUENCE: 921
CVSCVSSPCC                                                                           10

SEQ ID NO: 922          moltype = AA  length = 10
FEATURE                 Location/Qualifiers
source                  1..10
                        mol_type = protein
                        organism = Homo sapiens
SEQUENCE: 922
CVSRCCRPQC                                                                           10

SEQ ID NO: 923          moltype = AA  length = 10
FEATURE                 Location/Qualifiers
source                  1..10
                        mol_type = protein
                        organism = Homo sapiens
SEQUENCE: 923
CVSSCCKPQC                                                                           10

SEQ ID NO: 924          moltype = AA  length = 10
FEATURE                 Location/Qualifiers
source                  1..10
                        mol_type = protein
                        organism = Homo sapiens
SEQUENCE: 924
CVSSCCQHSC                                                                           10

SEQ ID NO: 925          moltype = AA  length = 10
FEATURE                 Location/Qualifiers
source                  1..10
                        mol_type = protein
                        organism = Homo sapiens
SEQUENCE: 925
CVSSCCQPFC                                                                           10

SEQ ID NO: 926          moltype = AA  length = 10
FEATURE                 Location/Qualifiers
source                  1..10
                        mol_type = protein
                        organism = Homo sapiens
SEQUENCE: 926
CVSSCCQPSC                                                                           10

SEQ ID NO: 927          moltype = AA  length = 10
FEATURE                 Location/Qualifiers
source                  1..10
                        mol_type = protein
                        organism = Homo sapiens
SEQUENCE: 927
CVSSCCRPQC                                                                           10

SEQ ID NO: 928          moltype = AA  length = 10
FEATURE                 Location/Qualifiers
source                  1..10
                        mol_type = protein
                        organism = Homo sapiens
SEQUENCE: 928
CVSTCCRPTC                                                                           10

SEQ ID NO: 929          moltype = AA  length = 10
FEATURE                 Location/Qualifiers
source                  1..10
                        mol_type = protein
                        organism = Homo sapiens
```

| | | |
|---|---|---|
| SEQUENCE: 929<br>CVTRCCSTPC | | 10 |
| SEQ ID NO: 930<br>FEATURE<br>source | moltype = AA  length = 10<br>Location/Qualifiers<br>1..10<br>mol_type = protein<br>organism = Homo sapiens | |
| SEQUENCE: 930<br>CVTSCCQPAC | | 10 |
| SEQ ID NO: 931<br>FEATURE<br>source | moltype = AA  length = 10<br>Location/Qualifiers<br>1..10<br>mol_type = protein<br>organism = Homo sapiens | |
| SEQUENCE: 931<br>CVTSCCQPSC | | 10 |
| SEQ ID NO: 932<br>FEATURE<br>source | moltype = AA  length = 10<br>Location/Qualifiers<br>1..10<br>mol_type = protein<br>organism = Homo sapiens | |
| SEQUENCE: 932<br>CVYSCCQPFC | | 10 |
| SEQ ID NO: 933<br>FEATURE<br>source | moltype = AA  length = 10<br>Location/Qualifiers<br>1..10<br>mol_type = protein<br>organism = Homo sapiens | |
| SEQUENCE: 933<br>CVYSCCQPSC | | 10 |
| SEQ ID NO: 934<br>FEATURE<br>source | moltype = AA  length = 10<br>Location/Qualifiers<br>1..10<br>mol_type = protein<br>organism = Homo sapiens | |
| SEQUENCE: 934<br>GCCGCSEGCG | | 10 |
| SEQ ID NO: 935<br>FEATURE<br>source | moltype = AA  length = 10<br>Location/Qualifiers<br>1..10<br>mol_type = protein<br>organism = Homo sapiens | |
| SEQUENCE: 935<br>GCCGCSGGCG | | 10 |
| SEQ ID NO: 936<br>FEATURE<br>source | moltype = AA  length = 10<br>Location/Qualifiers<br>1..10<br>mol_type = protein<br>organism = Homo sapiens | |
| SEQUENCE: 936<br>GCCGCSRGCG | | 10 |
| SEQ ID NO: 937<br>FEATURE<br>source | moltype = AA  length = 10<br>Location/Qualifiers<br>1..10<br>mol_type = protein<br>organism = Homo sapiens | |
| SEQUENCE: 937<br>GCCRPITCCP | | 10 |
| SEQ ID NO: 938<br>FEATURE<br>source | moltype = AA  length = 10<br>Location/Qualifiers<br>1..10<br>mol_type = protein<br>organism = Homo sapiens | |
| SEQUENCE: 938<br>GCGSSCCQCS | | 10 |
| SEQ ID NO: 939<br>FEATURE<br>source | moltype = AA  length = 10<br>Location/Qualifiers<br>1..10<br>mol_type = protein | |

```
                                  -continued

SEQUENCE: 939                                                          organism = Homo sapiens
GCGVPVCCCS                                                                                          10

SEQ ID NO: 940         moltype = AA   length = 10
FEATURE                Location/Qualifiers
source                 1..10
                       mol_type = protein
                       organism = Homo sapiens
SEQUENCE: 940
LCCPCQTTCS                                                                                          10

SEQ ID NO: 941         moltype = AA   length = 10
FEATURE                Location/Qualifiers
source                 1..10
                       mol_type = protein
                       organism = Homo sapiens
SEQUENCE: 941
PCCCLRPVCG                                                                                          10

SEQ ID NO: 942         moltype = AA   length = 10
FEATURE                Location/Qualifiers
source                 1..10
                       mol_type = protein
                       organism = Homo sapiens
SEQUENCE: 942
PCCCRPVTCQ                                                                                          10

SEQ ID NO: 943         moltype = AA   length = 10
FEATURE                Location/Qualifiers
source                 1..10
                       mol_type = protein
                       organism = Homo sapiens
SEQUENCE: 943
PCCCVRPVCG                                                                                          10

SEQ ID NO: 944         moltype = AA   length = 10
FEATURE                Location/Qualifiers
source                 1..10
                       mol_type = protein
                       organism = Homo sapiens
SEQUENCE: 944
PCCSQASCCV                                                                                          10

SEQ ID NO: 945         moltype = AA   length = 10
FEATURE                Location/Qualifiers
source                 1..10
                       mol_type = protein
                       organism = Homo sapiens
SEQUENCE: 945
PCCSQSRCCV                                                                                          10

SEQ ID NO: 946         moltype = AA   length = 10
FEATURE                Location/Qualifiers
source                 1..10
                       mol_type = protein
                       organism = Homo sapiens
SEQUENCE: 946
PCCSQSSCCK                                                                                          10

SEQ ID NO: 947         moltype = AA   length = 10
FEATURE                Location/Qualifiers
source                 1..10
                       mol_type = protein
                       organism = Homo sapiens
SEQUENCE: 947
PCCSQSSCCV                                                                                          10

SEQ ID NO: 948         moltype = AA   length = 10
FEATURE                Location/Qualifiers
source                 1..10
                       mol_type = protein
                       organism = Homo sapiens
SEQUENCE: 948
PCCWATTCCQ                                                                                          10

SEQ ID NO: 949         moltype = AA   length = 10
FEATURE                Location/Qualifiers
source                 1..10
```

```
                              mol_type = protein
                              organism = Homo sapiens
SEQUENCE: 949
QCSCCKPYCS                                                          10

SEQ ID NO: 950                moltype = AA   length = 10
FEATURE                       Location/Qualifiers
source                        1..10
                              mol_type = protein
                              organism = Homo sapiens
SEQUENCE: 950
RCYVPVCCCK                                                          10

SEQ ID NO: 951                moltype = AA   length = 10
FEATURE                       Location/Qualifiers
source                        1..10
                              mol_type = protein
                              organism = Homo sapiens
SEQUENCE: 951
SCCAPVYCCK                                                          10

SEQ ID NO: 952                moltype = AA   length = 10
FEATURE                       Location/Qualifiers
source                        1..10
                              mol_type = protein
                              organism = Homo sapiens
SEQUENCE: 952
SCCISSSCCP                                                          10

SEQ ID NO: 953                moltype = AA   length = 10
FEATURE                       Location/Qualifiers
source                        1..10
                              mol_type = protein
                              organism = Homo sapiens
SEQUENCE: 953
SCCVSSCRCP                                                          10

SEQ ID NO: 954                moltype = AA   length = 10
FEATURE                       Location/Qualifiers
source                        1..10
                              mol_type = protein
                              organism = Homo sapiens
SEQUENCE: 954
SCGCSQCSCY                                                          10

SEQ ID NO: 955                moltype = AA   length = 10
FEATURE                       Location/Qualifiers
source                        1..10
                              mol_type = protein
                              organism = Homo sapiens
SEQUENCE: 955
SCGLENCCCP                                                          10

SEQ ID NO: 956                moltype = AA   length = 10
FEATURE                       Location/Qualifiers
source                        1..10
                              mol_type = protein
                              organism = Homo sapiens
SEQUENCE: 956
VCCGASSCCQ                                                          10

SEQ ID NO: 957                moltype = AA   length = 10
FEATURE                       Location/Qualifiers
source                        1..10
                              mol_type = protein
                              organism = Homo sapiens
SEQUENCE: 957
VCCGDSSCCQ                                                          10

SEQ ID NO: 958                moltype = AA   length = 11
FEATURE                       Location/Qualifiers
source                        1..11
                              mol_type = protein
                              organism = Homo sapiens
SEQUENCE: 958
CASSCCTPSC C                                                        11

SEQ ID NO: 959                moltype = AA   length = 11
FEATURE                       Location/Qualifiers
```

```
source                   1..11
                         mol_type = protein
                         organism = Homo sapiens
SEQUENCE: 959
CCCPSCVVSS C                                                                      11

SEQ ID NO: 960           moltype = AA   length = 11
FEATURE                  Location/Qualifiers
source                   1..11
                         mol_type = protein
                         organism = Homo sapiens
SEQUENCE: 960
CCCPSYCVSS C                                                                      11

SEQ ID NO: 961           moltype = AA   length = 11
FEATURE                  Location/Qualifiers
source                   1..11
                         mol_type = protein
                         organism = Homo sapiens
SEQUENCE: 961
CCCSSGCGSS C                                                                      11

SEQ ID NO: 962           moltype = AA   length = 11
FEATURE                  Location/Qualifiers
source                   1..11
                         mol_type = protein
                         organism = Homo sapiens
SEQUENCE: 962
CCDTCPPPCC K                                                                      11

SEQ ID NO: 963           moltype = AA   length = 11
FEATURE                  Location/Qualifiers
source                   1..11
                         mol_type = protein
                         organism = Homo sapiens
SEQUENCE: 963
CCEPHCCALS C                                                                      11

SEQ ID NO: 964           moltype = AA   length = 11
FEATURE                  Location/Qualifiers
source                   1..11
                         mol_type = protein
                         organism = Homo sapiens
SEQUENCE: 964
CCEPPCCAPS C                                                                      11

SEQ ID NO: 965           moltype = AA   length = 11
FEATURE                  Location/Qualifiers
source                   1..11
                         mol_type = protein
                         organism = Homo sapiens
SEQUENCE: 965
CCEPPCCATS C                                                                      11

SEQ ID NO: 966           moltype = AA   length = 11
FEATURE                  Location/Qualifiers
source                   1..11
                         mol_type = protein
                         organism = Homo sapiens
SEQUENCE: 966
CCETSCCQPS C                                                                      11

SEQ ID NO: 967           moltype = AA   length = 11
FEATURE                  Location/Qualifiers
source                   1..11
                         mol_type = protein
                         organism = Homo sapiens
SEQUENCE: 967
CCGSSCCGSG C                                                                      11

SEQ ID NO: 968           moltype = AA   length = 11
FEATURE                  Location/Qualifiers
source                   1..11
                         mol_type = protein
                         organism = Homo sapiens
SEQUENCE: 968
CCGSSCCGSS C                                                                      11

SEQ ID NO: 969           moltype = AA   length = 11
```

```
                           -continued

FEATURE                Location/Qualifiers
source                 1..11
                       mol_type = protein
                       organism = Homo sapiens
SEQUENCE: 969
CCHPRCCISS C                                                              11

SEQ ID NO: 970         moltype = AA  length = 11
FEATURE                Location/Qualifiers
source                 1..11
                       mol_type = protein
                       organism = Homo sapiens
SEQUENCE: 970
CCHPSCCESS C                                                              11

SEQ ID NO: 971         moltype = AA  length = 11
FEATURE                Location/Qualifiers
source                 1..11
                       mol_type = protein
                       organism = Homo sapiens
SEQUENCE: 971
CCHPSCCISS C                                                              11

SEQ ID NO: 972         moltype = AA  length = 11
FEATURE                Location/Qualifiers
source                 1..11
                       mol_type = protein
                       organism = Homo sapiens
SEQUENCE: 972
CCHPSCCVSS C                                                              11

SEQ ID NO: 973         moltype = AA  length = 11
FEATURE                Location/Qualifiers
source                 1..11
                       mol_type = protein
                       organism = Homo sapiens
SEQUENCE: 973
CCHPTCCQNT C                                                              11

SEQ ID NO: 974         moltype = AA  length = 11
FEATURE                Location/Qualifiers
source                 1..11
                       mol_type = protein
                       organism = Homo sapiens
SEQUENCE: 974
CCHPTCCQTI C                                                              11

SEQ ID NO: 975         moltype = AA  length = 11
FEATURE                Location/Qualifiers
source                 1..11
                       mol_type = protein
                       organism = Homo sapiens
SEQUENCE: 975
CCISSCCKPS C                                                              11

SEQ ID NO: 976         moltype = AA  length = 11
FEATURE                Location/Qualifiers
source                 1..11
                       mol_type = protein
                       organism = Homo sapiens
SEQUENCE: 976
CCISSCCRPS C                                                              11

SEQ ID NO: 977         moltype = AA  length = 11
FEATURE                Location/Qualifiers
source                 1..11
                       mol_type = protein
                       organism = Homo sapiens
SEQUENCE: 977
CCISSSCCPS C                                                              11

SEQ ID NO: 978         moltype = AA  length = 11
FEATURE                Location/Qualifiers
source                 1..11
                       mol_type = protein
                       organism = Homo sapiens
SEQUENCE: 978
CCKAVCCVPT C                                                              11
```

```
SEQ ID NO: 979        moltype = AA   length = 11
FEATURE               Location/Qualifiers
source                1..11
                      mol_type = protein
                      organism = Homo sapiens
SEQUENCE: 979
CCKPCCSQAS C                                                              11

SEQ ID NO: 980        moltype = AA   length = 11
FEATURE               Location/Qualifiers
source                1..11
                      mol_type = protein
                      organism = Homo sapiens
SEQUENCE: 980
CCKPCCSQSR C                                                              11

SEQ ID NO: 981        moltype = AA   length = 11
FEATURE               Location/Qualifiers
source                1..11
                      mol_type = protein
                      organism = Homo sapiens
SEQUENCE: 981
CCKPCCSQSS C                                                              11

SEQ ID NO: 982        moltype = AA   length = 11
FEATURE               Location/Qualifiers
source                1..11
                      mol_type = protein
                      organism = Homo sapiens
SEQUENCE: 982
CCKPCCSSSG C                                                              11

SEQ ID NO: 983        moltype = AA   length = 11
FEATURE               Location/Qualifiers
source                1..11
                      mol_type = protein
                      organism = Homo sapiens
SEQUENCE: 983
CCKPCSCFSG C                                                              11

SEQ ID NO: 984        moltype = AA   length = 11
FEATURE               Location/Qualifiers
source                1..11
                      mol_type = protein
                      organism = Homo sapiens
SEQUENCE: 984
CCKPCSCSSG C                                                              11

SEQ ID NO: 985        moltype = AA   length = 11
FEATURE               Location/Qualifiers
source                1..11
                      mol_type = protein
                      organism = Homo sapiens
SEQUENCE: 985
CCKPCYCSSG C                                                              11

SEQ ID NO: 986        moltype = AA   length = 11
FEATURE               Location/Qualifiers
source                1..11
                      mol_type = protein
                      organism = Homo sapiens
SEQUENCE: 986
CCKPICCVPV C                                                              11

SEQ ID NO: 987        moltype = AA   length = 11
FEATURE               Location/Qualifiers
source                1..11
                      mol_type = protein
                      organism = Homo sapiens
SEQUENCE: 987
CCKPQCCQSV C                                                              11

SEQ ID NO: 988        moltype = AA   length = 11
FEATURE               Location/Qualifiers
source                1..11
                      mol_type = protein
                      organism = Homo sapiens
SEQUENCE: 988
CCKPVCCKPI C                                                              11
```

```
SEQ ID NO: 989            moltype = AA   length = 11
FEATURE                   Location/Qualifiers
source                    1..11
                          mol_type = protein
                          organism = Homo sapiens
SEQUENCE: 989
CCKPYCCQSS C                                                              11

SEQ ID NO: 990            moltype = AA   length = 11
FEATURE                   Location/Qualifiers
source                    1..11
                          mol_type = protein
                          organism = Homo sapiens
SEQUENCE: 990
CCKPYCSQCS C                                                              11

SEQ ID NO: 991            moltype = AA   length = 11
FEATURE                   Location/Qualifiers
source                    1..11
                          mol_type = protein
                          organism = Homo sapiens
SEQUENCE: 991
CCMPVCCKPV C                                                              11

SEQ ID NO: 992            moltype = AA   length = 11
FEATURE                   Location/Qualifiers
source                    1..11
                          mol_type = protein
                          organism = Homo sapiens
SEQUENCE: 992
CCMPVCCKTV C                                                              11

SEQ ID NO: 993            moltype = AA   length = 11
FEATURE                   Location/Qualifiers
source                    1..11
                          mol_type = protein
                          organism = Homo sapiens
SEQUENCE: 993
CCMSSCCKPQ C                                                              11

SEQ ID NO: 994            moltype = AA   length = 11
FEATURE                   Location/Qualifiers
source                    1..11
                          mol_type = protein
                          organism = Homo sapiens
SEQUENCE: 994
CCNPCCSQSS C                                                              11

SEQ ID NO: 995            moltype = AA   length = 11
FEATURE                   Location/Qualifiers
source                    1..11
                          mol_type = protein
                          organism = Homo sapiens
SEQUENCE: 995
CCPGDCFTCC T                                                              11

SEQ ID NO: 996            moltype = AA   length = 11
FEATURE                   Location/Qualifiers
source                    1..11
                          mol_type = protein
                          organism = Homo sapiens
SEQUENCE: 996
CCPSCVVSSC C                                                              11

SEQ ID NO: 997            moltype = AA   length = 11
FEATURE                   Location/Qualifiers
source                    1..11
                          mol_type = protein
                          organism = Homo sapiens
SEQUENCE: 997
CCPSYCVSSC C                                                              11

SEQ ID NO: 998            moltype = AA   length = 11
FEATURE                   Location/Qualifiers
source                    1..11
                          mol_type = protein
                          organism = Homo sapiens
SEQUENCE: 998
```

CCQNTCCRTT C 11

SEQ ID NO: 999    moltype = AA  length = 11
FEATURE           Location/Qualifiers
source            1..11
                  mol_type = protein
                  organism = Homo sapiens

SEQUENCE: 999
CCQPACCVSS C 11

SEQ ID NO: 1000   moltype = AA  length = 11
FEATURE           Location/Qualifiers
source            1..11
                  mol_type = protein
                  organism = Homo sapiens

SEQUENCE: 1000
CCQPCCHPTC Y 11

SEQ ID NO: 1001   moltype = AA  length = 11
FEATURE           Location/Qualifiers
source            1..11
                  mol_type = protein
                  organism = Homo sapiens

SEQUENCE: 1001
CCQPCCRPTS C 11

SEQ ID NO: 1002   moltype = AA  length = 11
FEATURE           Location/Qualifiers
source            1..11
                  mol_type = protein
                  organism = Homo sapiens

SEQUENCE: 1002
CCQPICGSSC C 11

SEQ ID NO: 1003   moltype = AA  length = 11
FEATURE           Location/Qualifiers
source            1..11
                  mol_type = protein
                  organism = Homo sapiens

SEQUENCE: 1003
CCQPICVTSC C 11

SEQ ID NO: 1004   moltype = AA  length = 11
FEATURE           Location/Qualifiers
source            1..11
                  mol_type = protein
                  organism = Homo sapiens

SEQUENCE: 1004
CCQPNCCRPS C 11

SEQ ID NO: 1005   moltype = AA  length = 11
FEATURE           Location/Qualifiers
source            1..11
                  mol_type = protein
                  organism = Homo sapiens

SEQUENCE: 1005
CCQPSCCETS C 11

SEQ ID NO: 1006   moltype = AA  length = 11
FEATURE           Location/Qualifiers
source            1..11
                  mol_type = protein
                  organism = Homo sapiens

SEQUENCE: 1006
CCQPSCCRPA C 11

SEQ ID NO: 1007   moltype = AA  length = 11
FEATURE           Location/Qualifiers
source            1..11
                  mol_type = protein
                  organism = Homo sapiens

SEQUENCE: 1007
CCQPSCCSTP C 11

SEQ ID NO: 1008   moltype = AA  length = 11
FEATURE           Location/Qualifiers
source            1..11
                  mol_type = protein
                  organism = Homo sapiens -continued

```
SEQUENCE: 1008
CCQPSCCSTT C                                                                    11

SEQ ID NO: 1009       moltype = AA  length = 11
FEATURE               Location/Qualifiers
source                1..11
                      mol_type = protein
                      organism = Homo sapiens
SEQUENCE: 1009
CCQPSCCVPS C                                                                    11

SEQ ID NO: 1010       moltype = AA  length = 11
FEATURE               Location/Qualifiers
source                1..11
                      mol_type = protein
                      organism = Homo sapiens
SEQUENCE: 1010
CCQPSCCVSS C                                                                    11

SEQ ID NO: 1011       moltype = AA  length = 11
FEATURE               Location/Qualifiers
source                1..11
                      mol_type = protein
                      organism = Homo sapiens
SEQUENCE: 1011
CCQPTCCHPS C                                                                    11

SEQ ID NO: 1012       moltype = AA  length = 11
FEATURE               Location/Qualifiers
source                1..11
                      mol_type = protein
                      organism = Homo sapiens
SEQUENCE: 1012
CCQPTCCQPT C                                                                    11

SEQ ID NO: 1013       moltype = AA  length = 11
FEATURE               Location/Qualifiers
source                1..11
                      mol_type = protein
                      organism = Homo sapiens
SEQUENCE: 1013
CCQPTCCRPR C                                                                    11

SEQ ID NO: 1014       moltype = AA  length = 11
FEATURE               Location/Qualifiers
source                1..11
                      mol_type = protein
                      organism = Homo sapiens
SEQUENCE: 1014
CCQPTCCRPS C                                                                    11

SEQ ID NO: 1015       moltype = AA  length = 11
FEATURE               Location/Qualifiers
source                1..11
                      mol_type = protein
                      organism = Homo sapiens
SEQUENCE: 1015
CCQPTCCRPT C                                                                    11

SEQ ID NO: 1016       moltype = AA  length = 11
FEATURE               Location/Qualifiers
source                1..11
                      mol_type = protein
                      organism = Homo sapiens
SEQUENCE: 1016
CCQPTCCRTT C                                                                    11

SEQ ID NO: 1017       moltype = AA  length = 11
FEATURE               Location/Qualifiers
source                1..11
                      mol_type = protein
                      organism = Homo sapiens
SEQUENCE: 1017
CCQPTCLSSC C                                                                    11

SEQ ID NO: 1018       moltype = AA  length = 11
FEATURE               Location/Qualifiers
source                1..11
                      mol_type = protein
```

```
                                           -continued organism = Homo sapiens
SEQUENCE: 1018
CCQPTCLTSC C                                                              11

SEQ ID NO: 1019         moltype = AA  length = 11
FEATURE                 Location/Qualifiers
source                  1..11
                        mol_type = protein
                        organism = Homo sapiens
SEQUENCE: 1019
CCQPTCVASC C                                                              11

SEQ ID NO: 1020         moltype = AA  length = 11
FEATURE                 Location/Qualifiers
source                  1..11
                        mol_type = protein
                        organism = Homo sapiens
SEQUENCE: 1020
CCQPTCVTSC C                                                              11

SEQ ID NO: 1021         moltype = AA  length = 11
FEATURE                 Location/Qualifiers
source                  1..11
                        mol_type = protein
                        organism = Homo sapiens
SEQUENCE: 1021
CCQPYCHPTC C                                                              11

SEQ ID NO: 1022         moltype = AA  length = 11
FEATURE                 Location/Qualifiers
source                  1..11
                        mol_type = protein
                        organism = Homo sapiens
SEQUENCE: 1022
CCQSMCCQPT C                                                              11

SEQ ID NO: 1023         moltype = AA  length = 11
FEATURE                 Location/Qualifiers
source                  1..11
                        mol_type = protein
                        organism = Homo sapiens
SEQUENCE: 1023
CCQSNCCVPV C                                                              11

SEQ ID NO: 1024         moltype = AA  length = 11
FEATURE                 Location/Qualifiers
source                  1..11
                        mol_type = protein
                        organism = Homo sapiens
SEQUENCE: 1024
CCQSSCCKPC S                                                              11

SEQ ID NO: 1025         moltype = AA  length = 11
FEATURE                 Location/Qualifiers
source                  1..11
                        mol_type = protein
                        organism = Homo sapiens
SEQUENCE: 1025
CCQSSCCKPS C                                                              11

SEQ ID NO: 1026         moltype = AA  length = 11
FEATURE                 Location/Qualifiers
source                  1..11
                        mol_type = protein
                        organism = Homo sapiens
SEQUENCE: 1026
CCQSSCCKPY C                                                              11

SEQ ID NO: 1027         moltype = AA  length = 11
FEATURE                 Location/Qualifiers
source                  1..11
                        mol_type = protein
                        organism = Homo sapiens
SEQUENCE: 1027
CCQSSCCQSS C                                                              11

SEQ ID NO: 1028         moltype = AA  length = 11
FEATURE                 Location/Qualifiers
source                  1..11
```

```
                            mol_type = protein
                            organism = Homo sapiens
SEQUENCE: 1028
CCQSSCCVPV C                                                            11

SEQ ID NO: 1029             moltype = AA   length = 11
FEATURE                     Location/Qualifiers
source                      1..11
                            mol_type = protein
                            organism = Homo sapiens
SEQUENCE: 1029
CCQSSCFKPC C                                                            11

SEQ ID NO: 1030             moltype = AA   length = 11
FEATURE                     Location/Qualifiers
source                      1..11
                            mol_type = protein
                            organism = Homo sapiens
SEQUENCE: 1030
CCQSSCSKPC C                                                            11

SEQ ID NO: 1031             moltype = AA   length = 11
FEATURE                     Location/Qualifiers
source                      1..11
                            mol_type = protein
                            organism = Homo sapiens
SEQUENCE: 1031
CCQSSCYKPC C                                                            11

SEQ ID NO: 1032             moltype = AA   length = 11
FEATURE                     Location/Qualifiers
source                      1..11
                            mol_type = protein
                            organism = Homo sapiens
SEQUENCE: 1032
CCQSVCCQPT C                                                            11

SEQ ID NO: 1033             moltype = AA   length = 11
FEATURE                     Location/Qualifiers
source                      1..11
                            mol_type = protein
                            organism = Homo sapiens
SEQUENCE: 1033
CCQTICRSTC C                                                            11

SEQ ID NO: 1034             moltype = AA   length = 11
FEATURE                     Location/Qualifiers
source                      1..11
                            mol_type = protein
                            organism = Homo sapiens
SEQUENCE: 1034
CCQTTCCRPS C                                                            11

SEQ ID NO: 1035             moltype = AA   length = 11
FEATURE                     Location/Qualifiers
source                      1..11
                            mol_type = protein
                            organism = Homo sapiens
SEQUENCE: 1035
CCQTTCCRTT C                                                            11

SEQ ID NO: 1036             moltype = AA   length = 11
FEATURE                     Location/Qualifiers
source                      1..11
                            mol_type = protein
                            organism = Homo sapiens
SEQUENCE: 1036
CCRPACCETT C                                                            11

SEQ ID NO: 1037             moltype = AA   length = 11
FEATURE                     Location/Qualifiers
source                      1..11
                            mol_type = protein
                            organism = Homo sapiens
SEQUENCE: 1037
CCRPACCQNT C                                                            11

SEQ ID NO: 1038             moltype = AA   length = 11
FEATURE                     Location/Qualifiers
```

-continued

```
source                  1..11
                        mol_type = protein
                        organism = Homo sapiens
SEQUENCE: 1038
CCRPLCCQTT C                                                                    11

SEQ ID NO: 1039         moltype = AA   length = 11
FEATURE                 Location/Qualifiers
source                  1..11
                        mol_type = protein
                        organism = Homo sapiens
SEQUENCE: 1039
CCRPQCCQSV C                                                                    11

SEQ ID NO: 1040         moltype = AA   length = 11
FEATURE                 Location/Qualifiers
source                  1..11
                        mol_type = protein
                        organism = Homo sapiens
SEQUENCE: 1040
CCRPQCCQTT C                                                                    11

SEQ ID NO: 1041         moltype = AA   length = 11
FEATURE                 Location/Qualifiers
source                  1..11
                        mol_type = protein
                        organism = Homo sapiens
SEQUENCE: 1041
CCRPSCCESS C                                                                    11

SEQ ID NO: 1042         moltype = AA   length = 11
FEATURE                 Location/Qualifiers
source                  1..11
                        mol_type = protein
                        organism = Homo sapiens
SEQUENCE: 1042
CCRPSCCETT C                                                                    11

SEQ ID NO: 1043         moltype = AA   length = 11
FEATURE                 Location/Qualifiers
source                  1..11
                        mol_type = protein
                        organism = Homo sapiens
SEQUENCE: 1043
CCRPSCCGSS C                                                                    11

SEQ ID NO: 1044         moltype = AA   length = 11
FEATURE                 Location/Qualifiers
source                  1..11
                        mol_type = protein
                        organism = Homo sapiens
SEQUENCE: 1044
CCRPSCCISS C                                                                    11

SEQ ID NO: 1045         moltype = AA   length = 11
FEATURE                 Location/Qualifiers
source                  1..11
                        mol_type = protein
                        organism = Homo sapiens
SEQUENCE: 1045
CCRPSCCKPQ C                                                                    11

SEQ ID NO: 1046         moltype = AA   length = 11
FEATURE                 Location/Qualifiers
source                  1..11
                        mol_type = protein
                        organism = Homo sapiens
SEQUENCE: 1046
CCRPSCCQTT C                                                                    11

SEQ ID NO: 1047         moltype = AA   length = 11
FEATURE                 Location/Qualifiers
source                  1..11
                        mol_type = protein
                        organism = Homo sapiens
SEQUENCE: 1047
CCRPSCCVSR C                                                                    11

SEQ ID NO: 1048         moltype = AA   length = 11
```

```
FEATURE              Location/Qualifiers
source               1..11
                     mol_type = protein
                     organism = Homo sapiens
SEQUENCE: 1048
CCRPSCCVSS C                                                              11

SEQ ID NO: 1049      moltype = AA  length = 11
FEATURE              Location/Qualifiers
source               1..11
                     mol_type = protein
                     organism = Homo sapiens
SEQUENCE: 1049
CCRPTCCQNT C                                                              11

SEQ ID NO: 1050      moltype = AA  length = 11
FEATURE              Location/Qualifiers
source               1..11
                     mol_type = protein
                     organism = Homo sapiens
SEQUENCE: 1050
CCRPTCCQTT C                                                              11

SEQ ID NO: 1051      moltype = AA  length = 11
FEATURE              Location/Qualifiers
source               1..11
                     mol_type = protein
                     organism = Homo sapiens
SEQUENCE: 1051
CCRPVCCDPC S                                                              11

SEQ ID NO: 1052      moltype = AA  length = 11
FEATURE              Location/Qualifiers
source               1..11
                     mol_type = protein
                     organism = Homo sapiens
SEQUENCE: 1052
CCRTTCCQPT C                                                              11

SEQ ID NO: 1053      moltype = AA  length = 11
FEATURE              Location/Qualifiers
source               1..11
                     mol_type = protein
                     organism = Homo sapiens
SEQUENCE: 1053
CCRTTCCRPS C                                                              11

SEQ ID NO: 1054      moltype = AA  length = 11
FEATURE              Location/Qualifiers
source               1..11
                     mol_type = protein
                     organism = Homo sapiens
SEQUENCE: 1054
CCRTTCCRTT C                                                              11

SEQ ID NO: 1055      moltype = AA  length = 11
FEATURE              Location/Qualifiers
source               1..11
                     mol_type = protein
                     organism = Homo sapiens
SEQUENCE: 1055
CCSCSSCGSC A                                                              11

SEQ ID NO: 1056      moltype = AA  length = 11
FEATURE              Location/Qualifiers
source               1..11
                     mol_type = protein
                     organism = Homo sapiens
SEQUENCE: 1056
CCSPGCQPTC C                                                              11

SEQ ID NO: 1057      moltype = AA  length = 11
FEATURE              Location/Qualifiers
source               1..11
                     mol_type = protein
                     organism = Homo sapiens
SEQUENCE: 1057
CCSQSSCCKP C                                                              11
```

| | | |
|---|---|---|
| SEQ ID NO: 1058<br>FEATURE<br>source<br><br>SEQUENCE: 1058<br>CCSSGCGSCC Q | moltype = AA   length = 11<br>Location/Qualifiers<br>1..11<br>mol_type = protein<br>organism = Homo sapiens | 11 |
| SEQ ID NO: 1059<br>FEATURE<br>source<br><br>SEQUENCE: 1059<br>CCSSGCGSSC C | moltype = AA   length = 11<br>Location/Qualifiers<br>1..11<br>mol_type = protein<br>organism = Homo sapiens | 11 |
| SEQ ID NO: 1060<br>FEATURE<br>source<br><br>SEQUENCE: 1060<br>CCSTPCCQPT C | moltype = AA   length = 11<br>Location/Qualifiers<br>1..11<br>mol_type = protein<br>organism = Homo sapiens | 11 |
| SEQ ID NO: 1061<br>FEATURE<br>source<br><br>SEQUENCE: 1061<br>CCVPACSCSS C | moltype = AA   length = 11<br>Location/Qualifiers<br>1..11<br>mol_type = protein<br>organism = Homo sapiens | 11 |
| SEQ ID NO: 1062<br>FEATURE<br>source<br><br>SEQUENCE: 1062<br>CCVPACSCTS C | moltype = AA   length = 11<br>Location/Qualifiers<br>1..11<br>mol_type = protein<br>organism = Homo sapiens | 11 |
| SEQ ID NO: 1063<br>FEATURE<br>source<br><br>SEQUENCE: 1063<br>CCVPICCKPI C | moltype = AA   length = 11<br>Location/Qualifiers<br>1..11<br>mol_type = protein<br>organism = Homo sapiens | 11 |
| SEQ ID NO: 1064<br>FEATURE<br>source<br><br>SEQUENCE: 1064<br>CCVPICCKPV C | moltype = AA   length = 11<br>Location/Qualifiers<br>1..11<br>mol_type = protein<br>organism = Homo sapiens | 11 |
| SEQ ID NO: 1065<br>FEATURE<br>source<br><br>SEQUENCE: 1065<br>CCVPVCCKPI C | moltype = AA   length = 11<br>Location/Qualifiers<br>1..11<br>mol_type = protein<br>organism = Homo sapiens | 11 |
| SEQ ID NO: 1066<br>FEATURE<br>source<br><br>SEQUENCE: 1066<br>CCVPVCCKPV C | moltype = AA   length = 11<br>Location/Qualifiers<br>1..11<br>mol_type = protein<br>organism = Homo sapiens | 11 |
| SEQ ID NO: 1067<br>FEATURE<br>source<br><br>SEQUENCE: 1067<br>CCVPVCCKSN C | moltype = AA   length = 11<br>Location/Qualifiers<br>1..11<br>mol_type = protein<br>organism = Homo sapiens | 11 |

-continued

| | | |
|---|---|---|
| SEQ ID NO: 1068<br>FEATURE<br>source | moltype = AA   length = 11<br>Location/Qualifiers<br>1..11<br>mol_type = protein<br>organism = Homo sapiens | |
| SEQUENCE: 1068<br>CCVPVCCKTV C | | 11 |
| SEQ ID NO: 1069<br>FEATURE<br>source | moltype = AA   length = 11<br>Location/Qualifiers<br>1..11<br>mol_type = protein<br>organism = Homo sapiens | |
| SEQUENCE: 1069<br>CCVPVCCSSS C | | 11 |
| SEQ ID NO: 1070<br>FEATURE<br>source | moltype = AA   length = 11<br>Location/Qualifiers<br>1..11<br>mol_type = protein<br>organism = Homo sapiens | |
| SEQUENCE: 1070<br>CCVPVCCVPV C | | 11 |
| SEQ ID NO: 1071<br>FEATURE<br>source | moltype = AA   length = 11<br>Location/Qualifiers<br>1..11<br>mol_type = protein<br>organism = Homo sapiens | |
| SEQUENCE: 1071<br>CCVSSCCKPQ C | | 11 |
| SEQ ID NO: 1072<br>FEATURE<br>source | moltype = AA   length = 11<br>Location/Qualifiers<br>1..11<br>mol_type = protein<br>organism = Homo sapiens | |
| SEQUENCE: 1072<br>CCVSSCCQHS C | | 11 |
| SEQ ID NO: 1073<br>FEATURE<br>source | moltype = AA   length = 11<br>Location/Qualifiers<br>1..11<br>mol_type = protein<br>organism = Homo sapiens | |
| SEQUENCE: 1073<br>CCVSSCCQPS C | | 11 |
| SEQ ID NO: 1074<br>FEATURE<br>source | moltype = AA   length = 11<br>Location/Qualifiers<br>1..11<br>mol_type = protein<br>organism = Homo sapiens | |
| SEQUENCE: 1074<br>CCVSSCCRPQ C | | 11 |
| SEQ ID NO: 1075<br>FEATURE<br>source | moltype = AA   length = 11<br>Location/Qualifiers<br>1..11<br>mol_type = protein<br>organism = Homo sapiens | |
| SEQUENCE: 1075<br>CCVSTCCRPT C | | 11 |
| SEQ ID NO: 1076<br>FEATURE<br>source | moltype = AA   length = 11<br>Location/Qualifiers<br>1..11<br>mol_type = protein<br>organism = Homo sapiens | |
| SEQUENCE: 1076<br>CCVSVCCKPV C | | 11 |
| SEQ ID NO: 1077<br>FEATURE<br>source | moltype = AA   length = 11<br>Location/Qualifiers<br>1..11<br>mol_type = protein<br>organism = Homo sapiens | |
| SEQUENCE: 1077 | | |

CDSSCCQPSC C                                                                                           11

SEQ ID NO: 1078         moltype = AA  length = 11
FEATURE                 Location/Qualifiers
source                  1..11
                        mol_type = protein
                        organism = Homo sapiens SEQUENCE: 1078
CEPCCRPVCC D                                                                                           11

SEQ ID NO: 1079         moltype = AA  length = 11
FEATURE                 Location/Qualifiers
source                  1..11
                        mol_type = protein
                        organism = Homo sapiens SEQUENCE: 1079
CFKPCCCQSS C                                                                                           11

SEQ ID NO: 1080         moltype = AA  length = 11
FEATURE                 Location/Qualifiers
source                  1..11
                        mol_type = protein
                        organism = Homo sapiens SEQUENCE: 1080
CGDGCCCPSC Y                                                                                           11

SEQ ID NO: 1081         moltype = AA  length = 11
FEATURE                 Location/Qualifiers
source                  1..11
                        mol_type = protein
                        organism = Homo sapiens SEQUENCE: 1081
CGGGCCGSSC C                                                                                           11

SEQ ID NO: 1082         moltype = AA  length = 11
FEATURE                 Location/Qualifiers
source                  1..11
                        mol_type = protein
                        organism = Homo sapiens SEQUENCE: 1082
CGGSCCGSSC C                                                                                           11

SEQ ID NO: 1083         moltype = AA  length = 11
FEATURE                 Location/Qualifiers
source                  1..11
                        mol_type = protein
                        organism = Homo sapiens SEQUENCE: 1083
CGLENCCCPS C                                                                                           11

SEQ ID NO: 1084         moltype = AA  length = 11
FEATURE                 Location/Qualifiers
source                  1..11
                        mol_type = protein
                        organism = Homo sapiens SEQUENCE: 1084
CGQSCCRPAC C                                                                                           11

SEQ ID NO: 1085         moltype = AA  length = 11
FEATURE                 Location/Qualifiers
source                  1..11
                        mol_type = protein
                        organism = Homo sapiens SEQUENCE: 1085
CGQSCCRPVC C                                                                                           11

SEQ ID NO: 1086         moltype = AA  length = 11
FEATURE                 Location/Qualifiers
source                  1..11
                        mol_type = protein
                        organism = Homo sapiens SEQUENCE: 1086
CGSCCQSSCC N                                                                                           11

SEQ ID NO: 1087         moltype = AA  length = 11
FEATURE                 Location/Qualifiers
source                  1..11
                        mol_type = protein
                        organism = Homo sapiens

```
SEQUENCE: 1087
CGSCGCSQCN C                                                                11

SEQ ID NO: 1088        moltype = AA  length = 11
FEATURE                Location/Qualifiers
source                 1..11
                       mol_type = protein
                       organism = Homo sapiens
SEQUENCE: 1088
CGSCGCSQCS C                                                                11

SEQ ID NO: 1089        moltype = AA  length = 11
FEATURE                Location/Qualifiers
source                 1..11
                       mol_type = protein
                       organism = Homo sapiens
SEQUENCE: 1089
CGSGCCGPVC C                                                                11

SEQ ID NO: 1090        moltype = AA  length = 11
FEATURE                Location/Qualifiers
source                 1..11
                       mol_type = protein
                       organism = Homo sapiens
SEQUENCE: 1090
CGSGCCVPVC C                                                                11

SEQ ID NO: 1091        moltype = AA  length = 11
FEATURE                Location/Qualifiers
source                 1..11
                       mol_type = protein
                       organism = Homo sapiens
SEQUENCE: 1091
CGSNCCQPCC R                                                                11

SEQ ID NO: 1092        moltype = AA  length = 11
FEATURE                Location/Qualifiers
source                 1..11
                       mol_type = protein
                       organism = Homo sapiens
SEQUENCE: 1092
CGSSCCQPCC H                                                                11

SEQ ID NO: 1093        moltype = AA  length = 11
FEATURE                Location/Qualifiers
source                 1..11
                       mol_type = protein
                       organism = Homo sapiens
SEQUENCE: 1093
CGSSCCQPCC R                                                                11

SEQ ID NO: 1094        moltype = AA  length = 11
FEATURE                Location/Qualifiers
source                 1..11
                       mol_type = protein
                       organism = Homo sapiens
SEQUENCE: 1094
CGSSCCQPCY C                                                                11

SEQ ID NO: 1095        moltype = AA  length = 11
FEATURE                Location/Qualifiers
source                 1..11
                       mol_type = protein
                       organism = Homo sapiens
SEQUENCE: 1095
CGSSCCQPSC C                                                                11

SEQ ID NO: 1096        moltype = AA  length = 11
FEATURE                Location/Qualifiers
source                 1..11
                       mol_type = protein
                       organism = Homo sapiens
SEQUENCE: 1096
CGSSCCQSSC C                                                                11

SEQ ID NO: 1097        moltype = AA  length = 11
FEATURE                Location/Qualifiers
source                 1..11
                       mol_type = protein
```

```
                       organism = Homo sapiens
SEQUENCE: 1097
CGSSCCVPIC C                                                                    11

SEQ ID NO: 1098        moltype = AA   length = 11
FEATURE                Location/Qualifiers
source                 1..11
                       mol_type = protein
                       organism = Homo sapiens
SEQUENCE: 1098
CGSSCCVPVC C                                                                    11

SEQ ID NO: 1099        moltype = AA   length = 11
FEATURE                Location/Qualifiers
source                 1..11
                       mol_type = protein
                       organism = Homo sapiens
SEQUENCE: 1099
CGSSCSQCSC C                                                                    11

SEQ ID NO: 1100        moltype = AA   length = 11
FEATURE                Location/Qualifiers
source                 1..11
                       mol_type = protein
                       organism = Homo sapiens
SEQUENCE: 1100
CGVPVCCCSC S                                                                    11

SEQ ID NO: 1101        moltype = AA   length = 11
FEATURE                Location/Qualifiers
source                 1..11
                       mol_type = protein
                       organism = Homo sapiens
SEQUENCE: 1101
CHPRCCISSC C                                                                    11

SEQ ID NO: 1102        moltype = AA   length = 11
FEATURE                Location/Qualifiers
source                 1..11
                       mol_type = protein
                       organism = Homo sapiens
SEQUENCE: 1102
CHPSCCESSC C                                                                    11

SEQ ID NO: 1103        moltype = AA   length = 11
FEATURE                Location/Qualifiers
source                 1..11
                       mol_type = protein
                       organism = Homo sapiens
SEQUENCE: 1103
CHPSCCISSC C                                                                    11

SEQ ID NO: 1104        moltype = AA   length = 11
FEATURE                Location/Qualifiers
source                 1..11
                       mol_type = protein
                       organism = Homo sapiens
SEQUENCE: 1104
CHPTCCQNTC C                                                                    11

SEQ ID NO: 1105        moltype = AA   length = 11
FEATURE                Location/Qualifiers
source                 1..11
                       mol_type = protein
                       organism = Homo sapiens
SEQUENCE: 1105
CISSCCHPSC C                                                                    11

SEQ ID NO: 1106        moltype = AA   length = 11
FEATURE                Location/Qualifiers
source                 1..11
                       mol_type = protein
                       organism = Homo sapiens
SEQUENCE: 1106
CISSCCKPSC C                                                                    11

SEQ ID NO: 1107        moltype = AA   length = 11
FEATURE                Location/Qualifiers
source                 1..11
```

```
                            mol_type = protein
                            organism = Homo sapiens
SEQUENCE: 1107
CISSCCRPSC C                                                             11

SEQ ID NO: 1108             moltype = AA  length = 11
FEATURE                     Location/Qualifiers
source                      1..11
                            mol_type = protein
                            organism = Homo sapiens
SEQUENCE: 1108
CISSSCCPSC C                                                             11

SEQ ID NO: 1109             moltype = AA  length = 11
FEATURE                     Location/Qualifiers
source                      1..11
                            mol_type = protein
                            organism = Homo sapiens
SEQUENCE: 1109
CKPCCCSSGC G                                                             11

SEQ ID NO: 1110             moltype = AA  length = 11
FEATURE                     Location/Qualifiers
source                      1..11
                            mol_type = protein
                            organism = Homo sapiens
SEQUENCE: 1110
CKPCCSQASC C                                                             11

SEQ ID NO: 1111             moltype = AA  length = 11
FEATURE                     Location/Qualifiers
source                      1..11
                            mol_type = protein
                            organism = Homo sapiens
SEQUENCE: 1111
CKPCCSQSRC C                                                             11

SEQ ID NO: 1112             moltype = AA  length = 11
FEATURE                     Location/Qualifiers
source                      1..11
                            mol_type = protein
                            organism = Homo sapiens
SEQUENCE: 1112
CKPCCSQSSC C                                                             11

SEQ ID NO: 1113             moltype = AA  length = 11
FEATURE                     Location/Qualifiers
source                      1..11
                            mol_type = protein
                            organism = Homo sapiens
SEQUENCE: 1113
CKPQCCQSMC C                                                             11

SEQ ID NO: 1114             moltype = AA  length = 11
FEATURE                     Location/Qualifiers
source                      1..11
                            mol_type = protein
                            organism = Homo sapiens
SEQUENCE: 1114
CKPQCCQSVC C                                                             11

SEQ ID NO: 1115             moltype = AA  length = 11
FEATURE                     Location/Qualifiers
source                      1..11
                            mol_type = protein
                            organism = Homo sapiens
SEQUENCE: 1115
CKPVCCCVPA C                                                             11

SEQ ID NO: 1116             moltype = AA  length = 11
FEATURE                     Location/Qualifiers
source                      1..11
                            mol_type = protein
                            organism = Homo sapiens
SEQUENCE: 1116
CKPVCCKPIC C                                                             11

SEQ ID NO: 1117             moltype = AA  length = 11
FEATURE                     Location/Qualifiers
```

```
                      -continued source               1..11
                     mol_type = protein
                     organism = Homo sapiens
SEQUENCE: 1117
CKPVCCMPVC C                                                    11

SEQ ID NO: 1118      moltype = AA   length = 11
FEATURE              Location/Qualifiers
source               1..11
                     mol_type = protein
                     organism = Homo sapiens
SEQUENCE: 1118
CKPVCCVPVC C                                                    11

SEQ ID NO: 1119      moltype = AA   length = 11
FEATURE              Location/Qualifiers
source               1..11
                     mol_type = protein
                     organism = Homo sapiens
SEQUENCE: 1119
CKPVCCVSVC C                                                    11

SEQ ID NO: 1120      moltype = AA   length = 11
FEATURE              Location/Qualifiers
source               1..11
                     mol_type = protein
                     organism = Homo sapiens
SEQUENCE: 1120
CKPYCSQCSC C                                                    11

SEQ ID NO: 1121      moltype = AA   length = 11
FEATURE              Location/Qualifiers
source               1..11
                     mol_type = protein
                     organism = Homo sapiens
SEQUENCE: 1121
CLPCCRPTCC Q                                                    11

SEQ ID NO: 1122      moltype = AA   length = 11
FEATURE              Location/Qualifiers
source               1..11
                     mol_type = protein
                     organism = Homo sapiens
SEQUENCE: 1122
CLTSCCQPSC C                                                    11

SEQ ID NO: 1123      moltype = AA   length = 11
FEATURE              Location/Qualifiers
source               1..11
                     mol_type = protein
                     organism = Homo sapiens
SEQUENCE: 1123
CMSSCCKPQC C                                                    11

SEQ ID NO: 1124      moltype = AA   length = 11
FEATURE              Location/Qualifiers
source               1..11
                     mol_type = protein
                     organism = Homo sapiens
SEQUENCE: 1124
CNPCCSQSSC C                                                    11

SEQ ID NO: 1125      moltype = AA   length = 11
FEATURE              Location/Qualifiers
source               1..11
                     mol_type = protein
                     organism = Homo sapiens
SEQUENCE: 1125
CPACCVSSCC Q                                                    11

SEQ ID NO: 1126      moltype = AA   length = 11
FEATURE              Location/Qualifiers
source               1..11
                     mol_type = protein
                     organism = Homo sapiens
SEQUENCE: 1126
CPESCCEPHC C                                                    11

SEQ ID NO: 1127      moltype = AA   length = 11
```

```
FEATURE                 Location/Qualifiers
source                  1..11
                        mol_type = protein
                        organism = Homo sapiens
SEQUENCE: 1127
CPESCCEPPC C                                                               11

SEQ ID NO: 1128         moltype = AA   length = 11
FEATURE                 Location/Qualifiers
source                  1..11
                        mol_type = protein
                        organism = Homo sapiens
SEQUENCE: 1128
CPSCCESSCC R                                                               11

SEQ ID NO: 1129         moltype = AA   length = 11
FEATURE                 Location/Qualifiers
source                  1..11
                        mol_type = protein
                        organism = Homo sapiens
SEQUENCE: 1129
CPSCCQTTCC R                                                               11

SEQ ID NO: 1130         moltype = AA   length = 11
FEATURE                 Location/Qualifiers
source                  1..11
                        mol_type = protein
                        organism = Homo sapiens
SEQUENCE: 1130
CPSCCVSSCC R                                                               11

SEQ ID NO: 1131         moltype = AA   length = 11
FEATURE                 Location/Qualifiers
source                  1..11
                        mol_type = protein
                        organism = Homo sapiens
SEQUENCE: 1131
CQCSCCKPYC S                                                               11

SEQ ID NO: 1132         moltype = AA   length = 11
FEATURE                 Location/Qualifiers
source                  1..11
                        mol_type = protein
                        organism = Homo sapiens
SEQUENCE: 1132
CQETCCRPSC C                                                               11

SEQ ID NO: 1133         moltype = AA   length = 11
FEATURE                 Location/Qualifiers
source                  1..11
                        mol_type = protein
                        organism = Homo sapiens
SEQUENCE: 1133
CQNTCCRTTC C                                                               11

SEQ ID NO: 1134         moltype = AA   length = 11
FEATURE                 Location/Qualifiers
source                  1..11
                        mol_type = protein
                        organism = Homo sapiens
SEQUENCE: 1134
CQPACCTASC C                                                               11

SEQ ID NO: 1135         moltype = AA   length = 11
FEATURE                 Location/Qualifiers
source                  1..11
                        mol_type = protein
                        organism = Homo sapiens
SEQUENCE: 1135
CQPACCTSSC C                                                               11

SEQ ID NO: 1136         moltype = AA   length = 11
FEATURE                 Location/Qualifiers
source                  1..11
                        mol_type = protein
                        organism = Homo sapiens
SEQUENCE: 1136
CQPACCTTSC C                                                               11
```

| | | |
|---|---|---|
| SEQ ID NO: 1137<br>FEATURE<br>source | moltype = AA   length = 11<br>Location/Qualifiers<br>1..11<br>mol_type = protein<br>organism = Homo sapiens | |
| SEQUENCE: 1137<br>CQPACCVPVC C | | 11 |
| SEQ ID NO: 1138<br>FEATURE<br>source | moltype = AA   length = 11<br>Location/Qualifiers<br>1..11<br>mol_type = protein<br>organism = Homo sapiens | |
| SEQUENCE: 1138<br>CQPACCVSSC C | | 11 |
| SEQ ID NO: 1139<br>FEATURE<br>source | moltype = AA   length = 11<br>Location/Qualifiers<br>1..11<br>mol_type = protein<br>organism = Homo sapiens | |
| SEQUENCE: 1139<br>CQPCCHPTCC Q | | 11 |
| SEQ ID NO: 1140<br>FEATURE<br>source | moltype = AA   length = 11<br>Location/Qualifiers<br>1..11<br>mol_type = protein<br>organism = Homo sapiens | |
| SEQUENCE: 1140<br>CQPCCRPACC E | | 11 |
| SEQ ID NO: 1141<br>FEATURE<br>source | moltype = AA   length = 11<br>Location/Qualifiers<br>1..11<br>mol_type = protein<br>organism = Homo sapiens | |
| SEQUENCE: 1141<br>CQPCCRPACC Q | | 11 |
| SEQ ID NO: 1142<br>FEATURE<br>source | moltype = AA   length = 11<br>Location/Qualifiers<br>1..11<br>mol_type = protein<br>organism = Homo sapiens | |
| SEQUENCE: 1142<br>CQPCCRPTCC Q | | 11 |
| SEQ ID NO: 1143<br>FEATURE<br>source | moltype = AA   length = 11<br>Location/Qualifiers<br>1..11<br>mol_type = protein<br>organism = Homo sapiens | |
| SEQUENCE: 1143<br>CQPCYCPACC V | | 11 |
| SEQ ID NO: 1144<br>FEATURE<br>source | moltype = AA   length = 11<br>Location/Qualifiers<br>1..11<br>mol_type = protein<br>organism = Homo sapiens | |
| SEQUENCE: 1144<br>CQPICCGSSC C | | 11 |
| SEQ ID NO: 1145<br>FEATURE<br>source | moltype = AA   length = 11<br>Location/Qualifiers<br>1..11<br>mol_type = protein<br>organism = Homo sapiens | |
| SEQUENCE: 1145<br>CQPRCCETSC C | | 11 |
| SEQ ID NO: 1146<br>FEATURE<br>source | moltype = AA   length = 11<br>Location/Qualifiers<br>1..11<br>mol_type = protein<br>organism = Homo sapiens | |
| SEQUENCE: 1146<br>CQPSCCETSC C | | 11 |

```
SEQ ID NO: 1147           moltype = AA  length = 11
FEATURE                   Location/Qualifiers
source                    1..11
                          mol_type = protein
                          organism = Homo sapiens SEQUENCE: 1147
CQPSCCRPAC C                                                              11

SEQ ID NO: 1148           moltype = AA  length = 11
FEATURE                   Location/Qualifiers
source                    1..11
                          mol_type = protein
                          organism = Homo sapiens SEQUENCE: 1148
CQPSCCVPSC C                                                              11

SEQ ID NO: 1149           moltype = AA  length = 11
FEATURE                   Location/Qualifiers
source                    1..11
                          mol_type = protein
                          organism = Homo sapiens SEQUENCE: 1149
CQPSCCVSSC C                                                              11

SEQ ID NO: 1150           moltype = AA  length = 11
FEATURE                   Location/Qualifiers
source                    1..11
                          mol_type = protein
                          organism = Homo sapiens SEQUENCE: 1150
CQPTCCCPSY C                                                              11

SEQ ID NO: 1151           moltype = AA  length = 11
FEATURE                   Location/Qualifiers
source                    1..11
                          mol_type = protein
                          organism = Homo sapiens SEQUENCE: 1151
CQPTCCGSSC C                                                              11

SEQ ID NO: 1152           moltype = AA  length = 11
FEATURE                   Location/Qualifiers
source                    1..11
                          mol_type = protein
                          organism = Homo sapiens SEQUENCE: 1152
CQPTCCHPSC C                                                              11

SEQ ID NO: 1153           moltype = AA  length = 11
FEATURE                   Location/Qualifiers
source                    1..11
                          mol_type = protein
                          organism = Homo sapiens SEQUENCE: 1153
CQPTCCQPTC C                                                              11

SEQ ID NO: 1154           moltype = AA  length = 11
FEATURE                   Location/Qualifiers
source                    1..11
                          mol_type = protein
                          organism = Homo sapiens SEQUENCE: 1154
CQPTCCRPSC C                                                              11

SEQ ID NO: 1155           moltype = AA  length = 11
FEATURE                   Location/Qualifiers
source                    1..11
                          mol_type = protein
                          organism = Homo sapiens SEQUENCE: 1155
CQPTCCRPTC C                                                              11

SEQ ID NO: 1156           moltype = AA  length = 11
FEATURE                   Location/Qualifiers
source                    1..11
                          mol_type = protein
                          organism = Homo sapiens

SEQUENCE: 1156
```

| | | |
|---|---|---|
| CQPTCCRTTC C | | 11 |
| SEQ ID NO: 1157<br>FEATURE<br>source<br><br>SEQUENCE: 1157<br>CQQACCMPVC C | moltype = AA  length = 11<br>Location/Qualifiers<br>1..11<br>mol_type = protein<br>organism = Homo sapiens | <br><br><br><br><br>11 |
| SEQ ID NO: 1158<br>FEATURE<br>source<br><br>SEQUENCE: 1158<br>CQQACCVPIC C | moltype = AA  length = 11<br>Location/Qualifiers<br>1..11<br>mol_type = protein<br>organism = Homo sapiens | <br><br><br><br><br>11 |
| SEQ ID NO: 1159<br>FEATURE<br>source<br><br>SEQUENCE: 1159<br>CQQACCVPVC C | moltype = AA  length = 11<br>Location/Qualifiers<br>1..11<br>mol_type = protein<br>organism = Homo sapiens | <br><br><br><br><br>11 |
| SEQ ID NO: 1160<br>FEATURE<br>source<br><br>SEQUENCE: 1160<br>CQQSCCVPVC C | moltype = AA  length = 11<br>Location/Qualifiers<br>1..11<br>mol_type = protein<br>organism = Homo sapiens | <br><br><br><br><br>11 |
| SEQ ID NO: 1161<br>FEATURE<br>source<br><br>SEQUENCE: 1161<br>CQQSCCVSVC C | moltype = AA  length = 11<br>Location/Qualifiers<br>1..11<br>mol_type = protein<br>organism = Homo sapiens | <br><br><br><br><br>11 |
| SEQ ID NO: 1162<br>FEATURE<br>source<br><br>SEQUENCE: 1162<br>CQSNCCVPVC C | moltype = AA  length = 11<br>Location/Qualifiers<br>1..11<br>mol_type = protein<br>organism = Homo sapiens | <br><br><br><br><br>11 |
| SEQ ID NO: 1163<br>FEATURE<br>source<br><br>SEQUENCE: 1163<br>CQSSCCCPAS C | moltype = AA  length = 11<br>Location/Qualifiers<br>1..11<br>mol_type = protein<br>organism = Homo sapiens | <br><br><br><br><br>11 |
| SEQ ID NO: 1164<br>FEATURE<br>source<br><br>SEQUENCE: 1164<br>CQSSCCKPCC S | moltype = AA  length = 11<br>Location/Qualifiers<br>1..11<br>mol_type = protein<br>organism = Homo sapiens | <br><br><br><br><br>11 |
| SEQ ID NO: 1165<br>FEATURE<br>source<br><br>SEQUENCE: 1165<br>CQSSCCKPCS C | moltype = AA  length = 11<br>Location/Qualifiers<br>1..11<br>mol_type = protein<br>organism = Homo sapiens | <br><br><br><br><br>11 |
| SEQ ID NO: 1166<br>FEATURE<br>source | moltype = AA  length = 11<br>Location/Qualifiers<br>1..11<br>mol_type = protein<br>organism = Homo sapiens | |

```
SEQUENCE: 1166
CQSSCCKPYC C                                                                                   11

SEQ ID NO: 1167          moltype = AA  length = 11
FEATURE                  Location/Qualifiers
source                   1..11
                         mol_type = protein
                         organism = Homo sapiens
SEQUENCE: 1167
CQSSCCNPCC S                                                                                   11

SEQ ID NO: 1168          moltype = AA  length = 11
FEATURE                  Location/Qualifiers
source                   1..11
                         mol_type = protein
                         organism = Homo sapiens
SEQUENCE: 1168
CQSSCCQSSC C                                                                                   11

SEQ ID NO: 1169          moltype = AA  length = 11
FEATURE                  Location/Qualifiers
source                   1..11
                         mol_type = protein
                         organism = Homo sapiens
SEQUENCE: 1169
CQSSCCVPVC C                                                                                   11

SEQ ID NO: 1170          moltype = AA  length = 11
FEATURE                  Location/Qualifiers
source                   1..11
                         mol_type = protein
                         organism = Homo sapiens
SEQUENCE: 1170
CQSSCFKPCC C                                                                                   11

SEQ ID NO: 1171          moltype = AA  length = 11
FEATURE                  Location/Qualifiers
source                   1..11
                         mol_type = protein
                         organism = Homo sapiens
SEQUENCE: 1171
CQSSCSKPCC C                                                                                   11

SEQ ID NO: 1172          moltype = AA  length = 11
FEATURE                  Location/Qualifiers
source                   1..11
                         mol_type = protein
                         organism = Homo sapiens
SEQUENCE: 1172
CQSSCYKPCC C                                                                                   11

SEQ ID NO: 1173          moltype = AA  length = 11
FEATURE                  Location/Qualifiers
source                   1..11
                         mol_type = protein
                         organism = Homo sapiens
SEQUENCE: 1173
CQSVCCQPTC C                                                                                   11

SEQ ID NO: 1174          moltype = AA  length = 11
FEATURE                  Location/Qualifiers
source                   1..11
                         mol_type = protein
                         organism = Homo sapiens
SEQUENCE: 1174
CQTTCCCPSC V                                                                                   11

SEQ ID NO: 1175          moltype = AA  length = 11
FEATURE                  Location/Qualifiers
source                   1..11
                         mol_type = protein
                         organism = Homo sapiens
SEQUENCE: 1175
CQTTCCRPSC C                                                                                   11

SEQ ID NO: 1176          moltype = AA  length = 11
FEATURE                  Location/Qualifiers
source                   1..11
                         mol_type = protein
```

```
                                     organism = Homo sapiens
SEQUENCE: 1176
CQTTCCRTTC C                                                                              11

SEQ ID NO: 1177         moltype = AA  length = 11
FEATURE                 Location/Qualifiers
source                  1..11
                        mol_type = protein
                        organism = Homo sapiens
SEQUENCE: 1177
CRPACCETTC C                                                                              11

SEQ ID NO: 1178         moltype = AA  length = 11
FEATURE                 Location/Qualifiers
source                  1..11
                        mol_type = protein
                        organism = Homo sapiens
SEQUENCE: 1178
CRPACCQNTC C                                                                              11

SEQ ID NO: 1179         moltype = AA  length = 11
FEATURE                 Location/Qualifiers
source                  1..11
                        mol_type = protein
                        organism = Homo sapiens
SEQUENCE: 1179
CRPCCCLRPV C                                                                              11

SEQ ID NO: 1180         moltype = AA  length = 11
FEATURE                 Location/Qualifiers
source                  1..11
                        mol_type = protein
                        organism = Homo sapiens
SEQUENCE: 1180
CRPCCCVRPV C                                                                              11

SEQ ID NO: 1181         moltype = AA  length = 11
FEATURE                 Location/Qualifiers
source                  1..11
                        mol_type = protein
                        organism = Homo sapiens
SEQUENCE: 1181
CRPCCWATTC C                                                                              11

SEQ ID NO: 1182         moltype = AA  length = 11
FEATURE                 Location/Qualifiers
source                  1..11
                        mol_type = protein
                        organism = Homo sapiens
SEQUENCE: 1182
CRPLCCQTTC C                                                                              11

SEQ ID NO: 1183         moltype = AA  length = 11
FEATURE                 Location/Qualifiers
source                  1..11
                        mol_type = protein
                        organism = Homo sapiens
SEQUENCE: 1183
CRPQCCQSVC C                                                                              11

SEQ ID NO: 1184         moltype = AA  length = 11
FEATURE                 Location/Qualifiers
source                  1..11
                        mol_type = protein
                        organism = Homo sapiens
SEQUENCE: 1184
CRPQCCQTTC C                                                                              11

SEQ ID NO: 1185         moltype = AA  length = 11
FEATURE                 Location/Qualifiers
source                  1..11
                        mol_type = protein
                        organism = Homo sapiens
SEQUENCE: 1185
CRPRCCISSC C                                                                              11

SEQ ID NO: 1186         moltype = AA  length = 11
FEATURE                 Location/Qualifiers
source                  1..11
```

```
                        mol_type = protein
                        organism = Homo sapiens
SEQUENCE: 1186
CRPSCCESSC C                                                                11

SEQ ID NO: 1187         moltype = AA   length = 11
FEATURE                 Location/Qualifiers
source                  1..11
                        mol_type = protein
                        organism = Homo sapiens
SEQUENCE: 1187
CRPSCCISSC C                                                                11

SEQ ID NO: 1188         moltype = AA   length = 11
FEATURE                 Location/Qualifiers
source                  1..11
                        mol_type = protein
                        organism = Homo sapiens
SEQUENCE: 1188
CRPSCCKPQC C                                                                11

SEQ ID NO: 1189         moltype = AA   length = 11
FEATURE                 Location/Qualifiers
source                  1..11
                        mol_type = protein
                        organism = Homo sapiens
SEQUENCE: 1189
CRPSCCPSCC Q                                                                11

SEQ ID NO: 1190         moltype = AA   length = 11
FEATURE                 Location/Qualifiers
source                  1..11
                        mol_type = protein
                        organism = Homo sapiens
SEQUENCE: 1190
CRPSCCQTTC C                                                                11

SEQ ID NO: 1191         moltype = AA   length = 11
FEATURE                 Location/Qualifiers
source                  1..11
                        mol_type = protein
                        organism = Homo sapiens
SEQUENCE: 1191
CRPSCCRPQC C                                                                11

SEQ ID NO: 1192         moltype = AA   length = 11
FEATURE                 Location/Qualifiers
source                  1..11
                        mol_type = protein
                        organism = Homo sapiens
SEQUENCE: 1192
CRPSCCVSRC C                                                                11

SEQ ID NO: 1193         moltype = AA   length = 11
FEATURE                 Location/Qualifiers
source                  1..11
                        mol_type = protein
                        organism = Homo sapiens
SEQUENCE: 1193
CRPSCCVSSC C                                                                11

SEQ ID NO: 1194         moltype = AA   length = 11
FEATURE                 Location/Qualifiers
source                  1..11
                        mol_type = protein
                        organism = Homo sapiens
SEQUENCE: 1194
CRPTCCQNTC C                                                                11

SEQ ID NO: 1195         moltype = AA   length = 11
FEATURE                 Location/Qualifiers
source                  1..11
                        mol_type = protein
                        organism = Homo sapiens
SEQUENCE: 1195
CRPVCCCEPT C                                                                11

SEQ ID NO: 1196         moltype = AA   length = 11
FEATURE                 Location/Qualifiers
```

```
source                    1..11
                          mol_type = protein
                          organism = Homo sapiens
SEQUENCE: 1196
CRPVCCCYSC E                                                                      11

SEQ ID NO: 1197           moltype = AA   length = 11
FEATURE                   Location/Qualifiers
source                    1..11
                          mol_type = protein
                          organism = Homo sapiens
SEQUENCE: 1197
CRTTCCHPSC C                                                                      11

SEQ ID NO: 1198           moltype = AA   length = 11
FEATURE                   Location/Qualifiers
source                    1..11
                          mol_type = protein
                          organism = Homo sapiens
SEQUENCE: 1198
CRTTCCRPSC C                                                                      11

SEQ ID NO: 1199           moltype = AA   length = 11
FEATURE                   Location/Qualifiers
source                    1..11
                          mol_type = protein
                          organism = Homo sapiens
SEQUENCE: 1199
CSCCKPYCSQ C                                                                      11

SEQ ID NO: 1200           moltype = AA   length = 11
FEATURE                   Location/Qualifiers
source                    1..11
                          mol_type = protein
                          organism = Homo sapiens
SEQUENCE: 1200
CSKPCCCQSS C                                                                      11

SEQ ID NO: 1201           moltype = AA   length = 11
FEATURE                   Location/Qualifiers
source                    1..11
                          mol_type = protein
                          organism = Homo sapiens
SEQUENCE: 1201
CSPCCQPTCC R                                                                      11

SEQ ID NO: 1202           moltype = AA   length = 11
FEATURE                   Location/Qualifiers
source                    1..11
                          mol_type = protein
                          organism = Homo sapiens
SEQUENCE: 1202
CSPCCVSSCC Q                                                                      11

SEQ ID NO: 1203           moltype = AA   length = 11
FEATURE                   Location/Qualifiers
source                    1..11
                          mol_type = protein
                          organism = Homo sapiens
SEQUENCE: 1203
CSQCSCCKPC Y                                                                      11

SEQ ID NO: 1204           moltype = AA   length = 11
FEATURE                   Location/Qualifiers
source                    1..11
                          mol_type = protein
                          organism = Homo sapiens
SEQUENCE: 1204
CSQCSCYKPC C                                                                      11

SEQ ID NO: 1205           moltype = AA   length = 11
FEATURE                   Location/Qualifiers
source                    1..11
                          mol_type = protein
                          organism = Homo sapiens
SEQUENCE: 1205
CSQSNCCKPC C                                                                      11

SEQ ID NO: 1206           moltype = AA   length = 11
```

```
FEATURE                 Location/Qualifiers
source                  1..11
                        mol_type = protein
                        organism = Homo sapiens
SEQUENCE: 1206
CSQSSCCKPC C                                                                    11

SEQ ID NO: 1207         moltype = AA  length = 11
FEATURE                 Location/Qualifiers
source                  1..11
                        mol_type = protein
                        organism = Homo sapiens
SEQUENCE: 1207
CSSSCCQPSC C                                                                    11

SEQ ID NO: 1208         moltype = AA  length = 11
FEATURE                 Location/Qualifiers
source                  1..11
                        mol_type = protein
                        organism = Homo sapiens
SEQUENCE: 1208
CTPSCCQPAC C                                                                    11

SEQ ID NO: 1209         moltype = AA  length = 11
FEATURE                 Location/Qualifiers
source                  1..11
                        mol_type = protein
                        organism = Homo sapiens
SEQUENCE: 1209
CVASCCQPSC C                                                                    11

SEQ ID NO: 1210         moltype = AA  length = 11
FEATURE                 Location/Qualifiers
source                  1..11
                        mol_type = protein
                        organism = Homo sapiens
SEQUENCE: 1210
CVPICCCKPV C                                                                    11

SEQ ID NO: 1211         moltype = AA  length = 11
FEATURE                 Location/Qualifiers
source                  1..11
                        mol_type = protein
                        organism = Homo sapiens
SEQUENCE: 1211
CVPSCCQPCC H                                                                    11

SEQ ID NO: 1212         moltype = AA  length = 11
FEATURE                 Location/Qualifiers
source                  1..11
                        mol_type = protein
                        organism = Homo sapiens
SEQUENCE: 1212
CVPVCCCKPM C                                                                    11

SEQ ID NO: 1213         moltype = AA  length = 11
FEATURE                 Location/Qualifiers
source                  1..11
                        mol_type = protein
                        organism = Homo sapiens
SEQUENCE: 1213
CVPVCCCKPV C                                                                    11

SEQ ID NO: 1214         moltype = AA  length = 11
FEATURE                 Location/Qualifiers
source                  1..11
                        mol_type = protein
                        organism = Homo sapiens
SEQUENCE: 1214
CVPVCCKPVC C                                                                    11

SEQ ID NO: 1215         moltype = AA  length = 11
FEATURE                 Location/Qualifiers
source                  1..11
                        mol_type = protein
                        organism = Homo sapiens
SEQUENCE: 1215
CVSSCCKPQC C                                                                    11
```

| | | |
|---|---|---|
| SEQ ID NO: 1216<br>FEATURE<br>source | moltype = AA   length = 11<br>Location/Qualifiers<br>1..11<br>mol_type = protein<br>organism = Homo sapiens | |
| SEQUENCE: 1216<br>CVSSCCQHSC C | | 11 |
| SEQ ID NO: 1217<br>FEATURE<br>source | moltype = AA   length = 11<br>Location/Qualifiers<br>1..11<br>mol_type = protein<br>organism = Homo sapiens | |
| SEQUENCE: 1217<br>CVSSCCQPCC H | | 11 |
| SEQ ID NO: 1218<br>FEATURE<br>source | moltype = AA   length = 11<br>Location/Qualifiers<br>1..11<br>mol_type = protein<br>organism = Homo sapiens | |
| SEQUENCE: 1218<br>CVSSCCQPCC R | | 11 |
| SEQ ID NO: 1219<br>FEATURE<br>source | moltype = AA   length = 11<br>Location/Qualifiers<br>1..11<br>mol_type = protein<br>organism = Homo sapiens | |
| SEQUENCE: 1219<br>CVSSCCQPFC C | | 11 |
| SEQ ID NO: 1220<br>FEATURE<br>source | moltype = AA   length = 11<br>Location/Qualifiers<br>1..11<br>mol_type = protein<br>organism = Homo sapiens | |
| SEQUENCE: 1220<br>CVSSCCQPSC C | | 11 |
| SEQ ID NO: 1221<br>FEATURE<br>source | moltype = AA   length = 11<br>Location/Qualifiers<br>1..11<br>mol_type = protein<br>organism = Homo sapiens | |
| SEQUENCE: 1221<br>CVSSCCRPQC C | | 11 |
| SEQ ID NO: 1222<br>FEATURE<br>source | moltype = AA   length = 11<br>Location/Qualifiers<br>1..11<br>mol_type = protein<br>organism = Homo sapiens | |
| SEQUENCE: 1222<br>CVTRCCSTPC C | | 11 |
| SEQ ID NO: 1223<br>FEATURE<br>source | moltype = AA   length = 11<br>Location/Qualifiers<br>1..11<br>mol_type = protein<br>organism = Homo sapiens | |
| SEQUENCE: 1223<br>CVTSCCQPAC C | | 11 |
| SEQ ID NO: 1224<br>FEATURE<br>source | moltype = AA   length = 11<br>Location/Qualifiers<br>1..11<br>mol_type = protein<br>organism = Homo sapiens | |
| SEQUENCE: 1224<br>CVTSCCQPSC C | | 11 |
| SEQ ID NO: 1225<br>FEATURE<br>source | moltype = AA   length = 11<br>Location/Qualifiers<br>1..11<br>mol_type = protein<br>organism = Homo sapiens | |
| SEQUENCE: 1225<br>CVYSCCQPFC C | | 11 |

```
SEQ ID NO: 1226           moltype = AA   length = 11
FEATURE                   Location/Qualifiers
source                    1..11
                          mol_type = protein
                          organism = Homo sapiens
SEQUENCE: 1226
CVYSCCQPSC C                                                                  11

SEQ ID NO: 1227           moltype = AA   length = 11
FEATURE                   Location/Qualifiers
source                    1..11
                          mol_type = protein
                          organism = Homo sapiens
SEQUENCE: 1227
CYCPACCVSS C                                                                  11

SEQ ID NO: 1228           moltype = AA   length = 11
FEATURE                   Location/Qualifiers
source                    1..11
                          mol_type = protein
                          organism = Homo sapiens
SEQUENCE: 1228
CYKPCCCQSS C                                                                  11

SEQ ID NO: 1229           moltype = AA   length = 11
FEATURE                   Location/Qualifiers
source                    1..11
                          mol_type = protein
                          organism = Homo sapiens
SEQUENCE: 1229
CYKPCCCSSG C                                                                  11

SEQ ID NO: 1230           moltype = AA   length = 11
FEATURE                   Location/Qualifiers
source                    1..11
                          mol_type = protein
                          organism = Homo sapiens
SEQUENCE: 1230
MCCCVPACSC S                                                                  11

SEQ ID NO: 1231           moltype = AA   length = 11
FEATURE                   Location/Qualifiers
source                    1..11
                          mol_type = protein
                          organism = Homo sapiens
SEQUENCE: 1231
NCCVPVCCQC K                                                                  11

SEQ ID NO: 1232           moltype = AA   length = 11
FEATURE                   Location/Qualifiers
source                    1..11
                          mol_type = protein
                          organism = Homo sapiens
SEQUENCE: 1232
QCSCCKPCYC S                                                                  11

SEQ ID NO: 1233           moltype = AA   length = 11
FEATURE                   Location/Qualifiers
source                    1..11
                          mol_type = protein
                          organism = Homo sapiens
SEQUENCE: 1233
QCSCYKPCCC S                                                                  11

SEQ ID NO: 1234           moltype = AA   length = 11
FEATURE                   Location/Qualifiers
source                    1..11
                          mol_type = protein
                          organism = Homo sapiens
SEQUENCE: 1234
SCCVPICCQC K                                                                  11

SEQ ID NO: 1235           moltype = AA   length = 11
FEATURE                   Location/Qualifiers
source                    1..11
                          mol_type = protein
                          organism = Homo sapiens
SEQUENCE: 1235
```

```
SCCVPVCCQC K                                                                     11

SEQ ID NO: 1236       moltype = AA  length = 11
FEATURE               Location/Qualifiers
source                1..11
                      mol_type = protein
                      organism = Homo sapiens
SEQUENCE: 1236
SCGCSQCNCC K                                                                     11

SEQ ID NO: 1237       moltype = AA  length = 11
FEATURE               Location/Qualifiers
source                1..11
                      mol_type = protein
                      organism = Homo sapiens
SEQUENCE: 1237
SCGCSQCSCC K                                                                     11

SEQ ID NO: 1238       moltype = AA  length = 11
FEATURE               Location/Qualifiers
source                1..11
                      mol_type = protein
                      organism = Homo sapiens
SEQUENCE: 1238
VCCCVPACSC S                                                                     11

SEQ ID NO: 1239       moltype = AA  length = 11
FEATURE               Location/Qualifiers
source                1..11
                      mol_type = protein
                      organism = Homo sapiens
SEQUENCE: 1239
VCCCVPACSC T                                                                     11
```

PEPTIDE COMPOSITION AND RESPECTIVE USES

CROSS-REFERENCE

This application is a continuation of U.S. application Ser. No. 18/194,372, filed Mar. 31, 2023, which is a continuation of U.S. application Ser. No. 16/439,889, filed Jun. 13, 2019, now U.S. Pat. No. 11,642,298, issued May 9, 2023, which is a continuation of U.S. application Ser. No. 15/030,313, filed Apr. 18, 2016, now U.S. Pat. No. 10,709,655, issued Jul. 14, 2020, which is a U.S. National Stage Entry of International Application PCT/IB2014/065375, filed Oct. 16, 2014, which claims priority to Portuguese Application No. 107244, filed Oct. 18, 2013, all of which are hereby incorporated by reference in their entirety.

SEQUENCE LISTING

The instant application contains a Sequence Listing which has been submitted electronically in XML format and is hereby incorporated by reference in its entirety. Said XML copy, created on Feb. 2, 2023, is named 63230-710-303_SL.xml and is 1,068.431 bytes in size.

TECHNICAL FIELD

The current application corresponds to a composition that comprises at least one peptide, based on keratin and keratin associated proteins, containing 2 to 5 cysteines with the purpose of treatment and cosmetics of animal hair, in preference human hair.

BACKGROUND

Human hair has a significant social role in most of the various world cultures, particularly for female population. Thus, there is a constant desire to improve and change hair characteristics, such as its natural texture. There are several differences in hair characteristics between different human ethnicities, as well as between individuals of the same ethnicity, such as length, thickness, color and texture.

Hair is composed of approximately 65% to 95% protein. The remaining constituents include water, lipids, pigments and trace elements. The majority of the proteins present in human hair correspond to keratin and keratin-associated proteins.

Human hair fiber's structure consists of cuticle, cortex and medulla. The cuticle constitutes about 15% by weight of the hair and consists of overlapping layers of cells, similar to a system of scales, with high content of cysteine. It provides a protective character to the hair fiber. The cortex is the middle region of the hair being responsible for the strength, elasticity and hair color. It is composed of several cell types and represents about 80% of the weight of the hair. The medulla corresponds to a central beam of cells and is absent in some hairs.

Keratins and mainly keratin-associated proteins have high sulfur content, present in the cysteine amino acid. The presence of sulfur is essential to the hair structure, as it allows the formation of disulfide bonds between amino acids of the polypeptide chains, due to oxidation of cysteine. The existence of these bonds is largely responsible for the structure and texture of the hair.

There are several hair styling methods that involve breakage and reestablishment of disulfide bonds, allowing relaxation and straightening of the hair. However, the most effective methods currently used to modulate hair contain harmful chemicals such as sodium hydroxide, potassium hydroxide, lithium hydroxide, guanidine hydroxide, ammonium thioglycolate or sodium sulfate. These methods can damage the scalp and the hair fiber, leading to its weakening and reducing its tensile strength. Formaldehyde, an extremely toxic chemical, is also used in hair straightening products. Other hair treatments that do not involve so much damage to the hair and the consumer are usually very expensive, time-consuming and/or have low efficacy. Thus, there is a constant demand for formulations that efficiently model the hair fiber without damage.

Peptides, proteins, amino acids and its derivatives have also been used in compositions for personal care products, namely hair conditioning and strengthening. For example, the document WO 00/23039 discloses a composition for hair treatment containing intermediate filament proteins, namely artificial keratin. The document EP 0488242 discloses a hair treating agent containing 3% to 10% by weight of cysteine and salts thereof, a polyhydric alcohol or a saccharide containing four to twenty carbon atoms, three or more hydroxyl groups in the molecule and no aldehyde or ketone group.

The current invention is distinguished by the use of peptides, while the other applications refer the use of, respectively, proteins and amino acids in isolation and together with other types of compounds. The peptides in this innovation peptide can penetrate into the human hair in order to improve hair fiber resistance.

The document WO 00/51556 discloses a hair treatment composition that contains four or more discrete amino acids selected from histidine, lysine, methionine, tyrosine, tryptophan or cysteine. This document describes peptides without referring sequences and providing a composition essentially based on histidine, lysine, methionine, tyrosine, tryptophan or cysteine.

The document PT 103484 describes a formulation for cosmetic applications that uses hydrophobic binding domains and/or carbohydrates, in order to enhance its properties and to repair hair damage. The binding domains used are hydrolyzed milk protein, a model of human surfactant protein as well as biologically active and synthetic peptides. The current invention is distinguished by the innovative use of synthetic peptide sequences analogous to keratin proteins instead of surfactant proteins. Furthermore, it does not rely on hydrophobic binding domains and/or carbohydrates, but in other interactions, namely disulfide bonds.

Enzymes have also been used as activating agents for hair treatment, such as in the document WO 00/64405. The document WO 2012/13593 discloses a cosmetic kit for hair conformational change that acts specifically in the disulfide bonds of the hair keratin, through enzyme activating agents and proteolytic enzymes.

As described in the last document there are hair treatments that include actions at the level of the hair disulfide bonds. Below we highlight some examples.

The document WO 97/11672 reports a method for permanent hair processing using tris(2-carboxyethyl)phosphine (TCEP), and other water-soluble tertiary phosphines to break disulfide bonds, whose reaction occurs in acidicic environment. The document U.S. Pat. No. 5,635,170 discloses a composition for permanent shaping of hair based on a keratin reducing agent, which contains N-glycyl-L-cysteine and/or L-cysteinyl-glycine. The pH range of this composition is 6.5 to 9.0. The document WO 2008/081348 refers a method and composition for permanent modulation of hair, through the use of 1% to 30% of N-alkyl-2-mercapto acetamide as a keratin reducing agent. It also contains at least one cationic surfactant for permanently shaping hair and the resulting process. The document WO 2006/001536 describes an agent for permanent hair processing that contains a derivative of mercaptocarboxylic acid, which allows processing and reduction of hair keratin in the acidic and neutral range of the pH. The document U.S. 2010/0272666 discloses a hair cosmetic composition for hair treatment, containing 5 to 50 amino acids, without containing cysteine or its derivatives. Thus, this invention is distinguished by the existence of specific amino acid sequences, which contain cysteine, allowing the formation of disulfide bonds that stabilize and protect the hair fiber.

In a previous article by Fernandes et al. (Fernandes, Lima, Loureiro, Gomes, & Cavaco-Paulo, 2012), it is performed the toxicology evaluation of a peptide sequence for hair care use, containing 13 amino acids with two cysteines in its composition. However, in this article it is not mentioned or suggested that the percentage of cysteine in a peptide sequence may have some effect on the resistance of the hair. Also, in the present innovation, the number of amino acids of each peptide sequence is 6 to 12.

SUMMARY

Thus, the present invention aims to provide a composition for treatment of the hair, including animal and human hair, without the use of chemicals harmful to the hair fiber and consumer health and that does not present the drawbacks found in the state of the art.

The compositions described in the current invention, after prolonged use, provide hair with soft, shiny, undamaged texture and with the desired features. The peptide compositions with a specific number of amino acids and cysteines act synergically providing resistance to strength, toughness and elasticity to the hair. Therefore, the compositions of the current invention are particularly relevant for hair treatment, hair dying, hair perms, etc.

The present application describes a peptide composition for hair treatment, in particular human or animal hair, which comprises at least one peptide with 6-12 amino acids length (namely 6, 7, 8, 9, 10, 11, 12 amino acids), where 2-5 of those amino acids correspond to cysteine, preferably 2, 3, 4 or 5 of those amino acids are cysteines and dermatologically suitable excipients, which penetrates the hair, increasing it resistance and reducing it breakage.

In the embodiment, for improved results, the peptide (or peptides) of the peptide composition for hair care can comprise 10-11 amino acids.

In the embodiment of the peptide composition for hair care treatment, the referred peptides can also contain a percentage of hydrophobic amino acids, not higher than 60%, and preferably less than 41% for better results. Preferably, the composition can also comprise at least one hydrophobic amino acid selected from the following list: phenylalanine, alanine, leucine, methionine, isoleucine, tryptophan, proline, valine or their mixtures.

In yet another embodiment, the amount of cysteine of the peptide composition for hair treatment may vary from 10% to 50% of the total of amino acids of the peptide sequence, preferably 20-30%, and even more preferably 25%.

In an embodiment of the composition, with better results of the peptide (or peptides) of the peptide composition for hair treatment, the sequence of peptide(s) can comprise at least one sequence of the following list with a with a degree of homology greater than or equal to 90%: SEQ.ID NO:1-SEQ.ID NO:1239, preferably with a degree of homology greater than or equal to 91%, 92%, 93%, 94%, 95%, 96%, 97%, 98%, 99%, 100%.

In an embodiment, improved results for the peptide (or peptides) of the peptide composition for hair treatment can comprise at least one of the sequences of the following list with a degree of homology equal or greater than 90%: SEQ.ID NO:5, SEQ.ID NO:75; SEQ.ID NO:94; SEQ.ID NO: 409; SEQ.ID NO:411; SEQ.ID NO:412; SEQ ID. NO:432; SEQ.ID NO:618; SEQ.ID NO:717; SEQ.ID NO:951; SEQ.ID NO:1088; SEQ.ID NO:1131; SEQ.ID NO:1149, preferably with a degree of homology equal or greater than 91%, 92%, 93%, 94%, 95%, 96%, 97%, 98%, 99%, 100%.

In other embodiment, the concentration of the peptide of the peptide composition for hair treatment can vary between 0.001%-20% (w/w), preferably 0.01-5% (w/w).

In yet other embodiment, the peptide composition for hair treatment can comprise at least one excipient, selected from the following list: surfactants, emulsifiers, preservatives, thickeners, organic polymers, humectants, silicones, oils, fragrances, vitamins, buffers.

In another embodiment, the peptide composition for hair treatment can comprise at least one anionic surfactant selected from the following list: alkylbenzene sulfonates, ammonium lauryl sulfate, ammonium lauryl sulfate, ammonium xylenesulfonate, sodium C14-16 olefin sulfonate, sodium cocoyl sarcosinate, sodium laureth sulfate, sodium lauryl sulfate, sodium lauryl sulfoacetate, sodium myreth sulfate, sodium xylenesulfonate, TEA-dodecylbenzenesulfonate, ethyl PEG-15 cocamine sulfate, dioctyl sodium sulfosuccinate, or any mixture thereof.

In an embodiment, the peptide composition for hair treatment can comprise at least one amphoteric surfactant selected from the following list: cocamidopropyl betaine, coco betaine, cocoamphoacetate, cocoamphodipropionate, disodium cocoamphodiacetate, disodium cocoamphodipropionate, lauroamphoacetate, sodium cocoyl isethionate, or any mixture thereof.

In other embodiment, the peptide composition for hair treatment can comprise at least one cationic surfactant selected from the following list: quaternary ammonium compounds, behentrimonium chloride, behentrimonium methosulfate, benzalkonium chloride, betrimonium chloride, binnamidopropyltrimonium chloride, cocotrimonium chloride, dicetyldimonium chloride, dicocodimonium chloride, dihydrogenated tallow dimethylammonium chloride, hydrogenated Palm trimethylammonium chloride, laurtrimonium chloride, quaternium-15, quaternium-18 bentonite, quaternium-22 hectonite, stearalkonium chloride, tallowtrimonium chloride, tricetyldimonium chloride, or any mixture thereof.

In yet other embodiment, the peptide composition for hair treatment can comprise at least one non-ionic surfactant selected from the following list: decyl glucoside, laureth-10 (lauryl ether 10), laureth-23, Laureth-4, PEG-10 sorbitan laurate, polysorbate-(20, 21, 40, 60, 61, 65, 80, 81), PPG-1 trideceth-6, sorbitol, steareth-(2, 10, 15, 20), C11-21 pareth-(3-30), C12-20 acid PEG-8 ester, or their mixtures.

In yet other embodiment, the peptide composition for hair treatment can comprise at least one emulsifier selected from the following list: caprylic/capric/diglyceryl succinate, C10-15 pareth-(2,4,6,8) phosphate, C14-16 glycol palmitate, C18-20 glycol isostearate, ceteareth-(4-60), cocamidopropyl lauryl ether, deceth-(3-10), DIPA-hydrogenated cocoate, dipentaerythrityl hydroxystearate, dipentaerythrityl hydroxyisostearate, dipentaerythrityl hexacaprate/caprylate, dodoxynol-(5,6,7,9,12), nonoxynol-(1-35), octoxynol-(1-70), Octyldodeceth-(2,5,16,20,25), Palm kernel glycerides, or any mixture thereof.

In other embodiment, the peptide composition for hair treatment can comprise at least one preservative selected from the following list: butyl paraben, diazolidinyl urea, DMDM hydantoin, ethyl paraben, imidazolidinyl urea, iodopropynyl butylcarbamate, isobutyl paraben, methyl paraben, methylchloroisothiazolinone, methylisothiazolinone, phenoxyethanol, propyl paraben, sodium benzoate, or any mixture thereof.

In other embodiment, the peptide composition for hair treatment can comprise at least one thickener selected from the following list: aluminum stearates/isostearates/myristates/laurates/palmitates, glycol distearate, hydrogenated castor oil, hydrogenated castor oil hydroxystearate, hydrogenated castor oil isostearate, hydrogenated castor oil stearate, hydrogenated castor PEG-8 esters, PEG-150 distearate, or any mixture thereof.

In other embodiment, the peptide composition for hair treatment can comprise at least one natural polymer derived selected from the following list: carboxymethyl hydroxyethyl celulose, carboxymethyl hydroxypropyl guar, cellulose, ethyl celulose, hydroxybutyl methylcellulose, hydroxyethylcellulose, hydroxymethylcellulose, lauryl polyglucose, or any mixture thereof.

In other embodiment, the peptide composition for hair treatment can comprise at least one humectant selected from the following list: 1,2,6 hexanetriol, dipropylene glycol, glycerin, hexylene glycol, panthenol, phytantriol, propylene glycol, sodium PCA, sorbitol, triethylene glycol, polyglyceryl sorbitol, glucose, fructose, polydextrose, potassium PCA, hydrogenated honey, hyaluronic acid, inositol, hexanediol beeswax, hexanetriol beeswax, hydrolyzed elastin, hydrolyzed collagen, hydrolyzed silk, hydrolyzed keratin, erythritol, capryl glycol, isoceteth-(3-10, 20, 30), isolaureth-(3-10, 20, 30), laneth-(5-50), laureth-(1-30), steareth-(4-20), trideceth-(5-50), or any mixture thereof.

In other embodiment, the peptide composition for hair treatment can comprise at least one cationic polymer selected from the following list: polyquaternium-10, polyquaternium-7, polyquaternium-11 m guar hydroxypropyltrimonium chloride, or any mixture thereof.

In other embodiment, the peptide composition for hair treatment can comprise at least one silicone selected from the following list: amodimethicone, amodimethicone, trideceth-12, cetrimonium, chloride mixture, behenoxy, dimethicone sparingly, cetearyl methicone, cetyl dimethicone, cyclomethicone, cyclopentasiloxane, dimethicone, dimethicone copolyol, dimethicone copolyol, dimethiconol, hydrolyzed wheat protein hydroxypropyl polysiloxane, stearoxy dimethicone sparingly, stearyl dimethicone, trimethylsilylamodimethicone, lauryl methicone copolyol, or any mixture thereof.

In yet other embodiment, the peptide composition for hair treatment can comprise at least one organic oil selected from the following list: mineral oil, paraffin, petrolatum, or any mixture thereof.

In yet other embodiment, the peptide composition for hair treatment can comprise at least one protein selected from the following list: cocodimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed keratin, cocodimonium hydroxypropyl hydrolyzed rice protein, cocodimonium hydroxypropyl hydrolyzed silk, cocodimonium hydroxypropyl hydrolyzed soy protein, cocodimonium hydroxypropyl hydrolyzed wheat protein, cocodimonium hydroxypropyl silk amino acids, cocoyl hydrolyzed collagen, cocoyl hydrolyzed keratin, hydrolyzed keratin, hydrolyzed oat flour, hydrolyzed silk, hydrolyzed silk protein, hydrolyzed soy protein, hydrolyzed wheat protein, hydrolyzed wheat protein, keratin, potassium cocoyl hydrolyzed collagen, TEA-cocoyl hydrolyzed collagen, TEA-cocoyl hydrolyzed soy protein, or any mixture thereof.

In other embodiment, the peptide composition for hair treatment can comprise at least one vitamin selected from the following list: retinol, retinyl palmitate tocopherol acetate, or any mixture thereof.

In other embodiment, the peptide composition for hair treatment can comprise at least one ester emollient selected from the following list: butyl myristate, butyl stearate, C12-15 alkyl benzoate, caprylic/capric triglyceride, cetyl octanoate, cetyl stearate, cetearyl stearate, decyl oleate, dimethyl lauramine isostearate, glyceryl stearate, glyceryl adipate, glyceryl arachidate, glyceryl arachidonate, glyceryl behenate, glyceryl caprate, glyceryl caprylate, glyceryl caprylate/caprate, glyceryl citrate/lactate/linoleate/oleate, glyceryl cocoate, glyceryl diarachidate, glyceryl dibehenate, glyceryl dierucate, glyceryl dihydroxystearate, glyceryl diisopalmitate, glyceryl diisostearate, glyceryl dilaurate, glyceryl dilinoleate, glyceryl dimyristate, glyceryl dioleate, glyceryl dipalmitate, glyceryl dipalmitoleate, glyceryl diricinoleate, glyceryl distearate, glyceryl erucate, glycol stearate, isocetyl stearate, isopropyl myristate, isopropyl palmitate, isopropyl stearate, isostearyl stearate, octyl palmitate, octyl stearate, propylene glycol dicaprylate/dicaprate, sorbitan benzoate, sorbitan caprylate, sorbitan isostearate, Sorbitan laurate, sorbitan tristearate, stearyl stearate, tocopheryl linoleate, or any mixture thereof.

In other embodiment, the peptide composition for hair treatment can comprise at least one alkanolamide selected from the following list: acetamide MEA, cocamide DEA, cocamide MEA, lactamide MEA, lauramide DEA, lauramide DEA, propylene glycol, lauramide MEA, lecithinamide DEA, linoleamide DEA, linoleamide MEA, linoleamide MIPA, myristamide DEA, myristamide MEA, myristamide MIPA, oleamide DEA, oleamide DEA, oleamide MEA, oleamide MIPA, soyamide DEA, stearamide MEA, or any mixture thereof.

In yet other embodiment, the peptide composition for hair treatment can comprise at least one amine selected from the following list: behentamidopropyl dimethylamine, cocamidopropyl dimethylamine, isostearamidopropyl dimethylamine, lauramidopropyl dimethylamine, myristamidopropyl dimethylamine, oleamidopropyl dimethylamine, palmitamidopropyl dimethylamine, stearamidopropyl dimethylamine, tallamidopropyl dimethylamine, or any mixture thereof.

In yet other embodiment, the peptide composition for hair treatment can comprise at least one pH adjuster selected from the following list: ascorbic acid, citric acid, sodium hydroxide, triethanolamine, or any mixture thereof.

In yet other embodiment, the peptide composition for hair treatment can comprise at least one salt selected from the following list: calcium chloride, magnesium chloride, magnesium sulfate, potassium chloride, potassium glycol sulfate, sodium chloride, or any mixture thereof.

In yet other embodiment, the peptide composition for hair treatment can comprise at least one aliphatic alcohol selected from the following list: behenyl alcohol, cetearyl alcohol, cetyl alcohol, isocetyl alcohol, isostearyl alcohol, lauryl alcohol, myristyl alcohol, stearyl alcohol, C30-50 alcohols, lanolin alcohol, or any mixture thereof.

In another embodiment, the peptide composition for hair treatment can comprise at least one UV filter/sunscreen selected from the following list: benzophenone-(2, 3, 4, 5, 6, 7, 8, 9, or 10), benzophenone-4, benzyl salicylate, benzylidene camphor sulfonic acid, bornelone, ethyl cinnamate, ethylhexyl methoxycinnamate (octyl methoxycinnamate), octoxynol-40, octoxynol-20, octyl methoxycinnamate, octyl salicylate, oxybenzone, phenyl ketone, PEG-25 PABA, polyacrylamidomethyl benzylidene camphor, or any mixture thereof.

In other embodiment, the peptide composition for hair treatment can comprise at least one natural oil selected from the following list: coconut oil, jojoba oil, olive oil, palm Oil, safflower oil, sesame seed oil, shea butter, sweet almond oil, wheat germ oil, or any mixture thereof.

In yet other embodiment, the peptide composition for hair treatment can comprise at least one amine oxide selected from the following list: cocamine oxide, lauramine oxide, or any mixture thereof.

In other embodiment, the peptide composition for hair treatment can comprise at least one chelate selected from the following list: diiospropyl oxalate, disodium EDTA, disodium EDTA-copper, HEDTA, oxalic acid, potassium citrate, sodium citrate, dodium oxalate, TEA-EDTA, tetrasodium EDTA, trisodium EDTA, trisodium HEDTA, or any mixture thereof.

In other embodiment, the peptide composition for hair treatment can comprise at least one fatty acid selected from the following list: arichidonic acid, capric acid, coconut fatty acid, lauric acid, linoleic acid, linolenic acid, myristic acid, palmitic acid, pantothenic acid, stearic acid, caproic acid, capryleth-(4, 6, 9) carboxylic acid, isostearic acid, or any mixture thereof In other embodiment, the peptide composition for hair treatment can comprise at least one agent antimicrobial/antibacterial selected from the following list: glyoxal, triclosan, or any mixture thereof.

In other embodiment, the peptide composition for hair treatment can comprise at least one PEG-modified material selected from the following list: PEG-150 pentaerythirtyl tetrastearate, PEG-(-2, -3, -4, -6, -8, -12, -20, -32, -50, -150, -175) distearate, PEG-10 castor oil, PEG-10 cocamine, PEG-10 cocoate, PEG-10 coconut oil esters, PEG-10 glyceryl oleate, PEG-10 glyceryl pibsa tallate, PEG-10 glyceryl stearate, PEG-10 hydrogenated lanolin, PEG-10 hydrogenated tallow amine, PEG-10 isolauryl thioether, PEG-10 isostearate, PEG-10 lanolate, PEG-10 lanolin, PEG-10 laurate, PEG-10 oleate, PEG-10 olive glycerides, PEG-10 polyglyceryl-2 laurate, PEG-10 propylene glycol, PEG-10 sorbitan laurate, PEG-10 soya sterol, PEG-10 soyamine, PEG-10 stearamine, PEG-10 stearate, PEG-10 stearyl benzonium chloride, PEG-10 tallate, PEG-10 tallow aminopropylamine, PEG-100, PEG-100 castor oil, PEG-100 hydrogenated castor oil, PEG-100 lanolin, PEG-100 stearate, PEG-40 hydrogenated castor Oil, PEG-60, PEG-55 propylene glycol distearate, or any mixture thereof.

In other embodiment, the peptide composition for hair treatment can comprise at least one polymer selected from the following list: carbomer, dodecanedioic acid/cetearyl alcohol/glycol copolymer, hydrogenated C6-14 olefin polymers, hydrogenated ethylene/propylene/styrene copolymer: polyacrylic acid, polymethyl methacrylate: polymer, polyvinyl acetate, polyvinyl alcohol, PPG, PPG-25-laureth-25, PPG-5 pentaerithrityl ether, PPG-75-PEG-300-hexylene glycol, polyvinylpyrrolidone, PVP/VA (polyvinylpyrrolidone/vinyl acetate copolymer), sodium carbomer, TEA-carbomer, poloxamer (100-407), poloxamine, polyacrylamidomethylpropane sulfonic acid, polyethylene terephthalate, or any mixture thereof.

In other embodiment, the peptide composition for hair treatment can comprise at least one antistatic agent selected from the following list: apricotamidopropyl ethyldimonium ethosulfate, apricotamidopropyl ethyldimonium lactate, cocamidopropyl ethyldimonium ethosulfate, cocamidopropyl ethyldimonium lactate, lauramidopropyl ethyldimonium ethosulfate, lauramidopropyl ethyldimonium lactate, linoleamidopropyl ethyldimonium ethosulfate, linoleamidopropyl ethyldimonium lactate, myristamidopropyl ethyldimonium ethosulfate, myristamidopropyl ethyldimonium lactate, oleamidopropyl ethyldimonium ethosulfate, oleamidopropyl ethyldimonium lactate, stearamidopropyl ethyldimonium ethosulfate, stearamidopropyl ethyldimonium lactate, or any mixture thereof.

In other embodiment, the peptide composition for hair treatment can comprise at least one alcohol selected from the following list: SD alcohol 40, witch hazel, isopropanol, or any mixture thereof.

In yet other embodiment, the peptide composition for hair treatment can comprise fragrances, oils or any mixture thereof.

In other embodiment, the peptide composition for hair treatment can be used in medicine, veterinary and/or for cosmetics, preferably for the treatment of hair, mainly for animal or human, particularly for treating diseases of the scalp, particularly scalp irritation, alopecia areata, lichen planus, folliculitis keloid of the neck, trichorrhexis nodosa, tricodistrophy, pili torti, tricorrexis invaginata, moniletrix, uncombable hair syndrome.[0058] In other embodiment, the composition may comprise a dye agent linked to the N or C-terminal of the referred peptides.

In yet other embodiment is the use of the described composition for hair coloring.

Other aspect of the embodiment is the use of the described composition as a hair strengthener or as fixer of perms and/or curly hairs.

It is also described in this application shampoo, lotion, serum, cream, conditioner, foam, elixir, oil, aerosol or mask comprising the composition presented in this application.

The present application discloses a composition for hair treatment that comprise, in whole or in part, one or more peptide sequences of 6 to 12 amino acid residues based on keratin and keratin-associated proteins having 2 to 5 cysteine residues, preferably having 3 to 5 residues of cysteine, for treatment and cosmetics of the hair, preferably human hair, chemically pre-treated or not. Thus, the presence of cysteine in the peptide sequence (higher than 10%, preferably more than 15%) in combination with a percentage of hydrophobic amino acids ensures that the peptides can have a lasting fixation in the hair, improving the human hair properties such as elasticity and strength.

Surprisingly, the described peptide compositions in which the peptide(s) comprising 2 to 5 cysteines allow penetration of the peptide(s) and enhance the properties of hair, preferably 3-5 cysteines. Thus, described peptide(s) containing 2-5 cysteine in order to allow hair penetration and enrichment of the hair properties, such as elasticity, resistance, reduce eventual hair damage, as well as improve and change hair characteristics.

The peptide compositions described in the present application surprisingly enrich and improve the properties and characteristics of the hair, such as elasticity, strength and appearance, repairing damaged keratinous fiber. Therefore, formulation's high cysteine content is used to improve and/or change its characteristics, such as hair curl or uncurl. The sequence of peptides can have also preferably a percentage of hydrophobic amino acids not exceeding 60%, improving even further the results. Examples of hydrophobic amino acids are phenylalanine, alanine, leucine, methionine, isoleucine, tryptophan, proline, valine, and others.

In the context of the present description, the peptide composition can also be applied to the hair and in particular to the human hair as, but not limited to, aqueous solution or conventional shampoo or conditioner. It can also be used as a lotion, foam, aerosol, gel, mask, and application formulation with or without subsequent rinsing.

The concentration of peptide to be used depends on several features such as the condition of the hair, the origin and the formulation of the hair care product.

DETAILED DESCRIPTION

It should be understood that the detailed description and specific examples are indicative of preferred embodiments of the invention and are provided to be illustrative only. This patent is not limited to those mentioned applications.

The present application describes a composition for hair treatment that comprises different peptides, which are based in the structure of keratin and keratin associated proteins.

The compositions described in the present application allow surprisingly the dermo-cosmetic treatment of animal hair, including human hair, chemically pre-treated or not. The composition described in the present invention, through the use of specific peptides, allows the preparation of keratinous fiber damages, due to the high binding capacity of the keratin peptides, including through disulfide bridges.

The described compositions improve the properties and characteristics of the hair, such as elasticity, resistance and appearance, repairing putative damages of the hair.

The peptides here defined are peptide sequences which bind with a certain affinity to the hair. The peptides used in this invention are composed by 6 to 12 amino acids and are constituted by a minimum of 2 and a maximum of 5 cysteines, preferably 3-5 cysteines.

The peptide composition for hair treatment described allows a resistance increase due to the presence of the cysteine-rich peptide, which leads to the resistance of the hair even after several rinsing.

Every peptide can be used together or separately, as well as all or part of the peptide sequence in the hair composition. Each peptide sequence contains amino acids with sulfur, specifically cysteine, which interacts with the hair and allows the formation of intermolecular cross-linking, stabilizing the keratinous fiber.

The peptide composition described uses a high content on cysteine in order to enrich the hair properties, such as improve elasticity and resistance, reduce putative damage of the hair, improve and/or change hair characteristics. Regarding the interaction with the keratinous fibers, the cysteine is 10% to 50% of the total amount of amino acids of the peptide sequence. Additionally, the number of amino acids of the peptide sequence is preferable from 6 to 12.

The peptides can be used separately or in combination of two or more peptides. The concentration of the peptide to be used depends on several characteristics, such as hair condition, origin and the formulation of the product for hair treatment. The content of the hair composition of the present invention is as example 1-0.001% (w/w) in mass.

The peptides of the present invention can be prepared by conventional methods of peptide synthesis, well known in the state of the art.

Additionally, many companies provide customized services for peptide synthesis.

An embodiment of the current invention describes peptides that link to the hair, and which sequence of amino acids includes cysteines where the sequence is selected from the group between the sequences ID NO:1 to sequence ID NO:1239.

The sequence of the 1239 peptides referred is listed in the table of the FIG. 1.

As example of hair, it was used virgin human hair tresses, acquired from the International Hair Importers and Products, Inc. (New York). The term virgin hair is applied to all the hair that was never subject or was at least 10 years without making any chemical treatment. Several different hair samples such as African, Asian and Caucasian hair are commercially available in several companies, such as the company mentioned above. Optionally, the hair samples can be treated, for example, using hydrogen peroxide to bleach the hair, needed for techniques such as hair dying.

In the context of this invention, the peptides can be applied to the hair, such as the human hair in the form of, but not limited to, aqueous or conventional preparation of shampoo or conditioner. It can also be in the form of lotion, foam, spray, gel, mask, formulation applied with or without subsequent rinsing.

This invention can be prepared by peptide coupling with an agent of these preparations directly or via a spacer.

This coupling interaction can be performed by covalent or non-covalent bonds, such as hydrogen bond, electrostatic interactions, hydrophobic interactions or van der Waals interactions. The spacer can be used to separate the peptide from the preparation agent, ensuring that the agent does not interfere with the peptide linkage to the hair.

The present invention can be understood more clearly and accurately by reading the following examples, which are indicative of preferred embodiments of the invention. They are provided for illustration in greater detail of the present invention, without introducing any limitation and without being limited to those applications.

EXAMPLES

The examples that are within the scope of the claims represent different embodiments of the invention; all other examples are comparative examples.

Example 1

The present application treats human hair through several commercial formulations with and without the use of the peptides from the sequence ID NO: 5. As The hair was supplied from International Hair Importers and Products, Inc. (New York).

The tests were performed with in human hair after 8 treatments of bleaching, at 50° C. in 0.1 M Na2CO3/NaHCO3 buffer, at pH=9, 10% H2O2, for 1 hour.

Several formulations were tested:
hair serum with 15% PG;
hair mask.

The mask used in this application was a basic commercial formulation with water, denaturing alcohol, propylene glycol, ether dicaprylic, cetylstearyl alcohol, behentrimonium chloride, cetyl ester, polysorbate 20, hydrolyzed wheat protein, hydrolyzed wheat starch, benzyl alcohol and fragrance.

The hair serum used in this application was a basic commercial formulation with water, denaturing alcohol, propylene glycol, polysorbate 20, hydrolyzed wheat protein, hydrolyzed wheat starch, crosslinked polymer alkyl acrylate/C10-30, triethanolamine, benzyl alcohol, fragrance.

Each of the formulations was tested with and without the peptide sequence ID NO:5, which contains in the sequence 15% of cysteine. The formulations containing the peptide SEQ ID NO:5 had a concentration of peptide of 0.1 mg/mL, in a ratio 1:1 (v/v).

To demonstrate the effect was also tested:
a peptide whose sequence does not contain cysteine, with approximately 41% hydrophobic amino acids;
a peptide which contains in it sequence 8% cysteine, with approximately 58% hydrophobic amino acids.

The hair mask was applied to the hair after 8 bleaching treatments, being left to act for 15 minutes, mimicking the procedure indicated in commercial masks. Posteriorly, the hair was washed. The serum was applied to the hair after 8 bleaching treatments, being left to act for 1 hour at 37° C. Posteriorly, the hair was not washed, as in typical commercial procedures the serum should be applied in dry hair. The hair was also tested after 5 applications.

The peptide from the sequence ID NO: 5 was able to penetrate in the hair fiber for all the formulations.

After the treatment, mechanical tests were performed, using a cell with 2.5 N maximum load and a deformation rate of 1.5 mm/min. Each hair was individually mounted in the tensile jig by means of a paper template with a fixed gauge length of 20 mm.

TABLE 1

Young modulus of virgin hair without treatments and after 8 times bleaching treatments.

| Hair type | Young modulus (MPa) |
| --- | --- |
| Virgin hair | 6579 |
| Hair after 8 time bleaching | 5294 |
| Serum(with a 15% cysteine and 50% hydrophobic amino acids peptide) | 7149 |
| Serum for comparison(with a 41% hydrophobic amino acid without cysteine peptide) | 6180 |
| Serum for comparison (with a 8% cysteine and 58% hydrophobic amino acid peptide) | 6456 |
| Serum for comparison (without peptide) | 6034 |

TABLE 2

Young modulus for different types of hair treatment.

| Type of treatment | Young modulus after 1 application (MPa) | Young modulus after 5 applications (MPa) |
| --- | --- | --- |
| Serum (with a 15% cysteine and 50% hydrophobic amino acid peptide) | 7149 | 7318 |
| Serum for comparison (without peptide) | 6034 | 6112 |
| Mask (with a 15% cysteine and 50% hydrophobic amino acid peptide) | 6175 | 7075 |
| Mask for comparison(without peptide) | 5514 | 5685 |

The peptide in these treatments is the peptide from sequence ID NO: 5. The formulations which contain the sequence ID NO:5 induce an increase in mechanical resistance of the damaged hair. After 5 applications, the hair treated with the sequence ID NO: 5 maintain the high resistance, having a higher increase in the resistance than without the peptide.

Example 2

This example discloses the treatment of human hair with peptides containing cysteine, and in this case the peptide containing the sequence ID NO: 409, based in the assumption that small peptides are able to penetrate in the hair fiber cuticle.

The hair was supplied from International Hair Importers and Products, Inc. (New York). Hair fibers were pre-treated by bleaching. The formulation was tested in different hair types:
virgin hair washed, with the cuticle intact and absence of chemical damages;
hair after 8 bleaching treatments, at 50° C. in 0.1 M Na2CO3/NaHCO3 buffer, at pH=9, 10% H2O2, for 1 hour.

The incorporation of the peptides was performed by direct application in the hair surface. The mechanical resistance tests were performed after the treatment of the hair with the peptide.

The measurements of mechanical resistance were performed using a cell with 2.5 N maximum load and a deformation rate of 1.5 mm/min. Each hair was individually mounted in the tensile jig by means of a paper template with a fixed gauge length of 20 mm.

As for the results obtained for the mechanical test showed that compared to the control, i.e., virgin hair without bleaching or peptide treatment (Young modulus: 4142±590 MPa), bleaching reduced the Young modulus (2478±567 MPa), while the treatment with the peptide sequence ID NO: 409 after bleaching increased the Young modulus to higher valued than the virgin hair with no treatment (5649±1022 MPa).

Example 3

This example discloses the treatment of human hair with a composition comprising peptides. In this example, the peptide with the sequence ID NO: 412 was tested. The hair was supplied from International Hair Importers and Products, Inc. (New York).

The formulation was tested in different hair types:
virgin hair washed, with the cuticle intact and absence of chemical damages;
hair after reduction treatment, at 37° C. in phosphate buffer at pH=8, with 3M GndHCl and 0.05M DTT for 2 hours.

For the treatment with the peptide SEQ ID NO: 412, concentrations of 0.01% (w/w) were used.

The average of the Young's modulus for relaxed hair is 3002 MPa, while for relaxed hair fiber after peptide treatment at 0.01% is 4190 MPa. The Young modulus value for virgin hair without treatment is 5214 MPa.

In the maximum load test, for the relaxed hair fiber, the maximum resistance was 96 MPa, while for the hair fiber relaxed after peptide treatment 126 MPa and for the virgin hair with no treatment 203 MPa.

Regarding hair stretching, the relaxed hair has an average of 51%, while after treatment with the peptide sequence ID NO: 412, has a stretching of 72%. For virgin hair, the average of hair stretching is 58%.

Therefore, it is evident that the peptides are capable to prevent the hair surface degradation and consequently, the hair treated with these peptides has a longer life span.

Example 4

In order to assess the interactions between the keratin and some peptides, a keratin solution was prepared. This procedure was performed by immersing African hair, acquired from the International Hair Importers and Products, Inc. (New York), in a solution containing 8 M urea, 0.2 M sodium dodecyl sulfate and 0.5 M sodium bisulfate. The mixture was heated to 50° C. for 24 h in a shaker bath. The solution was dialyzed for several days against double-distilled water. The keratin solution was then concentrated using AMICON with a 3 kDa cut-off. The keratin was then conjugated with Alexa Fluor 647 carboxylic acid, succinimidyl ester in DMSO anhydrous 5%.

The reaction was incubated for 1 h 30 min at room temperature and in the dark. The Alexa Fluor 647 that did not link to the keratin solution was separated by centrifugation in AMICON with a 3 kDa cut-off for 1 h at 25° C. and 5000×g.

The keratin was then diluted to 1 µg/mL in blocking buffer (3% BSA in tris-buffered saline (TBS) with 0.05% Tween 20). The peptides tested were SEQ.ID NO:179, SEQ.ID NO:75, SEQ.ID NO:432, SEQ.ID NO:951, SEQ.ID NO:1108, SEQ.ID NO:1131 and a peptide containing 13 amino acids, including 2 cysteines (X3CX5CX3), where X represents one of known amino acid residues, with the exception of cysteine residue that is represented by the letter C. This peptide is similar to the one tested in Fernandes et al. (Fernandes, Lima, Loureiro, Gomes, & Cavaco-Paulo, 2012).

Several peptides in a concentration of 15 fmol/mm2, were attached to a glass through a hydrophilic linked moiety, and were then incubated with the keratin, marked with Alexa Fluor 647, for 2 hours at 37° C.

After incubation, the glasses were rinsed in successive washing solutions: TBS+0.1% Tween 20 and blocking buffer with 3% BSA in TBS+0.1% Tween 20, for 3 minutes in each solution.

The imaging of the glasses was performed in Agilent G2565CA Microarray Scanner System. Three replicas of each peptide incubation were performed and analyzed.

TABLE 3

Normalized intensity levels of peptide sequences.

| Sequence | Number of amino acids | Cysteine content | Hydrophobic amino acids content | Intensity level (average ± standard deviation) |
|---|---|---|---|---|
| SEQ. ID NO: 179 | 10 | 20% | 50% | 0.990 ± 0.014 |
| SEQ. ID NO: 75 | 10 | 30% | 60% | 1.000 ± 0.000 |
| SEQ. ID NO: 432 | 10 | 30% | 40% | 1.000 ± 0.000 |
| SEQ. ID NO: 951 | 10 | 40% | 30% | 1.000 ± 0.000 |
| SEQ. ID NO: 1108 | 11 | 46% | 18% | 1.000 ± 0.000 |
| SEQ. ID NO: 1131 | 11 | 46% | 9% | 1.000 ± 0.000 |
| $X_3CX_5CX_3$ | 13 | 15% | 38% | 0.184 ± 0.084 |

The peptides SEQ.ID NO:75, SEQ.ID NO:432, SEQ.ID NO:951, SEQ.ID NO:1108, SEQ.ID NO:1131, with percentage of cysteine ranging from 30% to 46%, such as and percentage of hydrophobic amino acids ranging from 9% to 60% were able to obtain an intensity of 1, indicating a very high affinity to keratin. The peptide SEQ.ID NO:179, with 20% and 50% of cysteine and hydrophobic content, respectively showed a slightly inferior but still very high intensity (0.990±0.014). These peptides were compared with a peptide similar to the one described in Fernandes et al. (Fernandes, Lima, Loureiro, Gomes, & Cavaco-Paulo, 2012) containing 2 cysteines in a 13 amino acids sequence. The reduced percentage of cysteine (15%) and higher number of amino acids in the sequence (13 amino acids) lead to a decrease in the intensity to 0.184±0.084, showing an inferior affinity to keratin. This suggests that the higher number of amino acids difficult the reaction of the peptide with the hair keratins. This inferior affinity to keratin leads to less fixation of the peptides in the hair in posterior treatments and consequently providing less improvements in the recovery of the hair characteristics.

LIST OF PEPTIDE SEQUENCES

The sequences of peptides are described by one letter code of amino acids. The code is as follows:

```
Amino acid-One Letter Code
Histidine-H
Arginine-R
Lysine-K
Isoleucine-I
Phenylalanine-F
Leucine-L
Tryptophan-W
Alanine-A
Methionine-M
Proline-P
Valine-V
Cysteine-C
Asparagine-N
Glycine-G
Serine-S
Glutamine-Q
Tyrosine-Y
Threonine-T
Aspartic acid-D
Glutamic acid-E
```

SEQ. ID NO: 1

APCAPRPSCG

SEQ. ID NO: 2

EACVPSVPCP

SEQ. ID NO: 3

ESCGTASGCA

SEQ. ID NO: 4

GLCAGTSACL

SEQ. ID NO: 5

GVCGPSPPCI

SEQ. ID NO: 6

HGCTLPGACN

SEQ. ID NO: 7

HSCTLPGACN

SEQ. ID NO: 8

KDCLQNSLCE

SEQ. ID NO: 9

LPCLPAASCG

| | |
|---|---|
| LPCYFTGSCN | SEQ. ID NO: 10 |
| NFCLPSLSCR | SEQ. ID NO: 11 |
| NPCATTNACD | SEQ. ID NO: 12 |
| NPCATTNACE | SEQ. ID NO: 13 |
| NPCATTNACS | SEQ. ID NO: 14 |
| NPCGLRARCG | SEQ. ID NO: 15 |
| NPCGPRSRCG | SEQ. ID NO: 16 |
| NPCSTPASCT | SEQ. ID NO: 17 |
| NPCSTSPSCV | SEQ. ID NO: 18 |
| PACTSSSPCS | SEQ. ID NO: 19 |
| SKCHESTVCP | SEQ. ID NO: 20 |
| SPCVPRTVCV | SEQ. ID NO: 21 |
| SSCSVETACL | SEQ. ID NO: 22 |
| SVCSSGVNCR | SEQ. ID NO: 23 |
| TACPLPGTCH | SEQ. ID NO: 24 |
| TNCSPRPICV | SEQ. ID NO: 25 |
| TSCVPPAPCT | SEQ. ID NO: 26 |
| TTCTSSNTCE | SEQ. ID NO: 27 |
| VPCVPSVPCT | SEQ. ID NO: 28 |
| ATCGPSACIT | SEQ. ID NO: 29 |
| GPCISNPCGL | SEQ. ID NO: 30 |
| GPCLSNPCTS | SEQ. ID NO: 31 |
| GSCVTNPCGP | SEQ. ID NO: 32 |
| LTCFSITCSS | SEQ. ID NO: 33 |
| NPCSTPSCTT | SEQ. ID NO: 34 |
| PSCVTAPCAP | SEQ. ID NO: 35 |
| SDCSSTHCSP | SEQ. ID NO: 36 |
| SLCLPPTCHT | SEQ. ID NO: 37 |
| SLCNLGSCGP | SEQ. ID NO: 38 |
| SPCLVGNCAW | SEQ. ID NO: 39 |
| TACLPGTCAT | SEQ. ID NO: 40 |
| TSCLPALCLP | SEQ. ID NO: 41 |
| TSCSSRPCVP | SEQ. ID NO: 42 |
| TTCGGGSCGV | SEQ. ID NO: 43 |
| VNCRPELCLG | SEQ. ID NO: 44 |
| YVCQPMACLP | SEQ. ID NO: 45 |
| AFSCISACGP | SEQ. ID NO: 46 |
| GSVCSAPCNG | SEQ. ID NO: 47 |
| GVVCGDLCAS | SEQ. ID NO: 48 |
| GVVCGDLCVS | SEQ. ID NO: 49 |
| LTGCLLPCYF | SEQ. ID NO: 50 |
| NEDCKLPCNP | SEQ. ID NO: 51 |
| NFSCVSACGP | SEQ. ID NO: 52 |
| PPTCHTACPL | SEQ. ID NO: 53 |
| PQPCATACKP | SEQ. ID NO: 54 |
| SEDCKLPCNP | SEQ. ID NO: 55 |
| SLGCRTSCSS | SEQ. ID NO: 56 |
| SLSCRTSCSS | SEQ. ID NO: 57 |
| SSSCPLGCTM | SEQ. ID NO: 58 |
| TGSCNSPCLV | SEQ. ID NO: 59 |
| TSSCPLGCTM | SEQ. ID NO: 60 |
| VGSCGSSCRK | SEQ. ID NO: 61 |
| VGVCGGSCKR | SEQ. ID NO: 62 |
| VSNCNWFCEG | SEQ. ID NO: 63 |

-continued

| Sequence | SEQ. ID NO. |
|---|---|
| ACGPRPGRCC | 64 |
| ACGPRPSRCC | 65 |
| CAPRPSCGPC | 66 |
| CEPCSAYVIC | 67 |
| CGLRARCGPC | 68 |
| CGPRPGRCCI | 69 |
| CGPRPSRCCI | 70 |
| CGPRSRCGPC | 71 |
| CGTSQKGCCN | 72 |
| CHGCTLPGAC | 73 |
| CHSCTLPGAC | 74 |
| CLPCLPAASC | 75 |
| CLPPTCHTAC | 76 |
| CLSNPCTSCV | 77 |
| CLVGNCAWCE | 78 |
| CNPCSTPASC | 79 |
| CNPCSTPSCT | 80 |
| CNPCSTSPSC | 81 |
| CNSPCLVGNC | 82 |
| CRTSCSSRPC | 83 |
| CSLKEHCSAC | 84 |
| CSPRPICVPC | 85 |
| CSSTMSYSCC | 86 |
| CSTPASCTSC | 87 |
| CSTPSCTTCV | 88 |
| CTSCVPPAPC | 89 |
| CTSSNTCEPC | 90 |

-continued

| Sequence | SEQ. ID NO. |
|---|---|
| CVPPAPCTPC | 91 |
| CVPPSCHGCT | 92 |
| CVPPSCHSCT | 93 |
| DCKLPCNPCA | 94 |
| DCKLPCNPCS | 95 |
| PCGTSQKGCC | 96 |
| PCLSNPCTSC | 97 |
| PCLVGNCAWC | 98 |
| PCNPCSTPSC | 99 |
| PCSTPSCTTC | 100 |
| PCTTCGPTCG | 101 |
| PCVPPSCHGC | 102 |
| PCVPPSCHSC | 103 |
| SCCLPSLGCR | 104 |
| SCSEELQCCQ | 105 |
| SCSPCSTTCT | 106 |
| ASCSTSGTCG | 107 |
| ASCYIPVGCQ | 108 |
| ASCYVPVSCQ | 109 |
| AVCTLPSSCQ | 110 |
| DLCPTSVSCG | 111 |
| EICWEPTSCQ | 112 |
| ETCGEPTSCQ | 113 |
| ETCNETTSCQ | 114 |
| ETCWRPNSCQ | 115 |
| GYCGYRPFCF | 116 |
| KTCWEPASCQ | 117 |

-continued

| | |
|---|---|
| KTCWEPTSCQ | SEQ. ID NO: 118 |
| LDCVDTTPCK | SEQ. ID NO: 119 |
| LGCYGSFCG | SEQ. ID NO: 120 |
| NSCGYGSGCG | SEQ. ID NO: 121 |
| NYCPSNTMCE | SEQ. ID NO: 122 |
| PACVTSYSCR | SEQ. ID NO: 123 |
| PDCHVEGTCL | SEQ. ID NO: 124 |
| PDCRVEGTCL | SEQ. ID NO: 125 |
| PICSEPSPCS | SEQ. ID NO: 126 |
| PICYIFKPCQ | SEQ. ID NO: 127 |
| PLCYISNSCQ | SEQ. ID NO: 128 |
| PPCGQPTPCS | SEQ. ID NO: 129 |
| PPCHIPQPCV | SEQ. ID NO: 130 |
| PSCGRLASCG | SEQ. ID NO: 131 |
| PSCSESSICQ | SEQ. ID NO: 132 |
| PSCSEVTSCP | SEQ. ID NO: 133 |
| PSCSTSGTCG | SEQ. ID NO: 134 |
| PSCSVSSGCQ | SEQ. ID NO: 135 |
| PSCTESDSCK | SEQ. ID NO: 136 |
| PSCYQTSSCG | SEQ. ID NO: 137 |
| PTCFLLNSCQ | SEQ. ID NO: 138 |
| PTCSVTSSCQ | SEQ. ID NO: 139 |
| PTCWLLNNCH | SEQ. ID NO: 140 |
| PTCYQRTSCV | SEQ. ID NO: 141 |
| PTCYRRTSCV | SEQ. ID NO: 142 |
| PTCYVVKRCP | SEQ. ID NO: 143 |
| PVCFEATICE | SEQ. ID NO: 144 |
| PVCFEATVCE | SEQ. ID NO: 145 |
| PVCSRPASCS | SEQ. ID NO: 146 |
| PVCSWVPACS | SEQ. ID NO: 147 |
| QTCNESSYCL | SEQ. ID NO: 148 |
| QTCWEPTSCQ | SEQ. ID NO: 149 |
| SFCRLGYGCG | SEQ. ID NO: 150 |
| SFCRRGSGCG | SEQ. ID NO: 151 |
| SLCGYGYGCG | SEQ. ID NO: 152 |
| SLCSTEVSCG | SEQ. ID NO: 153 |
| SNCFGQLNCL | SEQ. ID NO: 154 |
| SPCGQPTPCS | SEQ. ID NO: 155 |
| SSCDQSSSCA | SEQ. ID NO: 156 |
| SSCGQSSSCA | SEQ. ID NO: 157 |
| SVCPEPVSCP | SEQ. ID NO: 158 |
| TFCSFDKSCR | SEQ. ID NO: 159 |
| TICSSDKSCR | SEQ. ID NO: 160 |
| TLCVESSPCH | SEQ. ID NO: 161 |
| TPCYQQSSCQ | SEQ. ID NO: 162 |
| VTCSRQTTCI | SEQ. ID NO: 163 |
| YGCGYGSGCG | SEQ. ID NO: 164 |
| YGCGYGSGCR | SEQ. ID NO: 165 |
| YGCIHSTHCG | SEQ. ID NO: 166 |
| AACEPSACQS | SEQ. ID NO: 167 |
| AACEPSPCQS | SEQ. ID NO: 168 |
| AACTMSVCSS | SEQ. ID NO: 169 |
| ADCLGGICLP | SEQ. ID NO: 170 |
| ALCLPSSCHS | SEQ. ID NO: 171 |

| Sequence | SEQ ID NO |
|---|---|
| ALCSPSTCQL | SEQ. ID NO: 172 |
| APCLALVCAP | SEQ. ID NO: 173 |
| APCLSLVCTP | SEQ. ID NO: 174 |
| APCLTLVCTP | SEQ. ID NO: 175 |
| APCVALLCRP | SEQ. ID NO: 176 |
| ASCGSLLCRP | SEQ. ID NO: 177 |
| ASCLSFLCRP | SEQ. ID NO: 178 |
| ASCVSLLCRP | SEQ. ID NO: 179 |
| AVCEPSPCQS | SEQ. ID NO: 180 |
| AVCLPVSCQS | SEQ. ID NO: 181 |
| AVCVPVRCQS | SEQ. ID NO: 182 |
| AVCVPVSCQS | SEQ. ID NO: 183 |
| DLCSPSTCQL | SEQ. ID NO: 184 |
| DSCGSSSCGP | SEQ. ID NO: 185 |
| DSCVQSNCFP | SEQ. ID NO: 186 |
| FNCSTRNCSS | SEQ. ID NO: 187 |
| GGCGSYGCSQ | SEQ. ID NO: 188 |
| GSCGFGSCYG | SEQ. ID NO: 189 |
| GSCSSRKCFS | SEQ. ID NO: 190 |
| GVCLPSTCPH | SEQ. ID NO: 191 |
| HSCEGYLCYS | SEQ. ID NO: 192 |
| IVCAAPSCQS | SEQ. ID NO: 193 |
| KTCSTTGCDP | SEQ. ID NO: 194 |
| LACVSQPCQS | SEQ. ID NO: 195 |
| LGCGYGGCGY | SEQ. ID NO: 196 |
| LSCGSRSCSS | SEQ. ID NO: 197 |
| LVCTPVSCVS | SEQ. ID NO: 198 |
| NGCQETYCEP | SEQ. ID NO: 199 |
| NSCRSLSCGS | SEQ. ID NO: 200 |
| PACVISTCPR | SEQ. ID NO: 201 |
| PGCLNQSCGS | SEQ. ID NO: 202 |
| PPCGTAPCLT | SEQ. ID NO: 203 |
| PPCTTALCRP | SEQ. ID NO: 204 |
| PPCYLVSCTP | SEQ. ID NO: 205 |
| PRCTRPICEP | SEQ. ID NO: 206 |
| PSCPVSSCAQ | SEQ. ID NO: 207 |
| PSCQPSVCVP | SEQ. ID NO: 208 |
| PSCSVSNCYQ | SEQ. ID NO: 209 |
| PSCSVSSCAQ | SEQ. ID NO: 210 |
| PSCTSVLCRP | SEQ. ID NO: 211 |
| PTCKSPSCEP | SEQ. ID NO: 212 |
| PTCVISSCPR | SEQ. ID NO: 213 |
| PTCVISTCPR | SEQ. ID NO: 214 |
| PTCYQTICFR | SEQ. ID NO: 215 |
| PVCGGVSCHT | SEQ. ID NO: 216 |
| PVCGRVSCHT | SEQ. ID NO: 217 |
| PVCNKPVCFV | SEQ. ID NO: 218 |
| PVCPTPTCSV | SEQ. ID NO: 219 |
| PVCRSTYCVP | SEQ. ID NO: 220 |
| PVCSKSVCYV | SEQ. ID NO: 221 |
| PVCSRPACYS | SEQ. ID NO: 222 |
| PVCYVPTCSE | SEQ. ID NO: 223 |
| QFCLSKSCQP | SEQ. ID NO: 224 |
| RPCERTACQS | SEQ. ID NO: 225 |

| Sequence | SEQ ID NO |
|---|---|
| RSCQTSFCGF | SEQ. ID NO: 226 |
| RSCSSLGCGS | SEQ. ID NO: 227 |
| RSCYSVGCGS | SEQ. ID NO: 228 |
| RVCLPGSCDS | SEQ. ID NO: 229 |
| SFCGFPSCST | SEQ. ID NO: 230 |
| SFCGYPSCST | SEQ. ID NO: 231 |
| SGCDPASCQP | SEQ. ID NO: 232 |
| SGCGGSGCGG | SEQ. ID NO: 233 |
| SGCQPSSCLA | SEQ. ID NO: 234 |
| SHCQPPHCQL | SEQ. ID NO: 235 |
| SICQPATCVA | SEQ. ID NO: 236 |
| SLCVPVSCRP | SEQ. ID NO: 237 |
| SNCLPTSCQP | SEQ. ID NO: 238 |
| SPCLVSSCQP | SEQ. ID NO: 239 |
| SPCQQSSCQE | SEQ. ID NO: 240 |
| SPCQQSYCVP | SEQ. ID NO: 241 |
| SPCSPAVCVS | SEQ. ID NO: 242 |
| SRCQQPSCQP | SEQ. ID NO: 243 |
| SRCYRPHCGQ | SEQ. ID NO: 244 |
| SSCAPIYCRR | SEQ. ID NO: 245 |
| SSCAPVYCRR | SEQ. ID NO: 246 |
| SSCGKGGCGS | SEQ. ID NO: 247 |
| SSCGKRGCGS | SEQ. ID NO: 248 |
| SSCLPVSCRP | SEQ. ID NO: 249 |
| SSCQPAYCTS | SEQ. ID NO: 250 |
| SSCQPSYCRQ | SEQ. ID NO: 251 |
| SSCQPVVCEP | SEQ. ID NO: 252 |
| SSCTAVVCRP | SEQ. ID NO: 253 |
| SSCYQPFCRS | SEQ. ID NO: 254 |
| SSCYRPICGS | SEQ. ID NO: 255 |
| SSCYRPTCGS | SEQ. ID NO: 256 |
| SVCMSGSCQA | SEQ. ID NO: 257 |
| SVCSDQGCDQ | SEQ. ID NO: 258 |
| SVCSDQGCGL | SEQ. ID NO: 259 |
| SVCSDQGCGQ | SEQ. ID NO: 260 |
| SVCSDQGCSQ | SEQ. ID NO: 261 |
| SVCSDQSCGQ | SEQ. ID NO: 262 |
| SVCSHQGCGQ | SEQ. ID NO: 263 |
| SVCSHQGCGR | SEQ. ID NO: 264 |
| SVCVPVSCRP | SEQ. ID NO: 265 |
| SYCRQASCVS | SEQ. ID NO: 266 |
| TACEPSACQS | SEQ. ID NO: 267 |
| TICTASPCQP | SEQ. ID NO: 268 |
| TSCPETSCLP | SEQ. ID NO: 269 |
| TSCQMTNCEQ | SEQ. ID NO: 270 |
| TSCQPVHCET | SEQ. ID NO: 271 |
| TSCQPVLCKS | SEQ. ID NO: 272 |
| TSCQPVLCVP | SEQ. ID NO: 273 |
| TSCVGFVCQP | SEQ. ID NO: 274 |
| TSCVSNPCQV | SEQ. ID NO: 275 |
| TTCFQPTCVS | SEQ. ID NO: 276 |
| TTCFQPTCVT | SEQ. ID NO: 277 |
| TTCFQPTCVY | SEQ. ID NO: 278 |
| TTCISNPCST | SEQ. ID NO: 279 |

| | |
|---|---|
| TWCQGSSCQP | SEQ. ID NO: 280 |
| VGCQSSVCVP | SEQ. ID NO: 281 |
| VPCQPSTCVF | SEQ. ID NO: 282 |
| VSCEPSPCQS | SEQ. ID NO: 283 |
| VSCGGPICLP | SEQ. ID NO: 284 |
| VSCKPVLCVA | SEQ. ID NO: 285 |
| VSCPSTSCRP | SEQ. ID NO: 286 |
| VSCQSSVCMP | SEQ. ID NO: 287 |
| VSCTRIVCVA | SEQ. ID NO: 288 |
| VTCEPSPCQS | SEQ. ID NO: 289 |
| VTCQTTVCRP | SEQ. ID NO: 290 |
| YGCYEGCRY | SEQ. ID NO: 291 |
| AGSCQPSCSE | SEQ. ID NO: 292 |
| ALLCRPLCGV | SEQ. ID NO: 293 |
| ALVCEPVCLR | SEQ. ID NO: 294 |
| ATICEPSCSV | SEQ. ID NO: 295 |
| ATTCEPSCSV | SEQ. ID NO: 296 |
| ATVCEPSCSV | SEQ. ID NO: 297 |
| EGTCLPPCYL | SEQ. ID NO: 298 |
| FSTCRPSCSG | SEQ. ID NO: 299 |
| GFVCQPMCSH | SEQ. ID NO: 300 |
| GLDCGYGCGY | SEQ. ID NO: 301 |
| GLGCGYGCGY | SEQ. ID NO: 302 |
| GLGCSYGCGH | SEQ. ID NO: 303 |
| GLGCSYGCGL | SEQ. ID NO: 304 |
| GSGCGYGCGY | SEQ. ID NO: 305 |
| GTGCGYGCGY | SEQ. ID NO: 306 |
| GVSCHTTCYR | SEQ. ID NO: 307 |
| GYACNFPCSY | SEQ. ID NO: 308 |
| GYGCYGCGF | SEQ. ID NO: 309 |
| HSPCQASCYV | SEQ. ID NO: 310 |
| HTSCSPACQP | SEQ. ID NO: 311 |
| HTSCSSGCQP | SEQ. ID NO: 312 |
| IRWCHPDCHV | SEQ. ID NO: 313 |
| IRWCRPDCRV | SEQ. ID NO: 314 |
| ISSCGTGCGI | SEQ. ID NO: 315 |
| KGGCGSGCGG | SEQ. ID NO: 316 |
| KGGCGSSCSQ | SEQ. ID NO: 317 |
| LVTCQDSCGS | SEQ. ID NO: 318 |
| LVTCQESCQP | SEQ. ID NO: 319 |
| MSICSSACTD | SEQ. ID NO: 320 |
| MSICSSACTN | SEQ. ID NO: 321 |
| MSVCSSACSD | SEQ. ID NO: 322 |
| PAICEPSCSV | SEQ. ID NO: 323 |
| PASCQKSCYR | SEQ. ID NO: 324 |
| PIYCRRTCYH | SEQ. ID NO: 325 |
| PNSCQTLCVE | SEQ. ID NO: 326 |
| PQPCVPTCFL | SEQ. ID NO: 327 |
| PSACQSGCTS | SEQ. ID NO: 328 |
| PSPCEPSCSE | SEQ. ID NO: 329 |
| PSPCQASCYI | SEQ. ID NO: 330 |
| PSPCQSGCIS | SEQ. ID NO: 331 |
| PSPCQSGCTD | SEQ. ID NO: 332 |
| PSPCQSGCTS | SEQ. ID NO: 333 |

-continued

| | |
|---|---|
| PTACQPTCYQ | SEQ. ID NO: 334 |
| PTACQPTCYR | SEQ. ID NO: 335 |
| PTPCSTTCRT | SEQ. ID NO: 336 |
| PTSCQKSCYR | SEQ. ID NO: 337 |
| PTSCQPSCES | SEQ. ID NO: 338 |
| PTSCQTSCTL | SEQ. ID NO: 339 |
| PVICEPSCSV | SEQ. ID NO: 340 |
| PVSCVPVCSG | SEQ. ID NO: 341 |
| PVTCVPRCTR | SEQ. ID NO: 342 |
| PVYCRRTCYH | SEQ. ID NO: 343 |
| PVYCRRTCYY | SEQ. ID NO: 344 |
| PVYCVPVCSG | SEQ. ID NO: 345 |
| QPGCESPCEP | SEQ. ID NO: 346 |
| QQSCVSSCRR | SEQ. ID NO: 347 |
| QTSCGSSCGQ | SEQ. ID NO: 348 |
| QTTCHPSCGM | SEQ. ID NO: 349 |
| QTTCRPSCGV | SEQ. ID NO: 350 |
| RGGCGSGCGG | SEQ. ID NO: 351 |
| RLACYSLCSG | SEQ. ID NO: 352 |
| RPACYRPCYS | SEQ. ID NO: 353 |
| RPFCFRRCYS | SEQ. ID NO: 354 |
| RPICRPICSG | SEQ. ID NO: 355 |
| RPLCYRRCYS | SEQ. ID NO: 356 |
| RSPCQASCYV | SEQ. ID NO: 357 |
| RVSCHTTCYR | SEQ. ID NO: 358 |
| SAICRPTCPR | SEQ. ID NO: 359 |
| SDSCKRDCKK | SEQ. ID NO: 360 |
| SEGCGSGCGG | SEQ. ID NO: 361 |
| SFLCRPACSR | SEQ. ID NO: 362 |
| SGGCGSGCGG | SEQ. ID NO: 363 |
| SGGCGSSCGG | SEQ. ID NO: 364 |
| SGSCQAACGQ | SEQ. ID NO: 365 |
| SLLCHPVCKS | SEQ. ID NO: 366 |
| SLLCHPVCRS | SEQ. ID NO: 367 |
| SLLCRPACSP | SEQ. ID NO: 368 |
| SLLCRPACSR | SEQ. ID NO: 369 |
| SLLCRPICRP | SEQ. ID NO: 370 |
| SLLCRPMCSR | SEQ. ID NO: 371 |
| SLLCRPTCSR | SEQ. ID NO: 372 |
| SLLCRPVCQP | SEQ. ID NO: 373 |
| SLLCRPVCRP | SEQ. ID NO: 374 |
| SLLCRPVCRS | SEQ. ID NO: 375 |
| SLLCRPVCSR | SEQ. ID NO: 376 |
| SNPCQVTCSR | SEQ. ID NO: 377 |
| SRGCGSGCGG | SEQ. ID NO: 378 |
| SRSCQSPCYR | SEQ. ID NO: 379 |
| SRSCQSSCYR | SEQ. ID NO: 380 |
| SSGCGYGCGY | SEQ. ID NO: 381 |
| SSGCPMACPG | SEQ. ID NO: 382 |
| SSICQPICSE | SEQ. ID NO: 383 |
| SSPCHTSCYY | SEQ. ID NO: 384 |
| SSPCQPTCYV | SEQ. ID NO: 385 |
| SSPCQQSCYV | SEQ. ID NO: 386 |
| SSPCQTSCYR | SEQ. ID NO: 387 |

| | | | |
|---|---|---|---|
| SSSCQQSCRV | SEQ. ID NO: 388 | CAPSPCQPAC | SEQ. ID NO: 415 |
| STVCQPACGV | SEQ. ID NO: 389 | CAPVYCRRTC | SEQ. ID NO: 416 |
| TDNCQETCGE | SEQ. ID NO: 390 | CASSPCQQAC | SEQ. ID NO: 417 |
| TQPCYEPCLP | SEQ. ID NO: 391 | CASSSCQPAC | SEQ. ID NO: 418 |
| TSSCGTGCGI | SEQ. ID NO: 392 | CASSSCQQSC | SEQ. ID NO: 419 |
| TSSCQPSCGR | SEQ. ID NO: 393 | CCGNFSSHSC | SEQ. ID NO: 420 |
| TSSCTTPCYQ | SEQ. ID NO: 394 | CCGYGGLGCG | SEQ. ID NO: 421 |
| TSVCLPGCLN | SEQ. ID NO: 395 | CCNYYGNSCG | SEQ. ID NO: 422 |
| TTVCLPGCLN | SEQ. ID NO: 396 | CCNYYRNSCG | SEQ. ID NO: 423 |
| VANCQAPCST | SEQ. ID NO: 397 | CCSRNFSSCS | SEQ. ID NO: 424 |
| VDDCPESCWP | SEQ. ID NO: 398 | CDAGSCQPSC | SEQ. ID NO: 425 |
| VKRCPSVCPE | SEQ. ID NO: 399 | CDPCSLQEGC | SEQ. ID NO: 426 |
| VSSCQPSCSE | SEQ. ID NO: 400 | CDPSPCEPSC | SEQ. ID NO: 427 |
| YEGCRYGCGH | SEQ. ID NO: 401 | CDPVICEPSC | SEQ. ID NO: 428 |
| YGRCRHGCHS | SEQ. ID NO: 402 | CDQGLCQETC | SEQ. ID NO: 429 |
| YGYCRPSCYG | SEQ. ID NO: 403 | CEATTCEPSC | SEQ. ID NO: 430 |
| YRDCQKTCWE | SEQ. ID NO: 404 | CELPCGTPSC | SEQ. ID NO: 431 |
| YRGCQEICWE | SEQ. ID NO: 405 | CEPAICEPSC | SEQ. ID NO: 432 |
| YRGCQETCWR | SEQ. ID NO: 406 | CEPPCGTAPC | SEQ. ID NO: 433 |
| YRGCQQTCWE | SEQ. ID NO: 407 | CEPPCSAPSC | SEQ. ID NO: 434 |
| YRSCRPSCYG | SEQ. ID NO: 408 | CEPRSCASSC | SEQ. ID NO: 435 |
| GGVCGPSPPC | SEQ. ID NO: 409 | CEPSACQSGC | SEQ. ID NO: 436 |
| GVCGPSPPCI | SEQ. ID NO: 410 | CEPSCSVSNC | SEQ. ID NO: 437 |
| VCGPSPPCIT | SEQ. ID NO: 411 | CEPSCSVSSC | SEQ. ID NO: 438 |
| CGPSPPCITT | SEQ. ID NO: 412 | CEPSPCQSGC | SEQ. ID NO: 439 |
| CAPIYCRRTC | SEQ. ID NO: 413 | CEPTACQPTC | SEQ. ID NO: 440 |
| CAPSPCQASC | SEQ. ID NO: 414 | CEPTSCQTSC | SEQ. ID NO: 441 |

-continued

| | |
|---|---|
| CEPVCLRPVC | SEQ. ID NO: 442 |
| CETSSCQPRC | SEQ. ID NO: 443 |
| CETTCFQPTC | SEQ. ID NO: 444 |
| CFQPTCVSSC | SEQ. ID NO: 445 |
| CFQPTCVTSC | SEQ. ID NO: 446 |
| CFQPTCVYSC | SEQ. ID NO: 447 |
| CGCGFRRLGC | SEQ. ID NO: 448 |
| CGCGYRGLDC | SEQ. ID NO: 449 |
| CGCNGYYGCY | SEQ. ID NO: 450 |
| CGFGSCYGCG | SEQ. ID NO: 451 |
| CGGSGCGGSC | SEQ. ID NO: 452 |
| CGGSGSSCCV | SEQ. ID NO: 453 |
| CGGVSCHTTC | SEQ. ID NO: 454 |
| CGKGGCGSCG | SEQ. ID NO: 455 |
| CGKRGCGSCG | SEQ. ID NO: 456 |
| CGQDLCQETC | SEQ. ID NO: 457 |
| CGQTSCGSSC | SEQ. ID NO: 458 |
| CGQVLCQETC | SEQ. ID NO: 459 |
| CGRDLCQETC | SEQ. ID NO: 460 |
| CGRVSCHTTC | SEQ. ID NO: 461 |
| CGSCGFGSCY | SEQ. ID NO: 462 |
| CGSCGGSKGC | SEQ. ID NO: 463 |
| CGSGCGVPVC | SEQ. ID NO: 464 |
| CGSLLCRPTC | SEQ. ID NO: 465 |
| CGSRCYVPVC | SEQ. ID NO: 466 |
| CGSSSCGPQC | SEQ. ID NO: 467 |
| CGSVCSDQGC | SEQ. ID NO: 468 |
| CGSVCSDQSC | SEQ. ID NO: 469 |
| CGSVCSHQGC | SEQ. ID NO: 470 |
| CGSYGCSQCS | SEQ. ID NO: 471 |
| CGVCLPSTCP | SEQ. ID NO: 472 |
| CGYEGCRYGC | SEQ. ID NO: 473 |
| CGYGCYGCG | SEQ. ID NO: 474 |
| CGYGGCGYGC | SEQ. ID NO: 475 |
| CGYGSFCGCG | SEQ. ID NO: 476 |
| CGYGSGCGCG | SEQ. ID NO: 477 |
| CHPSCGMSSC | SEQ. ID NO: 478 |
| CHPSCSISSC | SEQ. ID NO: 479 |
| CHPTCYQTIC | SEQ. ID NO: 480 |
| CHTSCSPACQ | SEQ. ID NO: 481 |
| CHTSCSSGCQ | SEQ. ID NO: 482 |
| CHTTCYRPAC | SEQ. ID NO: 483 |
| CHTTCYRPTC | SEQ. ID NO: 484 |
| CIHSPCQASC | SEQ. ID NO: 485 |
| CIHSTHCGCN | SEQ. ID NO: 486 |
| CIRSPCQASC | SEQ. ID NO: 487 |
| CISSCYRPQC | SEQ. ID NO: 488 |
| CISSPCQQSC | SEQ. ID NO: 489 |
| CKPCSSQSSC | SEQ. ID NO: 490 |
| CKPSCSQSSC | SEQ. ID NO: 491 |
| CKPVCFKPIC | SEQ. ID NO: 492 |
| CKPVCYVPTC | SEQ. ID NO: 493 |
| CKPVSCVPVC | SEQ. ID NO: 494 |
| CKPVYCVPVC | SEQ. ID NO: 495 |

-continued

| | |
|---|---|
| CKTVYCKPIC | SEQ. ID NO: 496 |
| CLNQSCGSNC | SEQ. ID NO: 497 |
| CLNQSCGSSC | SEQ. ID NO: 498 |
| CLPGCLNQSC | SEQ. ID NO: 499 |
| CLPGSCDSCS | SEQ. ID NO: 500 |
| CLPPCYLVSC | SEQ. ID NO: 501 |
| CLPTSCQPSC | SEQ. ID NO: 502 |
| CLSFLCRPAC | SEQ. ID NO: 503 |
| CLVSSCQPSC | SEQ. ID NO: 504 |
| CMPSPCQPAC | SEQ. ID NO: 505 |
| CMSGSCQAAC | SEQ. ID NO: 506 |
| CNESSYCLPC | SEQ. ID NO: 507 |
| CPASCVSLLC | SEQ. ID NO: 508 |
| CPMACPGSPC | SEQ. ID NO: 509 |
| CPSSCTAVVC | SEQ. ID NO: 510 |
| CPVTCEPSPC | SEQ. ID NO: 511 |
| CQAACEPSAC | SEQ. ID NO: 512 |
| CQAACEPSPC | SEQ. ID NO: 513 |
| CQAACGQSVC | SEQ. ID NO: 514 |
| CQAPCSTKNC | SEQ. ID NO: 515 |
| CQAVCEPSPC | SEQ. ID NO: 516 |
| CQDSCGSSSC | SEQ. ID NO: 517 |
| CQHSSCQPTC | SEQ. ID NO: 518 |
| CQISSCGTGC | SEQ. ID NO: 519 |
| CQKSSCQPAC | SEQ. ID NO: 520 |
| CQPMCSHAAC | SEQ. ID NO: 521 |
| CQPPCTTALC | SEQ. ID NO: 522 |
| CQPSCESSFC | SEQ. ID NO: 523 |
| CQPSCSESTC | SEQ. ID NO: 524 |
| CQPSCTSVLC | SEQ. ID NO: 525 |
| CQPTCGGSSC | SEQ. ID NO: 526 |
| CQPTCSRPSC | SEQ. ID NO: 527 |
| CQPVCPTPTC | SEQ. ID NO: 528 |
| CQPVLCKSSC | SEQ. ID NO: 529 |
| CQPVVCEPSC | SEQ. ID NO: 530 |
| CQQPSCQPAC | SEQ. ID NO: 531 |
| CQQSCRVPVC | SEQ. ID NO: 532 |
| CQQSCYVPVC | SEQ. ID NO: 533 |
| CQQSGCQPAC | SEQ. ID NO: 534 |
| CQQSSCHPAC | SEQ. ID NO: 535 |
| CQQSSCKPAC | SEQ. ID NO: 536 |
| CQQSSCQLAC | SEQ. ID NO: 537 |
| CQQSSCQPAC | SEQ. ID NO: 538 |
| CQQSSCQPTC | SEQ. ID NO: 539 |
| CQQSSCQSAC | SEQ. ID NO: 540 |
| CQQSSCVSCV | SEQ. ID NO: 541 |
| CQQSYCVPVC | SEQ. ID NO: 542 |
| CQSGCISSCT | SEQ. ID NO: 543 |
| CQSGCTDSCT | SEQ. ID NO: 544 |
| CQSGCTSSCT | SEQ. ID NO: 545 |
| CQSSCYRPTC | SEQ. ID NO: 546 |
| CQSVCYQPTC | SEQ. ID NO: 547 |
| CQSVYCQPTC | SEQ. ID NO: 548 |
| CQTACEPSAC | SEQ. ID NO: 549 |

| | |
|---|---|
| CQTSSCGTGC | SEQ. ID NO: 550 |
| CQTTCHPSCG | SEQ. ID NO: 551 |
| CQTTCRPSCG | SEQ. ID NO: 552 |
| CQTTCYRTTC | SEQ. ID NO: 553 |
| CQTTRCRTTC | SEQ. ID NO: 554 |
| CQVTCEPSPC | SEQ. ID NO: 555 |
| CRNTSCQPTC | SEQ. ID NO: 556 |
| CRPACSPLAC | SEQ. ID NO: 557 |
| CRPACSRLAC | SEQ. ID NO: 558 |
| CRPACSRPAC | SEQ. ID NO: 559 |
| CRPMCSRPAC | SEQ. ID NO: 560 |
| CRPSCGQTTC | SEQ. ID NO: 561 |
| CRPSCGVSSC | SEQ. ID NO: 562 |
| CRPSCSISSC | SEQ. ID NO: 563 |
| CRPSCSQTTC | SEQ. ID NO: 564 |
| CRPSYCGQSC | SEQ. ID NO: 565 |
| CRPSYCISSC | SEQ. ID NO: 566 |
| CRPSYCQTTC | SEQ. ID NO: 567 |
| CRPTCSRLAC | SEQ. ID NO: 568 |
| CRPTCSSGSC | SEQ. ID NO: 569 |
| CRPTSCQNTC | SEQ. ID NO: 570 |
| CRPVCRSTYC | SEQ. ID NO: 571 |
| CRPVCSRPAC | SEQ. ID NO: 572 |
| CRPVTCVPRC | SEQ. ID NO: 573 |
| CRQSSCQPAC | SEQ. ID NO: 574 |
| CRTTCFHPIC | SEQ. ID NO: 575 |
| CRTTCFQPTC | SEQ. ID NO: 576 |
| CRTTCYRPSC | SEQ. ID NO: 577 |
| CRTTYCRPSC | SEQ. ID NO: 578 |
| CRVTCEPSPC | SEQ. ID NO: 579 |
| CRYGCGHRGC | SEQ. ID NO: 580 |
| CSAPCVALLC | SEQ. ID NO: 581 |
| CSDDSGSCCQ | SEQ. ID NO: 582 |
| CSEDSSSCCQ | SEQ. ID NO: 583 |
| CSEDSYSCCQ | SEQ. ID NO: 584 |
| CSEGCGSGCG | SEQ. ID NO: 585 |
| CSESSPSCCQ | SEQ. ID NO: 586 |
| CSESSSSCCQ | SEQ. ID NO: 587 |
| CSFDKSCRCG | SEQ. ID NO: 588 |
| CSGASSLCCQ | SEQ. ID NO: 589 |
| CSGASSPCCQ | SEQ. ID NO: 590 |
| CSGASSSCCQ | SEQ. ID NO: 591 |
| CSGASTSCCQ | SEQ. ID NO: 592 |
| CSGGCGSGCG | SEQ. ID NO: 593 |
| CSGGCGSSCG | SEQ. ID NO: 594 |
| CSGISSSCCQ | SEQ. ID NO: 595 |
| CSKDSSSCCQ | SEQ. ID NO: 596 |
| CSKGACGSCG | SEQ. ID NO: 597 |
| CSLSCGSRSC | SEQ. ID NO: 598 |
| CSQDLCQETC | SEQ. ID NO: 599 |
| CSRGCGSGCG | SEQ. ID NO: 600 |
| CSRLSSACCG | SEQ. ID NO: 601 |
| CSSCGKGGCG | SEQ. ID NO: 602 |
| CSSCGKRGCG | SEQ. ID NO: 603 |

| | |
|---|---|
| CSSDKSCRCG | SEQ. ID NO: 604 |
| CSSGNFSSCC | SEQ. ID NO: 605 |
| CSSSGCGSFC | SEQ. ID NO: 606 |
| CSSSGCGSSC | SEQ. ID NO: 607 |
| CSTPCYQPIC | SEQ. ID NO: 608 |
| CSTTCRTSSC | SEQ. ID NO: 609 |
| CSWVPACSCT | SEQ. ID NO: 610 |
| CTFSPCQQAC | SEQ. ID NO: 611 |
| CTMSVCSSAC | SEQ. ID NO: 612 |
| CTRPICEPCR | SEQ. ID NO: 613 |
| CTSSPCQHAC | SEQ. ID NO: 614 |
| CTSSPCQQAC | SEQ. ID NO: 615 |
| CTSSPCQQSC | SEQ. ID NO: 616 |
| CTSSSCQQAC | SEQ. ID NO: 617 |
| CVALLCRPLC | SEQ. ID NO: 618 |
| CVALVCEPVC | SEQ. ID NO: 619 |
| CVFSSCNTTC | SEQ. ID NO: 620 |
| CVGFVCQPMC | SEQ. ID NO: 621 |
| CVPRCTRPIC | SEQ. ID NO: 622 |
| CVPSPCQVAC | SEQ. ID NO: 623 |
| CVPSRCQASC | SEQ. ID NO: 624 |
| CVPSSCQASC | SEQ. ID NO: 625 |
| CVPVCNKPVC | SEQ. ID NO: 626 |
| CVPVCSKSVC | SEQ. ID NO: 627 |
| CVPVRCKPVC | SEQ. ID NO: 628 |
| CVSLLCRPAC | SEQ. ID NO: 629 |
| CVSLLCRPMC | SEQ. ID NO: 630 |
| CVSLLCRPTC | SEQ. ID NO: 631 |
| CVSLLCRPVC | SEQ. ID NO: 632 |
| CVSNPCQVTC | SEQ. ID NO: 633 |
| CVSRCYRPHC | SEQ. ID NO: 634 |
| CVSSCFRPQC | SEQ. ID NO: 635 |
| CVSSICQPIC | SEQ. ID NO: 636 |
| CVSSPCQPTC | SEQ. ID NO: 637 |
| CVVSCTPPSC | SEQ. ID NO: 638 |
| CVVSCTPPTC | SEQ. ID NO: 639 |
| CYCPKNSIFC | SEQ. ID NO: 640 |
| CYEPCLPRGC | SEQ. ID NO: 641 |
| CYRRCYSSCY | SEQ. ID NO: 642 |
| GCCGYGGLGC | SEQ. ID NO: 643 |
| GCGGCGSGCA | SEQ. ID NO: 644 |
| GCGGCGSGCG | SEQ. ID NO: 645 |
| GCGGCGSSCG | SEQ. ID NO: 646 |
| GCGGCSSSCG | SEQ. ID NO: 647 |
| GCGGSGSSCC | SEQ. ID NO: 648 |
| GCGSGCAGCG | SEQ. ID NO: 649 |
| GCGSGCGGCG | SEQ. ID NO: 650 |
| GCGSGCGGCS | SEQ. ID NO: 651 |
| GCGSSCGGCD | SEQ. ID NO: 652 |
| GCGSSCGGCG | SEQ. ID NO: 653 |
| GCGSSCSQCS | SEQ. ID NO: 654 |
| GCGYSSSCCG | SEQ. ID NO: 655 |
| GCKGGCGSCG | SEQ. ID NO: 656 |
| GCSGCSGGCG | SEQ. ID NO: 657 |

| | |
|---|---|
| ICSGASSLCC | SEQ. ID NO: 658 |
| ICSGASSPCC | SEQ. ID NO: 659 |
| MCCNYYGNSC | SEQ. ID NO: 660 |
| MCCNYYRNSC | SEQ. ID NO: 661 |
| MCYGYGCGCG | SEQ. ID NO: 662 |
| NCCSRNFSSC | SEQ. ID NO: 663 |
| PCSLQEGCCR | SEQ. ID NO: 664 |
| PCSSQSSCCV | SEQ. ID NO: 665 |
| SCCAPASSCQ | SEQ. ID NO: 666 |
| SCCAPASTCQ | SEQ. ID NO: 667 |
| SCCAPTSSCQ | SEQ. ID NO: 668 |
| SCCGYRPLCY | SEQ. ID NO: 669 |
| SCCVPASSCQ | SEQ. ID NO: 670 |
| SCCVPTSSCQ | SEQ. ID NO: 671 |
| SCGCSKGACG | SEQ. ID NO: 672 |
| SCGGCDSSCG | SEQ. ID NO: 673 |
| SCGGCGSGCG | SEQ. ID NO: 674 |
| SCGGCGSSCG | SEQ. ID NO: 675 |
| SCGGCKGGCG | SEQ. ID NO: 676 |
| SCGGSKGCCG | SEQ. ID NO: 677 |
| SCGSGCRGCG | SEQ. ID NO: 678 |
| SCYGCGYGCI | SEQ. ID NO: 679 |
| TCCVPVPSCG | SEQ. ID NO: 680 |
| TCSDDSGSCC | SEQ. ID NO: 681 |
| TCSEDSSSCC | SEQ. ID NO: 682 |
| TCSEDSYSCC | SEQ. ID NO: 683 |
| TCSESSPSCC | SEQ. ID NO: 684 |
| TCSESSSSCC | SEQ. ID NO: 685 |
| TCSKDSSSCC | SEQ. ID NO: 686 |
| TCSRLSSACC | SEQ. ID NO: 687 |
| VCCQPTPICD | SEQ. ID NO: 688 |
| VCSEDSSSCC | SEQ. ID NO: 689 |
| VCSGASSLCC | SEQ. ID NO: 690 |
| VCSGASSPCC | SEQ. ID NO: 691 |
| VCSGASSSCC | SEQ. ID NO: 692 |
| VCSGASTSCC | SEQ. ID NO: 693 |
| VCSGDSSCCQ | SEQ. ID NO: 694 |
| VCSGISSSCC | SEQ. ID NO: 695 |
| YCVPIPSCCA | SEQ. ID NO: 696 |
| CASSCCTPSC | SEQ. ID NO: 697 |
| CCDNCPPPCH | SEQ. ID NO: 698 |
| CCEPCLPRGC | SEQ. ID NO: 699 |
| CCGAASSCCR | SEQ. ID NO: 700 |
| CCGCGGSGCG | SEQ. ID NO: 701 |
| CCGPSSSCCQ | SEQ. ID NO: 702 |
| CCGSGCGGCG | SEQ. ID NO: 703 |
| CCKPYCSQCS | SEQ. ID NO: 704 |
| CCMPVSSCCA | SEQ. ID NO: 705 |
| CCNYYRNCCG | SEQ. ID NO: 706 |
| CCPSCVVSSC | SEQ. ID NO: 707 |
| CCPSYCVSSC | SEQ. ID NO: 708 |
| CCQPICGSSC | SEQ. ID NO: 709 |
| CCQPICVTSC | SEQ. ID NO: 710 |
| CCQPTCLSSC | SEQ. ID NO: 711 |

| | |
|---|---|
| CCQPTCLTSC | SEQ. ID NO: 712 |
| CCQPTCVASC | SEQ. ID NO: 713 |
| CCQPTCVTSC | SEQ. ID NO: 714 |
| CCQPYCHPTC | SEQ. ID NO: 715 |
| CCQQSSCVSC | SEQ. ID NO: 716 |
| CCQSSCFKPC | SEQ. ID NO: 717 |
| CCQSSCSKPC | SEQ. ID NO: 718 |
| CCQSSCYKPC | SEQ. ID NO: 719 |
| CCQTICRSTC | SEQ. ID NO: 720 |
| CCQTTCHPSC | SEQ. ID NO: 721 |
| CCQTTCRPSC | SEQ. ID NO: 722 |
| CCRVPTCSCS | SEQ. ID NO: 723 |
| CCSPGCQPTC | SEQ. ID NO: 724 |
| CCSSGCGSSC | SEQ. ID NO: 725 |
| CCSSSCGSCG | SEQ. ID NO: 726 |
| CCTQEQNCCE | SEQ. ID NO: 727 |
| CCVPIPSCCA | SEQ. ID NO: 728 |
| CCVPISSCCA | SEQ. ID NO: 729 |
| CCVPVCYQCK | SEQ. ID NO: 730 |
| CCVPVPSCCA | SEQ. ID NO: 731 |
| CCVPVPSCCV | SEQ. ID NO: 732 |
| CCVPVSSCCA | SEQ. ID NO: 733 |
| CDSSCCQPSC | SEQ. ID NO: 734 |
| CDTCPPPCCK | SEQ. ID NO: 735 |
| CEPCRRPVCC | SEQ. ID NO: 736 |
| CEPSCCQPVC | SEQ. ID NO: 737 |
| CEPSCCSAVC | SEQ. ID NO: 738 |
| CETSCCQPSC | SEQ. ID NO: 739 |
| CETTCCRTTC | SEQ. ID NO: 740 |
| CFSGCGSSCC | SEQ. ID NO: 741 |
| CGCSQSNCCK | SEQ. ID NO: 742 |
| CGCSQSSCCK | SEQ. ID NO: 743 |
| CGGCGGCGGC | SEQ. ID NO: 744 |
| CGGCGGGCCG | SEQ. ID NO: 745 |
| CGGCGSGCCV | SEQ. ID NO: 746 |
| CGGCGSSCCV | SEQ. ID NO: 747 |
| CGGGCCGSSC | SEQ. ID NO: 748 |
| CGGSCCGSSC | SEQ. ID NO: 749 |
| CGQSCCRPAC | SEQ. ID NO: 750 |
| CGQSCCRPVC | SEQ. ID NO: 751 |
| CGSCGCSQCN | SEQ. ID NO: 752 |
| CGSCGCSQCS | SEQ. ID NO: 753 |
| CGSFCCQSSC | SEQ. ID NO: 754 |
| CGSGCCVPVC | SEQ. ID NO: 755 |
| CGSSCCGSGC | SEQ. ID NO: 756 |
| CGSSCCQPCY | SEQ. ID NO: 757 |
| CGSSCCQPIC | SEQ. ID NO: 758 |
| CGSSCCQPSC | SEQ. ID NO: 759 |
| CGSSCCQSSC | SEQ. ID NO: 760 |
| CGSSCCVPIC | SEQ. ID NO: 761 |
| CGSSCCVPVC | SEQ. ID NO: 762 |
| CGSSCSQCSC | SEQ. ID NO: 763 |
| CGYGSCCGCG | SEQ. ID NO: 764 |
| CHPRCCISSC | SEQ. ID NO: 765 |

| | |
|---|---|
| CHPSCCESSC | SEQ. ID NO: 766 |
| CHPSCCISSC | SEQ. ID NO: 767 |
| CHPTCCQNTC | SEQ. ID NO: 768 |
| CHPTCCQTIC | SEQ. ID NO: 769 |
| CHPVCCQTTC | SEQ. ID NO: 770 |
| CHPVCKSTCC | SEQ. ID NO: 771 |
| CHPVCRSTCC | SEQ. ID NO: 772 |
| CISSCCHPSC | SEQ. ID NO: 773 |
| CISSCCKPSC | SEQ. ID NO: 774 |
| CISSCCRPSC | SEQ. ID NO: 775 |
| CISSCTPSCC | SEQ. ID NO: 776 |
| CISSSCCPSC | SEQ. ID NO: 777 |
| CKAVCCVPTC | SEQ. ID NO: 778 |
| CKPCCSQASC | SEQ. ID NO: 779 |
| CKPCCSQSRC | SEQ. ID NO: 780 |
| CKPCCSQSSC | SEQ. ID NO: 781 |
| CKPCCSSSGC | SEQ. ID NO: 782 |
| CKPCSCFSGC | SEQ. ID NO: 783 |
| CKPCSCSSGC | SEQ. ID NO: 784 |
| CKPCYCSSGC | SEQ. ID NO: 785 |
| CKPICCVPVC | SEQ. ID NO: 786 |
| CKPQCCQSVC | SEQ. ID NO: 787 |
| CKPSCCQTTC | SEQ. ID NO: 788 |
| CKPVCCAPTC | SEQ. ID NO: 789 |
| CKPVCCKPIC | SEQ. ID NO: 790 |
| CKPVCCKSIC | SEQ. ID NO: 791 |
| CKPVCCLPTC | SEQ. ID NO: 792 |
| CKPVCCVPTC | SEQ. ID NO: 793 |
| CKPVCCVPVC | SEQ. ID NO: 794 |
| CKPVCCVSTC | SEQ. ID NO: 795 |
| CKPYCCQSSC | SEQ. ID NO: 796 |
| CKPYCSQCSC | SEQ. ID NO: 797 |
| CKSNCCKPVC | SEQ. ID NO: 798 |
| CKTVCCKPVC | SEQ. ID NO: 799 |
| CLPPCCVVSC | SEQ. ID NO: 800 |
| CLTSCCQPSC | SEQ. ID NO: 801 |
| CNPCCSQSSC | SEQ. ID NO: 802 |
| CPESCCELPC | SEQ. ID NO: 803 |
| CPESCCEPHC | SEQ. ID NO: 804 |
| CPESCCEPPC | SEQ. ID NO: 805 |
| CPFSCPTTCC | SEQ. ID NO: 806 |
| CPGDCFTCCT | SEQ. ID NO: 807 |
| CPSCVVSSCC | SEQ. ID NO: 808 |
| CPSYCVSSCC | SEQ. ID NO: 809 |
| CPTTCCRTTC | SEQ. ID NO: 810 |
| CQETCCRPSC | SEQ. ID NO: 811 |
| CQHACCVPVC | SEQ. ID NO: 812 |
| CQNTCCRTTC | SEQ. ID NO: 813 |
| CQPACCQPTC | SEQ. ID NO: 814 |
| CQPACCTASC | SEQ. ID NO: 815 |
| CQPACCTSSC | SEQ. ID NO: 816 |
| CQPACCTTSC | SEQ. ID NO: 817 |
| CQPACCVPVC | SEQ. ID NO: 818 |
| CQPACCVSSC | SEQ. ID NO: 819 |

| | |
|---|---|
| CQPCCHPTCY | SEQ. ID NO: 820 |
| CQPCCRPTSC | SEQ. ID NO: 821 |
| CQPICCGSSC | SEQ. ID NO: 822 |
| CQPICGSSCC | SEQ. ID NO: 823 |
| CQPICVTSCC | SEQ. ID NO: 824 |
| CQPNCCRPSC | SEQ. ID NO: 825 |
| CQPRCCETSC | SEQ. ID NO: 826 |
| CQPSCCRPAC | SEQ. ID NO: 827 |
| CQPSCCSTPC | SEQ. ID NO: 828 |
| CQPSCCSTTC | SEQ. ID NO: 829 |
| CQPSCCVPSC | SEQ. ID NO: 830 |
| CQPSCCVSSC | SEQ. ID NO: 831 |
| CQPTCCGSSC | SEQ. ID NO: 832 |
| CQPTCCHPSC | SEQ. ID NO: 833 |
| CQPTCCQPTC | SEQ. ID NO: 834 |
| CQPTCCRPRC | SEQ. ID NO: 835 |
| CQPTCCRPSC | SEQ. ID NO: 836 |
| CQPTCCRTTC | SEQ. ID NO: 837 |
| CQPTCLSSCC | SEQ. ID NO: 838 |
| CQPTCLTSCC | SEQ. ID NO: 839 |
| CQPTCVASCC | SEQ. ID NO: 840 |
| CQPTCVTSCC | SEQ. ID NO: 841 |
| CQPVCCQPTC | SEQ. ID NO: 842 |
| CQPYCHPTCC | SEQ. ID NO: 843 |
| CQQACCMPVC | SEQ. ID NO: 844 |
| CQQACCVPIC | SEQ. ID NO: 845 |
| CQQACCVPVC | SEQ. ID NO: 846 |
| CQQSCCVPVC | SEQ. ID NO: 847 |
| CQQSCCVSVC | SEQ. ID NO: 848 |
| CQSMCCQPTC | SEQ. ID NO: 849 |
| CQSNCCVPVC | SEQ. ID NO: 850 |
| CQSSCCKPCS | SEQ. ID NO: 851 |
| CQSSCCQSSC | SEQ. ID NO: 852 |
| CQSSCCVPVC | SEQ. ID NO: 853 |
| CQSSCFKPCC | SEQ. ID NO: 854 |
| CQSSCSKPCC | SEQ. ID NO: 855 |
| CQSVCCQPTC | SEQ. ID NO: 856 |
| CQTICRSTCC | SEQ. ID NO: 857 |
| CQTTCCRPSC | SEQ. ID NO: 858 |
| CQTTCCRTTC | SEQ. ID NO: 859 |
| CRATCCRPSC | SEQ. ID NO: 860 |
| CRGCGPSCCA | SEQ. ID NO: 861 |
| CRPACCETTC | SEQ. ID NO: 862 |
| CRPACCQNTC | SEQ. ID NO: 863 |
| CRPCCWATTC | SEQ. ID NO: 864 |
| CRPICRPACC | SEQ. ID NO: 865 |
| CRPLCCQTTC | SEQ. ID NO: 866 |
| CRPQCCQSVC | SEQ. ID NO: 867 |
| CRPQCCQTTC | SEQ. ID NO: 868 |
| CRPRCCISSC | SEQ. ID NO: 869 |
| CRPSCCESSC | SEQ. ID NO: 870 |
| CRPSCCETTC | SEQ. ID NO: 871 |
| CRPSCCISSC | SEQ. ID NO: 872 |
| CRPSCCKPQC | SEQ. ID NO: 873 |

| | |
|---|---|
| CRPSCCMSSC | SEQ. ID NO: 874 |
| CRPSCCQTTC | SEQ. ID NO: 875 |
| CRPSCCRPSC | SEQ. ID NO: 876 |
| CRPSCCVSRC | SEQ. ID NO: 877 |
| CRPSCCVSSC | SEQ. ID NO: 878 |
| CRPTCCETTC | SEQ. ID NO: 879 |
| CRPTCCQNTC | SEQ. ID NO: 880 |
| CRPTCCQTTC | SEQ. ID NO: 881 |
| CRPVCCDPCS | SEQ. ID NO: 882 |
| CRPVCCQTTC | SEQ. ID NO: 883 |
| CRPVCQPACC | SEQ. ID NO: 884 |
| CRPVCRPACC | SEQ. ID NO: 885 |
| CRPVCRPTCC | SEQ. ID NO: 886 |
| CRPVCRSTCC | SEQ. ID NO: 887 |
| CRPYCCESSC | SEQ. ID NO: 888 |
| CRRPVCCDPC | SEQ. ID NO: 889 |
| CRSQCCQSVC | SEQ. ID NO: 890 |
| CRTTCCHPSC | SEQ. ID NO: 891 |
| CRTTCCQPIC | SEQ. ID NO: 892 |
| CRTTCCQPTC | SEQ. ID NO: 893 |
| CRTTCCRPSC | SEQ. ID NO: 894 |
| CRTTCCRTTC | SEQ. ID NO: 895 |
| CSCSSCGSCA | SEQ. ID NO: 896 |
| CSCSSCGSCG | SEQ. ID NO: 897 |
| CSCTSCGSCG | SEQ. ID NO: 898 |
| CSPACQPTCC | SEQ. ID NO: 899 |
| CSPGCQPTCC | SEQ. ID NO: 900 |
| CSPSCCQTTC | SEQ. ID NO: 901 |
| CSQCSCYKPC | SEQ. ID NO: 902 |
| CSQSNCCKPC | SEQ. ID NO: 903 |
| CSQSSCCKPC | SEQ. ID NO: 904 |
| CSSGCGSCCQ | SEQ. ID NO: 905 |
| CSSGCGSSCC | SEQ. ID NO: 906 |
| CSSGCQPACC | SEQ. ID NO: 907 |
| CSSSCCQPSC | SEQ. ID NO: 908 |
| CSTPCCQPTC | SEQ. ID NO: 909 |
| CSTTCCQPIC | SEQ. ID NO: 910 |
| CTAVVCRPCC | SEQ. ID NO: 911 |
| CTDSCTPSCC | SEQ. ID NO: 912 |
| CTPSCCQPAC | SEQ. ID NO: 913 |
| CTRPICEPCC | SEQ. ID NO: 914 |
| CTSSCTPSCC | SEQ. ID NO: 915 |
| CVPACSCSSC | SEQ. ID NO: 916 |
| CVPACSCTSC | SEQ. ID NO: 917 |
| CVPVCCKPVC | SEQ. ID NO: 918 |
| CVPVCCVPTC | SEQ. ID NO: 919 |
| CVPVCCVPVC | SEQ. ID NO: 920 |
| CVSCVSSPCC | SEQ. ID NO: 921 |
| CVSRCCRPQC | SEQ. ID NO: 922 |
| CVSSCCKPQC | SEQ. ID NO: 923 |
| CVSSCCQHSC | SEQ. ID NO: 924 |
| CVSSCCQPFC | SEQ. ID NO: 925 |
| CVSSCCQPSC | SEQ. ID NO: 926 |
| CVSSCCRPQC | SEQ. ID NO: 927 |

| | |
|---|---|
| CVSTCCRPTC | SEQ. ID NO: 928 |
| CVTRCCSTPC | SEQ. ID NO: 929 |
| CVTSCCQPAC | SEQ. ID NO: 930 |
| CVTSCCQPSC | SEQ. ID NO: 931 |
| CVYSCCQPFC | SEQ. ID NO: 932 |
| CVYSCCQPSC | SEQ. ID NO: 933 |
| GCCGCSEGCG | SEQ. ID NO: 934 |
| GCCGCSGGCG | SEQ. ID NO: 935 |
| GCCGCSRGCG | SEQ. ID NO: 936 |
| GCCRPITCCP | SEQ. ID NO: 937 |
| GCGSSCCQCS | SEQ. ID NO: 938 |
| GCGVPVCCCS | SEQ. ID NO: 939 |
| LCCPCQTTCS | SEQ. ID NO: 940 |
| PCCCLRPVCG | SEQ. ID NO: 941 |
| PCCCRPVTCQ | SEQ. ID NO: 942 |
| PCCCVRPVCG | SEQ. ID NO: 943 |
| PCCSQASCCV | SEQ. ID NO: 944 |
| PCCSQSRCCV | SEQ. ID NO: 945 |
| PCCSQSSCCK | SEQ. ID NO: 946 |
| PCCSQSSCCV | SEQ. ID NO: 947 |
| PCCWATTCCQ | SEQ. ID NO: 948 |
| QCSCCKPYCS | SEQ. ID NO: 949 |
| RCYVPVCCCK | SEQ. ID NO: 950 |
| SCCAPVYCCK | SEQ. ID NO: 951 |
| SCCISSSCCP | SEQ. ID NO: 952 |
| SCCVSSCRCP | SEQ. ID NO: 953 |
| SCGCSQCSCY | SEQ. ID NO: 954 |
| SCGLENCCCP | SEQ. ID NO: 955 |
| VCCGASSCCQ | SEQ. ID NO: 956 |
| VCCGDSSCCQ | SEQ. ID NO: 957 |
| CASSCCTPSCC | SEQ. ID NO: 958 |
| CCCPSCVVSSC | SEQ. ID NO: 959 |
| CCCPSYCVSSC | SEQ. ID NO: 960 |
| CCCSSGCGSSC | SEQ. ID NO: 961 |
| CCDTCPPPCCK | SEQ. ID NO: 962 |
| CCEPHCCALSC | SEQ. ID NO: 963 |
| CCEPPCCAPSC | SEQ. ID NO: 964 |
| CCEPPCCATSC | SEQ. ID NO: 965 |
| CCETSCCQPSC | SEQ. ID NO: 966 |
| CCGSSCCGSGC | SEQ. ID NO: 967 |
| CCGSSCCGSSC | SEQ. ID NO: 968 |
| CCHPRCCISSC | SEQ. ID NO: 969 |
| CCHPSCCESSC | SEQ. ID NO: 970 |
| CCHPSCCISSC | SEQ. ID NO: 971 |
| CCHPSCCVSSC | SEQ. ID NO: 972 |
| CCHPTCCQNTC | SEQ. ID NO: 973 |
| CCHPTCCQTIC | SEQ. ID NO: 974 |
| CCISSCCKPSC | SEQ. ID NO: 975 |
| CCISSCCRPSC | SEQ. ID NO: 976 |
| CCISSSCCPSC | SEQ. ID NO: 977 |
| CCKAVCCVPTC | SEQ. ID NO: 978 |
| CCKPCCSQASC | SEQ. ID NO: 979 |
| CCKPCCSQSRC | SEQ. ID NO: 980 |
| CCKPCCSQSSC | SEQ. ID NO: 981 |

| | |
|---|---|
| CCKPCCSSSGC | SEQ. ID NO: 982 |
| CCKPCSCFSGC | SEQ. ID NO: 983 |
| CCKPCSCSSGC | SEQ. ID NO: 984 |
| CCKPCYCSSGC | SEQ. ID NO: 985 |
| CCKPICCVPVC | SEQ. ID NO: 986 |
| CCKPQCCQSVC | SEQ. ID NO: 987 |
| CCKPVCCKPIC | SEQ. ID NO: 988 |
| CCKPYCCQSSC | SEQ. ID NO: 989 |
| CCKPYCSQCSC | SEQ. ID NO: 990 |
| CCMPVCCKPVC | SEQ. ID NO: 991 |
| CCMPVCCKTVC | SEQ. ID NO: 992 |
| CCMSSCCKPQC | SEQ. ID NO: 993 |
| CCNPCCSQSSC | SEQ. ID NO: 994 |
| CCPGDCFTCCT | SEQ. ID NO: 995 |
| CCPSCVVSSCC | SEQ. ID NO: 996 |
| CCPSYCVSSCC | SEQ. ID NO: 997 |
| CCQNTCCRTTC | SEQ. ID NO: 998 |
| CCQPACCVSSC | SEQ. ID NO: 999 |
| CCQPCCHPTCY | SEQ. ID NO: 1000 |
| CCQPCCRPTSC | SEQ. ID NO: 1001 |
| CCQPICGSSCC | SEQ. ID NO: 1002 |
| CCQPICVTSCC | SEQ. ID NO: 1003 |
| CCQPNCCRPSC | SEQ. ID NO: 1004 |
| CCQPSCCETSC | SEQ. ID NO: 1005 |
| CCQPSCCRPAC | SEQ. ID NO: 1006 |
| CCQPSCCSTPC | SEQ. ID NO: 1007 |
| CCQPSCCSTTC | SEQ. ID NO: 1008 |
| CCQPSCCVPSC | SEQ. ID NO: 1009 |
| CCQPSCCVSSC | SEQ. ID NO: 1010 |
| CCQPTCCHPSC | SEQ. ID NO: 1011 |
| CCQPTCCQPTC | SEQ. ID NO: 1012 |
| CCQPTCCRPRC | SEQ. ID NO: 1013 |
| CCQPTCCRPSC | SEQ. ID NO: 1014 |
| CCQPTCCRPTC | SEQ. ID NO: 1015 |
| CCQPTCCRTTC | SEQ. ID NO: 1016 |
| CCQPTCLSSCC | SEQ. ID NO: 1017 |
| CCQPTCLTSCC | SEQ. ID NO: 1018 |
| CCQPTCVASCC | SEQ. ID NO: 1019 |
| CCQPTCVTSCC | SEQ. ID NO: 1020 |
| CCQPYCHPTCC | SEQ. ID NO: 1021 |
| CCQSMCCQPTC | SEQ. ID NO: 1022 |
| CCQSNCCVPVC | SEQ. ID NO: 1023 |
| CCQSSCCKPCS | SEQ. ID NO: 1024 |
| CCQSSCCKPSC | SEQ. ID NO: 1025 |
| CCQSSCCKPYC | SEQ. ID NO: 1026 |
| CCQSSCCQSSC | SEQ. ID NO: 1027 |
| CCQSSCCVPVC | SEQ. ID NO: 1028 |
| CCQSSCFKPCC | SEQ. ID NO: 1029 |
| CCQSSCSKPCC | SEQ. ID NO: 1030 |
| CCQSSCYKPCC | SEQ. ID NO: 1031 |
| CCQSVCCQPTC | SEQ. ID NO: 1032 |
| CCQTICRSTCC | SEQ. ID NO: 1033 |
| CCQTTCCRPSC | SEQ. ID NO: 1034 |
| CCQTTCCRTTC | SEQ. ID NO: 1035 |

| Sequence | SEQ ID NO |
|---|---|
| CCRPACCETTC | SEQ. ID NO: 1036 |
| CCRPACCQNTC | SEQ. ID NO: 1037 |
| CCRPLCCQTTC | SEQ. ID NO: 1038 |
| CCRPQCCQSVC | SEQ. ID NO: 1039 |
| CCRPQCCQTTC | SEQ. ID NO: 1040 |
| CCRPSCCESSC | SEQ. ID NO: 1041 |
| CCRPSCCETTC | SEQ. ID NO: 1042 |
| CCRPSCCGSSC | SEQ. ID NO: 1043 |
| CCRPSCCISSC | SEQ. ID NO: 1044 |
| CCRPSCCKPQC | SEQ. ID NO: 1045 |
| CCRPSCCQTTC | SEQ. ID NO: 1046 |
| CCRPSCCVSRC | SEQ. ID NO: 1047 |
| CCRPSCCVSSC | SEQ. ID NO: 1048 |
| CCRPTCCQNTC | SEQ. ID NO: 1049 |
| CCRPTCCQTTC | SEQ. ID NO: 1050 |
| CCRPVCCDPCS | SEQ. ID NO: 1051 |
| CCRTTCCQPTC | SEQ. ID NO: 1052 |
| CCRTTCCRPSC | SEQ. ID NO: 1053 |
| CCRTTCCRTTC | SEQ. ID NO: 1054 |
| CCSCSSCGSCA | SEQ. ID NO: 1055 |
| CCSPGCQPTCC | SEQ. ID NO: 1056 |
| CCSQSSCCKPC | SEQ. ID NO: 1057 |
| CCSSGCGSCCQ | SEQ. ID NO: 1058 |
| CCSSGCGSSCC | SEQ. ID NO: 1059 |
| CCSTPCCQPTC | SEQ. ID NO: 1060 |
| CCVPACSCSSC | SEQ. ID NO: 1061 |
| CCVPACSCTSC | SEQ. ID NO: 1062 |
| CCVPICCKPIC | SEQ. ID NO: 1063 |
| CCVPICCKPVC | SEQ. ID NO: 1064 |
| CCVPVCCKPIC | SEQ. ID NO: 1065 |
| CCVPVCCKPVC | SEQ. ID NO: 1066 |
| CCVPVCCKSNC | SEQ. ID NO: 1067 |
| CCVPVCCKTVC | SEQ. ID NO: 1068 |
| CCVPVCCSSSC | SEQ. ID NO: 1069 |
| CCVPVCCVPVC | SEQ. ID NO: 1070 |
| CCVSSCCKPQC | SEQ. ID NO: 1071 |
| CCVSSCCQHSC | SEQ. ID NO: 1072 |
| CCVSSCCQPSC | SEQ. ID NO: 1073 |
| CCVSSCCRPQC | SEQ. ID NO: 1074 |
| CCVSTCCRPTC | SEQ. ID NO: 1075 |
| CCVSVCCKPVC | SEQ. ID NO: 1076 |
| CDSSCCQPSCC | SEQ. ID NO: 1077 |
| CEPCCRPVCCD | SEQ. ID NO: 1078 |
| CFKPCCCQSSC | SEQ. ID NO: 1079 |
| CGDGCCCPSCY | SEQ. ID NO: 1080 |
| CGGGCCGSSCC | SEQ. ID NO: 1081 |
| CGGSCCGSSCC | SEQ. ID NO: 1082 |
| CGLENCCCPSC | SEQ. ID NO: 1083 |
| CGQSCCRPACC | SEQ. ID NO: 1084 |
| CGQSCCRPVCC | SEQ. ID NO: 1085 |
| CGSCCQSSCCN | SEQ. ID NO: 1086 |
| CGSCGCSQCNC | SEQ. ID NO: 1087 |
| CGSCGCSQCSC | SEQ. ID NO: 1088 |
| CGSGCCGPVCC | SEQ. ID NO: 1089 |

-continued

| Sequence | SEQ ID NO |
|---|---|
| CGSGCCVPVCC | SEQ. ID NO: 1090 |
| CGSNCCQPCCR | SEQ. ID NO: 1091 |
| CGSSCCQPCCH | SEQ. ID NO: 1092 |
| CGSSCCQPCCR | SEQ. ID NO: 1093 |
| CGSSCCQPCYC | SEQ. ID NO: 1094 |
| CGSSCCQPSCC | SEQ. ID NO: 1095 |
| CGSSCCQSSCC | SEQ. ID NO: 1096 |
| CGSSCCVPICC | SEQ. ID NO: 1097 |
| CGSSCCVPVCC | SEQ. ID NO: 1098 |
| CGSSCSQCSCC | SEQ. ID NO: 1099 |
| CGVPVCCCSCS | SEQ. ID NO: 1100 |
| CHPRCCISSCC | SEQ. ID NO: 1101 |
| CHPSCCESSCC | SEQ. ID NO: 1102 |
| CHPSCCISSCC | SEQ. ID NO: 1103 |
| CHPTCCQNTCC | SEQ. ID NO: 1104 |
| CISSCCHPSCC | SEQ. ID NO: 1105 |
| CISSCCKPSCC | SEQ. ID NO: 1106 |
| CISSCCRPSCC | SEQ. ID NO: 1107 |
| CISSSCCPSCC | SEQ. ID NO: 1108 |
| CKPCCCSSGCG | SEQ. ID NO: 1109 |
| CKPCCSQASCC | SEQ. ID NO: 1110 |
| CKPCCSQSRCC | SEQ. ID NO: 1111 |
| CKPCCSQSSCC | SEQ. ID NO: 1112 |
| CKPQCCQSMCC | SEQ. ID NO: 1113 |
| CKPQCCQSVCC | SEQ. ID NO: 1114 |
| CKPVCCCVPAC | SEQ. ID NO: 1115 |
| CKPVCCKPICC | SEQ. ID NO: 1116 |
| CKPVCCMPVCC | SEQ. ID NO: 1117 |
| CKPVCCVPVCC | SEQ. ID NO: 1118 |
| CKPVCCVSVCC | SEQ. ID NO: 1119 |
| CKPYCSQCSCC | SEQ. ID NO: 1120 |
| CLPCCRPTCCQ | SEQ. ID NO: 1121 |
| CLTSCCQPSCC | SEQ. ID NO: 1122 |
| CMSSCCKPQCC | SEQ. ID NO: 1123 |
| CNPCCSQSSCC | SEQ. ID NO: 1124 |
| CPACCVSSCCQ | SEQ. ID NO: 1125 |
| CPESCCEPHCC | SEQ. ID NO: 1126 |
| CPESCCEPPCC | SEQ. ID NO: 1127 |
| CPSCCESSCCR | SEQ. ID NO: 1128 |
| CPSCCQTTCCR | SEQ. ID NO: 1129 |
| CPSCCVSSCCR | SEQ. ID NO: 1130 |
| CQCSCCKPYCS | SEQ. ID NO: 1131 |
| CQETCCRPSCC | SEQ. ID NO: 1132 |
| CQNTCCRTTCC | SEQ. ID NO: 1133 |
| CQPACCTASCC | SEQ. ID NO: 1134 |
| CQPACCTSSCC | SEQ. ID NO: 1135 |
| CQPACCTTSCC | SEQ. ID NO: 1136 |
| CQPACCVPVCC | SEQ. ID NO: 1137 |
| CQPACCVSSCC | SEQ. ID NO: 1138 |
| CQPCCHPTCCQ | SEQ. ID NO: 1139 |
| CQPCCRPACCE | SEQ. ID NO: 1140 |
| CQPCCRPACCQ | SEQ. ID NO: 1141 |
| CQPCCRPTCCQ | SEQ. ID NO: 1142 |
| CQPCYCPACCV | SEQ. ID NO: 1143 |

| Sequence | SEQ ID NO |
|---|---|
| CQPICCGSSCC | SEQ. ID NO: 1144 |
| CQPRCCETSCC | SEQ. ID NO: 1145 |
| CQPSCCETSCC | SEQ. ID NO: 1146 |
| CQPSCCRPACC | SEQ. ID NO: 1147 |
| CQPSCCVPSCC | SEQ. ID NO: 1148 |
| CQPSCCVSSCC | SEQ. ID NO: 1149 |
| CQPTCCCPSYC | SEQ. ID NO: 1150 |
| CQPTCCGSSCC | SEQ. ID NO: 1151 |
| CQPTCCHPSCC | SEQ. ID NO: 1152 |
| CQPTCCQPTCC | SEQ. ID NO: 1153 |
| CQPTCCRPSCC | SEQ. ID NO: 1154 |
| CQPTCCRPTCC | SEQ. ID NO: 1155 |
| CQPTCCRTTCC | SEQ. ID NO: 1156 |
| CQQACCMPVCC | SEQ. ID NO: 1157 |
| CQQACCVPICC | SEQ. ID NO: 1158 |
| CQQACCVPVCC | SEQ. ID NO: 1159 |
| CQQSCCVPVCC | SEQ. ID NO: 1160 |
| CQQSCCVSVCC | SEQ. ID NO: 1161 |
| CQSNCCVPVCC | SEQ. ID NO: 1162 |
| CQSSCCCPASC | SEQ. ID NO: 1163 |
| CQSSCCKPCCS | SEQ. ID NO: 1164 |
| CQSSCCKPCSC | SEQ. ID NO: 1165 |
| CQSSCCKPYCC | SEQ. ID NO: 1166 |
| CQSSCCNPCCS | SEQ. ID NO: 1167 |
| CQSSCCQSSCC | SEQ. ID NO: 1168 |
| CQSSCCVPVCC | SEQ. ID NO: 1169 |
| CQSSCFKPCCC | SEQ. ID NO: 1170 |
| CQSSCSKPCCC | SEQ. ID NO: 1171 |
| CQSSCYKPCCC | SEQ. ID NO: 1172 |
| CQSVCCQPTCC | SEQ. ID NO: 1173 |
| CQTTCCCPSCV | SEQ. ID NO: 1174 |
| CQTTCCRPSCC | SEQ. ID NO: 1175 |
| CQTTCCRTTCC | SEQ. ID NO: 1176 |
| CRPACCETTCC | SEQ. ID NO: 1177 |
| CRPACCQNTCC | SEQ. ID NO: 1178 |
| CRPCCCLRPVC | SEQ. ID NO: 1179 |
| CRPCCCVRPVC | SEQ. ID NO: 1180 |
| CRPCCWATTCC | SEQ. ID NO: 1181 |
| CRPLCCQTTCC | SEQ. ID NO: 1182 |
| CRPQCCQSVCC | SEQ. ID NO: 1183 |
| CRPQCCQTTCC | SEQ. ID NO: 1184 |
| CRPRCCISSCC | SEQ. ID NO: 1185 |
| CRPSCCESSCC | SEQ. ID NO: 1186 |
| CRPSCCISSCC | SEQ. ID NO: 1187 |
| CRPSCCKPQCC | SEQ. ID NO: 1188 |
| CRPSCCPSCCQ | SEQ. ID NO: 1189 |
| CRPSCCQTTCC | SEQ. ID NO: 1190 |
| CRPSCCRPQCC | SEQ. ID NO: 1191 |
| CRPSCCVSRCC | SEQ. ID NO: 1192 |
| CRPSCCVSSCC | SEQ. ID NO: 1193 |
| CRPTCCQNTCC | SEQ. ID NO: 1194 |
| CRPVCCCEPTC | SEQ. ID NO: 1195 |
| CRPVCCCYSCE | SEQ. ID NO: 1196 |
| CRTTCCHPSCC | SEQ. ID NO: 1197 |

| Sequence | SEQ ID NO |
|---|---|
| CRTTCCRPSCC | 1198 |
| CSCCKPYCSQC | 1199 |
| CSKPCCCQSSC | 1200 |
| CSPCCQPTCCR | 1201 |
| CSPCCVSSCCQ | 1202 |
| CSQCSCCKPCY | 1203 |
| CSQCSCYKPCC | 1204 |
| CSQSNCCKPCC | 1205 |
| CSQSSCCKPCC | 1206 |
| CSSSCCQPSCC | 1207 |
| CTPSCCQPACC | 1208 |
| CVASCCQPSCC | 1209 |
| CVPICCCKPVC | 1210 |
| CVPSCCQPCCH | 1211 |
| CVPVCCCKPMC | 1212 |
| CVPVCCCKPVC | 1213 |
| CVPVCCKPVCC | 1214 |
| CVSSCCKPQCC | 1215 |
| CVSSCCQHSCC | 1216 |
| CVSSCCQPCCH | 1217 |
| CVSSCCQPCCR | 1218 |
| CVSSCCQPFCC | 1219 |
| CVSSCCQPSCC | 1220 |
| CVSSCCRPQCC | 1221 |
| CVTRCCSTPCC | 1222 |
| CVTSCCQPACC | 1223 |
| CVTSCCQPSCC | 1224 |
| CVYSCCQPFCC | 1225 |
| CVYSCCQPSCC | 1226 |
| CYCPACCVSSC | 1227 |
| CYKPCCCQSSC | 1228 |
| CYKPCCCSSGC | 1229 |
| MCCCVPACSCS | 1230 |
| NCCVPVCCQCK | 1231 |
| QCSCCKPCYCS | 1232 |
| QCSCYKPCCCS | 1233 |
| SCCVPICCQCK | 1234 |
| SCCVPVCCQCK | 1235 |
| SCGCSQCNCCK | 1236 |
| SCGCSQCSCCK | 1237 |
| VCCCVPACSCS | 1238 |
| VCCCVPACSCT | 1239 |

The present invention is of course in any way restricted to the embodiments herein described and one with ordinary skill in the area can provide many possibilities to modifications and substitutions of technical characteristics by equivalent ones, depending on each situation, as defined in the claims.

The preferred embodiments described above may obviously be combined. The following claims define further preferred embodiments.

---

What is claimed is:

1. A method for treating hair, the method comprising:
applying to the hair of a subject a hair composition comprising,
at least one peptide sequence having at least 90% sequence identity with SEQ ID NO: 412 or SEQ ID NO: 409,
wherein the at least one peptide sequence has from about 15% to about 30% cysteine amino acid content.

2. The method of claim 1, wherein the at least one peptide has about 15-25% cysteine amino acid content.

3. The method of claim 1, wherein the at least one peptide forms one or more molecular interactions with the hair.

4. The method of claim 3, wherein the one or more molecular interactions is one or more disulfide bonds.

5. The method of claim 3, wherein the one or more molecular interactions improves one or more properties of the hair.

6. The method of claim 5, wherein the one or more properties of the hair is strength, elasticity, or appearance of the hair.

7. The method of claim 3, wherein the one or more interactions repairs damage to keratinous fiber.

8. The method of claim 1, wherein the hair composition further comprises at least one excipient suitable for dermatological use.

9. The method of claim 8, wherein the at least one excipient suitable for dermatological use is selected from the group consisting of non-naturally occurring surfactants, emulsifiers, preservatives, thickeners, organic polymers, humectants, silicones, oils, fragrances, vitamins and buffers.

10. The method of claim 1, wherein the hair composition is in the form of a shampoo, conditioner, lotion, foam, elixir, spray, gel, mask, aerosol, or any formulation applied with or without subsequent rinsing.

11. The method of claim 1, wherein the at least one peptide has at least 95% sequence identity with SEQ ID NO: 412 or SEQ ID NO: 409.

12. The method of claim 1, wherein the at least one peptide is SEQ ID NO: 412 or SEQ ID NO: 409.

13. A method for treating hair, the method comprising:
applying to the hair of a subject a hair composition comprising:
a keratin peptide fragment having 10% to 50% cysteine amino acid content, wherein the total number of cysteine amino acids in the keratin peptide fragment is 2-5 cysteine amino acids and the keratin peptide fragment comprises SEQ ID NO: 5, SEQ ID NO: 409, or SEQ ID NO: 412.

14. The method of claim 13, wherein the keratin peptide fragment penetrates the hair fiber of the subject.

15. The method of claim 13, wherein the keratin peptide fragment comprises SEQ ID NO: 412.

16. The method of claim 13, wherein treating hair comprises the keratin peptide fragment forming one or more disulfide bonds to keratin in the hair of the subject.

17. The method of claim 13, wherein the keratin peptide fragment is present in the composition at 0.01% to 5% (w/w).

18. The method of claim 13, wherein the tensile strength of the hair is increased after applying to the hair of the subject the hair composition.

19. The method of claim 13, wherein the keratin peptide fragment is present in the composition at 0.001% to 20% (w/w).

20. The method of claim 13, wherein the keratin peptide fragment comprises SEQ ID NO: 409.

* * * * *